(12) United States Patent
Kawasaki et al.

(10) Patent No.: US 7,378,423 B2
(45) Date of Patent: May 27, 2008

(54) PYRIMIDINE COMPOUND AND MEDICAL USE THEREOF

(75) Inventors: Hisashi Kawasaki, Osaka (JP); Hiroyuki Abe, Osaka (JP); Kazuhide Hayakawa, Osaka (JP); Tetsuya Iida, Osaka (JP); Shinichi Kikuchi, Osaka (JP); Takayuki Yamaguchi, Osaka (JP); Toyomichi Nanayama, Osaka (JP); Hironori Kurachi, Osaka (JP); Masahiro Tamaru, Osaka (JP); Yoshikazu Hori, Osaka (JP); Mitsuru Takahashi, Osaka (JP); Takayuki Yoshida, Yokohama (JP); Toshiyuki Sakai, Kyoto (JP)

(73) Assignee: Japan Tobacco Inc., Tokyo (JP)

( * ) Notice: Subject to any disclaimer, the term of this patent is extended or adjusted under 35 U.S.C. 154(b) by 95 days.

(21) Appl. No.: 11/150,792

(22) Filed: Jun. 10, 2005

(65) Prior Publication Data

US 2006/0014768 A1 Jan. 19, 2006

Related U.S. Application Data

(60) Provisional application No. 60/630,596, filed on Nov. 23, 2004.

(30) Foreign Application Priority Data

Jun. 11, 2004 (JP) ............................. 2004-174770
Nov. 10, 2004 (JP) ............................. 2004-327111

(51) Int. Cl.
*A61K 31/519* (2006.01)
*C07D 487/04* (2006.01)
*C07D 413/10* (2006.01)
*C07D 413/12* (2006.01)
*A61P 35/00* (2006.01)
*A61P 31/5355* (2006.01)

(52) U.S. Cl. ................... 514/264.1; 544/256; 544/279; 544/117; 514/236.2; 514/234.2

(58) Field of Classification Search ............ 514/262.1, 514/264.1, 236.2, 234.2; 544/256, 279, 117
See application file for complete search history.

(56) References Cited

U.S. PATENT DOCUMENTS

2004/0138285 A1 7/2004 Okazaki

FOREIGN PATENT DOCUMENTS

| CA | 2 385 412 A1 | 11/2002 |
|---|---|---|
| JP | 2002-532414 T | 10/2002 |
| JP | 2002-532415 T | 10/2002 |
| JP | 2002-534380 T | 10/2002 |
| JP | 2002-534381 T | 10/2002 |
| JP | 2002-332247 A | 11/2002 |
| JP | 2003-504401 T | 2/2003 |
| JP | 2004-504294 T | 2/2004 |
| WO | WO 00/35435 A1 | 6/2000 |
| WO | WO 00/35436 A2 | 6/2000 |
| WO | WO 00/40235 A2 | 7/2000 |
| WO | WO 00/40237 A1 | 7/2000 |
| WO | WO 01/05393 A2 | 1/2001 |
| WO | WO 02/03997 A1 | 1/2002 |
| WO | WO 02/06213 A2 | 1/2002 |
| WO | WO 02/06520 A1 | 1/2002 |
| WO | WO 02/087620 A1 | 11/2002 |
| WO | WO 02/094824 A1 | 11/2002 |
| WO | WO 03/062236 A1 | 7/2003 |

OTHER PUBLICATIONS

Calvet, J. Am. Soc. Nephrol, 17: 1498-1500, 2006.*
Guo, et al., Leukemia, 2006, 20, pp. 115-121.*
Boultwood, et al., Brit. J. of Haematol, 138, pp. 3-11, 2007.*
Wang, et al., J. Biol. Chem., vol. 280, No. 13, 2005, pp. 12339-12343.*

(Continued)

*Primary Examiner*—Mark L. Berch
*Assistant Examiner*—Cecilia M Jaisle
(74) *Attorney, Agent, or Firm*—Leydig, Voit & Mayer, Ltd.

(57) ABSTRACT

The present invention relates to a pyrimidine compound or a pharmaceutically acceptable salt thereof represented by the following formula [I]

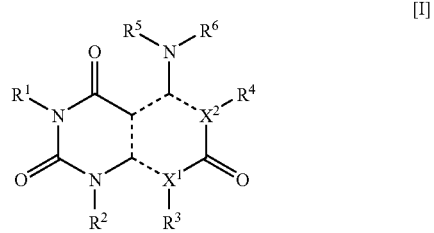

wherein each symbol is as defined in the specification and a method of therapeutically or prophylactically treating an undesirable cell proliferation, comprising administering such a compound. The compound of the present invention has superior activity in suppressing undesirable cell proliferation, particularly, an antitumor activity, and is useful as an antitumor agent for the prophylaxis or treatment of cancer, rheumatism, and the like. In addition, the compound of the present invention can be a more effective antitumor agent when used in combination with other antitumor agents such as an alkylating agent or metabolism antagonist.

26 Claims, No Drawings

OTHER PUBLICATIONS

Tamir, et al., Cell Growth & Differentiation, vol. 11, pp. 269-277, May 2000.*
Crees, Calif. St. J. Med., vol. V, No. II, 1907, pp. 292-293.*
Burova et al., *Chemistry of Heterocyclic Compounds*, 5: 674-680 (1991) [Translation pp. 538-544 (1991)].
Hannon et al., *Nature*, 371: 257-261 (Sep. 15, 1994).
Hitomi et al., *FEBS Letters*, 554: 347-350 (2003).
Hoshino et al., *Journal of Biological Chemistry*, 276(4): 2686-2692 (Jan. 26, 2001).
Khattab et al., *Journal für Praktische Chemie*, 338: 151-156 (1996).
Ogura et al., *Chem. Pharm. Bull.*, 21(9): 2014-2018 (1973).
Su et al., *Journal of Medicinal Chemistry*, 29(5): 709-715 (1986).

* cited by examiner

PYRIMIDINE COMPOUND AND MEDICAL USE THEREOF

TECHNICAL FIELD

The present invention relates to a novel pyrimidine compound or a pharmaceutically acceptable salt thereof useful as an agent for the prophylaxis or treatment of diseases caused by undesirable cell proliferation, particularly, an antitumor agent. Moreover, the present invention relates to novel use of a certain kind of pyrimidine compound or a pharmaceutically acceptable salt thereof as an agent for the prophylaxis or treatment of a disease caused by undesirable cell proliferation, particularly, as an antitumor agent. More particularly, the present invention relates to a pharmaceutical agent comprising a pyrimidine compound showing a p15 protein inducing action and/or a p27 protein inducing action and/or an MEK inhibitory action, or a pharmaceutically acceptable salt thereof.

BACKGROUND ART

A "cell cycle" means a cycle wherein the period for a cell to divide and once again divide is one cycle, and this cycle is also referred to as a "cell division cycle".

A cell cycle includes four phases in a determined order. They are DNA duplication preparation phase (G1 phase), DNA duplication phase (S phase), division preparation phase (G2 phase) and division phase (M phase), and regulated by many factors. Among them, the kinase activity of a cyclin/cyclin dependent kinase (CDK) complex is essential for the regulation of the cell cycle.

As a protein to inhibit the kinase activity, a CDK inhibitory protein is known. The CDK inhibitory proteins of mammalian cells are p21 family and p16 family, both of which are considered to negatively regulate the progress of cell cycle and responsible for cell differentiation, apoptosis and repair of DNA damage due to irradiation of X ray and the like. At present, p21, p27 and p57 have been reported as a p21 family, and p16, p15, p18 and p19 have been reported as a p16 family.

When these CDK inhibitory proteins are highly expressed in the cell, the cell proliferation is arrested at G1 phase.

The p21 family shows an inhibitory activity on a relatively wide range and plural cyclin/CDK complexes. For example, cyclin E/CDK 2 which is an important cyclin/CDK complex from G1 phase to G1/S transition phase, cyclin B/Cdc2 which is important for M phase and the like can be mentioned. The p16 family is a specific inhibitory factor against cyclin D/CDK 4 and cyclin D/CDK 6, which are one of the cyclin/CDKs in the G1 phase, and is considered to dissociate the cyclin/CDK complex by binding with CDK 4 and CDK 6, respectively.

From the examination of clinical materials of cancer of esophangus, pancreatic cancer, non-small cell lung cancer, skin cancer and the like, highly frequent incidence of genetic abnormality of P16 has been reported, and high cancer incidence in p16 knock out mice has been demonstrated, and therefore, clinical application of p16 inducer has been tried.

Under such situation, p15 protein (aka:INK4B, also simply referred to as p15) has been found as a p16 family. In 1994, induction of p15 expression by TGF-β stimulation was confirmed in human keratinocyte cell (HaCaT), and p15 was considered to be one of the factors negatively regulating the cell cycle. It is known that induction of G1 phase cell cycle arrest in HaCaT by TGF-β leads to the suppression of cell proliferation (Letters to Nature, Sep. 15, 1994, vol. 371, pp. 257-261).

While the histondeacetylase (HDAC) inhibitor is known to arrest cell cycles at G1 phase or G2 phase in human cancer cell, it has been found recently that trichostatin A, which is an HDAC inhibitor, induces p15 gene in human colon cancer cell (HCT116p21(−/−)), and the induction of p15 by trichostatin A is involved in the inhibition of the cell proliferation of the cancer cells (FEBS Letters, 2003, vol. 554, pp. 347-350).

In this way, a compound that induces p15 and/or p27 is expected to inhibit the cell proliferation of cancer cells and the like.

In the meantime, Mitogen-activated protein (MAP) Kinase/extracellular signal-regulated kinase (ERK) kinase (hereinafter to be referred to as MEK) is known to be involved in the regulation of cell proliferation as a kinase that mediates Raf-MEK-ERK signal transduction pathway, and the Raf family (B-Raf, C-Raf etc.) activates the MEK family (MEK-1, MEK-2 etc.) and the MEK family activates the ERK family (ERK-1 and ERK-2).

Activation of Raf-MEK-ERK signal transduction pathway in cancer, particularly colorectal cancer, pancreatic cancer, lung cancer, breast cancer and the like, has been frequently observed.

In addition, since the signals produced by signal molecules such as growth factor, cytokine and the like converge to the activation of MEK-ERK, inhibition of these functions is considered to more effectively suppress Raf-MEK-ERK signal transduction than the suppression of the function of RTK, Ras, Raf and the like in the upstream.

Moreover, it is also known in recent years that a compound having an MEK inhibitory activity extremely effectively induces inhibition of ERK1/2 activity and suppression of cell proliferation (The Journal of Biological Chemistry, vol. 276, No. 4, pp. 2686-2692, 2001), and the compound is expected to show effects on the disease caused by undesirable cell proliferation, such as tumor and the like. In addition, an MEK inhibitor is expected to inhibit infiltration or metastaticity of cells via promotion of expression of Matrix metalloproteinase (MMP) and CD44, and angiogenesis via promotion of expression of vascular endothelial growth factor (VEGF).

Furthermore, application to chronic pain (JP 2003-504401: WO 01/005393), application to diseases or symptoms mediated by neutrophile (JP2002-332247: CA-2385412), application to graft rejection (JP 2002-532414: WO 00/35435), application to arthritis (JP 2002-532415: WO 00/35436), application to asthma (JP 2002-534380: WO 00/40235), application to viral diseases (JP 2002-534381: WO 00/40237), application to diseases caused by deformation or injury of cartilage (WO2002/087620: U.S. 2004/138285), application to Peutz-Jeghers syndrome (WO02/006520) are expected.

However, such pharmaceutical agent has not been marked heretofore.

As an already commercially available antitumor agent, the following compound (Gefitinib) and the like are known (Iressa tablet 250 package insert).

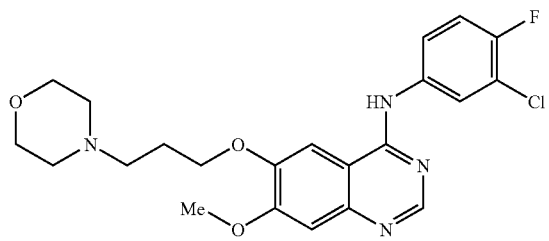

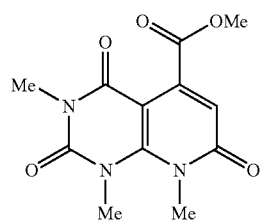

JP-A-2004-504294 (patent family: WO2002/006213) describe the following compound and the like as compounds having an antitumor activity. In addition, the MEK inhibitory activity of such compounds is described (JP-A-2004-504294, pp. 123-124, Example 39, Example 241).

In these literatures, however, the compound of the present invention is not disclosed, nor is there found a description suggestive thereof.

Furthermore, WO2002/094824 discloses the following compound and the like (WO2002/094824, p. 55, Example 9) as a therapeutic agent having a cytokine regulating action for immune, inflammatory or allergic disease.

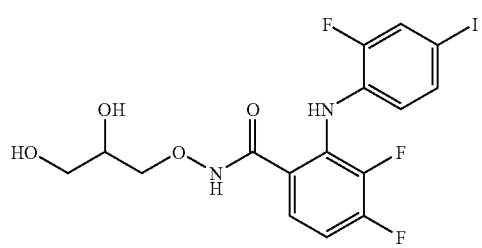

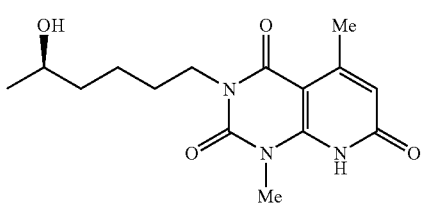

Known compounds relatively similar to the pharmaceutical agent of the present invention are described below.

In the literatures issued in 1991, the antitumor activity of pyrido[2,3-d]pyrimidine derivative has been studied and it is described, for example, that some of the following compounds and the like have an inhibitory activity in sarcoma, leukemia cells (Khimiia geterotsiklicheskikh soedinenii, 1991, No. 5, pp. 674-680 (English translation p. 542, lines 4-7; p. 538, compound IIIa)).

In the literatures issued in 1996, synthetic methods of the following compound and the like are disclosed (Journal fur Praktische Chemie, 1996, vol. 338, pp. 151-156 (p. 154, Table 1, compound 8f)).

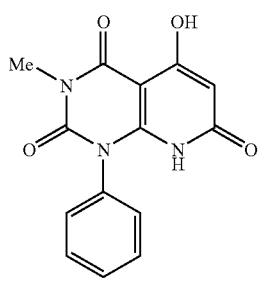

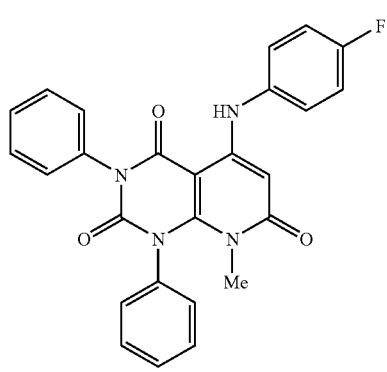

In the literatures issued in 1973, novel synthetic methods of the following compound and the like are disclosed and the antitumor activity of pyrido[2,3-d]pyrimidine derivative is described (Chem. Pharm. Bull., 1973, No. 21, vol. 9, pp. 2014-2018 (p. 2015, chart 2, compound VIII)).

In the literatures issued in 1986, synthetic methods of the following compound and the like as a synthetic intermediate for aminopterin analog having an antitumor activity are disclosed (Journal of Medicinal Chemistry, 1986, vol. 29, No. 5, pp. 709-715 (p. 709 abstract; p. 712, Table 1, compound 9b)).

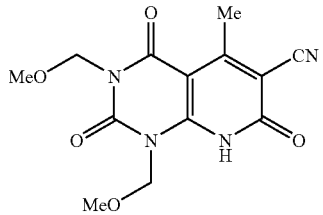

However, this literature does not contain a description relating to the use of these compounds as antitumor agents, the compound of the present invention is not disclosed and a description suggestive thereof is not found.

DISCLOSURE OF THE INVENTION

An object of the present invention is to provide a pharmaceutical agent containing a pyrimidine compound showing undesirable cell proliferation inhibitory action, particularly an antitumor action or a pharmaceutically acceptable salt thereof.

The present inventors have conducted intensive studies in an attempt to find a compound having such action and completed the present invention.

More particularly, the present invention provides the following (1) to (37).

(1) Use of a compound represented by the following formula [I] or a pharmaceutically acceptable salt thereof as an active ingredient for the production of a pharmaceutical agent for treating a tumor:

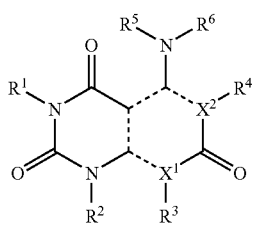

wherein
$X^1$ and $X^2$ are the same or different and each is a carbon atom or a nitrogen atom, wherein the

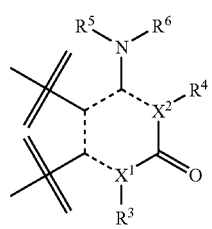

moiety is

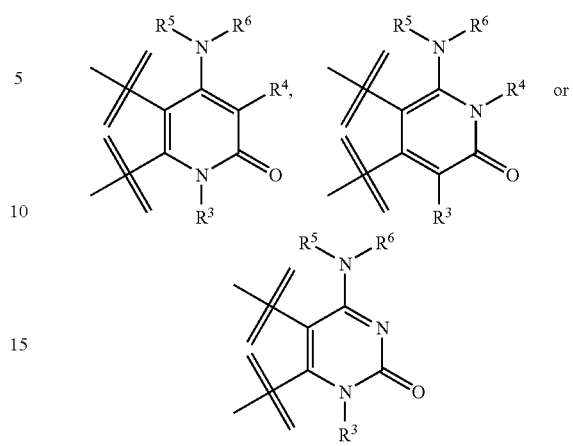

$R^1$, $R^2$, and $R^6$ are the same or different and each is
a $C_{1-6}$ alkyl group,
a $C_{2-6}$ alkenyl group,
wherein the $C_{1-6}$ alkyl group and the $C_{2-6}$ alkenyl group are optionally substituted by 1 to 3 substituents selected from the following group A, or

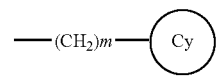

wherein m is 0 or an integer of 1 to 4,
ring Cy is a $C_{3-12}$ carbon ring group or a heterocyclic group,
wherein the heterocyclic group is a saturated or unsaturated ring group having, besides carbon atom, 1 to 4 hetero atoms selected from an oxygen atom, a nitrogen atom and a sulfur atom, the $C_{3-12}$ carbon ring group and the heterocyclic group are optionally substituted by 1 to 5 substituents selected from the following group B,
$R^3$, $R^4$, and $R^5$ are the same or different and each is
a hydrogen atom,
a hydroxyl group,
a $C_{1-6}$ alkyl group,
a $C_{2-6}$ alkenyl group,
wherein the $C_{1-6}$ alkyl group and the $C_{2-6}$ alkenyl group are optionally substituted by 1 to 3 substituents selected from the following group A,
a $C_{3-12}$ carbon ring group or
a heterocyclic group,
wherein the heterocyclic group is a saturated or unsaturated ring group having, besides carbon atom, 1 to 4 hetero atoms selected from an oxygen atom, a nitrogen atom and a sulfur atom, and the $C_{3-12}$ carbon ring group and the heterocyclic group are optionally substituted by 1 to 5 substituents selected from the following group B, or
$R^2$ and $R^3$ are optionally linked to form a $C_{1-4}$ alkylene group, or
$R^4$ and $R^5$ are optionally linked to form a $C_{1-4}$ alkylene group,
wherein group A is a group consisting of
1) a halogen atom,
2) a nitro group,
3) a cyano group, 4) a C$_{1-4}$ alkyl group,
5) —OR$^{A1}$ wherein R$^{A1}$ is a hydrogen atom or a C$_{1-4}$ alkyl group,
6) —SR$^{A2}$ wherein R$^{A2}$ is a hydrogen atom or a C$_{1-4}$ alkyl group,
7) —NR$^{A3}$R$^{A4}$ wherein R$^{A3}$ and R$^{A4}$ are the same or different and each is a hydrogen atom or a C$_{1-4}$ alkyl group,
8) —COOR$^{A5}$ wherein R$^{A5}$ is a hydrogen atom or a C$_{1-4}$ alkyl group,
9) —NR$^{A6}$COR$^{A7}$ wherein R$^{A6}$ is a hydrogen atom or a C$_{1-4}$ alkyl group, R$^{A7}$ is a C$_{1-4}$ alkyl group, a C$_{3-12}$ carbon ring group or a heterocyclic group,
10) —NR$^{A8}$COOR$^{A9}$ wherein R$^{A8}$ and R$^{A9}$ are the same or different and each is a hydrogen atom or a C$_{1-4}$ alkyl group,
11) a C$_{3-12}$ carbon ring group and
12) a heterocyclic group,
  wherein the heterocyclic group is a saturated or unsaturated ring group having, besides carbon atom, 1 to 4 hetero atoms selected from an oxygen atom, a nitrogen atom and a sulfur atom,
  each of the C$_{1-4}$ alkyl groups of the above-mentioned 4), R$^{A1}$, R$^{A2}$, R$^{A3}$, R$^{A4}$, R$^{A5}$, R$^{A6}$, R$^{A7}$, R$^{A8}$ and R$^{A9}$ is optionally substituted by the same or different 1 to 3 substituents selected from the following group C, and
  each of the C$_{3-12}$ carbon ring groups of the above-mentioned 11) and R$^{A7}$, and the heterocyclic groups of 12) and R$^{A7}$ is optionally substituted by the same or different 1 to 5 substituents selected from the following group C
group B is a group consisting of
1) a halogen atom,
2) a nitro group,
3) a cyano group,
4) a C$_{1-8}$ alkyl group,
5) a C$_{2-4}$ alkenyl group,
6) a C$_{2-4}$ alkynyl group,
7) —OR$^{B1}$ wherein R$^{B1}$ is a hydrogen atom or a C$_{1-4}$ alkyl group,
8) —SR$^{B2}$ wherein R$^{B2}$ is a hydrogen atom or a C$_{1-4}$ alkyl group,
9) —NR$^{B3}$R$^{B4}$ wherein R$^{B3}$ is a hydrogen atom, a C$_{1-4}$ alkyl group, a C$_{3-12}$ carbon ring group or a heterocyclic group, and R$^{B4}$ is a hydrogen atom or a C$_{1-4}$ alkyl group,
10) —NR$^{B5}$COR$^{B6}$ wherein R$^{B5}$ is a hydrogen atom or a C$_{1-4}$ alkyl group, and R$^{B6}$ is a hydrogen atom, a C$_{1-4}$ alkyl group, a C$_{3-12}$ carbon ring group or a heterocyclic group,
11) —NR$^{B7}$COOR$^{B8}$ wherein R$^{B7}$ and R$^{B8}$ are the same or different and each is a hydrogen atom or a C$_{1-4}$ alkyl group,
12) —NR$^{B9}$CONR$^{B10}$R$^{B11}$ wherein R$^{B9}$, R$^{B10}$ and R$^{B11}$ are the same or different and each is a hydrogen atom or a C$_{1-4}$ alkyl group,
13) —NR$^{B12}$CONR$^{B13}$OR$^{B14}$ wherein R$^{B12}$, R$^{B13}$ and R$^{B14}$ are the same or different and each is a hydrogen atom or a C$_{1-4}$ alkyl group,
14) —NR$^{B15}$SO$_2$R$^{B16}$ wherein R$^{B15}$ is a hydrogen atom or a C$_{1-4}$ alkyl group, and R$^{B16}$ is a C$_{1-4}$ alkyl group, a C$_{3-12}$ carbon ring group or a heterocyclic group,
15) —SO$_2$—R$^{B17}$ wherein R$^{B17}$ is a C$_{1-4}$ alkyl group or a heterocyclic group,
16) —SO$_2$NR$^{B18}$R$^{B19}$ wherein R$^{B18}$ and R$^{B19}$ are the same or different and each is a hydrogen atom or a C$_{1-4}$ alkyl group,
17) —P(=O)(R$^{B20}$)(R$^{B21}$) wherein R$^{B20}$ and R$^{B21}$ are the same or different and each is a C$_{1-4}$ alkyl group,
18) —COOR$^{B22}$ wherein R$^{B22}$ is a hydrogen atom or a C$_{1-4}$ alkyl group,
19) —CONR$^{B23}$R$^{B24}$ wherein R$^{B23}$ and R$^{B24}$ are the same or different and each is a hydrogen atom or a C$_{1-4}$ alkyl group,
20) —NR$^{B25}$SO$_2$NR$^{B26}$R$^{B27}$ wherein R$^{B25}$, R$^{B26}$ and R$^{B27}$ are the same or different and each is a hydrogen atom or a C$_{1-4}$ alkyl group,
21) —NR$^{B28}$SO$_2$NR$^{B29}$CONR$^{B30}$R$^{B31}$ wherein R$^{B28}$, R$^{B29}$, R$^{B30}$ and R$^{B31}$ are the same or different and each is a hydrogen atom or a C$_{1-4}$ alkyl group,
22) a C$_{3-12}$ carbon ring group and
23) a heterocyclic group
  wherein each of the "C$_{1-8}$ alkyl group" of the above-mentioned 4), and the C$_{1-4}$ alkyl groups for R$^{B1}$ to R$^{B31}$ is optionally substituted by the same or different 1 to 3 substituents selected from the above-mentioned group A,
  each of the C$_{2-4}$ alkenyl group of 5) and the C$_{2-4}$ alkynyl group of 6) is optionally substituted by the same or different 1 to 3 substituents selected from the above-mentioned group A,
  the heterocyclic group is a saturated or unsaturated ring group having, besides carbon atom, 1 to 4 hetero atoms selected from an oxygen atom, a nitrogen atom and a sulfur atom, and
  each of the C$_{3-12}$ carbon ring group of the above-mentioned 22), R$^{B3}$, R$^{B6}$ and R$^{B16}$, and the heterocyclic group of the above-mentioned 23), R$^{B3}$, R$^{B6}$, R$^{B16}$ and R$^{B17}$ is optionally substituted by the same or different 1 to 5 substituents selected from the following group C, and group C is a group consisting of
1) a halogen atom,
2) a cyano group,
3) a C$_{1-4}$ alkyl group,
4) —OR$^{C1}$ wherein R$^{C1}$ is a hydrogen atom or a C$_{1-4}$ alkyl group,
5) —NR$^{C2}$R$^{C3}$ wherein R$^{C2}$ and R$^{C3}$ are the same or different and each is a hydrogen atom or a C$_{1-4}$ alkyl group,
6) —COOR$^{C4}$ wherein R$^{C4}$ is a hydrogen atom or a C$_{1-4}$ alkyl group and
7) an oxo group.
(2) A compound represented by the following formula [I'] or a pharmaceutically acceptable salt thereof:

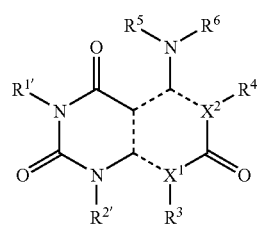

[I']

wherein
R$^{1'}$, R$^{2'}$ and R$^6$ are the same or different and each is
a C$_{1-6}$ alkyl group,
a C$_{2-6}$ alkenyl group,
  wherein the C$_{1-6}$ alkyl group and the C$_{2-6}$ alkenyl group are optionally substituted by 1 to 3 substituents selected from group A of the above-mentioned (1), or

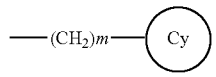

m is an integer of 0 or 1 to 4, ring Cy is a $C_{3-12}$ carbon ring group or a heterocyclic group
   wherein the heterocyclic group is a saturated or unsaturated ring having, besides carbon atom, 1 to 4 hetero atoms selected from an oxygen atom, a nitrogen atom and a sulfur atom, and the $C_{3-12}$ carbon ring group and the heterocyclic group are optionally substituted by 1 to 5 substituents selected from group B of the above-mentioned (1), provided that, when the

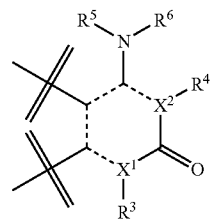

moiety is

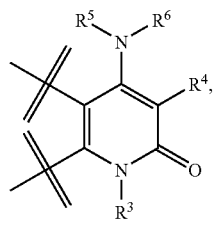

then $R^{2'}$ is not a methyl group, and when $R^{2'}$ is a phenyl group, then $R^{1'}$ is not a phenyl group, and other symbols are as defined in the above-mentioned (1).

(3) Use of the above-mentioned (1), wherein the compound is represented by the following formula [I-1]:

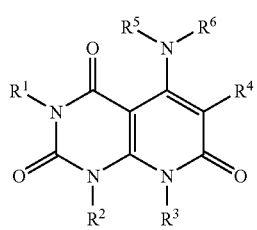

wherein each symbol in the formula is as defined in the above-mentioned (1).

(4) Use of the above-mentioned (1), wherein the compound is represented by the following formula [I-2]:

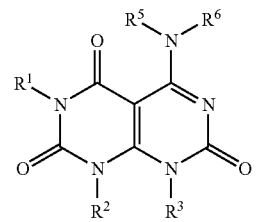

wherein each symbol in the formula is as defined in the above-mentioned (1).

(5) Use of the above-mentioned (1), wherein the compound is represented by the following formula [I-3]:

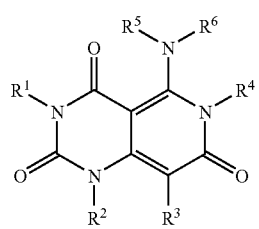

wherein each symbol in the formula is as defined in the above-mentioned (1).

(6) Use of the above-mentioned (1), wherein $R^1$ is a $C_{1-6}$ alkyl group.

(7) Use of the above-mentioned (1), wherein $R^1$ is

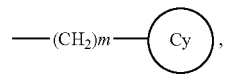

wherein m is 0, and ring Cy is a $C_{3-12}$ carbon ring group
   wherein the $C_{3-12}$ carbon ring group is optionally substituted by 1 to 5 substituents selected from group B of the above-mentioned (1).

(8) Use of the above-mentioned (1), wherein $R^1$ is a $C_{3-8}$ cycloalkyl group.

(9) Use of the above-mentioned (8), wherein $R^1$ is a cyclopropyl group.

(10) Use of the above-mentioned (1), wherein $R^2$ is

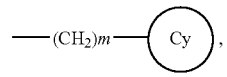

wherein m is 0, and ring Cy is a $C_{3-12}$ carbon ring group or a heterocyclic group
   wherein the $C_{3-12}$ carbon ring group and the heterocyclic group are optionally substituted by 1 to 5 substituents selected from group B of the above-mentioned (1).

(11) Use of the above-mentioned (1), wherein $R^3$ is a $C_{1-6}$ alkyl group.

(12) Use of the above-mentioned (1), wherein $R^4$ is a hydrogen atom.

(13) Use of the above-mentioned (1), wherein $R^5$ is a hydrogen atom.

(14) Use of the above-mentioned (1), wherein $R^6$ is

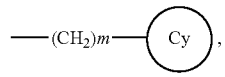

wherein m is 0, and ring Cy is a $C_{3-12}$ carbon ring group or a heterocyclic group
wherein the $C_{3-12}$ carbon ring group and the heterocyclic group are optionally substituted by 1 to 5 substituents selected from group B of the above-mentioned (1).

(15) Use of a compound of the formula [I] of the above-mentioned (1) or a pharmaceutically acceptable salt thereof as an active ingredient for the production of an antitumor agent.

(16) Use of a compound of the formula [I] of the above-mentioned (1) or a pharmaceutically acceptable salt thereof as an active ingredient for the production of a pharmaceutical agent capable of inhibiting MEK.

(17) Use of a compound of the formula [I] of the above-mentioned (1) or a pharmaceutically acceptable salt thereof as an active ingredient for the production of a pharmaceutical agent capable of inducing p15 protein.

(18) Use of a compound of the formula [I] of the above-mentioned (1) or a pharmaceutically acceptable salt thereof as an active ingredient for the production of a pharmaceutical agents for treating a disease caused by an undesirable cell proliferation.

(19) Use of the above-mentioned (18), wherein the disease causing by an undesirable cell proliferation is rheumatism.

(20) Use of a compound of the formula [I] of the above-mentioned (1) or a pharmaceutically acceptable salt thereof as an active ingredient for the production of a pharmaceutical agent capable of inhibiting undesirable cell proliferation.

(21) Use of a compound of the formula [I] of the above-mentioned (1) or a pharmaceutically acceptable salt thereof as an active ingredient for the production of a pharmaceutical agent capable of regulating cell cycle.

(22) A pharmaceutical composition which comprises a compound of the formula [I'] of the above-mentioned (2) or a pharmaceutically acceptable salt thereof, and a pharmaceutically acceptable carrier.

(23) A pharmaceutical composition for the treatment of a tumor, which comprises a compound of the formula [I] of the above-mentioned (1) or a pharmaceutically acceptable salt thereof, and a pharmaceutically acceptable carrier.

(24) A pharmaceutical composition for treating a disease causing by an undesirable cell proliferation, which comprises a compound of the formula [I] of the above-mentioned (1) or a pharmaceutically acceptable salt thereof, and a pharmaceutically acceptable carrier.

(25) A commercial package comprising a pharmaceutical composition of the above-mentioned (23) and a written matter associated therewith, the written matter stating that the pharmaceutical composition can or should be used for treating tumor.

(26) A commercial package comprising a pharmaceutical composition of the above-mentioned (24) and a written matter associated therewith, the written matter stating that the pharmaceutical composition can or should be used for treating disease causing by an undesirable cell proliferation.

(27) Use of (a) a compound of the formula [I] of the above-mentioned (1) or a pharmaceutically acceptable salt thereof as an active ingredient, which is used in combination with (b) at least one other antitumor compound, for the production of an antitumor agent.

(28) Use of (a) compound of the formula [I] of the above-mentioned (1) or a pharmaceutically acceptable salt thereof as an active ingredient and (b) at least one other antitumor compound, in combination, for the production of an antitumor agent.

(29) A pharmaceutical composition comprising, as an active ingredient, (a) a compound of the formula [I] of the above-mentioned (1) or a pharmaceutically acceptable salt thereof and (b) at least one other antitumor compound, and a pharmaceutical acceptable carrier, in combination.

(30) A kit for treating a tumor comprising (a) a pharmaceutical composition comprising, as an active ingredient, a compound of the formula [I] of the above-mentioned (1) or a pharmaceutically acceptable salt thereof and (b) a pharmaceutical composition comprising, as an active ingredient, at least one other antitumor agent, in combination.

(31) An antitumor agent comprising a compound of the formula [I] of the above-mentioned (1) or a pharmaceutically acceptable salt thereof as an active ingredient.

(32) A MEK inhibitor comprising a compound of the formula [I] of the above-mentioned (1) or a pharmaceutically acceptable salt thereof as an active ingredient.

(33) A p15 protein inducer comprising a compound of the formula [I] of the above-mentioned (1) or a pharmaceutically acceptable salt thereof as an active ingredient.

(34) An antitumor agent comprising, as an active ingredient, (a) a compound of the formula [I] of the above-mentioned (1) or a pharmaceutically acceptable salt thereof, which is used in combination with (b) at least one other antitumor compound.

(35) An antitumor agent comprising, as an active ingredient, (a) a compound of the formula [I] of the above-mentioned (1) or a pharmaceutically acceptable salt thereof, and (b) at least one other antitumor compound, in combination.

(36) The agent of the above-mentioned (34), wherein (a) a compound of the formula [I] of the above-mentioned (1) or a pharmaceutically acceptable salt thereof and (b) at least one other antitumor compound are administered to a mammal simultaneously or sequentially.

(37) The agent of the above-mentioned (35), wherein (a) a compound of the formula [I] of the above-mentioned (1) or a pharmaceutically acceptable salt thereof and (b) at least one other antitumor compound are administered to a mammal simultaneously or sequentially.

BEST MODE FOR EMBODYING THE INVENTION

The definitions of each substituent and each moiety used in the present specification are as follows.

$X^1$ and $X^2$ are the same or different, and each is a carbon atom or a nitrogen atom, wherein the moiety is

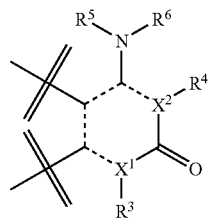

preferably,

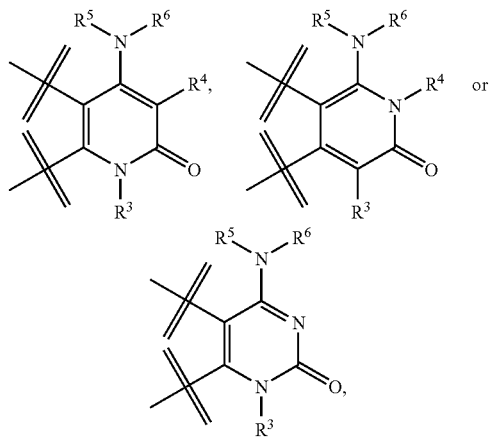

and particularly preferably

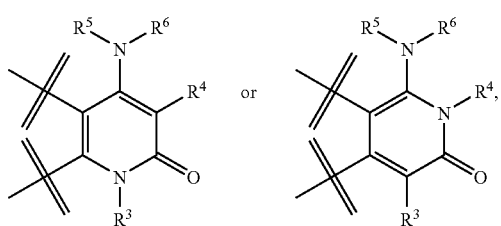

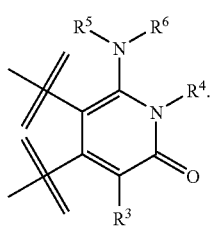

The "halogen atom" is a fluorine atom, a chlorine atom, a bromine atom or an iodine atom, which is preferably a fluorine atom, a chlorine atom or a bromine atom for 1) of group A and 1) of group C, more preferably a fluorine atom for 1) of group A, more preferably a fluorine atom or a bromine atom for 1) of group C, and preferably a fluorine atom or an iodine atom for 1) of group B.

The "$C_{1-6}$ alkyl group" is a straight chain or branched chain alkyl group having 1 to 6 carbon atoms, and specifically, methyl group, ethyl group, propyl group, isopropyl group, 2,2-dimethylpropyl group, butyl group, isobutyl group, sec-butyl group, tert-butyl group, pentyl group, hexyl group and the like can be mentioned.

As $R^1$, $R^{1\prime}$, $R^2$, $R^{2\prime}$ and $R^6$, methyl group, ethyl group, propyl group, isopropyl group, 2,2-dimethylpropyl group, butyl group and isobutyl group are preferable, methyl group and ethyl group are more preferable, and methyl group is particularly preferable. As $R^3$, $R^4$ and $R^5$, methyl group, ethyl group, propyl group and isobutyl group are preferable, and methyl group is more preferable.

The "$C_{1-4}$ alkyl group" is a straight chain or branched chain alkyl group having 1 to 4 carbon atoms, and specifically, methyl group, ethyl group, propyl group, isopropyl group, butyl group, isobutyl group, sec-butyl group, tert-butyl group and the like can be mentioned.

As 4) of group A and 3) of group C, methyl group and ethyl group are preferable and methyl group is more preferable. As $R^{A1}$, $R^{A2}$, $R^{A3}$, $R^{A4}$, $R^{A5}$, $R^{A6}$, $R^{A7}$, $R^{A8}$ and $R^{A9}$, methyl group, ethyl group and butyl group are preferable and methyl group is more preferable. As $R^{B1}$ to $R^{B31}$, methyl group, ethyl group, propyl group, isopropyl group and butyl group are preferable and methyl group, ethyl group and propyl group are more preferable. As $R^{C1}$, $R^{C2}$, $R^{C3}$, $R^{C4}$ and $R^{C5}$, methyl group and ethyl group are preferable and methyl group is more preferable.

The "$C_{1-8}$ alkyl group" is a straight chain or branched chain alkyl group having 1 to 8 carbon atoms, and specifically, methyl group, ethyl group, propyl group, isopropyl group, 1-ethyl-1-propyl group, butyl group, isobutyl group, sec-butyl group, tert-butyl group, 3-methylbutyl group, 1-propyl-1-butyl group, pentyl group, isopentyl group, hexyl group, heptyl group, octyl group and the like can be mentioned.

As 2) of group B, methyl group, ethyl group, propyl group, isopentyl group, 1-ethyl-1-propyl group, 3-methylbutyl group and 1-propyl-1-butyl group are preferable and methyl group and ethyl group are more preferable.

The "$C_{2-6}$ alkenyl group" is a straight chain or branched chain alkenyl group having 2 to 6 carbon atoms, and specifically, vinyl group, 1-propenyl group, 2-propenyl group, isopropenyl group, 1-butenyl group, 2-butenyl group, 3-butenyl group, 1-methyl-1-propenyl group, 1-methyl-2-propenyl group, 2-methyl-2-propenyl group, 1-ethylvinyl group, 1-pentenyl group, 2-pentenyl group, 3-pentenyl group, 4-pentenyl group, 1,2-dimethyl-1-propenyl group, 1,2-dimethyl-2-propenyl group, 1-ethyl-1-propenyl group, 1-ethyl-2-propenyl group, 1-methyl-1-butenyl group, 1-methyl-2-butenyl group, 2-methyl-1-butenyl group, 1-isopropylvinyl group, 2,4-pentadienyl group, 1-hexenyl group, 2-hexenyl group, 3-hexenyl group, 4-hexenyl group, 5-hexenyl group, 2,4-hexadienyl group, 1-methyl-1-pentenyl group and the like can be mentioned.

As $R^1$, $R^{1\prime}$, $R^2$, $R^{2\prime}$, $R^3$, $R^4$, $R^5$ and $R^6$, vinyl group, 1-propenyl group and 2-propenyl group are preferable and 2-propenyl group is more preferable.

The "$C_{2-4}$ alkenyl group" is a straight chain or branched chain alkenyl group having 2 to 4 carbon atoms, and specifically, vinyl group, 1-propenyl group, 2-propenyl group, isopropenyl group, 1-butenyl group, 2-butenyl group, 3-butenyl group, 1-methyl-1-propenyl group, 1-methyl-2-propenyl group, 2-methyl-2-propenyl group, 1-ethylvinyl group and the like can be mentioned.

As 5) of group B, vinyl group and 1-propenyl group are preferable, and vinyl group is more preferable.

The "C$_{2-4}$ alkynyl group" is a straight chain or branched chain alkynyl group having 2 to 4 carbon atoms, and specifically, ethynyl group, 1-propynyl group, 2-propynyl group, isopropynyl group, 1-butynyl group, 2-butynyl group, 3-butynyl group, 1-methyl-1-propynyl group, 1-methyl-2-propynyl group, 2-methyl-2-propynyl group, 1-ethylethynyl group and the like can be mentioned.

As 6) of group B, ethynyl group, 1-propynyl group and 1-butynyl group are preferable, and ethynyl group is more preferable.

The "C$_{1-4}$ alkylene group" optionally formed by R$^2$ in junction with R$^3$ and the "C$_{1-4}$ alkylene group" optionally formed by R$^4$ in junction with R$^5$ is a straight chain or branched chain alkylene group having 1 to 4 carbon atoms, and specifically, methylene group, ethylene group, trimethylene group, 2-methyltrimethylene group, tetramethylene group and the like can be mentioned.

The "C$_{1-4}$ alkylene group" optionally formed by R$^2$ in junction with R$^3$ is preferably methylene group, ethylene group or trimethylene group, more preferably trimethylene group.

The "C$_{1-4}$ alkylene group" optionally formed by R$^4$ in junction with R$^5$ is preferably methylene group, ethylene group or trimethylene group, more preferably ethylene group.

As m, preferred is 0 or an integer of 1 or 2, more preferably 0.

The "C$_{3-12}$ carbon ring group" is a saturated or unsaturated cyclic hydrocarbon group having 3 to 12 carbon atoms, which means a phenyl group, naphthyl group, C$_{3-8}$cycloalkyl group, or a fused ring group of C$_{3-8}$ cycloalkyl and benzene.

The "C$_{3-8}$ cycloalkyl group" is a saturated cyclic hydrocarbon group having 3 to 8 carbon atoms, and specifically, cyclopropyl group, cyclobutyl group, cyclopentyl group, cyclohexyl group, cycloheptyl group, cyclooctyl group, norbornanyl group and the like can be mentioned, and preferably cyclopropyl group, cyclobutyl group, cyclopentyl group or cyclohexyl group.

As the "fused ring group of C$_{3-8}$cycloalkyl and benzene", indanyl group, 1,2,3,4-tetrahydronaphthyl group (1,2,3,4-tetrahydro-2-naphthyl group, 5,6,7,8-tetrahydro-2-naphthyl group etc.) and the like can be specifically mentioned, which is preferably indanyl group, 1,2,3,4-tetrahydronaphthyl group and the like, and more preferably indanyl group.

As R$^1$, R$^2$, R$^3$, R$^4$, R$^5$ and R$^6$, phenyl group, cyclopropyl group, cyclobutyl group, cyclopentyl group and cyclohexyl group are preferable, and phenyl group and cyclopropyl group are more preferable. As R$^1$, cyclopropyl group is particularly preferable, and as R$^2$ and R$^6$, phenyl group is particularly preferable. As 11) of group A, R$^{A7}$, 22) of group B, R$^{B3}$, R$^{B6}$ and R$^{B16}$, phenyl group, cyclopropyl group, cyclobutyl group, cyclopentyl group and cyclohexyl group are preferable, and phenyl group and cyclopropyl group are more preferable.

The "heterocyclic group" is a saturated monocyclic ring or an unsaturated monocyclic ring having 5 or 6 ring-constituting atoms, which contains, besides carbon atom, 1 to 4 hetero atoms selected from an oxygen atom, a nitrogen atom and a sulfur atom, as a ring-constituting atom, a fused ring of the monocycle and a benzene ring or a spiro ring of these monocycles or fused rings and the above-mentioned C$_{3-12}$ carbon ring, each of which may have 1 to 4, preferably 1 or 2, oxo groups.

As the "heterocyclic group", which is a monocycle of a saturated ring, pyrrolidinyl group, tetrahydrofuryl group, tetrahydrothienyl group, imidazolidinyl group, 2-oxoimidazolidinyl group, 2,4-dioxoimidazolidinyl group, pyrazolidinyl group, 1,3-dioxolanyl group, 1,3-oxathiolanyl group, oxazolidinyl group, 2-oxooxazolidinyl group, thiazolidinyl group, piperidinyl group, piperazinyl group, 2-oxopiperazinyl group, tetrahydropyranyl group, tetrahydrothiopyranyl group, dioxanyl group, morpholinyl group, thiomorpholinyl group, 2-oxopyrrolidinyl group, 2-oxopiperidinyl group, 4-oxopiperidinyl group, 2,6-dioxopiperidinyl group, thiadiazolidinyl group (e.g., 1,1-dioxo-1,2,5-thiadiazolidin-2-yl group etc.) and the like can be mentioned. Preferably, pyrrolidinyl group, piperidinyl group, piperazinyl group and morpholinyl group can be mentioned.

As the "heterocyclic group", which is a monocycle of unsaturated ring, pyrrolyl group (e.g., 2-pyrrolyl group etc.), furyl group, thienyl group, imidazolyl group (e.g., 4-imidazolyl group etc.), 1,2-dihydro-2-oxoimidazolyl group, pyrazolyl group (e.g., 5-pyrazolyl group etc.), diazolyl group, oxazolyl group, isoxazolyl group, thiazolyl group, isothiazolyl group, 1,2,4-triazolyl group, 1,2,3-triazolyl group, tetrazolyl group, 1,3,4-oxadiazolyl group, 1,2,4-oxadiazolyl group, 1,3,4-thiadiazolyl group, 1,2,4-thiadiazolyl group, furazanyl group, pyridyl group (e.g., 3-pyridyl group etc.), pyrimidinyl group, 3,4-dihydro-4-oxopyrimidinyl group, pyridazinyl group, pyrazinyl group, 1,3,5-triazinyl group, imidazolinyl group (e.g., 2-imidazolinyl group etc.), pyrazolinyl group, oxazolinyl group (2-oxazolinyl group, 3-oxazolinyl group, 4-oxazolinyl group), isoxazolinyl group, thiophenyl group, thiazolinyl group, isothiazolinyl group, pyranyl group, 2-oxopyranyl group, 2-oxo-2,5-dihydrofuranyl group, 1,1-dioxo-1H-isothiazolyl group and the like can be mentioned. Preferably, pyrrolyl group, thienyl group, imidazolyl group, pyrazolyl group, oxazolyl group, isooxazolyl group, thiophenyl group, thiazolyl group, isothiazolyl group and pyridyl group can be mentioned.

As the "heterocyclic group" which is a fused ring of monocycle and benzene ring, indolyl groups (e.g., 4-indolyl group, 5-indolyl group, 6-indolyl group, 7-indolyl group etc.), isoindolyl group, 1,3-dihydro-1,3-dioxoisoindolyl group and benzofuranyl groups (e.g., 4-benzofuranyl group, 7-benzofuranyl group etc.), indazolyl group, isobenzofuranyl group and benzothiophenyl groups (e.g., 4-benzothiophenyl group, 5-benzothiophenyl group, 7-benzothiophenyl group etc.), benzoxazolyl groups (e.g., 4-benzoxazolyl group, 7-benzoxazolyl group etc.), benzimidazolyl groups (e.g., 4-benzimidazolyl group, 5-benzimidazolyl group, 7-benzimidazolyl group etc.), benzothiazolyl groups (e.g., 4-benzothiazolyl group, 7-benzothiazolyl group etc.), quinolyl group, isoquinolyl group, 1,2-dihydro-2-oxoquinolyl group, quinazolinyl group, quinoxalinyl group, cinnolinyl group, phthalazinyl group, 2,3-dihydroindolyl group, isoindolinyl group, 1,2,3,4-tetrahydroquinolyl group, 2-oxo-1,2,3,4-tetrahydroquinolyl group, benzo[1,3]dioxolyl group, chromanyl group, isochromanyl group,

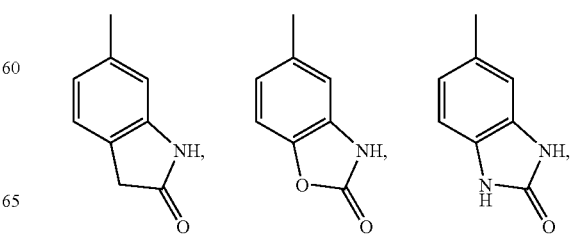

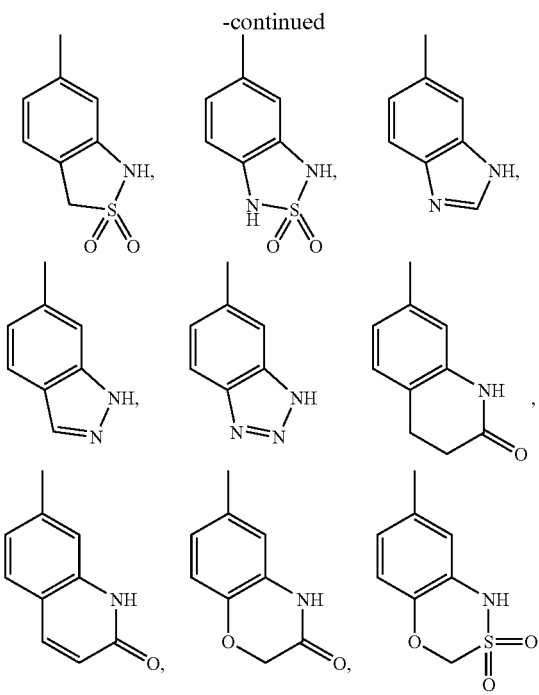

and the like can be mentioned.

As the Spiro ring of the above-mentioned monocycle or fused ring and the above-mentioned $C_{3-12}$ carbon ring, for example, groups represented by the following formulas can be mentioned.

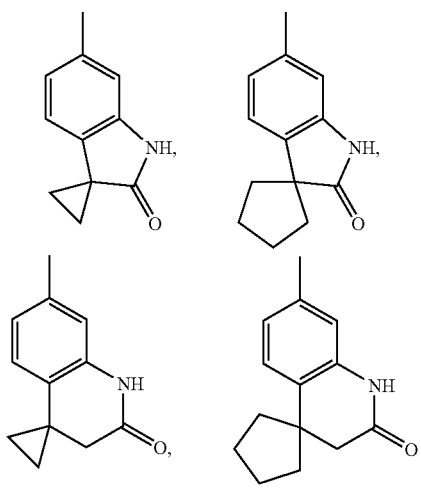

Preferably, it is a fused ring group of monocyclic 5- or 6-membered heterocycle and a benzene ring, which is specifically, indolyl group, indazolyl group, benzothiophenyl group, benzimidazolyl group, 2,3-dihydroindolyl group, 1,2,3,4-tetrahydroquinolyl group, benzo[1,3]dioxolyl group and the like.

As $R^1$, $R^2$, $R^3$, $R^4$, $R^5$ and $R^6$, pyrrolidinyl group, piperidinyl group, piperazinyl group, morpholinyl group, pyridinyl group, thiophenyl group, thiazolyl group, indolyl group, indazolyl group, benzothiophenyl group, benzimidazolyl group, 2,3-dihydroindolyl group, 1,2,3,4-tetrahydroquinolyl group and benzo[1,3]dioxolyl group are preferable, and piperidinyl group, pyridinyl group, thiophenyl group, thiazolyl group, indolyl group, indazolyl group, benzothiophenyl group, benzimidazolyl group, 2,3-dihydroindolyl group, 1,2,3,4-tetrahydroquinolyl group, benzo[1,3]dioxolyl group are more preferable. As 12) of group A, $R^{47}$ and 23) of group B, $R^{B3}$, $R^{B6}$, $R^{B16}$ and $R^{B17}$, pyrrolidinyl group, piperidinyl group, piperazinyl group, morpholinyl group, pyridyl group and oxazolinyl group are preferable, and pyrrolidinyl group, piperidinyl group, piperazinyl group and morpholinyl group are more preferable.

The "$C_{1-6}$ alkyl group" and "$C_{2-6}$ alkenyl group" for $R^1$, $R^2$ and $R^6$, and $R^3$, $R^4$ and $R^5$ are optionally substituted by 1 to 3 substituents selected from group A. That is, the above-defined "$C_{1-6}$ alkyl group" and "$C_{2-6}$ alkenyl group" may be substituted by 1 to 3 substituents selected from group A, and include unsubstituted "$C_{1-6}$ alkyl group" and unsubstituted "$C_{2-6}$ alkenyl group".

Each of the above-defined "$C_{1-8}$ alkyl group" for the below-defined 4) of group B, and the above-defined "$C_{1-4}$ alkyl group" for $R^{B1}$ to $R^{B31}$ is optionally substituted by the same or different 1 to 3 substituents selected from group A.

Each of the above-defined "$C_{2-4}$ alkenyl group" for the below-defined 5) of group B and the above-defined "$C_{2-4}$ alkynyl group" for 6) is optionally substituted by the same or different 1 to 3 substituents selected from group A.

The "group A" is a group consisting of 1) the above-defined "halogen atom", 2) nitro group, 3) cyano group, 4) the above-defined "$C_{1-4}$ alkyl group", 5) "—$OR^{41}$", 6) "—$SR^{42}$", 7) "—$NR^{43}R^{44}$", 8) "—$COOR^{45}$", 9) "—$NR^{46}COR^{47}$", 10) "—$NR^{48}COOR^{49}$", 11) the above-defined "$C_{3-12}$ carbon ring group" and 12) the above-defined "heterocyclic group", wherein $R^{41}$, $R^{42}$, $R^{43}$, $R^{44}$, $R^{45}$, $R^{46}$, $R^{48}$ and $R^{49}$ are the same or different and each is a hydrogen atom, or, the above-defined "$C_{1-4}$ alkyl group", $R^{47}$ is the above-defined "$C_{1-4}$ alkyl group", the above-defined "$C_{3-12}$ carbon ring group" or the above-defined "heterocyclic group".

As the "—$OR^{41}$", hydroxyl group, methoxy group, ethoxy group, propoxy group, isopropyloxy group, tert-butoxy group and the like can be specifically mentioned.

As the "—$SR^{42}$", mercapto group, methylsulfanyl group, ethylsulfanyl group, propylsulfanyl group, isopropylsulfanyl group, tert-butylsulfanyl group and the like can be specifically mentioned.

As the "—$NR^{43}R^{44}$", amino group, methylamino group, ethylamino group, propylamino group, isopropylamino group, tert-butylamino group, dimethylamino group, diethylamino group, N-ethyl-N-methylamino group, N-methyl-N-propylamino group, N-isopropyl-N-methylamino group and the like can be specifically mentioned.

As the "—$COOR^{45}$", carboxyl group, methoxycarbonyl group, ethoxycarbonyl group, propoxycarbonyl group, isopropoxycarbonyl group, tert-butoxycarbonyl group and the like can be specifically mentioned.

As the "—$NR^{46}COR^{47}$", acetylamino group, propionylamino group, butyrylamino group, isobutyrylamino group, pivaloylamino group, N-acetyl-N-methylamino group, butylcarbonylamino group and the like can be specifically mentioned.

As the "—$NR^{48}COOR^{49}$", carboxyamino group, carboxymethylamino group, carboxyethylamino group, methoxycarbonylamino group, methoxycarbonylmethylamino group and the like can be specifically mentioned.

As the "group A", preferably, fluorine atom, chlorine atom, bromine atom, methyl group, ethyl group, propyl group, hydroxyl group, methoxy group, ethoxy group, propoxy group, amino group, methylamino group, ethylamino group, dimethylamino group, diethylamino group, carboxyamino group, butylcarbonylamino group, carboxy group, phenyl group, 4-morpholinyl group, 1-pyrrolidinyl group, 1-piperidinyl group and 1-piperazinyl group can be mentioned.

As the "group A", particularly preferably, fluorine atom, chlorine atom, methyl group, hydroxyl group, methoxy group, amino group, dimethylamino group, diethylamino group, carboxyamino group, butylcarbonylamino group, carboxy group, phenyl group, 4-morpholinyl group, 1-pyrrolidinyl group, 1-piperidinyl group and 1-piperazinyl group can be mentioned.

The preferable number of the substituent is 1, and the substituent may be used at any substitutable position.

The "$C_{3-12}$ carbon ring group" and "heterocyclic group" for ring Cy, and "$C_{3-12}$ carbon ring group" and "heterocyclic group" for $R^3$, $R^4$ or $R^5$ are optionally substituted by 1 to 5 substituents selected from group B. That is, the above-defined "$C_{3-12}$ carbon ring group" and "heterocyclic group" may be substituted by 1 to 5 substituents selected from group B, and includes unsubstituted "$C_{3-12}$ carbon ring group" and unsubstituted "heterocyclic group".

The "group B" is a group consisting of 1) the above-defined "halogen atom", 2) a nitro group, 3) a cyano group, 4) the above-defined "$C_{1-8}$ alkyl group", 5) the above-defined "$C_{2-4}$ alkenyl group", 6) the above-defined "$C_{2-4}$ alkynyl group", 7) "—$OR^{B1}$", 8) "—$SR^{B2}$", 9) "—$NR^{B3}R^{B4}$", 10) "—$NR^{B5}COR^{B6}$", 11) "—$NR^{B7}COOR^{B8}$", 12) "—$NR^{B9}CONR^{B10}R^{B11}$", 13) "—$NR^{B12}CONR^{B13}OR^{B14}$", 14) "—$NR^{B15}SO_2R^{B16}$", 15) "—$SO_2$—$R^{B17}$", 16) "—$SO_2NR^{B18}R^{B19}$", 17) "—$P(=O)(R^{B20})(R^{B21})$", 18) "—$COOR^{B22}$", 19) "—$CONR^{B23}R^{B24}$", 20) "—$NR^{B25}SO_2NR^{B26}R^{B27}$", 21) "—$NR^{B28}SO_2NR^{B29}CONR^{B30}R^{B31}$", 22) the above-defined "$C_{3-12}$ carbon ring group" and 23) the above-defined "heterocyclic group", wherein $R^{B1}$, $R^{B2}$, $R^{B4}$, $R^{B5}$, $R^{B7}$, $R^{B8}$, $R^{B9}$, $R^{B10}$, $R^{B11}$, $R^{B12}$, $R^{B13}$, $R^{B14}$, $R^{B15}$, $R^{B18}$, $R^{B19}$, $R^{B22}$, $R^{B23}$, $R^{B24}$, $R^{B25}$, $R^{B26}$, $R^{B27}$, $R^{B28}$, $R^{B29}$, $R^{B30}$ and $R^{B31}$ are the same or different and each is a hydrogen atom or the above-defined "$C_{1-4}$ alkyl group", $R^{B3}$ and $R^{B6}$ are each a hydrogen atom, the above-defined "$C_{1-4}$ alkyl group", the above-defined "$C_{3-12}$ carbon ring group" or the above-defined "heterocyclic group", $R^{B16}$ is the above-defined "$C_{1-4}$ alkyl group", the above-defined "$C_{3-12}$ carbon ring group" or the above-defined "heterocyclic group", $R^{B17}$ is the above-defined "$C_{1-4}$ alkyl group" or the above-defined "heterocyclic group", and $R^{B20}$ and $R^{B21}$ are the same or different and each is the above-defined "$C_{1-4}$ alkyl group".

As the "—$OR^{B1}$", hydroxyl group, methoxy group, ethoxy group, propoxy group, isopropyloxy group, tert-butoxy group and the like can be specifically mentioned.

As the "—$SR^{B2}$", mercapto group, methylsulfanyl group, ethylsulfanyl group, propylsulfanyl group, isopropylsulfanyl group, tert-butylsulfanyl group and the like can be specifically mentioned.

As the "—$NR^{B3}R^{B4}$", amino group, methylamino group, ethylamino group, 2-aminoethylamino group, propylamino group, isopropylamino group, tert-butylamino group, dimethylamino group, diethylamino group, N-ethyl-N-methylamino group, N-methyl-N-propylamino group, N-isopropyl-N-methylamino group, N-(imidazolin-2-yl)amino group and the like can be specifically mentioned.

As the "—$NR^{B5}COR^{B6}$", amino group, formylamino group, acetylamino group, hydroxyacetylamino group, propionylamino group, butyrylamino group, isobutyrylamino group, pivaloylamino group, N-acetyl-N-methylamino group, 3-aminopropionylamino group, 3-(pentanoylamino) propionylamino group, 4-imidazolylcarbonylamino group, (1-methylpyrrol-2-yl)carbonylamino group, 4-pyrazolylcarbonylamino group and the like can be specifically mentioned.

As the "—$NR^{B7}COOR^{B8}$", carboxyamino group, carboxymethylamino group, carboxyethylamino group, methoxycarbonylamino group, methoxycarbonylmethylamino group and the like can be specifically mentioned.

As the "—$NR^{B9}CONR^{B10}R^{B11}$", aminocarbonylamino group, methylaminocarbonylamino group, dimethylaminocarbonylamino group, (methylaminocarbonyl)(methyl) amino group, (dimethylaminocarbonyl)(methyl)amino group, [(2-hydroxyethyl)carbamoyl]amino and the like can be specifically mentioned.

As the "—$NR^{B12}CONR^{B13}OR^{B14}$", methoxyaminocarbonylamino group, (methylmethoxyaminocarbonyl)(methyl) amino group, (methylmethoxyaminocarbonyl)amino group and the like can be specifically mentioned.

As the "—$NR^{B15}SO_2R^{B16}$", sulfonylamino group, methylsulfonylamino group, ethylsulfonylamino group, propylsulfonylamino group, N-methyl-N-sulfonylamino group, N-methyl-N-methylsulfonylamino group, N-ethyl-N-sulfonylamino group, N-ethyl-N-methylsulfonylamino group, 3-pyridylsulfonylamino group, morpholinosulfonylamino group, piperidinomorpholinosulfonylamino group, 2-morpholinoethylsulfonylamino group and the like can be specifically mentioned.

As the "—$SO_2$—$R^{B17}$", sulfonyl group, methylsulfonyl group, ethylsulfonyl group, propylsulfonyl group, butylsulfonyl group and the like can be specifically mentioned.

As the "—$SO_2NR^{B18}R^{B19}$", aminosulfonyl group, methylaminosulfonyl group, dimethylaminosulfonyl group, ethylmethylaminosulfonyl group and the like can specifically be mentioned.

As the "—$P(=O)(R^{B20})(R^{B21})$", phosphinoyl group, methylphosphinoyl group, dimethylphosphinoyl group, ethylphosphinoyl group, diethylphosphinoyl group and the like can be specifically mentioned.

As the "—$COOR^{B22}$", carboxyl group, methoxycarbonyl group, ethoxycarbonyl group, propoxycarbonyl group, isopropoxycarbonyl group, tert-butoxycarbonyl group and the like can be specifically mentioned.

As the "—$CONR^{B23}R^{B24}$", carbamoyl, methylcarbamoyl, dimethylcarbamoyl, ethylcarbamoyl, diethylcarbamoyl, propylcarbamoyl, butylcarbamoyl and the like can be specifically mentioned.

As the "—$NR^{B25}SO_2NR^{B26}R^{B27}$", sulfamoylamino group, dimethylsulfamoylamino group and the like can be specifically mentioned.

As the "—$NR^{B28}SO_2NR^{B29}CONR^{B30}R^{B31}$", {[(2-hydroxyethyl)carbamoyl](2-hydroxyethyl)sulfamoyl}amino group and the like can be specifically mentioned.

As the "group B", preferably, fluorine atom, chlorine atom, bromine atom, iodine atom, nitro group, cyano group, methyl group, ethyl group, propyl group, isopropyl group, butyl group, isobutyl group, pentyl group, isopentyl group, hexyl group, 1-ethylpropyl group, 1-propylbutyl group, vinyl group, 1-propenyl group, ethynyl group, 1-propynyl group, 1-butynyl group, hydroxyl group, methoxy group, ethoxy group, propoxy group, isopropoxy group, methylthio group, ethylthio group, amino group, methylamino group, ethylamino group, dimethylamino group, diethylamino group, ethylmethylamino group, methylcarbonylamino group, ethylcarbonylamino group, propylcarbonylamino group, isopropylcarbonylamino group, (methylcarbonyl)(methyl)amino group, ethoxycarbonylamino group, methylaminocarbonylamino group, dimethylaminocarbonylamino group, methoxyaminocarbonylamino group, methylsulfonylamino group, ethylsulfonylamino group, propylsulfonylamino group, isopropylsulfonylamino group, phenylsulfonylamino group, (methylsulfonyl)(methyl)amino group, methylsulfonyl group, piperazin-1-ylsulfonyl group, morpholin-4-ylsulfonyl group, piperidin-4-ylsulfonyl group, pyrrolidin-4-ylsulfonyl group, aminosulfonyl group, methylaminosulfonyl group, ethylaminosulfonyl group, dimethylaminosulfonyl group, dimethylphosphinoyl group, carboxy group, methoxycarbonyl group, carbamoyl group, methylaminocarbonyl group, ethylaminocarbonylamino group, dimethylaminosulfonylamino group, cyclopropyl group, cyclohexyl group, phenyl group, piperidinyl group, pyrrolidinyl group, piperidinyl group, piperazinyl group and morpholinyl group can be mentioned.

As the "group B", particularly preferably, fluorine atom, chlorine atom, bromine atom, iodine atom, nitro group, cyano group, methyl group, ethyl group, propyl group, isopropyl group, butyl group, 1-ethylpropyl group, 1-propylbutyl group, butyl group, isobutyl group, isopentyl group, vinyl group, ethynyl group, 1-propynyl group, 1-butynyl group, hydroxyl group, methoxy group, propoxy group, isopropoxy group, methylthio group, amino group, methylamino group, ethylamino group, dimethylamino group, diethylamino group, ethylmethylamino group, methylcarbonylamino group, ethylcarbonylamino group, propylcarbonylamino group, isopropylcarbonylamino group, (methylcarbonyl)(methyl)amino group, ethoxycarbonylamino group, methylaminocarbonylamino group, dimethylaminocarbonylamino group, methoxyaminocarbonylamino group, methylsulfonylamino group, ethylsulfonylamino group, propylsulfonylamino group, isopropylsulfonylamino group, phenylsulfonylamino group, (methylsulfonyl)(methyl)amino group, methylsulfonyl group, piperazin-1-ylsulfonyl group, morpholin-4-ylsulfonyl group, piperidin-4-ylsulfonyl group, pyrrolidin-4-ylsulfonyl group, aminosulfonyl group, methylaminosulfonyl group, ethylaminosulfonyl group, dimethylaminosulfonyl group, dimethylphosphinoyl group, carboxy group, methoxycarbonyl group, carbamoyl group, methylaminocarbonyl group, ethylaminocarbonylamino group, dimethylaminosulfonylamino group, cyclopropyl group, phenyl group, piperidinyl group, pyrrolidinyl group, piperidinyl group, piperazinyl group and morpholinyl group can be mentioned.

The preferable number of substituent is 1 or 2, and when the "$C_{3-12}$ carbon ring group" is a phenyl group, ring Cy is preferably mono-substituted at the 2-position, mono-substituted at the 3-position, mono-substituted at the 4-position, di-substituted at the 2,3-position, di-substituted at the 2,4-position, di-substituted at the 2,5-position or di-substituted at the 2,6-position, and particularly preferably mono-substituted at the 4-position or di-substituted at the 2,4-position, $R^2$ is more preferably mono-substituted at the 3-position, and $R^6$ is more preferably di-substituted at the 2,4-position.

Each of the above-defined "$C_{1-4}$ alkyl group" for 4) of the above-defined group A, and the above-defined "$C_{1-4}$ alkyl group" for $R^{A1}$, $R^{A2}$, $R^{A3}$, $R^{A4}$, $R^{A5}$, $R^{A6}$, $R^{A7}$, $R^{A8}$ or $R^{A9}$ is optionally substituted by the same or different 1 to 3 substituents selected from the below-defined "group C".

Each of the above-defined "$C_{3-12}$ carbon ring group" for 11) of group A and $R^{A7}$, and the above-defined "heterocyclic group" for 12) and $R^{A7}$ is optionally substituted by the same or different 1 to 5 substituents selected from the below-defined "group C".

Each of the above-defined "$C_{3-12}$ carbon ring group" for the above-mentioned 22) of group B, $R^{B3}$, $R^{B6}$ and $R^{B16}$, and the above-defined "heterocyclic group" for the above-mentioned 23), $R^{B3}$, $R^{B6}$, $R^{B16}$ and $R^{B17}$ is optionally substituted by the same or different 1 to 5 substituents selected from the below-defined "group C".

The "group C" is a group consisting of 1) the above-defined "halogen atom", 2) a cyano group, 3) the above-defined "$C_{1-4}$ alkyl group", 4) "—$OR^{C1}$", 5) "—$NR^{C2}R^{C3}$", 6) "—$COOR^{C4}$" and 7) an oxo group, wherein $R^{C1}$, $R^{C2}$, $R^{C3}$ and $R^{C4}$ are the same or different and each is a hydrogen atom or the above-defined "$C_{1-4}$ alkyl group".

As the "—$OR^{C1}$", hydroxyl group, methoxy group, ethoxy group, propoxy group, isopropoxy group, tert-butoxy group and the like can be specifically mentioned.

As the "—$NR^{C2}R^{C3}$", amino group, methylamino group, ethylamino group, propylamino group, isopropylamino group, tert-butylamino group, dimethylamino group, diethylamino group, N-ethyl-N-methylamino group, N-methyl-N-propylamino group, N-isopropyl-N-methylamino group and the like can be specifically mentioned.

As the "—$COOR^{C4}$", carboxyl group, methoxycarbonyl group, ethoxycarbonyl group, propoxycarbonyl group, isopropyloxycarbonyl group, tert-butoxycarbonyl group and the like can be specifically mentioned.

As the "group C", the group consisting of 1) the above-defined "halogen atom", 2) a cyano group, 3) the above-defined "$C_{1-4}$ alkyl group", 4) "—$OR^{C1}$", 5) "—$NR^{C2}R^{C3}$" and 6) "—$COOR^{C4}$" are preferable, and specifically, fluorine atom, chlorine atom, bromine atom, cyano group, methyl group, ethyl group, propyl group, hydroxyl group, methoxy group, ethoxy group, amino group, dimethylamino group, diethylamino group, carboxyl group and methoxycarbonyl group can be mentioned.

As the "group C", methyl group is particularly preferable.

The preferable number of the substituent is 1, and the substituent may be used at any substitutable position.

As the "$R^1$", preferably, a $C_{1-6}$ alkyl group (wherein the $C_{1-6}$ alkyl group is optionally substituted by 1 to 3 substituents selected from group A) or

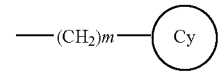

wherein each symbol is as defined above, can be mentioned.

Here, m is preferably 0, the "ring Cy" is preferably $C_{3-12}$ carbon ring group, and the "carbon ring group" is preferably cycloalkyl group (wherein the "$C_{3-12}$ carbon ring group" and "cycloalkyl group" are optionally substituted by 1 to 5 substituents selected from group B).

Specifically, as the "$R^1$", methyl group, ethyl group, 2,2,2-trifluoroethyl group, propyl group, isopropyl group, butyl group, 2-propenyl group, cyclopropyl group, 2-methylcyclopropyl group, cyclobutyl group, cyclopentyl group, cyclohexyl group, phenyl group, 4-chlorophenyl group, 4-fluorophenyl group, o-tolyl group, m-tolyl group, p-tolyl group, 4-methoxyphenyl group, thiophen-3-yl group, cyclopropylmethyl group, 2-methoxyethyl, carboxymethyl, 2-hydroxyethyl, 2-(dimethylamino)ethyl and benzyl group are preferable.

More preferably, methyl group, ethyl group, 2,2,2-trifluoroethyl group, propyl group, isopropyl group, butyl group, cyclopropyl group, 2-methylcyclopropyl group, cyclobutyl group, cyclopentyl group, cyclohexyl group, phenyl group, 4-chlorophenyl group, 4-fluorophenyl group, o-tolyl group, m-tolyl group, p-tolyl group, 4-methoxyphenyl group, thiophen-3-yl group, 2-methoxyethyl, carboxymethyl, 2-hydroxyethyl and 2-(dimethylamino)ethyl, particularly preferably, methyl group or cyclopropyl group can be mentioned.

As the "$R^2$",

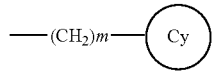

wherein each symbol is as defined above, is preferable. Here, m is preferably 0, the "ring Cy" is preferably $C_{3-12}$ carbon ring group, and the "carbon ring group" is preferably phenyl group (wherein the "$C_{3-12}$ carbon ring group" and "phenyl group" are optionally substituted by 1 to 5 substituents selected from group B, and as the "group B", "—$NR^{B3}R^{B4}$", "—$NR^{B5}COR^{B6}$", "—$NR^{B7}COOR^{B8}$", "—$NR^{B9}CONR^{B10}R^{B11}$", "—$NR^{B12}CONR^{B13}OR^{B14}$", "—$NR^{B15}SO_2R^{B16}$", "—$NR^{B25}SO_2NR^{B26}R^{B27}$", and "—$NR^{B28}SO_2NR^{B29}CONR^{B30}R^{B31}$" are preferable).

Specifically, as the "$R^2$", a hydrogen atom, methyl group, ethyl group, 2,2,2-trifluoroethyl group, isopropyl group, butyl group, isobutyl group, 2-propenyl group, cyclopropyl group, cyclobutyl group, cyclopentyl group, phenyl group, 4-chlorophenyl group, 2-fluorophenyl group, 4-fluorophenyl group, 4-bromophenyl group, 2,6-difluorophenyl group, o-tolyl group, m-tolyl group, p-tolyl group, 2,6-dimethylphenyl group, 2-ethylphenyl group, 3-(3-hydroxypropyl)phenyl group, 3-(2-carboxyethyl)phenyl group, 3-(3-morpholin-4-ylpropyl)phenyl group, 3-dimethylaminopropylphenyl group, 3-hydroxyphenyl group, 4-hydroxyphenyl group, 2-methoxyphenyl group, 3-methoxyphenyl group, 4-methoxyphenyl group, 3-dimethylaminoethoxyphenyl group, 3-carboxymethoxyphenyl group, 3-(3-dimethylaminopropoxy)phenyl group, 3-(2-morpholin-4-ylethoxy)phenyl group, 3-(2-pyrrolidin-1-ylethoxy)phenyl group, 3-(2-piperidin-1-ylethoxy)phenyl group, 3-(2-diethylaminoethoxy)phenyl group, 3-[3-(4-methylpiperazin-1-yl)propoxy]phenyl group, 3-aminophenyl group, 3-methylaminophenyl group, 3-dimethylaminophenyl group, 3-(methanesulfonyl)methylaminophenyl group, 3-methylcarbonylaminophenyl group, 3-methanesulfonylaminophenyl group, 4-chloro-3-methanesulfonylaminophenyl group, 3-ethanesulfonylaminophenyl group, 3-(propane-1-sulfonylamino)phenyl group, 3-(propane-2-sulfonylamino)phenyl group, 3-chloromethanesulfonylaminophenyl group, 3-trifluoromethanesulfonylaminophenyl group, 3-(2,2,2-trifluoroethanesulfonylamino)phenyl group, 3-(2-methoxyethyl)methylaminophenyl group, 3-methylcarbonylaminophenyl group, 3-ethylcarbonylaminophenyl group, 3-propylcarbonylaminophenyl group, 3-isopropylcarbonylaminophenyl group, 3-ethoxycarbonylaminophenyl group, 3-(hydroxymethylcarbonyl)aminophenyl group, 3-(2-hydroxyethylcarbonylamino)phenyl group, 3-ethylaminocarbonylaminophenyl group, 3-(2-dimethylaminoethylcarbonylamino)phenyl group, 3-(3-dimethylaminopropylcarbonylamino)phenyl group, 3-(methoxymethylcarbonylamino)phenyl group, 3-(butylcarbonylaminomethylcarbonylamino)phenyl group, 3-(2-butylcarbonylaminoethylcarbonylamino)phenyl group, 3-methylaminocarbonylaminophenyl group, 3-methoxyaminocarbonylaminophenyl group, 3-dimethylaminocarbonylaminophenyl group, 3-(dimethylaminomethylcarbonylamino)phenyl group, 3-(2-morpholin-4-ylethylamino)phenyl group, 3-(2-benzyloxycarbonylaminoethyl)sulfonylaminophenyl group, 3-(2-aminoethyl)sulfonylaminophenyl group, 3-(2-butylcarbonylaminoethyl)sulfonylaminophenyl group, 3-dimethylaminosulfonylaminophenyl group, 3-carboxyphenyl group, 3-carbamoylphenyl group, 3-methanesulfonylphenyl group, 4-methanesulfonylphenyl group, 3-ethanesulfonylphenyl group, 3-methylaminosulfonylphenyl group, 3-ethylaminosulfonylphenyl group, 3-benzenesulfonylaminophenyl group, 3-aminosulfonylphenyl group, 3-dimethylaminosulfonylphenyl group, 4-dimethylaminosulfonylphenyl group, 3-(4-methylpiperazine-1-sulfonyl)phenyl group, 3-(morpholine-4-sulfonyl)phenyl group, 3-(piperidine-1-sulfonyl)phenyl group, 3-(pyrrolidine-1-sulfonyl)phenyl group, 3-methylaminocarbonylphenyl group, 3-morpholin-4-ylphenyl group, 3-pyrrolidin-1-ylphenyl group, 3-piperidin-1-ylphenyl group, 3-(4-methylpiperazin-1-yl)phenyl group, 3-(2-oxopyrrolidin-1-yl)phenyl group, 3-(3-oxomorpholin-4-yl)phenyl group, thiophen-3-yl group, pyridin-3-yl group, benzyl group and the following groups:

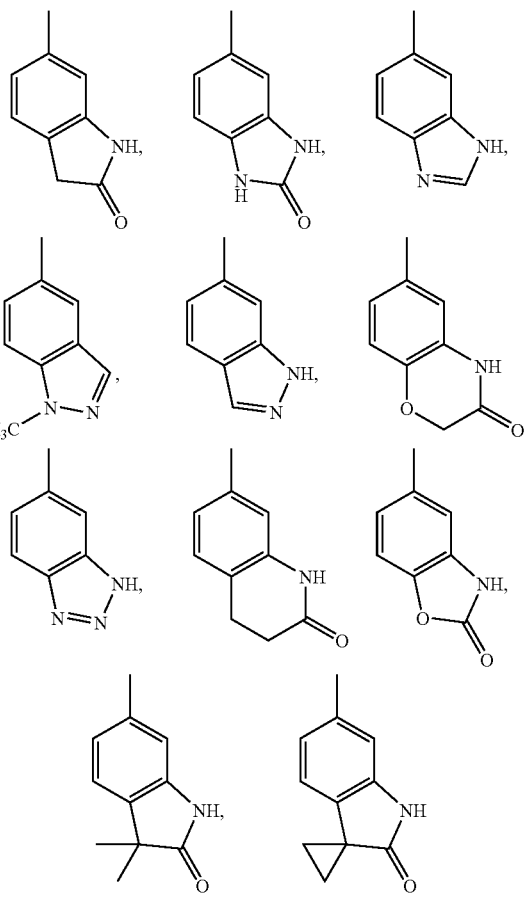

are preferable.

More preferably, phenyl group, 4-chlorophenyl group, 2-fluorophenyl group, 4-fluorophenyl group, 4-bromophenyl group, 2,6-difluorophenyl group, o-tolyl group, m-tolyl group, p-tolyl group, 2,6-dimethylphenyl group, 2-ethylphenyl group, 3-(3-hydroxypropyl)phenyl group, 3-(2-carboxyethyl)phenyl group, 3-(3-morpholin-4-ylpropyl)phenyl group, 3-dimethylaminopropylphenyl group, 3-hydroxyphenyl group, 4-hydroxyphenyl group, 2-methoxyphenyl group, 3-methoxyphenyl group, 4-methoxyphenyl group, 3-dimethylaminoethoxyphenyl group, 3-carboxymethoxyphenyl group, 3-(3-dimethylaminopropoxy)phenyl group, 3-(2-morpholin-4-ylethoxy)phenyl group, 3-(2-pyrrolidin-1-ylethoxy)phenyl group, 3-(2-piperidin-1-ylethoxy)phenyl group, 3-(2-diethylaminoethoxy)phenyl group, 3-[3-(4-methylpiperazin-1-yl)propoxy]phenyl group, 3-aminophenyl group, 3-methylaminophenyl group, 3-dimethylaminophenyl group, 3-(methanesulfonyl)methylaminophenyl group, 3-methylcarbonylaminophenyl group, 3-methanesulfonylaminophenyl group, 4-chloro-3-methanesulfonylaminophenyl group, 3-ethanesulfonylaminophenyl group, 3-(propane-1-sulfonylamino)phenyl group, 3-(propane-2-sulfonylamino)phenyl group, 3-chloromethanesulfonylaminophenyl group, 3-trifluoromethanesulfonylaminophenyl group, 3-(2,2,2-trifluoroethanesulfonylamino)phenyl group, 3-(2-methoxyethyl)methylaminophenyl group, 3-methylcarbonylaminophenyl group, 3-ethylcarbonylaminophenyl group, 3-propylcarbonylaminophenyl group, 3-isopropylcarbonylaminophenyl group, 3-ethoxycarbonylaminophenyl group, 3-(hydroxymethylcarbonyl)aminophenyl group, 3-(2-hydroxyethylcarbonylamino)phenyl group, 3-ethylaminocarbonylaminophenyl group, 3-(2-dimethylaminoethylcarbonylamino)phenyl group, 3-(3-dimethylaminopropylcarbonylamino)phenyl group, 3-(methoxymethylcarbonylamino)phenyl group, 3-(butylcarbonylaminomethylcarbonylamino)phenyl group, 3-(2-butylcarbonylaminoethylcarbonylamino)phenyl group, 3-methylaminocarbonylaminophenyl group, 3-methoxyaminocarbonylaminophenyl group, 3-dimethylaminocarbonylaminophenyl group, 3-(dimethylaminomethylcarbonylamino)phenyl group, 3-(2-morpholin-4-ylethylamino)phenyl group, 3-(2-benzyloxycarbonylaminoethyl)sulfonylaminophenyl group, 3-(2-aminoethyl)sulfonylaminophenyl group, 3-(2-butylcarbonylaminoethyl)sulfonylaminophenyl group, 3-dimethylaminosulfonylaminophenyl group, 3-carboxyphenyl group, 3-carbamoylphenyl group, 3-methanesulfonylphenyl group, 4-methanesulfonylphenyl group, 3-ethanesulfonylphenyl group, 3-methylaminosulfonylphenyl group, 3-ethylaminosulfonylphenyl group, 3-benzenesulfonylaminophenyl group, 3-aminosulfonylphenyl group, 3-dimethylaminosulfonylphenyl group, 4-dimethylaminosulfonylphenyl group, 3-(4-methylpiperazine-1-sulfonyl)phenyl group, 3-(morpholine-4-sulfonyl)phenyl group, 3-(piperidine-1-sulfonyl)phenyl group, 3-(pyrrolidine-1-sulfonyl)phenyl group, 3-methylaminocarbonylphenyl group, 3-morpholin-4-ylphenyl group, 3-pyrrolidin-1-ylphenyl group, 3-piperidin-1-ylphenyl group, 3-(4-methylpiperazin-1-yl)phenyl group, 3-(2-oxopyrrolidin-1-yl)phenyl group and 3-(3-oxomorpholin-4-yl)phenyl group can be mentioned.

As the "$R^6$",

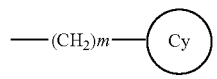

wherein each symbol is as defined above, is preferable. Here, m is preferably 0, the "ring Cy" is preferably $C_{3-12}$ carbon ring group and the "carbon ring group" is preferably phenyl group (wherein the "$C_{3-12}$ carbon ring group" and "phenyl group" are optionally substituted by 1 to 5 substituents selected from group B, where the "group B" preferably includes the above-defined "halogen atom", the above-defined "$C_{1-8}$ alkyl group" and the above-defined "$C_{2-4}$ alkynyl group").

Specifically, as the "$R^6$", 2-methoxyethyl group, 2,2-dimethylpropyl group, 3-dimethylaminopropyl group, cyclopropyl group, cyclohexyl group, phenyl group, 2-chlorophenyl group, 3-chlorophenyl group, 4-chlorophenyl group, 2,4-dichlorophenyl group, 3,4-dichlorophenyl group, 4-bromophenyl group, 2-fluorophenyl group, 4-fluorophenyl group, 4-iodophenyl group, o-tolyl group, p-tolyl group, 2-ethylphenyl group, 4-ethylphenyl group, 2-propylphenyl group, 2-isopropylphenyl group, 4-isopropylphenyl group, 2-butylphenyl group, 4-butylphenyl group, 2-isobutylphenyl group, 4-tert-butylphenyl group, 2-(3-methylbutyl)phenyl group, 4-trifluoromethylphenyl group, 4-(2-fluoroethyl)phenyl group, 4-(2,2-difluoroethyl)phenyl group, 4-(2,2,2-trifluoroethyl)phenyl group, 4-(1-ethylpropyl)phenyl group, 4-(1-propylbutyl)phenyl group, 4-ethynylphenyl group, 2,4-difluorophenyl group, 2,6-difluorophenyl group, 2,4-dichlorophenyl group, 4-bromo-2-fluorophenyl group, 4-bromo-3-fluorophenyl group, 4-bromo-2-chlorophenyl group, 4-chloro-2-fluorophenyl group, 2-fluoro-4-iodophenyl group, 2-chloro-4-methylphenyl group, 4-chloro-2-methylphenyl group, 4-bromo-2-methylphenyl group, 4-bromo-3-methylphenyl group, 2-fluoro-4-methylphenyl group, 2-fluoro-4-trifluoromethylphenyl group, 4-bromo-2-ethylphenyl group, 4-ethyl-2-fluorophenyl group, 4-(2-carboxyethyl)-2-fluorophenyl group, 2-fluoro-4-propylphenyl group, 2-fluoro-4-vinylphenyl group, 4-(2-carboxyvinyl)-2-fluorophenyl group, 4-ethynyl-2-fluorophenyl group, 2-fluoro-4-(prop-1-ynyl)phenyl group, 2-fluoro-4-(3-hydroxyprop-1-ynyl)phenyl group, 2-fluoro-4-(3-methoxyprop-1-ynyl)phenyl group, 4-cyclopropyl-2-fluorophenyl group, 2-fluoro-4-(3-hydroxy-3-methylbut-1-ynyl)phenyl group, 4-(3-dimethylaminoprop-1-ynyl)-2-fluorophenyl group, 4-chloro-2-dimethylaminomethylphenyl group, 4-dimethylamino-2-methylphenyl group, 4-hydroxyphenyl group, 2-methoxyphenyl group, 4-methoxyphenyl group, 4-trifluoromethoxyphenyl group, 4-isopropoxyphenyl group, 2,4-dimethoxyphenyl group, 4-methoxy-2-methylphenyl group, 2-fluoro-4-methoxyphenyl group, 4-bromo-2-hydroxyphenyl group, 4-bromo-2-methoxyphenyl group, 2-bromo-4-methoxyphenyl group, 4-methylthiophenyl group, 4-trifluoromethylthiophenyl group, 2-fluoro-4-methylthiophenyl group, 4-aminophenyl group, 4-methylaminophenyl group, 2-dimethylaminophenyl group, 3-dimethylaminophenyl group, 4-dimethylaminophenyl group, 4-ethylaminophenyl group, 4-diethylaminophenyl group, 4-ethylmethylamino-2-fluorophenyl group, 4-nitrophenyl group, 4-cyanophenyl group, 6-aminopyridin-3-yl group, 6-dimethylaminopyridin-3-yl group, 6-chloropyridin-2-yl group, 4-chloropyridin-3-yl group, 4-carboxyphenyl group, 4-methoxycarbonylphenyl group, 4-ethylaminophenyl group, 4-(methylcarbonyl)methylaminophenyl group, 4-methanesulfonylphenyl group, 4-trifluoromethanesulfonylphenyl group, 4-dimethylamino-2-methylphenyl group, 4-dimethylamino-3-methylphenyl group, 4-dimethylamino-3-trifluoromethylphenyl group, 4-dimethylamino-2-propylphenyl group, 4-dimethylamino-2-fluorophenyl group, 4-dimethylamino-3-fluorophenyl group, 4-dimethylphosphinoyl phenyl group, benzo[1,3]dioxol-5-yl group, 1,1'-biphenyl-4-yl group, 4-(piperidin-1-yl)phenyl group, 4-benzylphenyl group, 4-(morpholin-4-yl)phenyl group, 1-methylpiperidin-4-yl group, 1-isopropylpiperidin-4-yl group, thiazol-2-yl group, 2-dimethylaminothiazol-4-yl group, 1-methyl-1,2,3,4-tetrahydroquinolin-6-yl group, 1H-indol-5-yl group, 1-methyl-1H-indol-5-yl group, 1-ethyl-1H-indol-5-yl group, 1-methyl-1H-indol-6-yl group, 1-methyl-1H-indol-7-yl group, 1,2-dimethyl-1H-indol-5-yl group, 1,2,3-trimethyl-1H-indol-5-yl group, 6-fluoro-1H- indol-5-yl group, 1-methyl-1H-benzimidazol-5-yl group, 1-methyl-1H-indazol-5-yl group, 1-methyl-2,3-dihydro-1H-indol-5-yl group, benzo[b]thiophen-5-yl group, 4-chlorobenzyl group, 2-bromobenzyl group, 3-bromobenzyl group, 4-bromobenzyl group, 5-bromo-2-fluorobenzyl group, 2-morpholin-4-ylethyl group and pyridin-3-ylmethyl group are preferable.

More preferably, phenyl group, 2-chlorophenyl group, 3-chlorophenyl group, 4-chlorophenyl group, 2,4-dichlorophenyl group, 3,4-dichlorophenyl group, 4-bromophenyl group, 2-fluorophenyl group, 4-fluorophenyl group, 4-iodophenyl group, o-tolyl group, p-tolyl group, 2-ethylphenyl group, 4-ethylphenyl group, 2-propylphenyl group, 2-isopropylphenyl group, 4-isopropylphenyl group, 2-butylphenyl group, 4-butylphenyl group, 2-isobutylphenyl group, 4-tert-butylphenyl group, 2-(3-methylbutyl)phenyl group, 4-trifluoromethylphenyl group, 4-(2-fluoroethyl)phenyl group, 4-(2,2-difluoroethyl)phenyl group, 4-(2,2,2-trifluoroethyl)phenyl group, 4-(1-ethylpropyl)phenyl group, 4-(1-propylbutyl)phenyl group, 4-ethynylphenyl group, 2,4-difluorophenyl group, 2,6-difluorophenyl group, 2,4-dichlorophenyl group, 4-bromo-2-fluorophenyl group, 4-bromo-3-fluorophenyl group, 4-bromo-2-chlorophenyl group, 4-chloro-2-fluorophenyl group, 2-fluoro-4-iodophenyl group, 2-chloro-4-methylphenyl group, 4-chloro-2-methylphenyl group, 4-bromo-2-methylphenyl group, 4-bromo-3-methylphenyl group, 2-fluoro-4-methylphenyl group, 2-fluoro-4-trifluoromethylphenyl group, 4-bromo-2-ethylphenyl group, 4-ethyl-2-fluorophenyl group, 4-(2-carboxyethyl)-2-fluorophenyl group, 2-fluoro-4-propylphenyl group, 2-fluoro-4-vinylphenyl group, 4-(2-carboxyvinyl)-2-fluorophenyl group, 4-ethynyl-2-fluorophenyl group, 2-fluoro-4-(prop-1-ynyl)phenyl group, 2-fluoro-4-(3-hydroxyprop-1-ynyl)phenyl group, 2-fluoro-4-(3-methoxyprop-1-ynyl)phenyl group, 4-cyclopropyl-2-fluorophenyl group, 2-fluoro-4-(3-hydroxy-3-methylbut-1-ynyl)phenyl group, 4-(3-dimethylaminoprop-1-ynyl)-2-fluorophenyl group, 4-chloro-2-dimethylaminomethylphenyl group, 4-dimethylamino-2-methylphenyl group, 4-hydroxyphenyl group, 2-methoxyphenyl group, 4-methoxyphenyl group, 4-trifluoromethoxyphenyl group, 4-isopropoxyphenyl group, 2,4-dimethoxyphenyl group, 4-methoxy-2-methylphenyl group, 2-fluoro-4-methoxyphenyl group, 4-bromo-2-hydroxyphenyl group, 4-bromo-2-methoxyphenyl group, 2-bromo-4-methoxyphenyl group, 4-methylthiophenyl group, 4-trifluoromethylthiophenyl group, 2-fluoro-4-methylthiophenyl group, 4-aminophenyl group, 4-methylaminophenyl group, 2-dimethylaminophenyl group, 3-dimethylaminophenyl group, 4-dimethylaminophenyl group, 4-ethylaminophenyl group, 4-diethylaminophenyl group, 4-ethylmethylamino-2-fluorophenyl group, 4-nitrophenyl group, 4-cyanophenyl group, 6-aminopyridin-3-yl group, 6-dimethylaminopyridin-3-yl group, 6-chloropyridin-2-yl group, 4-chloropyridin-3-yl group, 4-carboxyphenyl group, 4-methoxycarbonylphenyl group, 4-ethylaminophenyl group, 4-(methylcarbonyl)methylaminophenyl group, 4-methanesulfonylphenyl group, 4-trifluoromethanesulfonylphenyl group, 4-dimethylamino-2-methylphenyl group, 4-dimethylamino-3-methylphenyl group, 4-dimethylamino-3-trifluoromethylphenyl group, 4-dimethylamino-2-propylphenyl group, 4-dimethylamino-2-fluorophenyl group, 4-dimethylamino-3-fluorophenyl group, 4-dimethylphosphinoylphenyl group, 1,1'-biphenyl-4-yl group, 4-(piperidin-1-yl)phenyl group, 4-benzylphenyl group and 4-(morpholin-4-yl)phenyl group can be mentioned.

As the "$R^3$", preferably, $C_{1-6}$ alkyl group (wherein the $C_{1-6}$ alkyl group is optionally substituted by 1 to 3 substituents selected from group A) can be mentioned.

Specifically, a hydrogen atom, methyl group, ethyl group, propyl group, isobutyl group, 2-methoxyethyl group, cyclopropyl group, 2-dimethylaminoethyl group and 2-propenyl group are preferable, and methyl group is particularly preferable.

As the "$R^4$", preferably, a $C_{1-6}$ alkyl group (wherein the $C_{1-6}$ alkyl group is optionally substituted by 1 to 3 substituents selected from group A) can be mentioned.

Specifically, a hydrogen atom, methyl group, propyl group and hydroxy group are preferable, and methyl group is particularly preferable.

As the "$R^5$", a hydrogen atom and methyl group are preferable, and a hydrogen atom is particularly preferable.

The "pharmaceutically acceptable salt thereof" may be any salt as long as it forms a non-toxic salt with the compounds of the above-mentioned formula [I], [I'] and [I-1]-[I-3] and can be obtained by a reaction with an inorganic acid such as hydrochloric acid, sulfuric acid, phosphoric acid, hydrobromic acid and the like; an organic acid such as oxalic acid, malonic acid, citric acid, fumaric acid, lactic acid, malic acid, succinic acid, tartaric acid, acetic acid, trifluoroacetic acid, gluconic acid, ascorbic acid, methanesulfonic acid, benzenesulfonic acid and the like; an inorganic base such as sodium hydroxide, potassium hydroxide, calcium hydroxide, magnesium hydroxide, ammonium hydroxide and the like; an organic base such as methylamine, diethylamine, triethylamine, triethanolamine, ethylenediamine, tris(hydroxymethyl)methylamine, guanidine, choline, cinchonine and the like; or an amino acid such as lysine, arginine, alanine and the like. The present invention also encompasses hydrate and solvate of each compound.

The present invention also encompasses prodrugs and metabolites of each compound.

By the "prodrug" is meant a derivative of the compound of the present invention, which has a chemically or metabolically decomposable group and which, after administration to a body, restores to the original compound to show its inherent efficacy, including a complex and a salt, not involving a covalent bond.

The prodrug is utilized for, for example, improving absorption by oral administration or targeting of a target site.

As the site to be modified, highly reactive functional groups in the compound of the present invention, such as hydroxyl group, carboxyl group, amino group, thiol group and the like, are mentioned.

For example, a compound wherein a hydroxyl group is substituted by —CO-alkyl, —CO$_2$-alkyl, —CONH-alkyl, —CO-alkenyl, —CO$_2$-alkenyl, —CONH-alkenyl, —CO-aryl, —CO$_2$-aryl, —CONH-aryl, —CO-heterocycle, —CO$_2$-heterocycle, —CONH-heterocycle (wherein alkyl, alkenyl, aryl and heterocycle are optionally substituted by halogen atom, alkyl group, hydroxyl group, alkoxy group, carboxy group, amino group, amino acid residue, —PO$_3$H$_2$, —SO$_3$H, —OPO$_3$H$_2$, —OSO$_3$H and the like) or —PO$_3$H$_2$ and the like, a compound wherein an amino group is substituted by —CO-alkyl, —CO$_2$-alkyl, —CO-alkenyl, —CO$_2$-alkenyl, —CO$_2$-aryl, —CO-aryl, —CO-heterocycle, —CO$_2$-heterocycle (wherein alkyl, alkenyl, aryl and heterocycle are optionally substituted by halogen atom, alkyl group, hydroxyl group, alkoxy group, carboxy group, amino group, amino acid residue, —PO$_3$H$_2$, —SO$_3$H, —OPO$_3$H$_2$, —OSO$_3$H and the like) or —PO$_3$H$_2$ and the like and the like can be mentioned.

Specifically, as the modifying group of hydroxyl group, acetyl group, propionyl group, isobutyryl group, pivaloyl group, palmitoyl group, benzoyl group, 4-methylbenzoyl group, dimethylcarbamoyl group, dimethylaminomethylcarbonyl group, sulfo group, alanyl group, fumaryl group and the like can be mentioned. The sodium salt of 3-carboxybenzoyl group or 2-carboxyethylcarbonyl group and the like can be also mentioned.

Specifically, as the modifying group of carboxyl group, methyl group, ethyl group, propyl group, isopropyl group, butyl group, isobutyl group, tert-butyl group, pivaloyloxymethyl group, carboxymethyl group, dimethylaminomethyl group, 1-(acetyloxy)ethyl group, 1-(ethoxycarbonyloxy) ethyl group, 1-(isopropyloxycarbonyloxy)ethyl group, 1-(cyclohexyloxycarbonyloxy)ethyl group, carboxylmethyl group, (5-methyl-2-oxo-1,3-dioxol-4-yl)methyl group, benzyl group, phenyl group, o-tolyl group, morpholinoethyl group, N,N-diethylcarbamoylmethyl group, phthalidyl group and the like can be mentioned.

Specifically, as the modifying group of amino group, tert-butyl group, docosanoyl group, pivaloylmethyloxy group, alanyl group, hexylcarbamoyl group, pentylcarbamoyl group, 3-methylthio-1-(acetylamino)propylcarbonyl group, 1-sulfo-1-(3-ethoxy-4-hydroxyphenyl)methyl group, (5-methyl-2-oxo-1,3-dioxol-4-yl)methyl group, (5-methyl-2-oxo-1,3-dioxol-4-yl)methoxycarbonyl group, tetrahydrofuranyl group, pyrrolidylmethyl group and the like can be mentioned.

The "tumor" used in the present specification includes malignant tumor, and the "antitumor agent" contains an anticancer agent and is a compound having an antitumor activity.

The compound of the present invention can be administered to a mammal (human, mouse, rat, hamster, rabbit, cat, dog, bovine, sheep, monkey etc.) and the like as an antitumor agent and the like.

When the compound of the present invention is used as a pharmaceutical preparation, it is generally admixed with pharmaceutically acceptable carriers, excipients, diluents, extending agents, disintegrants, stabilizers, preservatives, buffers, emulsifiers, flavoring agents, coloring agents, sweetening agents, thickeners, corrigents, dissolution aids, and other additives, that are known per se, such as water, vegetable oil, alcohol (e.g., ethanol, benzyl alcohol etc.), polyethylene glycol, glycerol triacetate, gelatin, carbohydrate (e.g., lactose, starch etc.), magnesium stearate, talc, lanolin, petrolatum and the like, formed into tablet, pill, powder, granule, suppository, injection, eye drop, liquid, capsule, troche, aerosol, elixir, suspension, emulsion, syrup and the like by a conventional method, and administered systemically or topically, and orally or parenterally.

While the dose varies depending on age, body weight, symptom, treatment effect, administration method and the like, it is generally 0.01 mg to 1 g once for an adult, which is given once to several times a day orally or in a dosage form of an injection such as intravenous injection and the like.

An antitumor agent is generally required to sustain its effect for a long time, so that can be effective not only for temporal suppression of the proliferation of cancer cells but also for the prohibition of the re-prohibition of cancer cells. This means that a prolonged administration is necessary and that a high single dose may be frequently inevitable to sustain effect for a longer period through the night. Such prolonged and high dose administration increases the risk of causing side effects.

In view of this, one of the preferable embodiments of the pyrimidine compound of the present invention is such compound as permitting high absorption by oral administration, and such compound capable of maintaining blood concentration of the administered compound for an extended period of time.

A compound capable of showing p15 protein induction and/or p27 protein induction and/or MEK inhibition in combination is preferable.

This compound is useful for the treatment of diseases caused by undesirable cell proliferation.

As the "diseases caused by undesirable cell proliferation", for example, tumor, specifically cerebral tumor (neuroglioma having a component of malignant astroglioma and oligodendroglioma and the like), cancer of esophangus, stomach cancer, liver cancer, pancreatic cancer, colorectal cancer(colon cancer, rectal cancer etc.), lung cancer(non-small cell lung cancer, small cell lung cancer, primary and metastatic squamous cancer etc.), renal cancer, breast cancer, ovarian cancer, prostate cancer, skin cancer, neuroblastoma, sarcoma, osteochondroma, osteoma, osteosarcoma, seminoma, extragonadal tumor, testicle tumor, uterine cancer (cervical cancer, endometrial cancer and the like), head and neck tumor (maxillary cancer, larynx cancer, pharyngeal cancer, lingual cancer, intraoral cancer and the like), multiple myeloma, malignant lymphoma (reticulosarcoma, lymphosarcoma, Hodgkin's disease etc.), polycythemia vera, leukemia (acute myeloid leukemia, chronic myeloid leukemia, acute lymphocytic leukemia, chronic lymphocytic leukemia etc.), goiter, renal pelvic cancer, ureteral tumor, bladder tumor, gallbladder cancer, bile duct cancer, chorioma, malignant melanoma, pediatric tumor (sarcoma of the ewing's family, Wilms' tumor, rhabdomyosarcoma, vascular sarcoma, embryonal testicle cancer, neuroblastoma, retinoblastoma, hepatoblastoma, nephroblastoma etc.) and the like can be mentioned.

Application to cerebral tumor (neuroglioma having a component of malignant astroglioma and oligodendroglioma etc.), cancer of esophangus, stomach cancer, liver cancer, pancreatic cancer, colorectal cancer(colon cancer, rectal cancer etc.), lung cancer(non-small cell lung cancer, small cell lung cancer etc.), renal cancer, breast cancer, ovarian cancer, prostate cancer, skin cancer, neuroblastoma, sarcoma and the like can be mentioned. more preferably, colon cancer, pancreas cancer, renal cancer, lung cancer, and breast cancer is preferable, and application to colon cancer and pancreas cancer is particularly preferable.

In addition, treatment of chronic pain, specifically, neuropathic pain, catapletic pain, pain associated with chronic alcoholism, vitamin deficiency, uremia and hypothyroidism can be mentioned. Furthermore, neutrophile-mediated disease or symptoms, specifically, ischemia reperfusion injury, chronic obstructive pulmonary disease, acute respiratory disease syndrome, cystic fibrosis, catapletic pulmonary fibrosis, sepsis, endotoxemia, lung emphysema and pulmonary asbestosis can be mentioned. Furthermore, graft rejection can be mentioned. Moreover, arthritis, specifically, rheumatoid arthritis and osteoarthritis can be mentioned. In addition, asthma can be mentioned. Moreover, viral diseases, specifically, herpes virus (HSV-1) infection, human cytomegalovirus (HCMV) infection, human immunodeficiency virus (HIV) infection can be mentioned. Furthermore, disease caused by denaturation or injury of cartilage, specifically, osteoarthrosis, rheumatoid arthritis, osteochondrosis dissecans and disease requiring chondrogenesis can be mentioned.

Besides the above, application to restenosis, psoriasis, atherosclerosis, cardiac failure, apoplexia and the like can be mentioned.

As the "diseases caused by undesirable cell proliferation", tumor and rheumatism are preferable.

As other "antitumor agent" used for multiple drug therapy, alkylating agent, platinum complex, metabolism antagonist, antibiotics, plant alkaloid, interferon, cyclooxygenase-2 (COX-2) inhibitor, hormonal anticancer agent, cancer cell vaccine, bacterial preparation, mushroom extract polysaccharides, cytokine agonist, interleukin preparation, antibody drug, immunomodulator, angiogenesis inhibitor, intracellular tube formation inhibitor, cell proliferation inhibitor, cell cycle regulator, apoptosis inducer, cancer gene therapy agent and the like can be mentioned.

As the alkylating agent, cyclophosphamide, ifosfamide, melpharan, buslfan, nimustine, ranimustine (MCNU), nitrogen mustard-N-oxide hydrochloride, thiotepa, procarbazine hydrochloride, carboquone, mitobronitol, improsulfan tosylate, estramustine phosphate sodium, dacarbazine, temozolomide, dacarbazine(DTIC), mustine hydrochride, treosulfan, temozolomide, MS-247, (−)-(S)-bromofosfamide and the like can be mentioned.

As the platinum complex, cisplatin, carboplatin, nedaplatin, paraplatin, etoposide, oxaliplatin, eptaplatin, miriplation, lobaplatin, picoplatin, oxaliplatin, satraplatin, SLIT-cisplatin and the like can be mentioned.

As the metabolism antagonist, methotrexate, 6-mercaptopurine, cytosine-arabinoside, enocitabine (BHAC), 5-fluorouracil, tegafur, tegafur-uracil (UFT), carmofur (HCFU), doxifluridine, gemcitabine hydrochloride, hydroxylcarbamide, procarbazine hydrochloride, pemetrexed disodium, L-MDAM, mercaptopurine riboside, fludarabine phosphate, tegafur-gimestat-otastat, levofolinate-fluorouracil, folinate calcium levofolinate, bemcitabine, calcium levolecucovorin, capecitabine, cytarabine, cytarabine ocfosfate, CS-682, 3'-ethynylcytidine, TAS-102, capecitabine, fulvestrant, idoxuridine, hydroxyurea, pemetrexeddisodium, 3-AP, benspm, lometrexol, troxacitabine, ABT-510, AP-2/09, AR-726, AVI-4126, belimumab, CA4P, colorectal cancer vaccine, COU-1, degarelix, DJ-927, DPC-974, EKB-569, enzastaurin hydrochloride, fentanyl citrate, fulvestrant, gallium maltolate, HuMax-EGFR, IDD-1, LE-AON, MDX-070, MT-201, NK-911, NV-07, Oncomyc-NG, pertuzumab, PX-103.1, renal cancer vaccine, SN-4071, TL-139, topixantrone dihydrochloride, ZYC-101a and the like can be mentioned.

As the antibiotics, actinomycin D, daunomycin, doxorubicin (adriamycin), epirubicin, aclacinomycin A, mitomycin C, bleomycin, pirarubicin hydrochloride, idarubicin hydrochloride, aclarubicin hydrochloride, amrubicin hydrochloride, peplomycin sulfate, neocarzinostatine, zinostatin stimalamer, valrubicin, liposormal doxorubicin, NK911, BMS-247550(epothilone derivative), KRN5500, KW-2170, annamycin, becatecarin, PK1, sabarubicin hydrochloride, CVS-10290 and the like can be mentioned.

As the plant alkaloid, vincristine, vinblastine, vindesine, etoposide, docetaxel, paclitaxel, irinotecan hydrochloride, vinorelbine tartrate, mitoxantrone hydrochloride, noscapine, vinflunine, docetaxel, E-7010, polyglutamated paclitaxel, soblidotin, Bay59-8862, E-7389, DJ-927, HTI-286, AC-7700, T-3782, ABI-007, batabulin sodium, DHA-paclitaxel, deoxyepothilone B, ixabepilone, MBT-0206, ortataxel, SB-715992, AI-850, synthadotin, lxabepilone, rubitecan, nogitecan hydrochloride, topotecan hydrochloride, sobuzoxane, etoposide phosphate disodium salt, dexrazoxane hydrochloride, rubitecan IST-622, exatecan mesylate, TOP-53, edotecarin, karenitecan, AG-7352, TAS-103, T-0128, NK-314, CKD-602, BNP-1350, lurtotecan, pegamotecan, rubitecan, LE-SN38, CPT-11 and the like can be mentioned.

As interferon, interferon α, interferon α-2a, interferon α-2b, interferon β and interferon γ, interferon γ-1a, interferon γ-1b, interferon γ-n1 and the like can be mentioned.

As the cyclooxygenase-2 inhibitor, rofecoxib, celecoxib, lumiracoxib, tiracoxib (tilmacozib), CS-502, CS-706, valdecoxib, parecoxib, R-109339, deguelin, ajulemic acid, p-54, E-6087, LM-4108, R-109339, CBX-AC, CBX-PR, CBX-BU, L-748706, DMNQ-S64, ON-09250, ON-09300 and the like can be mentioned.

As the hormonal anticancer agent, leuprorelin acetate, goserelin acetate, aminoglutethimide, triptorelin, goserelin, formestane, fabrozole monohydrochloride, letrozole, exemestane, deslorelin, buserelin acetate, cetrorelix acetate, histrelin acetate, abarelix, atrigel-leuprolide, estramustine phosphate sodium, chlormadinone acetate, fosfetrol, flutamide, bicartamide, cyproterone acetate, medroxyprogesterone acetate, tamoxifen citrate, toremifene citrate, mepithiostane, epithiostanol, medroxyprogesterone acetate, fluvestrant, ormeloxifene, raloxifene hydrochloride, miproxifene phosphate, TAS-108, FMPA, fadrozole, anastrozole, exemestane, letrozole, formestane, bosentan, atrasentan, dutasteride, ESI, KT5555, KAT-682 and the like can be mentioned.

As the cancer cell vaccine, cancer vaccine, activated lymphocyte, UL56 deficient HSV, vaccine for colorectal cancer treatment, cancer peptide vaccine and the like can be mentioned.

As the bacterial preparation, BCG, anti-malignant tumor streptococcal preparation, LC9018, tubercle *bacillus* hot water an extract and the like can be mentioned.

As the mushroom extract polysaccharides, lentinan, *Coriolus versicolor* polysaccharides(krestin), sizofiran, CM6271 and the like can be mentioned.

As the cytokine agonist, ubenimex and the like can be mentioned.

As the interleukin preparation, interleukin-2, teceleukin, interleukin-12 and the like can be mentioned.

As the antibody pharmaceutical agent, immunomodulator, trastuzumab, rituximab, gemtuzumab ozogamicin, iburitumomab tiuxetan, cetuximab, bevacizumab, caprpmab pendetide, capromab pendetide indium, pemetrexed disodium, yttrium 90 ibritumab tiuxetan, votumumab, humanized IL-6 receptor antibody, anti-TA226 human monoclonal antibody, F(ab') human antibody GAH, EMD72000, partuzumab, alemtuzumab, VEGF receptor FLt-1 antibody, KW-2871, humanized anti-GM2 antibody, humanized anti-GD2 antibody, KM2760, TRAIL receptor-2 monoclonal antibody, anti-TRAIL receptor DR5 antibody, TRAIL-R1mAb, humanized anti-HM1.24 antibody, humanized FasL antibody, humanized anti-CD26 monoclonal antibody, α-galactosylceramide, diphtheria toxin modified transferrin bond, CD47 monoclonal antibody, anti-human melanoma monoclonal antibody, HoAKs-1 (anti-lung cancer monoclonal antibody) and the like can be mentioned.

As the angiogenesis inhibitor, gefitinib (Iressa), thalidomide, cetuximab, semaxanib, TSU-68, KRN633, KRN951, marimastat, S-3304, erlotinib hydrochloride, ZD6474, GW572016, S-3304, E7820, SU6668, E7080, NK4, TAS-101, lapatinib, priomastat, RPI-4610, thalidomide, WX-UK1, 2-methoxyestradiol, SG-292, FYK-1388 and the like can be mentioned.

As the intracellular tube formation inhibitor, TAC-01, E-7820 and the like can be mentioned.

As the cell proliferation inhibitor, imatinib mesylate, trastuzumab, rituximab, gemtuzumab, AHM, mubritinib/TAK-165, KW-2871, KM8969, CP-724714 and the like can be mentioned.

As the cell cycle regulator, Boltezomib (NF-κβ Activation inhibitor), histone deacetylase HDAC inhibitor (FK-228, SAHA, CI-994, LAQ-824, pyroxamide, AN-9, PBA, MS-275 and the like), E-7070, flavopiritol, UCN-01, CGP41251, CCI-779, KT5555, HMN-214, Y-27632, vatalanib/PTK-787A, MGCD0130, temsirolimus, (R)-roscovitine, indisulam and the like can be mentioned.

As the apoptosis inducer, bortezomib, arglabin, R-115777, KW-2401, BMS-214662, tipifarnib, lonafarnib, arglabin, bexarotene, exisulind, glufosfamide, irofulven, MX-126374, MX-2167, GRN163, GM95, MST-312, (-)-EGCG(Teavigo) and the like can be mentioned.

As the cancer gene therapy agent, A-007, Ad/Q5-H-sDd, apaziquone, AVE-8062, MS-214662, combretastatin A-4, didox, dolastatin-10, ganglioside vaccine, GivaRex, ILX-23-7553, interleukins, itriglumide, KW-2401, MCC-465, miriplatin, MUC-1 vaccine, OSI-7904L, platelet factor 4, SR-271425, ZK-230211 and the like can be mentioned.

As other antitumor agents, anticancer agents, L-asparaginase, tretinoin, levoleucovorin calcium, celmoleukin, 1111n-pentetreotide, ibandronate sodium hydrate, aminolevulinic acid hydrochloride, ukrain, Stem cell factor, denileukin difftitox, menatetrenone, methoxsalen, trimetrexate glucuronate, IOR-R3, everolimus, cytokeratin 19, doxercalciferol, alitretinoin, bexarotene, verteporfin, morphine sulfate sustained-release, *Bacillus* Calmette Guerin, megestrol acetate, menadione, floxuridine, thyrotropin alfa, inositol hexaphosphate, augmerosen, Thio TEPA, chorionic gonadotropin, histamine dihydrochloride, lycopene, talaporfin sidium, tasonermin, arsenic trioxide, levamisole hydrochroride, folic acid, teniposide, mebendazole, morphine hydrochloride, ALA Me ester, anethole dithiolethion, testosterone propionate, cinacalcet hydrochloride, anethole dithiolethione, testosterone, mitotane, sodium thiosulfate, zevalin, bexxar, salmon calcitonin, novobiocin, aminoglutethimide, eflornithine hydrochloride, lonidamine, amoxnox, pirarubicin, vesnarinone, pamidronate sodium, clodronate disodium, zoledronic acid monohydrate, ambamustine hydrochloride, ubestatin, amifostine hydrate, deoxyspergualin hydrochloride, pentostatin, bisantrene, peplomycin, iobenguane, amsacrine, trilostane, tramadol hydrochloride, elliptinium acetate, ladakamycin, bromebrate sodium, nitracrin dihydrochloride hydrate, altretamine, OROS-oxyodone, fentanyl citrate, aspirin, AERx Morphine sulfate, carmustine, metoclopramide hydrochloride, loperamide hydrochloride, nilutamide, polysaccharide K, ranimustine, atvogen, pipobroman, imiquimod (interferon inducers), cladribine, tibolone, suramin sodium, leflunomide, fentanyl, octreotide acetate, inositol, ursodiol, feverfew, lentinan, tetranabinex, (cannabinoid receptor agonists), pegaspargase, triclosan, crbohydrate antigen 19-9, angiopeptin acetate, fotemustine, gallium nitrate, trabectebin, raltitrexed, zinostatin stimalamer, hexadecylphosphocholine, tazarotene, finasteride, clofarabine, temoporfin, SY-801, human angiotensin II, efaproxiral sodium, amonafide(DNA-Intercalating Drug), SP-1053C(DNA-Intercalating Drug), antineoplaston AS2-1, fenretinide(retinoids), trabectebin, mammastatin, DOS-47, ECO-04601, thymectacin, rhIGFBP-3, carboxyamidotriazole, CoFactor, davanat-1, tariquidar, ONT-093, minobronic acid, minodronic acid, dofequidar fumarate(MDR-1 inhibitors), tariquidar(MDR-1 Inhibitors), Davanat-1, ranpirnase, atrasentan, meclinertant, tacedinline, troxacitabine, DN-101, EB-1627, ACO-04601, MX-116407, STA-4783, Davanat-1, moverastin, mitoxantrone hydrochloride, procarbazine hydrochloride, octreotide acetate, porfimer sodium, pentostatin, cladribine, sobuzoxane, tretinoin, aceglatone, mitotane, porfimer sodium, elliptinium Acetate, AZD6126, tirapazamine, Bay43-9006, tipifarnib/R115777, midostaurin, BMS-214662, EKB-569, E7107, CBP501, HMN-214, FK-866, WF-536, SU-11248, MKT-077, phenoxodiol, NSC-330507, G-CSF, Edrecolomab(Monoclonal Antibodies), satumomab, sargramostin (GM-CSF), tamibarotene (retinoid derivative), arsenic trioxide, dutasteride, menatetrenone, ZD4054, NIK-333, NS-9, ABT-510, S-2678, methioninase, TAS-105, metastin, TOP-008, NCO-700, BCA and the like can be mentioned.

As "other antitumor agents" used for the multiple drug therapy with the compound of the present invention, platinum complex, alkylating agent and metabolism antagonist are preferable. It is possible to use 2 or 3 or more pharmaceutical agents can be used in combination, wherein a combination of pharmaceutical agents having different action mechanism is one of the preferable embodiments. Moreover, selection of pharmaceutical agents having non-overlapping side effects is preferable.

For a combined use of the compound of the present invention with "other antitumor agents", these two or more kinds of compounds may be contained in the same composition. In addition, a composition containing the compound of the present invention and a composition containing "other antitumor agents" may be simultaneously or sequentially administered.

When two agents are simultaneously administered, "simultaneous" includes administration of 2 agents, with administration of one agent and then the other agent in several minutes after the first administration. By "sequentially" is meant a lapse of a given time. For example, administration of the other agent several minutes to several dozen minutes after the administration of the first agent, and administration of the other agent several hours to several days after the administration of the first agent are included, wherein the lapse of time is not limited. For example, one agent may be administered once a day, and the other agent may be administered 2 or 3 times a day, or one agent may be administered once a week, and the other agent may be administered once a day and the like.

When the compound of the present invention is used as an antitumor agent, and when the compound of the present invention is used in combination with "other antitumor agents", radiotherapy, activation lymphocyte therapy and the like may be further added.

Some examples of the Production Methods of the compound used for embodiment of the present invention are shown in the following. However, the Production Methods of the compound of the present invention are not limited to these examples.

Even in the absence of description in the Production Methods, efficient production can be afforded by designs such as introducing, where necessary, a protecting group into a functional group followed by deprotection in a subsequent step; subjecting a functional group to each step as a precursor and converting the group to a desired functional group in a suitable step; exchanging the order of respective Production Methods and steps; and the like.

The work-up treatment in each step can be applied by a typical method, wherein isolation and purification is performed as necessary by selecting or combining conventional methods, such as crystallization, recrystallization, distillation, partitioning, silica gel chromatography, preparative HPLC and the like.

Production Method 1

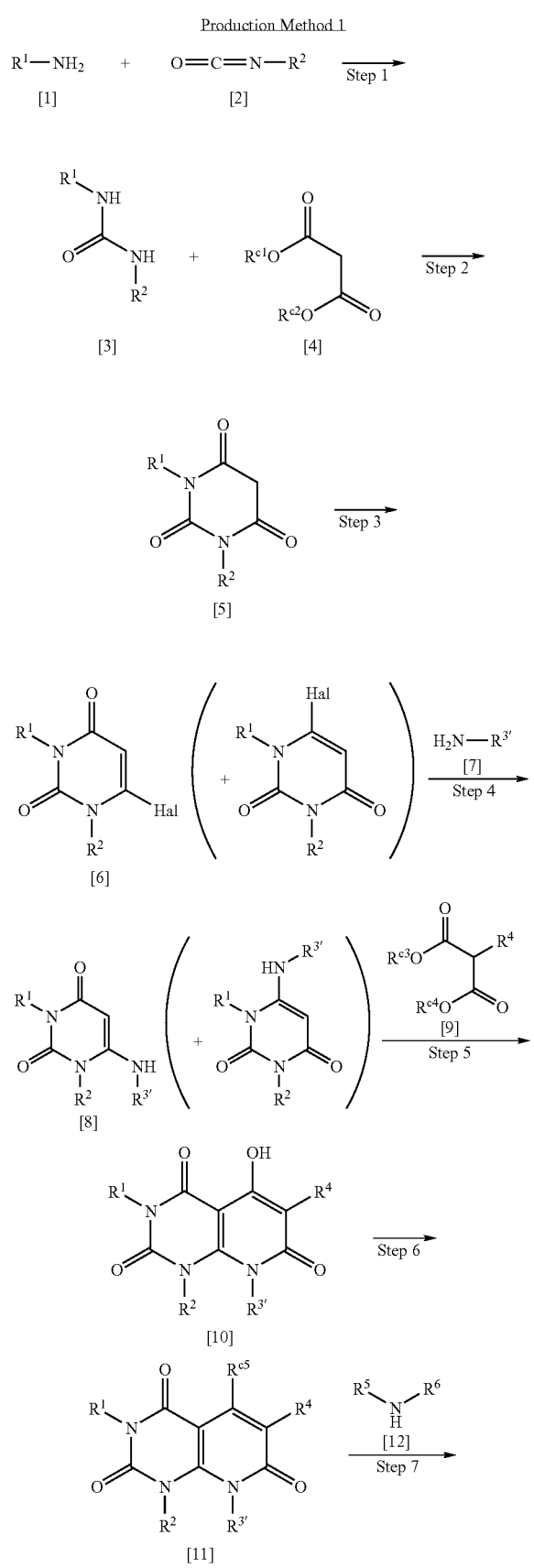

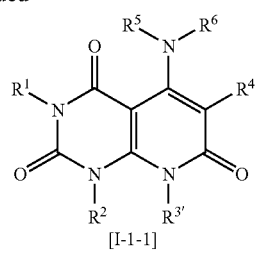

[I-1-1]

wherein Hal is a halogen atom such as chlorine atom, bromine atom and the like, $R^{c1}$, $R^{c2}$, $R^{c3}$ and $R^{c4}$ are the same or different and each is a hydrogen atom or the above-defined "$C_{1-6}$ alkyl group", $R^{3\prime}$ is $R^3$ other than a hydrogen atom, $R^{c5}$ is a leaving group such as a halogen atom, p-toluenesulfonyloxy, methanesulfonyloxy, trifluoromethanesulfonyloxy and the like, and other symbols are as defined above.

Step 1

The compound [3] can be obtained by reacting compound [1] with compound [2] in a solvent preferably under a nitrogen atmosphere from cooling to room temperature.

As the solvent, ether solvents such as 1,4-dioxane, diethyl ether, 1,2-dimethoxyethane, tetrahydrofuran (THF) and the like; hydrocarbon solvents such as benzene, toluene, xylene, hexane and the like; and the like can be mentioned.

Step 2

The compound [5] can be obtained by reacting compound [3] with compound [4] in a solvent preferably under a nitrogen atmosphere under heating.

As the solvent, acetic anhydride, acetyl chloride, phosphorus oxychloride and the like can be mentioned.

Step 3

Here, Hal is preferably bromine atom or chlorine atom. The compound [6] can be obtained by reacting compound [5] with a halogenating agent such as phosphorus oxychloride, N-bromosuccinimide, N-iodosuccinimide and the like, in a solvent such as trifluoromethanesulfonic acid, acetic acid, concentrated sulfuric acid, N,N-dimethylformamide (DMF), water and the like, at room temperature to under heating.

Step 4

The compound [8] can be obtained by reacting compound [6] with compound [7] in a solvent under heating.

As the solvent, alcohol solvents such as water-containing or nonaqueous methanol, ethanol and the like; ether solvents such as 1,4-dioxane, tetrahydrofuran(THF) and the like, and the like can be mentioned.

Step 5

The compound [10] can be obtained by reacting compound [8] with compound [9] in a solvent under heating.

As the solvent, ether solvents such as diphenylether and the like; acetic anhydride, acetyl chloride and the like can be mentioned.

Step 6

The compound [11] can be obtained by introducing a leaving group into compound [10] by a conventional method.

For example, compound [11] can be obtained by reacting compound [10] with methanesulfonyl chloride, p-toluenesulfonyl chloride, trifluoromethanesulfonic anhydride and the like, in the presence of base such as trimethylamine hydrochloride, triethylamine, pyridine and the like as necessary in a solvent.

As the solvent, acetonitrile; ether solvents such as tetrahydrofuran and the like; halogen solvents such as dichloromethane and the like, and the like can be mentioned.

Step 7

The compound [I-1-1] can be obtained by reacting compound [11] with compound [12] under heating as necessary in a solvent.

As the solvent, N,N-dimethylacetamide, chloroform and the like can be mentioned.

To improve reaction efficiency, 2,6-lutidine may be added.

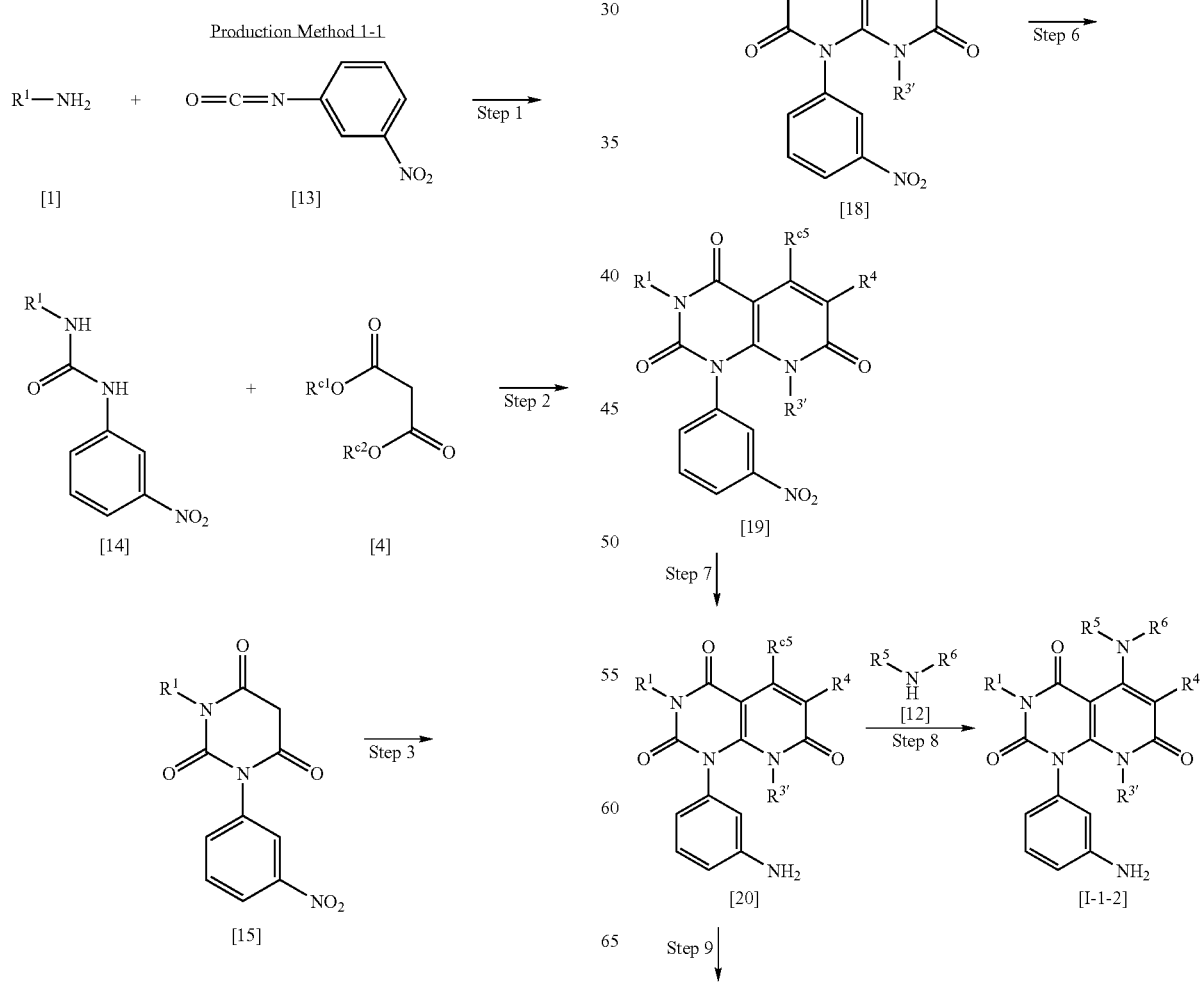

-continued

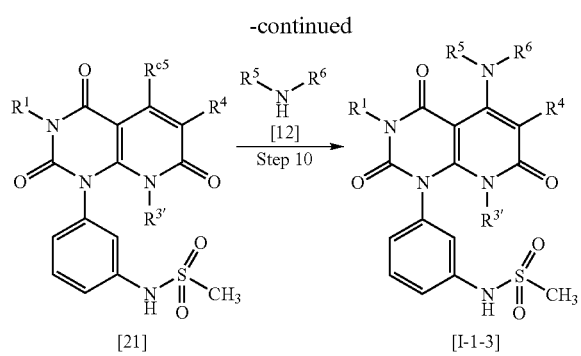

wherein each symbol is as defined above.

Step 1

The compound [14] can be obtained by reacting compound [1] with compound [13] in the same manner as in Production Method 1, Step 1.

Step 2

The compound [15] can be obtained by reacting compound [14] with compound [4] in the same manner as in Production Method 1, Step 2.

Step 3

The compound [16] can be obtained by reacting compound [15] in the same manner as in Production Method 1, Step 3.

Step 4

The compound [17] can be obtained by reacting compound [16] with compound [7] in the same manner as in Production Method 1, Step 4.

Step 5

The compound [18] can be obtained by reacting compound [17] with compound [9] in the same manner as in Production Method 1, Step 5.

Step 6

The compound [19] can be obtained by reacting compound [18] in the same manner as in Production Method 1, Step 6.

Step 7

The compound [20] can be obtained by reducing compound [19] by a conventional method such as reduction with zinc or iron in a neutral or alkaline condition; iron and acid; tin or tin (II) chloride and concentrated hydrochloric acid; alkali sulfide; alkaline hydrosulfite and the like, or hydrogenation under hydrogen atmosphere and the like.

For example, compound [20] can be obtained by adding acetic acid and zinc powder to compound [19] under cooling to allow to react at room temperature. Alternatively, compound [20] can be obtained by adding palladium-carbon to a solution of compound [19] in a mixed solvent of THF and methanol under hydrogen atmosphere to allow to react at room temperature.

Step 8

The compound [I-1-2] can be obtained by reacting compound [20] with compound [12] in the same manner as in Production Method 1, Step 7.

Step 9

The compound [21] can be obtained by reacting compound [20] with methanesulfonyl chloride in a solvent in the presence of base such as triethylamine, pyridine and the like under cooling.

As the solvent, acetonitrile; ether solvents such as tetrahydrofuran and the like; halogen solvents such as dichloromethane and the like, and the like can be mentioned.

Step 10

The compound [I-1-3] can be obtained by reacting compound [21] with compound [12] in the same manner as in Production Method 1, Step 7.

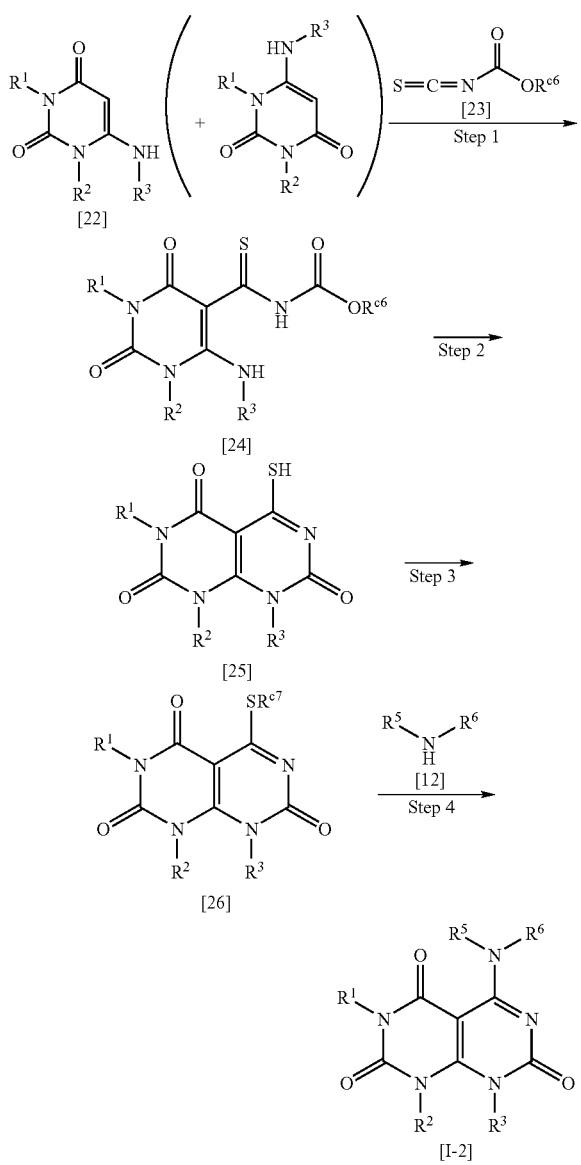

wherein $R^{c6}$ is a hydrogen atom or an $C_{1-4}$ alkyl group, $SR^{c7}$ ($R^{c7}$ is lower alkyl such as methyl, ethyl and the like or benzyl) is a leaving group, and other symbols are as defined above.

Step 1

The compound [24] can be obtained by reacting compound [22] obtained in the same manner as in Production Method 1, Step 1 to Step 4 with compound [23].

Step 2

The compound [25] can be obtained by cyclizing compound [24] by a conventional method. For example, compound [25] can be obtained by stirring compound [24] in a solvent such as N,N-dimethylformamide and the like in the presence of triethylamine at room temperature.

Step 3

The compound [26] can be obtained by reacting compound [25] with lower alkyl halide or benzyl halide in the presence of base.

As the base, potassium carbonate, sodium carbonate, lithium hydride, sodium hydride, potassium hydride and the like can be mentioned, potassium carbonate is preferable.

As the lower alkyl halide, methyl iodide, ethyl iodide, benzyl iodide and the like can be mentioned, methyl iodide is preferable.

Step 4

The compound [I-2] can be obtained by reacting compound [26] with compound [12] in the same manner as in Production Method 1, Step 7.

Production Method 3

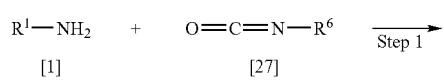

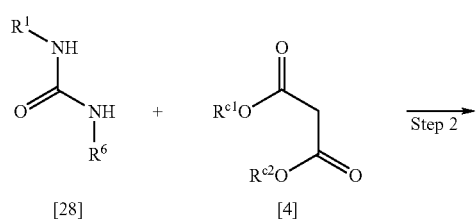

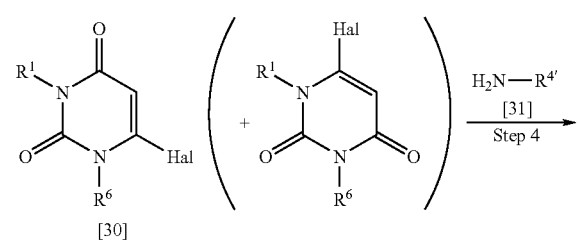

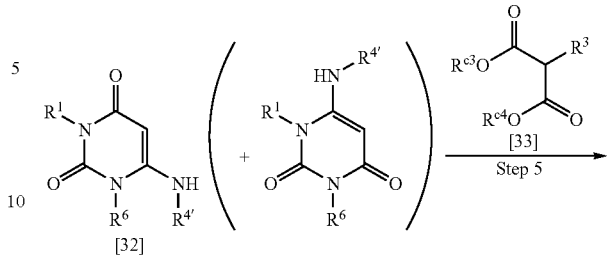

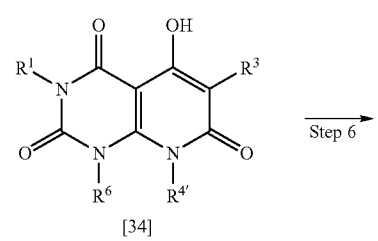

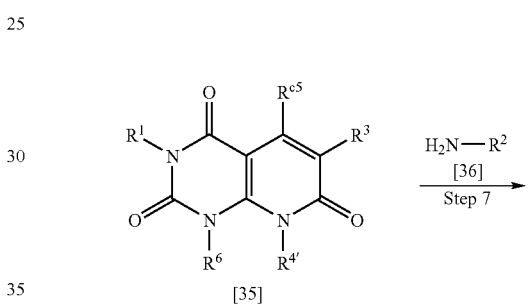

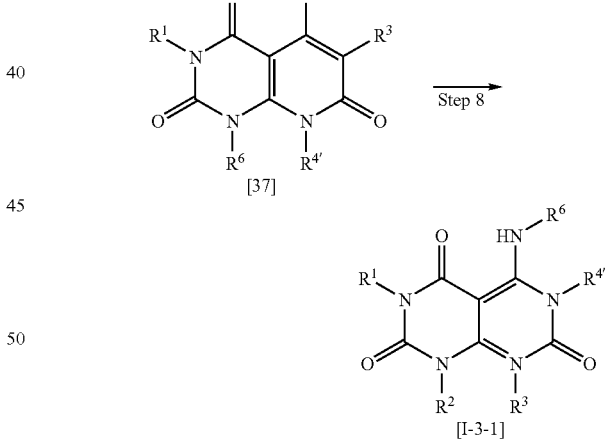

wherein $R^{4'}$ is $R^4$ other than a hydrogen atom, and other symbols are as defined above.

Step 1

The compound [28] can be obtained by reacting compound [1] with compound [27] in the same manner as in Production Method 1, Step 1.

Step 2

The compound [29] can be obtained by reacting compound [28] with compound [4] in the same manner as in Production Method 1, Step 2.

Step 3

The compound [30] can be obtained by reacting compound [29] in the same manner as in Production Method 1, Step 3.

Step 4

The compound [32] can be obtained by reacting compound [30] with compound [31] in the same manner as in Production Method 1, Step 4.

Step 5

The compound [34] can be obtained by reacting compound [32] with compound [33] in the same manner as in Production Method 1, Step 5.

Step 6

The compound [35] can be obtained by reacting compound [34] in the same manner as in Production Method 1, Step 6.

Step 7

The compound [37] can be obtained by reacting compound [35] with compound [36] in the same manner as in Production Method 1, Step 7.

Step 8

The compound [I-3-1] can be obtained by stirring compound [37] in a solvent, in the presence of base at room temperature to under reflux.

As the base, potassium carbonate, sodium carbonate, lithium hydride, sodium hydride, potassium hydride, sodium methoxide and the like can be mentioned, potassium carbonate and sodium methoxide are preferable.

As the solvent, alcohol solvents such as methanol, ethanol, n-propanol, isopropanol and the like; mixed solvents of these solvent and amide solvents such as N,N-dimethylformamide, N,N-dimethylacetamide and the like, halogen solvents such as dichloromethane, chloroform, carbon tetrachloride, 1,2-dichloroethane and the like or ether solvents such as tetrahydrofuran (THF) and the like, and the like can be mentioned.

Production Method 4-1

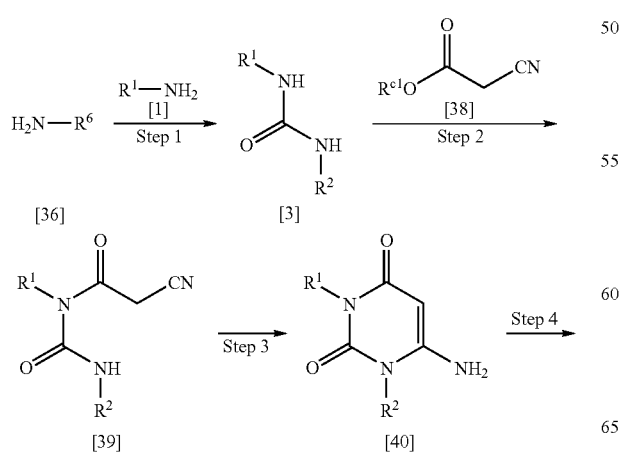

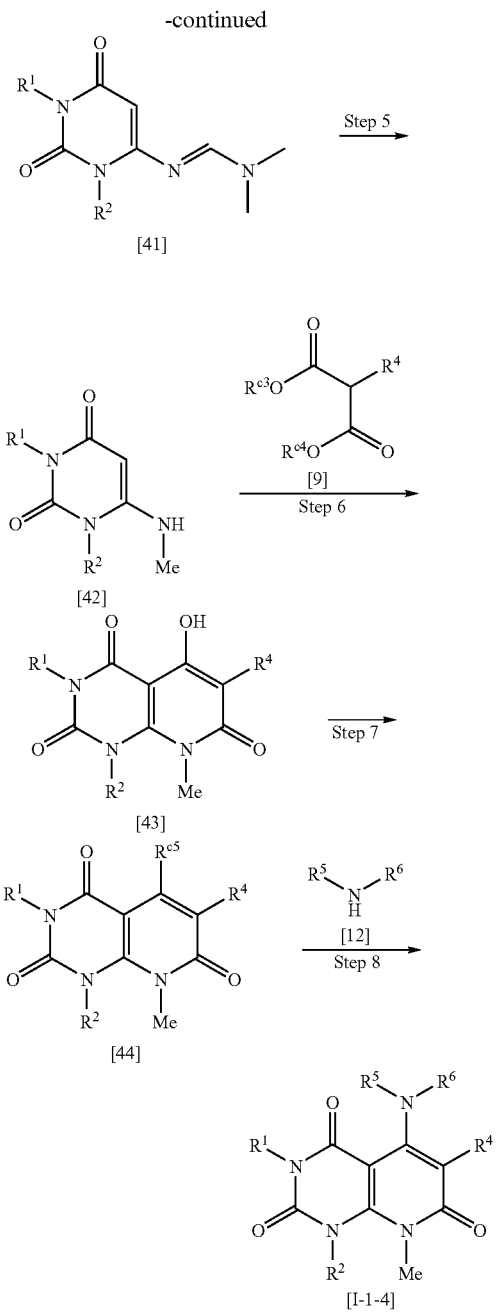

wherein each symbol is as defined above.

Step 1

The compound [3] can be obtained by reacting compound [36] with carbonyldiimidazole in a solvent in the presence of tertiary amine such as triethylamine and the like under nitrogen or argon atmosphere from cooling to room temperature, and then reacting with compound [1].

As the solvent, N,N-dimethylformamide, chloroform, dichloromethane, tetrahydrofuran and the like can be mentioned.

Step 2

The compound [39] can be obtained by acylating compound [3] with compound [38] preferably under a nitrogen atmosphere by a conventional method.

for example, when $R^{c1}$ is hydrogen, compound [38] can be condensed with compound [3] using acetic anhydride, acetyl chloride, pivaloyl chloride, methanesulfonyl chloride and the like, particularly methanesulfonyl chloride in a solvent such as N,N-dimethylformamide, N,N-dimethylacetamide and the like.

Step 3

The compound [40] can be obtained by reacting compound [39] in a solvent in the presence of base at room temperature to under heating.

As the solvent, water, ethanol-water, tetrahydrofuran-water and the like can be mentioned, water is preferable.

As the base, potassium carbonate, sodium carbonate, potassium hydroxide, sodium hydroxide, lithium hydride, sodium hydride, potassium hydride and the like can be mentioned, sodium hydroxide is preferable.

Step 4

The compound [41] can be obtained by reacting compound [40] with N,N-dimethylformamide dimethylacetal in a N,N-dimethylformamide solvent preferably under a nitrogen atmosphere.

Step 5

The compound [42] can be obtained by reducing compound [41] by a conventional method.

For example, compound [42] can be obtained by treating with a reducing agent such as sodium borohydride, sodium cyanoborohydride and the like in an alcohol solvent such as methanol, ethanol, isopropanol, tert-butanol and the like or a mixed solvent thereof under a nitrogen atmosphere.

Step 6

The compound [43] can be obtained by reacting compound [42] with compound [9] in the same manner as in Production Method 1, Step 5.

Step 7

The compound [44] can be obtained by reacting compound [43] in the same manner as in Production Method 1, Step 6.

Step 8

The compound [I-1-4] can be obtained by reacting compound [44] with compound [12] in the same manner as in Production Method 1, Step 7.

Production Method 4-2

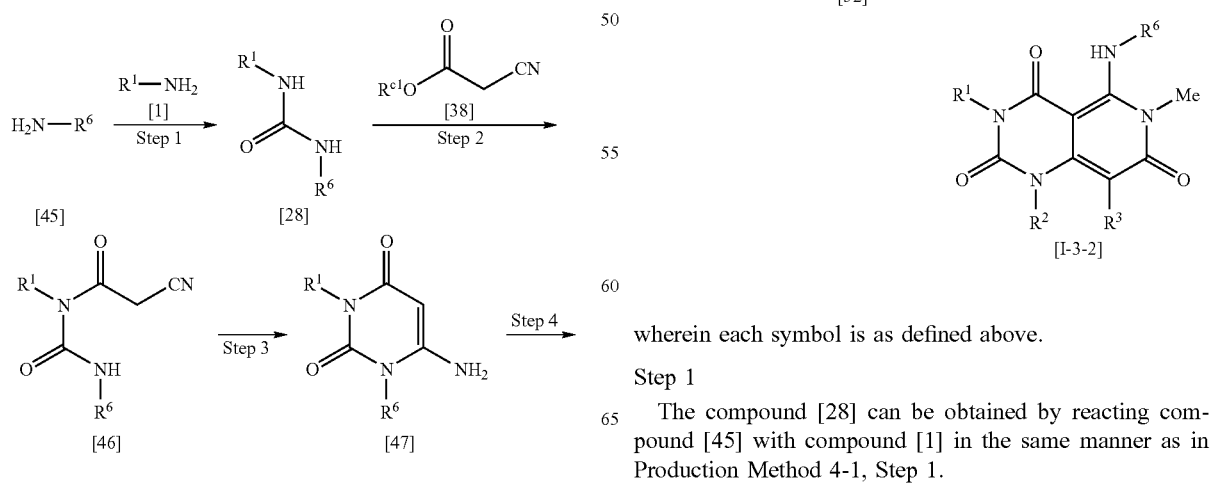

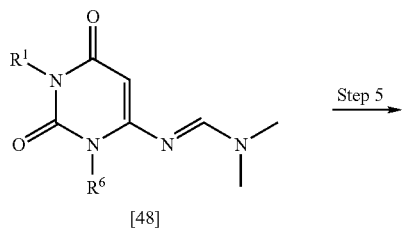

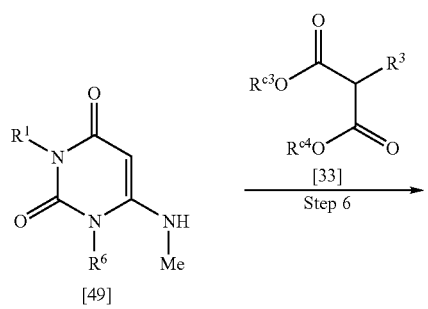

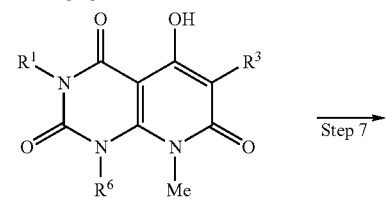

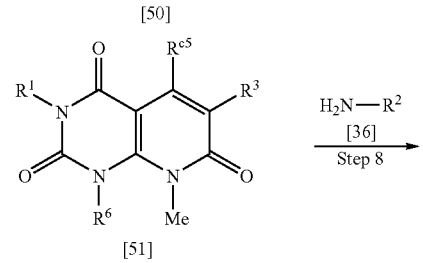

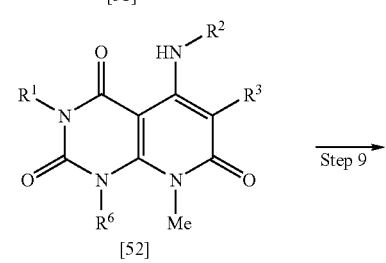

wherein each symbol is as defined above.

Step 1

The compound [28] can be obtained by reacting compound [45] with compound [1] in the same manner as in Production Method 4-1, Step 1.

Step 2

The compound [46] can be obtained by reacting compound [28] with compound [38] in the same manner as in Production Method 4-1, Step 2.

Step 3

The compound [47] can be obtained by reacting compound [46] in the same manner as in Production Method 4-1, Step 3.

Step 4

The compound [48] can be obtained by reacting compound [47] in the same manner as in Production Method 4-1, Step 4.

Step 5

The compound [49] can be obtained by reacting compound [48] in the same manner as in Production Method 4-1, Step 5.

Step 6

The compound [50] can be obtained by reacting compound [49] with compound [33] in the same manner as in Production Method 1, Step 5.

Step 7

The compound [51] can be obtained by reacting compound [50] in the same manner as in Production Method 1, Step 6.

Step 8

The compound [52] can be obtained by reacting compound [51] with compound [36] in the same manner as in Production Method 1, Step 7.

Step 9

The compound [I-3-2] can be obtained by reacting compound [52] in the same manner as in Production Method 3, Step 8.

Production Method 4-3

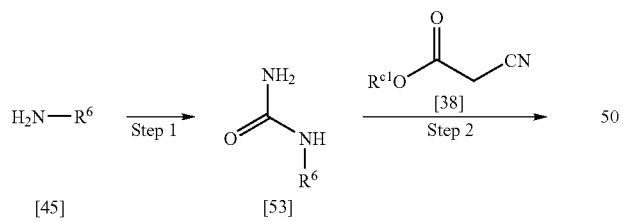

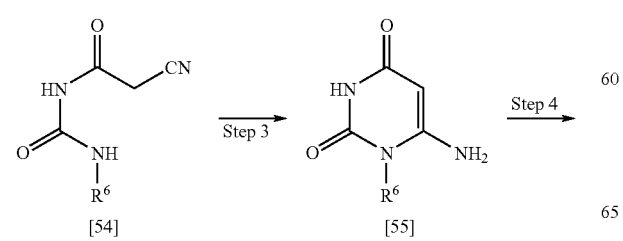

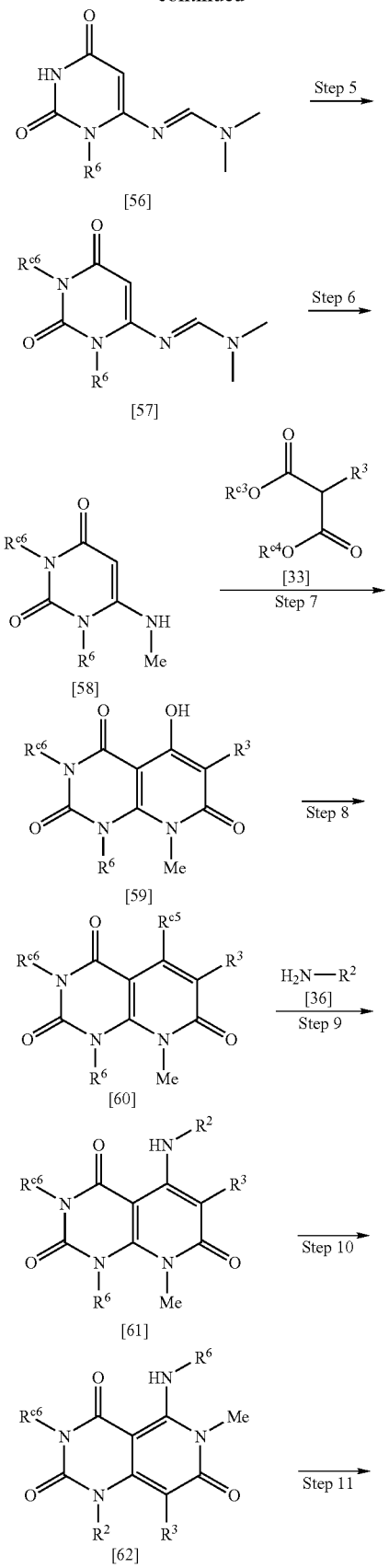

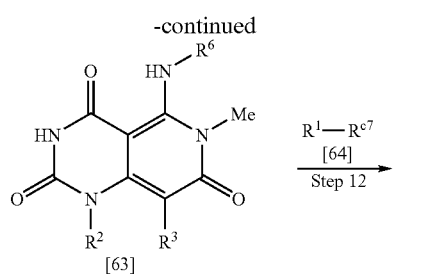

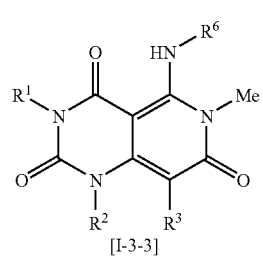

wherein $R^{c7}$ is a halogen atom such as bromine atom, chlorine atom and the like or a hydroxyl group and the other symbols are as defined above.

Step 1

The compound [53] can be obtained by reacting compound [45] with carbonyldiimidazole in a solvent in the presence of tertiary amine such as triethylamine and the like under a nitrogen or argon atmosphere from cooling to room temperature, and then reacting with ammonia.

As the solvent, N,N-dimethylformamide, chloroform, dichloromethane, tetrahydrofuran and the like can be mentioned.

Step 2

The compound [54] can be obtained by reacting compound [53] with compound [38] in the same manner as in Production Method 4-1, Step 2.

Step 3

The compound [55] can be obtained by reacting compound [54] in the same manner as in Production Method 4-1, Step 3.

Step 4

The compound [56] can be obtained by reacting compound [55] in the same manner as in Production Method 4-1, Step 4.

Step 5

The compound [57] can be obtained by introducing a protecting group into compound [56] by a conventional method.

Step 6

The compound [58] can be obtained by reacting compound [57] in the same manner as in Production Method 4-1, Step 5.

Step 7

The compound [59] can be obtained by reacting compound [58] with compound [33] in the same manner as in Production Method 1, Step 5.

Step 8

The compound [60] can be obtained by reacting compound [59] in the same manner as in Production Method 1, Step 6.

Step 9

The compound [61] can be obtained by reacting compound [60] with compound [36] in the same manner as in Production Method 1, Step 7.

Step 10

The compound [62] can be obtained by reacting compound [61] in the same manner as in Production Method 3, Step 8.

Step 11

The compound [63] can be obtained by deprotecting compound [62] by a conventional method.

Step 12

The compound [I-3-3] can be obtained by reacting compound [63] with compound [64] by a conventional method.

For example, when $R^{c7}$ is a hydroxyl group, compound [63] is reacted with a condensing agent such as diethyl azodicarboxylate, diisopropyl azodicarboxylate and the like and triphenylphosphine in a solvent such as N,N-dimethylformamide, acetonitrile, tetrahydrofuran and the like under a nitrogen or argon atmosphere according to Mitsunobu reaction.

EXAMPLES

Example 1-1

Synthesis of N-{3-[5-(4-bromo-2-fluoro-phenylamino)-3-cyclopropyl-8-methyl-2,4,7-trioxo-3,4,7,8-tetrahydro-2H-pyrido[2,3-d]pyrimidin-1-yl]phenyl}-methanesulfonamide Step 1 Synthesis of 1-cyclopropyl-3-(nitrophenyl)urea

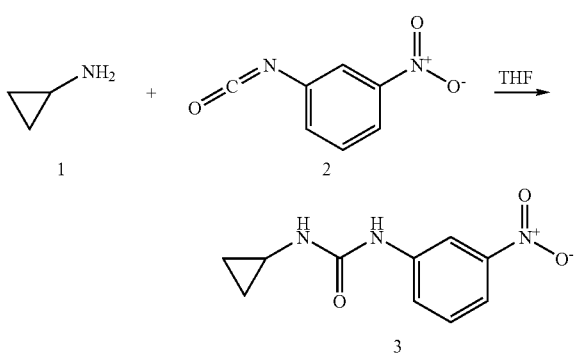

To a solution of cyclopropylamine 1 (9 g) in tetrahydrofuran (250 ml) was added 3-nitrophenylisocyanate 2 (25 g) by small portions, and the mixture was stirred at room temperature for 1 hr. The solid precipitated from the reaction mixture was filtered by suction, washed with ethyl acetate, and dried to give 1-cyclopropyl-3-(nitrophenyl)urea 3 (33 g, 99%) as a yellow solid.

Step 2 Synthesis of 1-cyclopropyl-3-(3-nitrophenyl)pyrimidine-2,4,6-trione

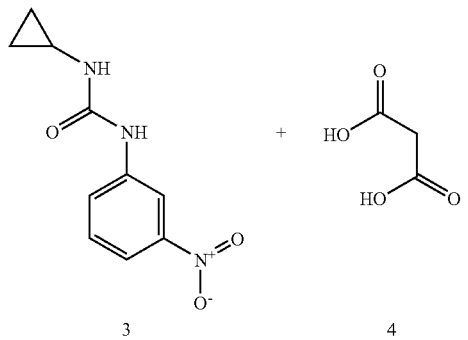

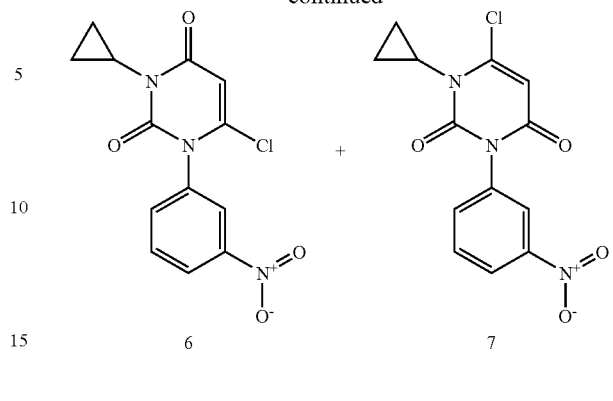

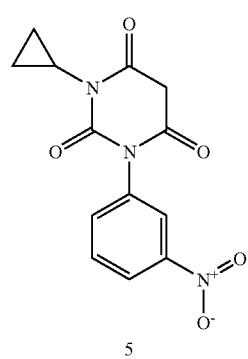

To 1-cyclopropyl-3-(nitrophenyl)urea 3 (33 g) obtained in Step 1 were added acetic anhydride (99 ml) and malonic acid 4 (17 g), and the mixture was stirred under heating at 110° C. for 4 hrs. The reaction mixture was concentrated under reduced pressure. Chloroform was added to the residue, and the mixture was stirred at room temperature for 10 min. Chloroform insoluble material was filtered by suction and dried to give 1-cyclopropyl-3-(3-nitrophenyl)pyrimidine-2,4,6-trione 5 (28 g, 65%) as a brown solid.

Step 3 Synthesis of 6-chloro-3-cyclopropyl-1-(3-nitrophenyl)-1H-pyrimidine-2,4-dione

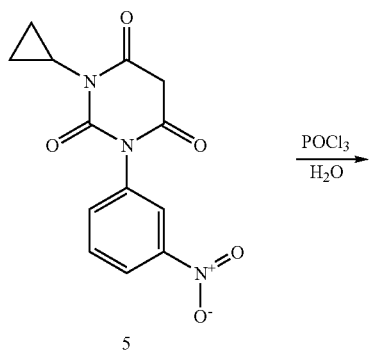

To 1-cyclopropyl-3-(3-nitrophenyl)pyrimidine-2,4,6-trione 5 (28 g) obtained in Step 2 was added water (3 ml), phosphorus oxychloride (72 ml) was added dropwise by small portions with stirring, and the mixture was stirred with heating at 110° C. for 1 hr. The reaction mixture was poured into ice water by small portions, and the precipitated solid was filtered by suction. The filtrate was dissolved in chloroform (300 ml), washed with water (30 ml) and brine (30 ml), and the organic layer was dried over anhydrous magnesium sulfate, and concentrated under reduced pressure. The residue was purified by column chromatography (chloroform:acetone=9:1) to give a 2:1 mixture (10 g, 34%) of 6-chloro-3-cyclopropyl-1-(3-nitrophenyl)-1H-pyrimidine-2,4-dione 6 and 4-chloro-3-cyclopropyl-1-(3-nitrophenyl)-1H-pyrimidine-2,6-dione 7 as a white solid.

Step 4 Synthesis of 3-cyclopropyl-6-methylamino-1-(3-nitrophenyl)-1H-pyrimidine-2,4-dione

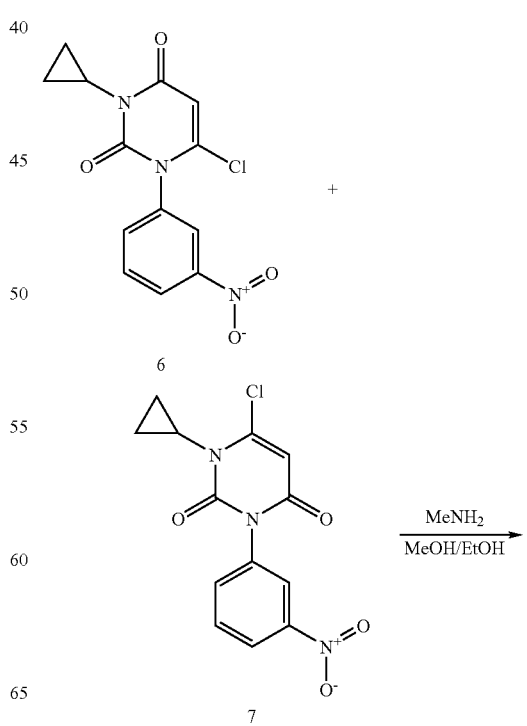

-continued

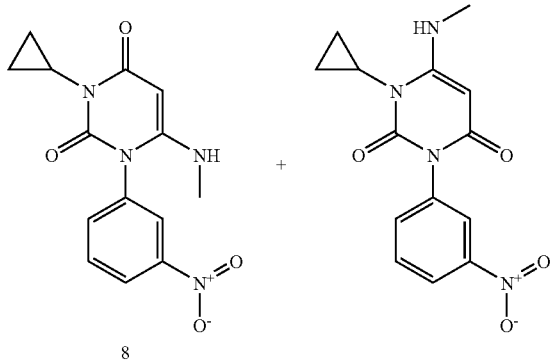

8

To the mixture (30 g) of 6-chloro-3-cyclopropyl-1-(3-nitrophenyl)-1H-pyrimidine-2,4-dione 6 and 4-chloro-3-cyclopropyl-1-(3-nitrophenyl)-1H-pyrimidine-2,6-dione 7 obtained in Step 3 were added ethanol (300 ml) and a 40% solution (150 ml) of methylamine in methanol, and the mixture was stirred with heating at 80° C. for 4.5 hrs, ice-cooled and the precipitated solid was filtered by suction. The residue was washed with water (1 liter) and dried to give 3-cyclopropyl-6-methylamino-1-(3-nitrophenyl)-1H-pyrimidine-2,4-dione 8 (16 g, 55%) as a white solid.

Step 5 Synthesis of 3-cyclopropyl-5-hydroxy-8-methyl-1-(3-nitrophenyl)-1H,8H-pyrido[2,3-d]pyrimidine-2,4,7-trione

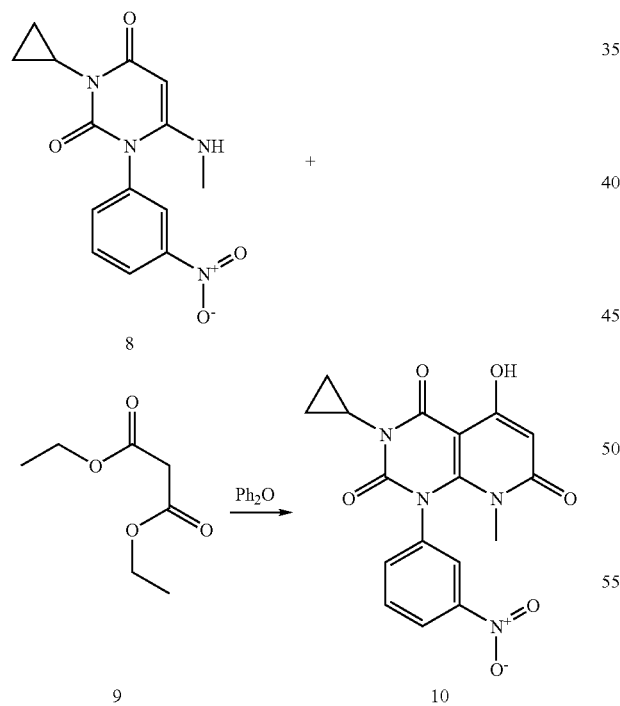

To 3-cyclopropyl-6-methylamino-1-(3-nitrophenyl)-1H-pyrimidine-2,4-dione 8 (16 g) obtained in Step 4 were added diphenyl ether (160 ml) and diethyl malonate 9 (40 ml), and the mixture was stirred under heating at 230° C. for 11 hrs while evaporating the resulting ethanol. The reaction mixture was purified by column chromatography (chloroform→chloroform:acetone=9:1) to give 3-cyclopropyl-5-hydroxy-8-methyl-1-(3-nitrophenyl)-1H,8H-pyrido[2,3-d]pyrimidine-2,4,7-trione 10 (10 g, 51%) as a brown foamy oil.

Step 6 Synthesis of toluene-4-sulfonic acid 3-cyclopropyl-8-methyl-1-(3-nitrophenyl)-2,4,7-trioxo-1,2,3,4,7,8-hexahydropyrido[2,3-d]pyrimidin-5-yl ester

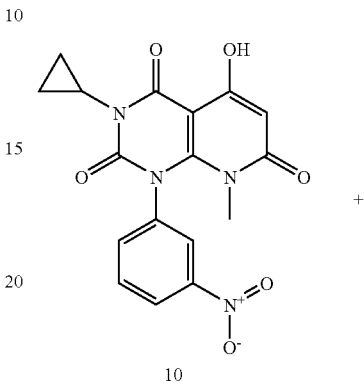

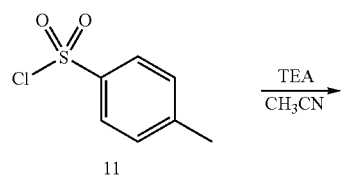

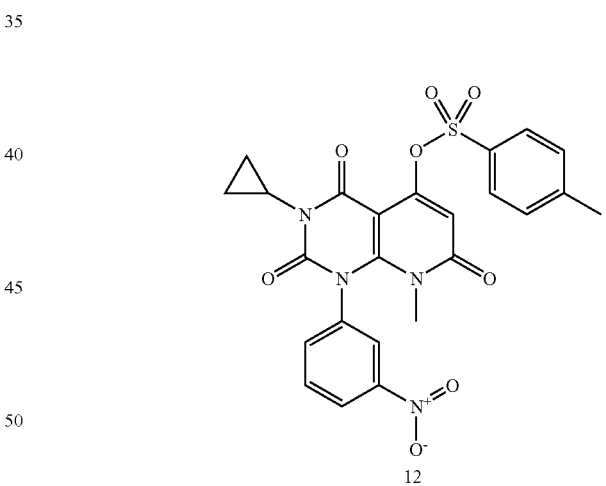

To 3-cyclopropyl-5-hydroxy-8-methyl-1-(3-nitrophenyl)-1H,8H-pyrido[2,3-d]pyrimidine-2,4,7-trione 10 (18 g) obtained in Step 5 were added acetonitrile (180 ml), tosyl chloride 11 (11 g) and triethylamine (8 ml), and the mixture was stirred with heating under reflux at 110° C. for 1 hr. The reaction mixture was concentrated under reduced pressure. Water (100 ml) was added to the residue and the mixture was extracted with chloroform (800 ml). The organic layer was washed with brine (50 ml), dried over anhydrous magnesium sulfate, and concentrated under reduced pressure. The residue was recrystallized from chloroform:diethyl ether=1:5 to give toluene-4-sulfonic acid 3-cyclopropyl-8- methyl-1-(3-nitrophenyl)-2,4,7-trioxo-1,2,3,4,7,8-hexahydro-pyrido[2,3-d]pyrimidin-5-yl ester 12 (21 g, 82%) as a white solid.

Step 7 Synthesis of toluene-4-sulfonic acid 1-(3-aminophenyl)-3-cyclopropyl-8-methyl-2,4,7-trioxo-1,2,3,4,7,8-hexahydro-pyrido[2,3-d]pyrimidin-5-yl ester

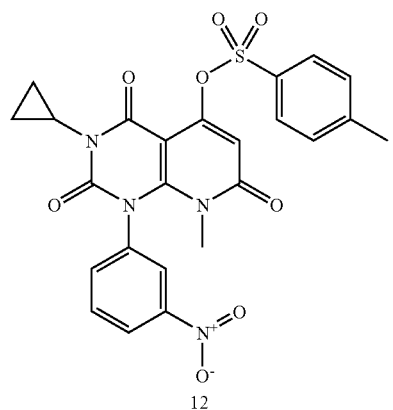

Step 8 Synthesis of toluene-4-sulfonic acid 3-cyclopropyl-1-(3-methanesulfonylaminophenyl)-8-methyl-2,4,7-trioxo-1,2,3,4,7,8-hexahydro-pyrido[2,3-d]pyrimidin-5-yl ester To a suspension of toluene-4-sulfonic acid 3-cyclopropyl-8-methyl-1-(3-nitrophenyl)-2,4,7-trioxo-1,2,3,4,7,8-hexahydro-pyrido[2,3-d]pyrimidin-5-yl ester 12 (21 g) obtained in Step 6 in tetrahydrofuran was added stannous chloride dihydrate (45 g), and the mixture was stirred at room temperature for 4 hrs. The reaction mixture was alkalified with saturated aqueous sodium hydrogen carbonate, an insoluble inorganic product was filtered off by suction using celite as a filtration aides, and the filtrate was extracted with ethyl acetate. The organic layer was washed with brine, dried over anhydrous magnesium sulfate and concentrated under reduced pressure. The residue was purified by column chromatography (chloroform:acetone=9:1) to give toluene-4-sulfonic acid 1-(3-aminophenyl)-3-cyclopropyl-8-methyl-2,4,7-trioxo-1,2,3,4,7,8-hexahydro-pyrido[2,3-d]pyrimidin-5-yl ester 13 (15 g, 74%) as a white solid.

To toluene-4-sulfonic acid 1-(3-aminophenyl)-3-cyclopropyl-8-methyl-2,4,7-trioxo-1,2,3,4,7,8-hexahydro-pyrido[2,3-d]pyrimidin-5-yl ester 13 (5 g) obtained in Step 7 was added pyridine (40 ml), a solution of methanesulfonyl chloride 14 (0.9 ml) in chloroform (10 ml) was added dropwise with stirring under ice-cooling, and the mixture was stirred for 3 hrs in an ice bath. The reaction mixture was concentrated under reduced pressure, 2N hydrochloric acid was added and the mixture was extracted with chloroform. The organic layer was washed with brine, dried over anhydrous magnesium sulfate and concentrated under reduced pressure. The resultant solid was suspended in diethyl ether:hexane=1:1, and filtered by suction to give toluene-4-sulfonic acid 3-cyclopropyl-1-(3-methanesulfonylaminophenyl)-8-methyl-2,4,7-trioxo-1,2,3,4,7,8-hexahydro-pyrido[2,3-d]pyrimidin-5-yl ester 15 (5.5 g, 95%) as a white solid.-

Step 9 Synthesis of N-{3-[5-(4-bromo-2-fluoro-phenylamino)-3-cyclopropyl-8-methyl-2,4,7-trioxo-3,4,7,8-tetrahydro-2H-pyrido[2,3-d]pyrimidin-1-yl]phenyl}-methanesulfonamide

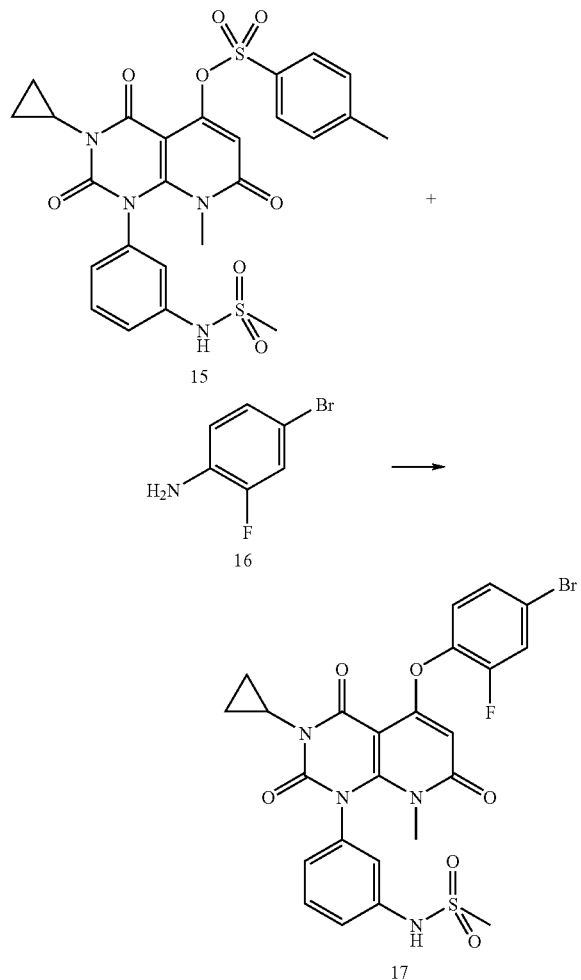

To toluene-4-sulfonic acid 3-cyclopropyl-1-(3-methanesulfonylaminophenyl)-8-methyl-2,4,7-trioxo-1,2,3,4,7,8-hexahydropyrido[2,3-d]pyrimidin-5-yl ester 15 (3.5 g) obtained in Step 8 was added 2-fluoro-4-bromoaniline 16 (23 g), and the mixture was stirred under heating at 135° C. for 3 hrs. The reaction mixture was purified by column chromatography (chloroform:acetone=9:1) to give N-{3-[5-(4-bromo-2-fluoro-phenylamino)-3-cyclopropyl-8-methyl-2,4,7-trioxo-3,4,7,8-tetrahydro-2H-pyrido[2,3-d]pyrimidin-1-yl]phenyl}-methanesulfonamide 17 (3.0 g, 83%) as a white solid.

MS ESI m/e: 590, 592 (M+H), 588, 590 (M−H).

$^1$H-NMR (DMSO-$d_6$, 300 MHz) δ 0.71-0.79 (m, 2H), 0.99-1.08 (m, 2H), 2.66 (s, 1H), 3.02 (s, 1H), 5.36 (s, 1H), 7.13 (d, J=9.0 Hz, 1H), 7.24-7.30 (m, 2H), 7.43-7.54 (m, 3H), 7.74 (d, J=9.0 Hz, 1H), 10.00 (brs, 1H), 10.53 (brs, 1H).

Examples 1-2 to 1-343

In the same manner as in Example 1-1, the compounds of Examples 1-2 to 1-343 were obtained. The structural formulas thereof are shown in Tables 1-1 to 1-58 with Example 1-1.

TABLE 1-1

| Ex. No. | structural formula |
|---|---|
| 1-1 | |
| 1-2 | |
| 1-3 | |
| 1-4 | |

TABLE 1-1-continued

| Ex. No. | structural formula |
|---|---|
| 1-5 | 3-chlorophenylamino pyrido[2,3-d]pyrimidine-2,4,7-trione, 1,3-diphenyl-8-methyl |
| 1-6 | 4-methylphenylamino pyrido[2,3-d]pyrimidine-2,4,7-trione, 1,3-diphenyl-8-methyl |

TABLE 1-2

| Ex. No. | structural formula |
|---|---|
| 1-7 | 4-(dimethylamino)phenylamino pyrido[2,3-d]pyrimidine-2,4,7-trione, 1,3-diphenyl-8-methyl |

TABLE 1-2-continued

| Ex. No. | structural formula |
|---|---|
| 1-8 | 4-fluorophenylamino pyrido[2,3-d]pyrimidine-2,4,7-trione, 1,3-diphenyl-8-methyl |
| 1-9 | 4-methoxyphenylamino pyrido[2,3-d]pyrimidine-2,4,7-trione, 1,3-diphenyl-8-methyl |
| 1-10 | 4-chlorobenzylamino pyrido[2,3-d]pyrimidine-2,4,7-trione, 1,3-diphenyl-8-methyl |
| 1-11 | 4-bromophenylamino pyrido[2,3-d]pyrimidine-2,4,7-trione, 1,3-diphenyl-8-methyl |

TABLE 1-2-continued

| Ex. No. | structural formula |
|---|---|
| 1-12 | (structure) |

TABLE 1-3

| Ex. No. | structural formula |
|---|---|
| 1-13 | (structure) |
| 1-14 | (structure) |
| 1-15 | (structure) |

TABLE 1-3-continued

| Ex. No. | structural formula |
|---|---|
| 1-16 | (structure) |
| 1-17 | (structure) |
| 1-18 | (structure) |

TABLE 1-4

| Ex. No. | structural formula |
|---|---|
| 1-19 | (structure) |
| 1-20 | (structure) |
| 1-21 | (structure) |
| 1-22 | (structure) |
| 1-23 | (structure) |
| 1-24 | (structure) |

TABLE 1-5

| Ex. No. | structural formula |
|---|---|
| 1-25 | (structure) |

TABLE 1-5-continued

| Ex. No. | structural formula |
|---|---|
| 1-26 | (structure: 5-(2,4-dichlorophenylamino)-1,3-diphenyl-8-methylpyrido[2,3-d]pyrimidine-2,4,7-trione) |
| 1-27 | (structure: 5-[4-(piperidin-1-yl)phenylamino]-1,3-diphenyl-8-methylpyrido[2,3-d]pyrimidine-2,4,7-trione) |
| 1-28 | (structure: 5-[4-(diethylamino)phenylamino]-1,3-diphenyl-8-methylpyrido[2,3-d]pyrimidine-2,4,7-trione) |
| 1-29 | (structure: 5-(4-benzylphenylamino)-1,3-diphenyl-8-methylpyrido[2,3-d]pyrimidine-2,4,7-trione) |

TABLE 1-5-continued

| Ex. No. | structural formula |
|---|---|
| 1-30 | (structure: 5-[4-(morpholin-4-yl)phenylamino]-1,3-diphenyl-8-methylpyrido[2,3-d]pyrimidine-2,4,7-trione) |

TABLE 1-6

| Ex. No. | structural formula |
|---|---|
| 1-31 | (structure: 5-(4-butylphenylamino)-1,3-diphenyl-8-methylpyrido[2,3-d]pyrimidine-2,4,7-trione) |
| 1-32 | (structure: 5-(4-chlorophenylamino)-3-phenyl-1,8-dimethylpyrido[2,3-d]pyrimidine-2,4,7-trione) |

TABLE 1-6-continued

| Ex. No. | structural formula |
|---|---|
| 1-33 | (structure) |
| 1-34 | (structure) |
| 1-35 | (structure) |
| 1-36 | (structure) |

TABLE 1-7

| Ex. No. | structural formula |
|---|---|
| 1-37 | (structure) |
| 1-38 | (structure) |
| 1-39 | (structure) |

TABLE 1-7-continued

| Ex. No. | structural formula |
|---|---|
| 1-40 | (structure) |
| 1-41 | (structure) |
| 1-42 | (structure) |

TABLE 1-8

| Ex. No. | structural formula |
|---|---|
| 1-43 | (structure) |
| 1-44 | (structure) |
| 1-45 | (structure) |
| 1-46 | (structure) · HCl |

TABLE 1-8-continued

| Ex. No. | structural formula |
|---|---|
| 1-47 | |
| 1-48 | |

TABLE 1-9

| Ex. No. | structural formula |
|---|---|
| 1-49 | |

TABLE 1-9-continued

| Ex. No. | structural formula |
|---|---|
| 1-50 | |
| 1-51 | |
| 1-52 | |
| 1-53 | |

TABLE 1-9-continued

| Ex. No. | structural formula |
|---|---|
| 1-54 | |

TABLE 1-10

| Ex. No. | structural formula |
|---|---|
| 1-55 | |
| 1-56 | |

TABLE 1-10-continued

| Ex. No. | structural formula |
|---|---|
| 1-57 | |
| 1-58 | |
| 1-59 | |
| 1-60 | |

TABLE 1-11
| Ex. No. | structural formula |
|---|---|
| 1-61 | 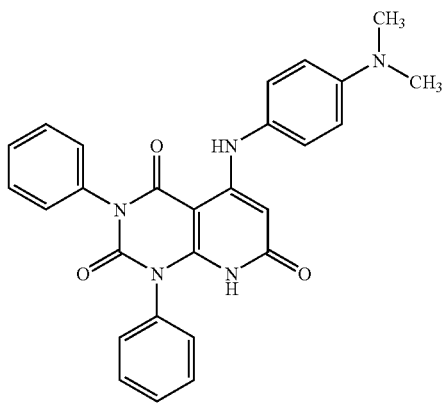 |
| 1-62 | 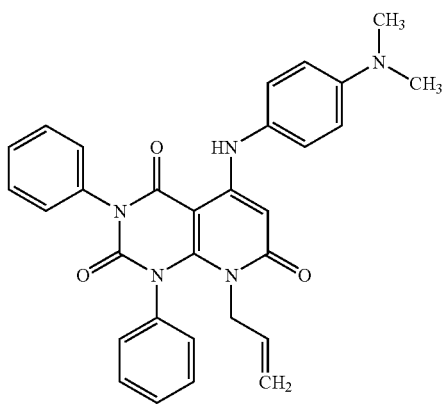 |
| 1-63 | 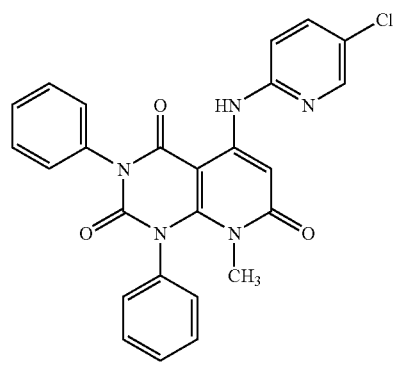 |
TABLE 1-11-continued
| Ex. No. | structural formula |
|---|---|
| 1-64 | 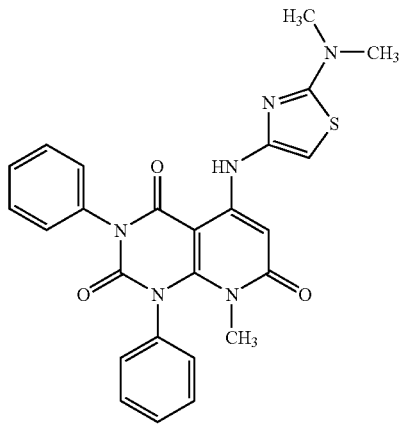 |
| 1-65 | 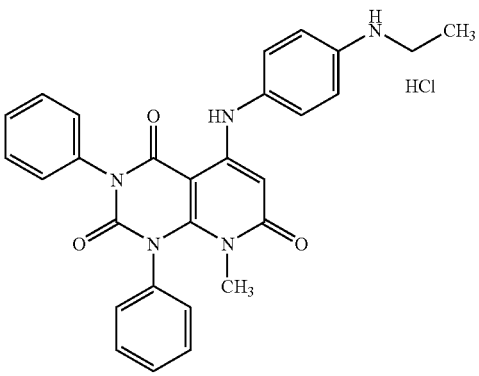 |
| 1-66 | 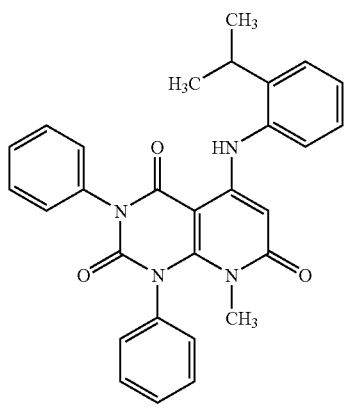 |

TABLE 1-12

| Ex. No. | structural formula |
|---|---|
| 1-67 | (structure) |
| 1-68 | (structure) |
| 1-69 | (structure) |
| 1-70 | (structure) |

TABLE 1-12-continued

| Ex. No. | structural formula |
|---|---|
| 1-71 | (structure) |
| 1-72 | (structure) |

TABLE 1-13

| Ex. No. | structural formula |
|---|---|
| 1-73 | (structure) |

TABLE 1-13-continued
| Ex. No. | structural formula |
|---|---|
| 1-74 | 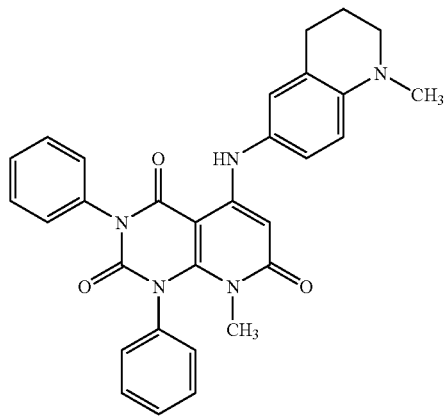 |
| 1-75 | 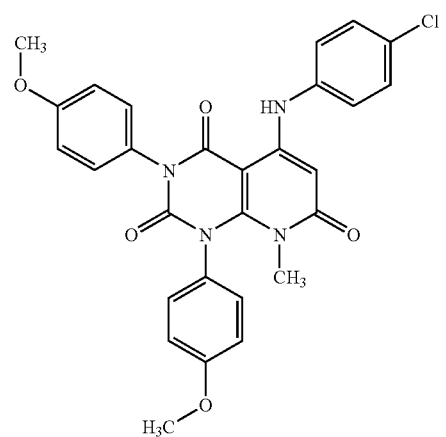 |
| 1-76 | 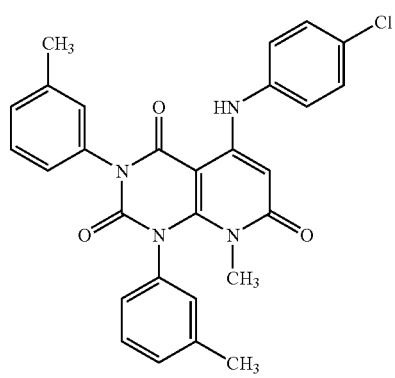 |
TABLE 1-13-continued
| Ex. No. | structural formula |
|---|---|
| 1-77 | 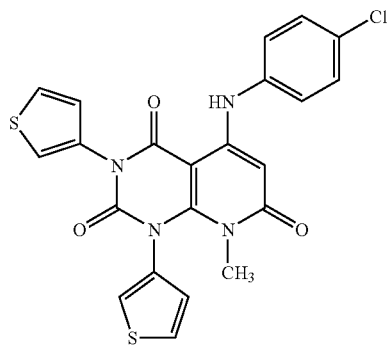 |
| 1-78 | 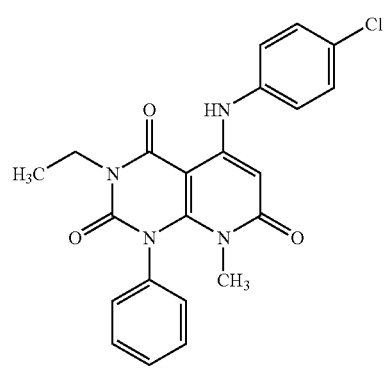 |
TABLE 1-14
| Ex. No. | structural formula |
|---|---|
| 1-79 | 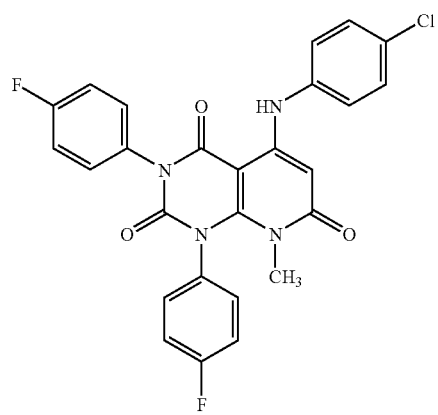 |

TABLE 1-14-continued

| Ex. No. | structural formula |
|---|---|
| 1-80 | (cyclopentyl-N, phenyl-N, methyl-N, 5-(4-chlorophenylamino) pyrido[2,3-d]pyrimidine-2,4,7-trione) |
| 1-81 | (isopropyl-N, phenyl-N, methyl-N, 5-(4-chlorophenylamino) pyrido[2,3-d]pyrimidine-2,4,7-trione) |
| 1-82 | (n-propyl-N, phenyl-N, methyl-N, 5-(4-chlorophenylamino) pyrido[2,3-d]pyrimidine-2,4,7-trione) |
| 1-83 | (n-butyl-N, phenyl-N, methyl-N, 5-(4-chlorophenylamino) pyrido[2,3-d]pyrimidine-2,4,7-trione) |

TABLE 1-14-continued

| Ex. No. | structural formula |
|---|---|
| 1-84 | (cyclopropyl-N, phenyl-N, methyl-N, 5-(4-chlorophenylamino) pyrido[2,3-d]pyrimidine-2,4,7-trione) |

TABLE 1-15

| Ex. No. | structural formula |
|---|---|
| 1-85 | (methyl-N, 2-methylphenyl-N, methyl-N, 5-(4-chlorophenylamino) pyrido[2,3-d]pyrimidine-2,4,7-trione) |
| 1-86 | (methyl-N, 3-methylphenyl-N, methyl-N, 5-(4-chlorophenylamino) pyrido[2,3-d]pyrimidine-2,4,7-trione) |

TABLE 1-15-continued

| Ex. No. | structural formula |
|---|---|
| 1-87 | (structure) |
| 1-88 | (structure) |
| 1-89 | (structure) |
| 1-90 | (structure) |

TABLE 1-16

| Ex. No. | structural formula |
|---|---|
| 1-91 | (structure) |
| 1-92 | (structure) |
| 1-93 | (structure) |
| 1-94 | (structure) |

TABLE 1-16-continued

| Ex. No. | structural formula |
|---|---|
| 1-95 | |
| 1-96 | |

TABLE 1-17

| Ex. No. | structural formula |
|---|---|
| 1-97 | |

TABLE 1-17-continued

| Ex. No. | structural formula |
|---|---|
| 1-98 | |
| 1-99 | |
| 1-100 | |
| 1-101 | |

TABLE 1-17-continued

| Ex. No. | structural formula |
|---|---|
| 1-102 | |

TABLE 1-18

| Ex. No. | structural formula |
|---|---|
| 1-103 | |
| 1-104 | |

TABLE 1-18-continued

| Ex. No. | structural formula |
|---|---|
| 1-105 | |
| 1-106 | |
| 1-107 | |
| 1-108 | |

TABLE 1-19
| Ex. No. | structural formula |
|---|---|
| 1-109 | 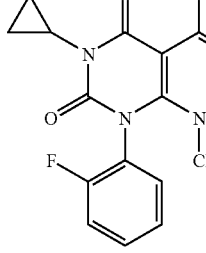 |
| 1-110 | |
| 1-111 | |
| 1-112 | |
TABLE 1-19-continued
| Ex. No. | structural formula |
|---|---|
| 1-113 | 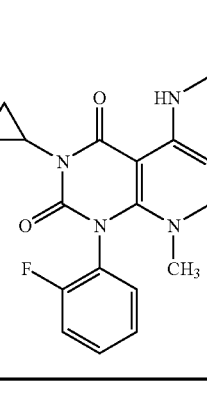 |
| 1-114 | |
TABLE 1-20
| Ex. No. | structural formula |
|---|---|
| 1-115 | 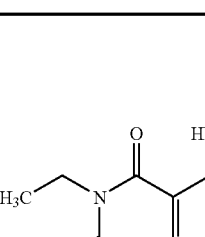 |

TABLE 1-20-continued
| Ex. No. | structural formula |
|---|---|
| 1-116 | 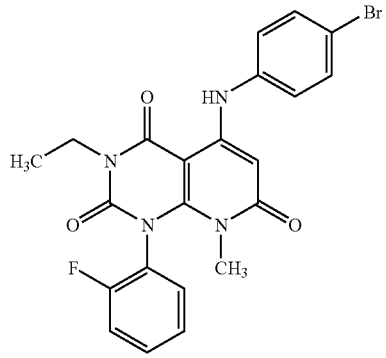 |
| 1-117 | 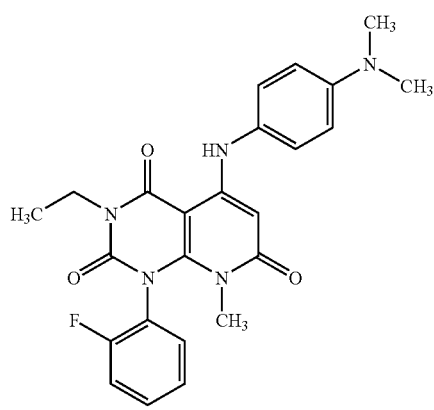 |
| 1-118 | 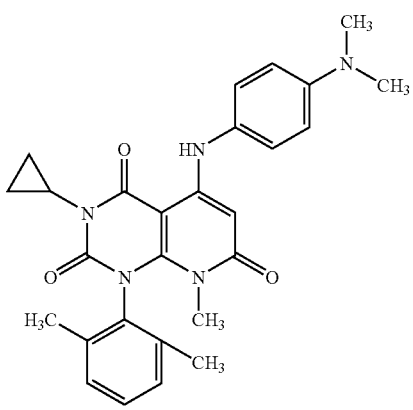 |
TABLE 1-20-continued
| Ex. No. | structural formula |
|---|---|
| 1-119 | 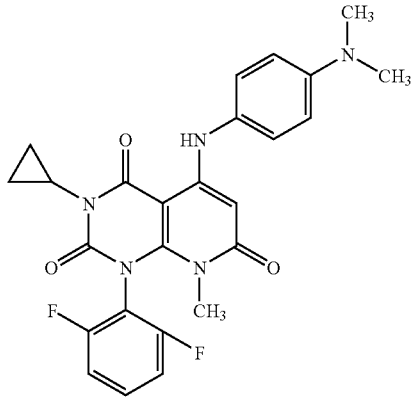 |
| 1-120 | 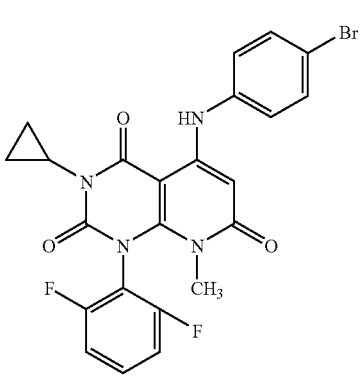 |
TABLE 1-21
| Ex. No. | structural formula |
|---|---|
| 1-121 | 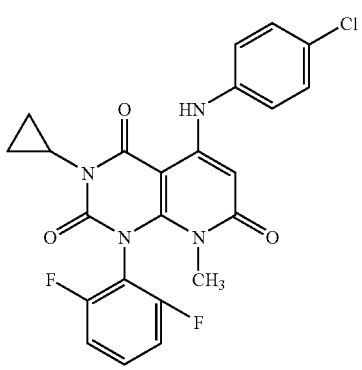 |

TABLE 1-21-continued

| Ex. No. | structural formula |
|---|---|
| 1-122 | (structure) |
| 1-123 | (structure) |
| 1-124 | (structure) |
| 1-125 | (structure) |

TABLE 1-21-continued

| Ex. No. | structural formula |
|---|---|
| 1-126 | (structure) |

TABLE 1-22

| Ex. No. | structural formula |
|---|---|
| 1-127 | (structure) |
| 1-128 | (structure) |

TABLE 1-22-continued

| Ex. No. | structural formula |
|---|---|
| 1-129 | (structure) |
| 1-130 | (structure) |
| 1-131 | (structure) |
| 1-132 | (structure) |

TABLE 1-23

| Ex. No. | structural formula |
|---|---|
| 1-133 | (structure) |
| 1-134 | (structure) |
| 1-135 | (structure) HCl |
| 1-136 | (structure) HCl |

TABLE 1-23-continued
| Ex. No. | structural formula |
|---|---|
| 1-137 | 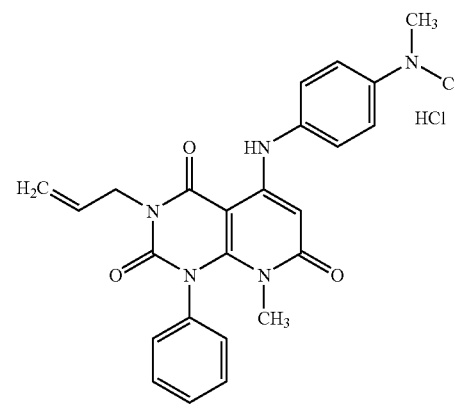 |
| 1-138 | |
TABLE 1-24
| Ex. No. | structural formula |
|---|---|
| 1-139 | |
TABLE 1-24-continued
| Ex. No. | structural formula |
|---|---|
| 1-140 | 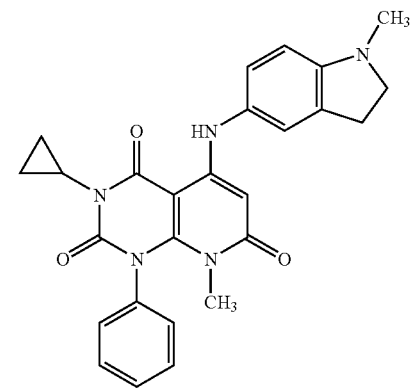 |
| 1-141 | |
| 1-142 | |

TABLE 1-24-continued
| Ex. No. | structural formula |
|---|---|
| 1-143 | 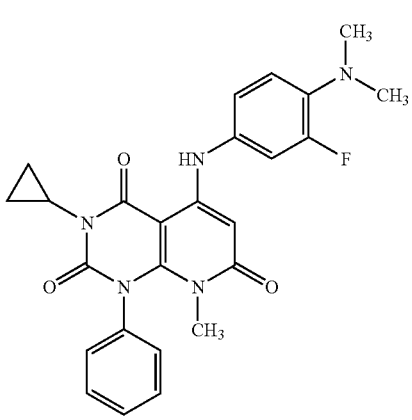 |
| 1-144 | 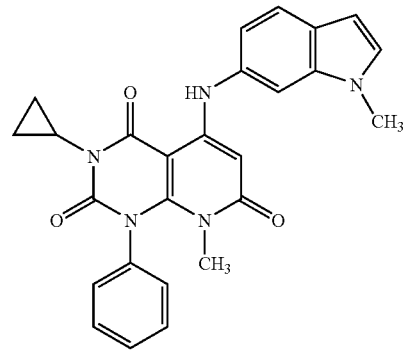 |
TABLE 1-25
| Ex. No. | structural formula |
|---|---|
| 1-145 | 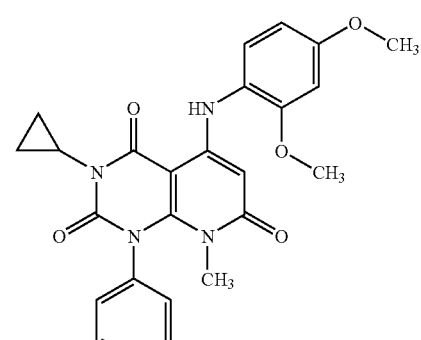 |
TABLE 1-25-continued
| Ex. No. | structural formula |
|---|---|
| 1-146 | 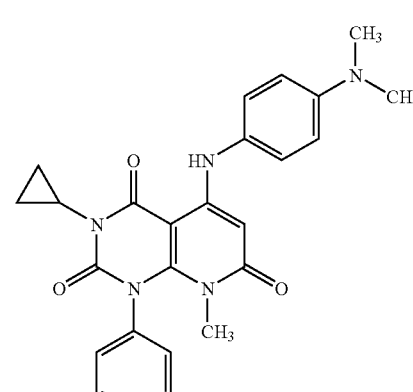 |
| 1-147 | 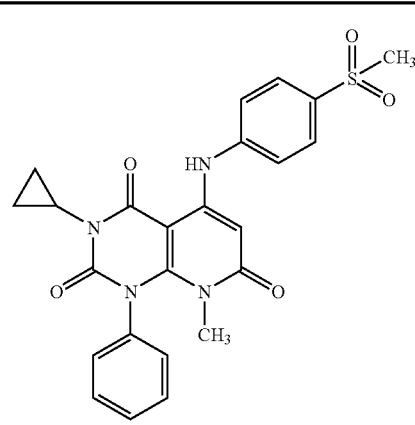 |
| 1-148 | 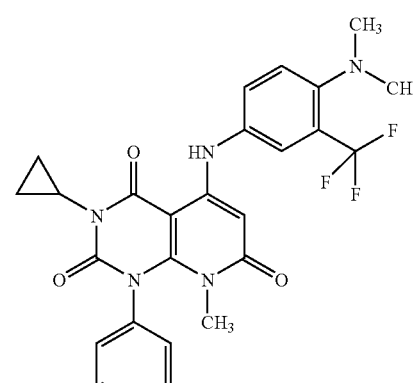 |

TABLE 1-25-continued
| Ex. No. | structural formula |
|---|---|
| 1-149 | 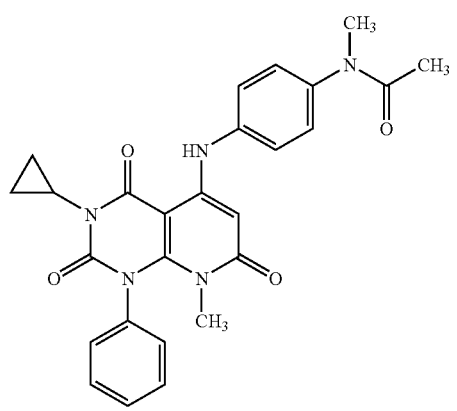 |
| 1-150 | 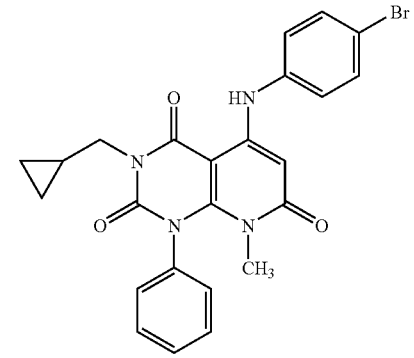 |
TABLE 1-26
| Ex No. | structural formula |
|---|---|
| 1-151 | 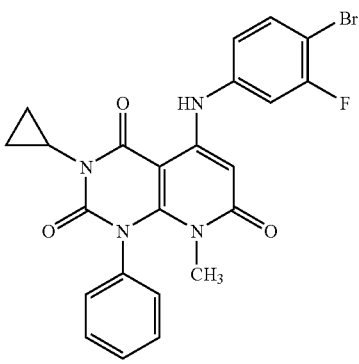 |
TABLE 1-26-continued
| Ex No. | structural formula |
|---|---|
| 1-152 | 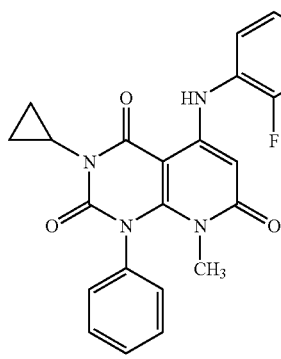 |
| 1-153 | 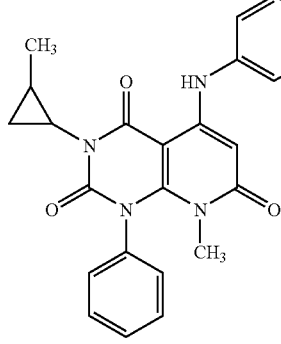 |
| 1-154 | 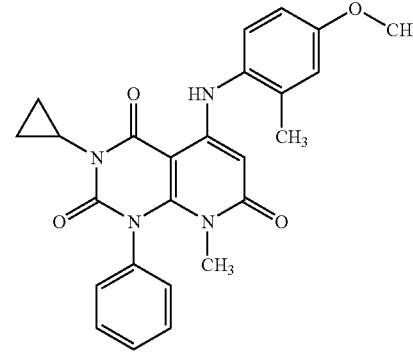 |
| 1-155 | 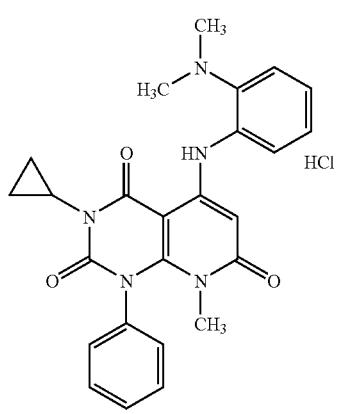 |

TABLE 1-26-continued

| Ex No. | structural formula |
|---|---|
| 1-156 | (structure) |

TABLE 1-27

| Ex. No. | structural formula |
|---|---|
| 1-157 | (structure) |
| 1-158 | (structure) |

TABLE 1-27-continued

| Ex. No. | structural formula |
|---|---|
| 1-159 | (structure) |
| 1-160 | (structure) |
| 1-161 | (structure) |
| 1-162 | (structure) |

TABLE 1-28

| Ex. No. | structural formula |
|---|---|
| 1-163 | (cyclopropyl-N, N-methyl-N-phenyl pyrido-pyrimidine-trione with 2,4-dichlorophenylamino substituent) |
| 1-164 | (3-ethyl-1-phenyl-8-methyl pyrido-pyrimidine-trione with 4-bromo-2-fluorophenylamino substituent) |
| 1-165 | (3-cyclopropyl-1-phenyl-8-methyl pyrido-pyrimidine-trione with 1H-indol-5-ylamino substituent) |
| 1-166 | (3-cyclopropyl-1-(2-methoxyphenyl)-8-methyl pyrido-pyrimidine-trione with 4-bromo-2-fluorophenylamino substituent) |

TABLE 1-28-continued

| Ex. No. | structural formula |
|---|---|
| 1-167 | (3-cyclopropyl-1-phenyl-8-methyl pyrido-pyrimidine-trione with 1-ethyl-1H-indol-5-ylamino substituent) |
| 1-168 | (3-cyclopropyl-1-phenyl-8-methyl pyrido-pyrimidine-trione with 2-fluoro-4-methylphenylamino substituent) |

TABLE 1-29

| Ex. No. | structural formula |
|---|---|
| 1-169 | (3-cyclopropyl-1-phenyl-8-methyl pyrido-pyrimidine-trione with 2-morpholinoethylamino substituent) |

TABLE 1-29-continued

| Ex. No. | structural formula |
|---|---|
| 1-170 | (structure) |
| 1-171 | (structure) |
| 1-172 | (structure) |
| 1-173 | (structure) |

TABLE 1-29-continued

| Ex. No. | structural formula |
|---|---|
| 1-174 | (structure) |

TABLE 1-30

| Ex. No. | structural formula |
|---|---|
| 1-175 | (structure) |
| 1-176 | (structure) |

TABLE 1-30-continued
| Ex. No. | structural formula |
|---|---|
| 1-177 | 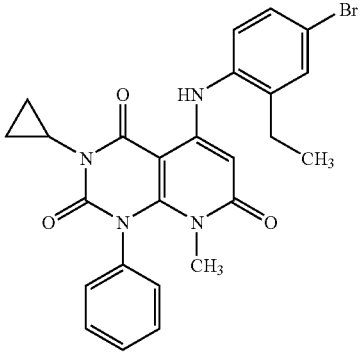 |
| 1-178 | 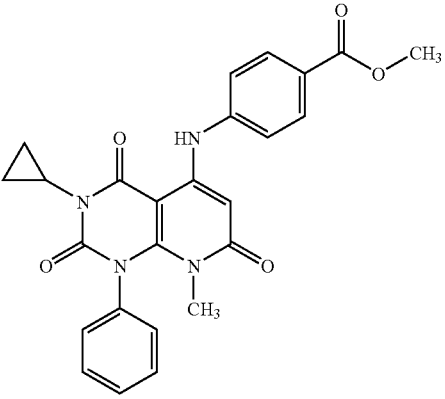 |
| 1-179 | 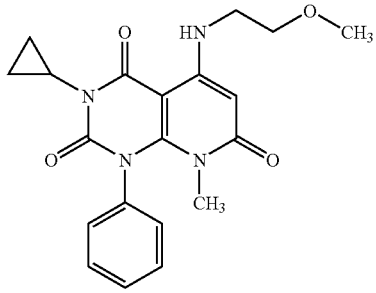 |
| 1-180 | 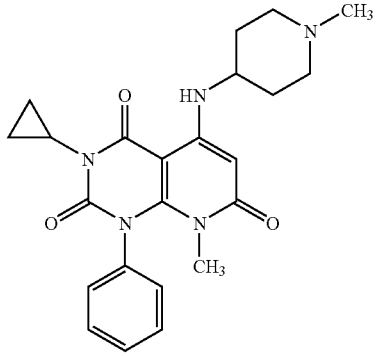 |
TABLE 1-31
| Ex. No. | structural formula |
|---|---|
| 1-181 | 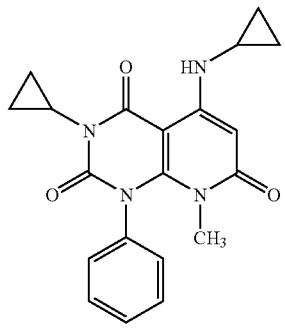 |
| 1-182 | 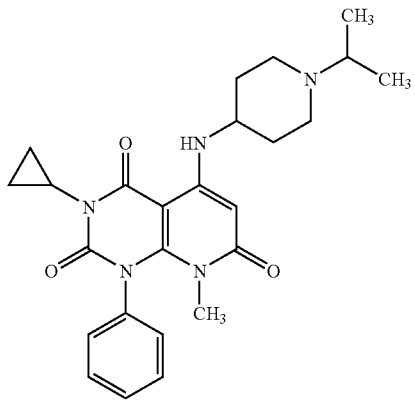 |
| 1-183 | 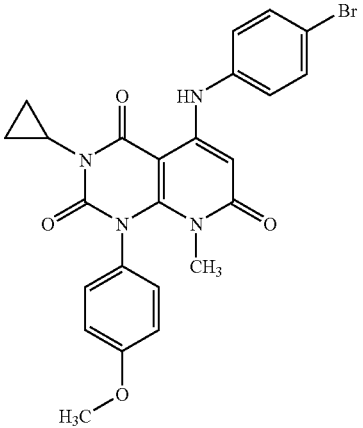 |
| 1-184 | 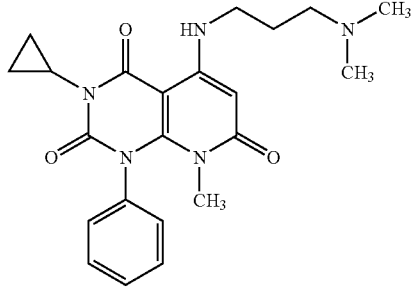 |

TABLE 1-31-continued

| Ex. No. | structural formula |
|---|---|
| 1-185 | |
| 1-186 | |

TABLE 1-32

| Ex. No. | structural formula |
|---|---|
| 1-187 | |

TABLE 1-32-continued

| Ex. No. | structural formula |
|---|---|
| 1-188 | |
| 1-189 | |
| 1-190 | |
| 1-191 | |

TABLE 1-32-continued

| Ex. No. | structural formula |
|---|---|
| 1-192 | (structure) |

TABLE 1-33

| Ex. No. | structural formula |
|---|---|
| 1-193 | (structure) |
| 1-194 | (structure) |

TABLE 1-33-continued

| Ex. No. | structural formula |
|---|---|
| 1-195 | (structure) |
| 1-196 | (structure) |
| 1-197 | (structure) |
| 1-198 | (structure) |

TABLE 1-34
| Ex. No. | structural formula |
|---|---|
| 1-199 | 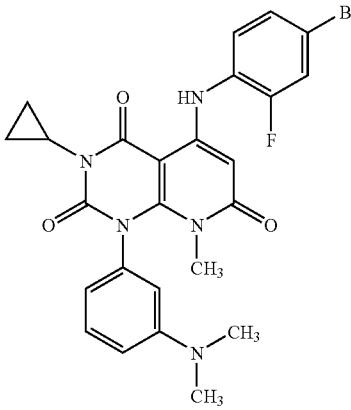 |
| 1-200 | 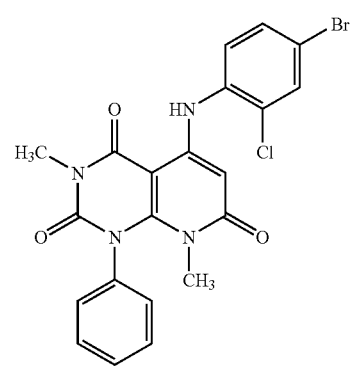 |
| 1-201 | 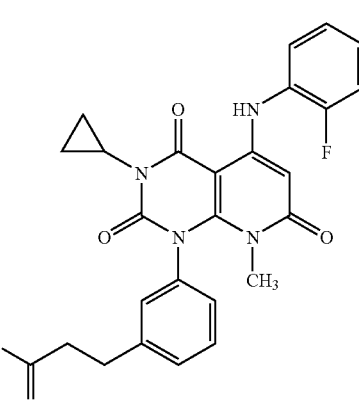 |
| 1-202 | 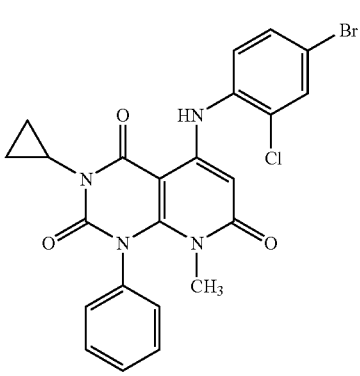 |
TABLE 1-34-continued
| Ex. No. | structural formula |
|---|---|
| 1-203 | 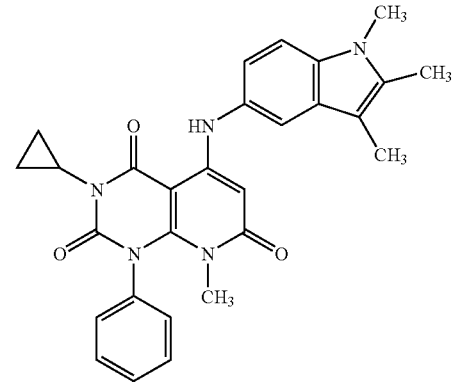 |
| 1-204 | 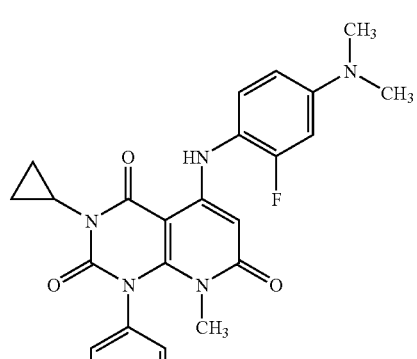 |
TABLE 1-35
| Ex. No. | structural formula |
|---|---|
| 1-205 | 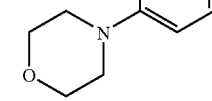 |

TABLE 1-35-continued
| Ex. No. | structural formula |
|---|---|
| 1-206 | 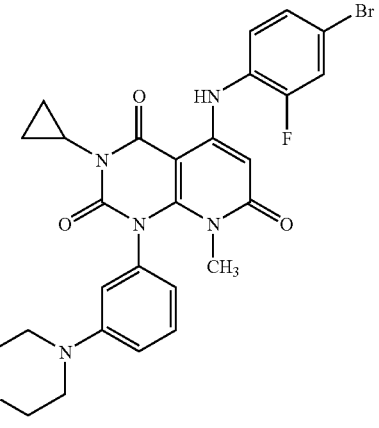 |
| 1-207 | 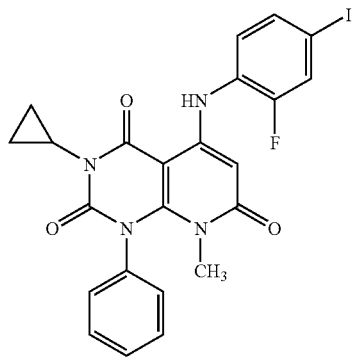 |
| 1-208 | 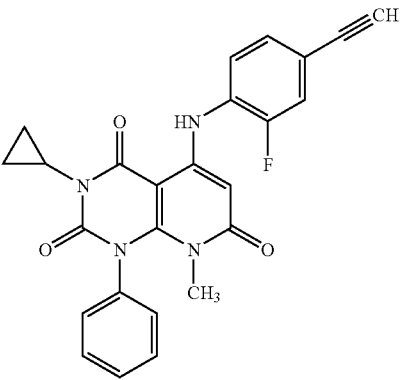 |
| 1-209 | 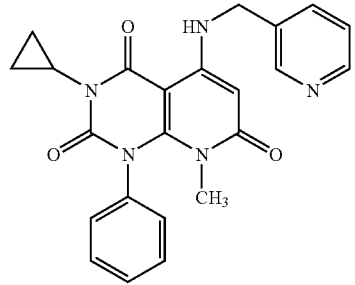 |
TABLE 1-35-continued
| Ex. No. | structural formula |
|---|---|
| 1-210 | 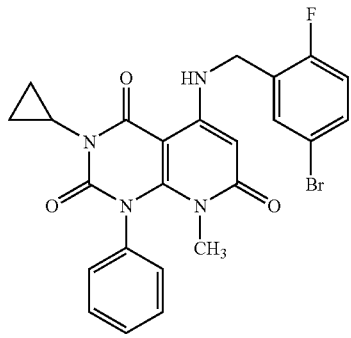 |
TABLE 1-36
| Ex. No. | structural formula |
|---|---|
| 1-211 | 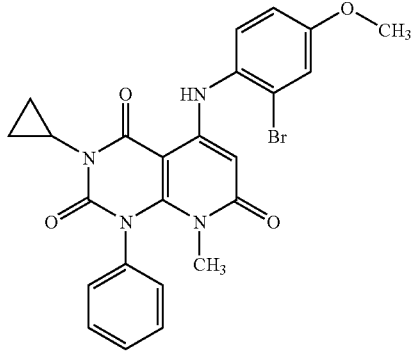 |
| 1-212 | 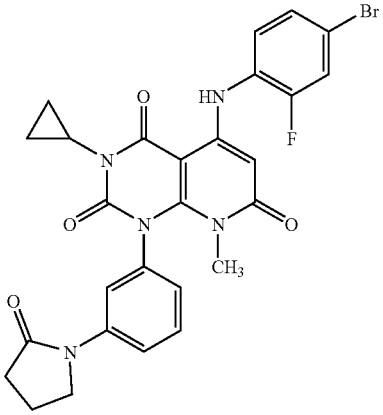 |

TABLE 1-36-continued

| Ex. No. | structural formula |
|---|---|
| 1-213 | (structure) |
| 1-214 | (structure) |
| 1-215 | (structure) |

TABLE 1-36-continued

| Ex. No. | structural formula |
|---|---|
| 1-216 | (structure) |

TABLE 1-37

| Ex. No. | structural formula |
|---|---|
| 1-217 | (structure) |
| 1-218 | (structure) |

TABLE 1-37-continued

| Ex. No. | structural formula |
|---|---|
| 1-219 | (structure) |
| 1-220 | (structure) |
| 1-221 | (structure) |

TABLE 1-37-continued

| Ex. No. | structural formula |
|---|---|
| 1-222 | (structure) |

TABLE 1-38

| Ex. No. | structural formula |
|---|---|
| 1-223 | (structure) |
| 1-224 | (structure) |

TABLE 1-38-continued

| Ex. No. | structural formula |
|---|---|
| 1-225 | (structure) |
| 1-226 | (structure) |
| 1-227 | (structure) |

TABLE 1-38-continued

| Ex. No. | structural formula |
|---|---|
| 1-228 | (structure) |

TABLE 1-39

| Ex. No. | structural formula |
|---|---|
| 1-229 | (structure) |
| 1-230 | (structure) |

TABLE 1-39-continued

| Ex. No. | structural formula |
|---|---|
| 1-231 | (cyclopropyl-pyrido[2,3-d]pyrimidine-2,4,7-trione with N-CH₃, N-phenyl, and 5-NH-(4-cyanophenyl) substituents) |
| 1-232 | (cyclopropyl-pyrido[2,3-d]pyrimidine-2,4,7-trione with N-CH₃, 5-NH-(4-bromo-2-fluorophenyl), and N-[3-(2-morpholinoethoxy)phenyl] substituents) |
| 1-233 | (cyclopropyl-pyrido[2,3-d]pyrimidine-2,4,7-trione with N-CH₃, 5-NH-(4-bromo-2-fluorophenyl), and N-[3-(2-pyrrolidinylethoxy)phenyl] substituents) |
| 1-234 | (cyclopropyl-pyrido[2,3-d]pyrimidine-2,4,7-trione with N-CH₃, 5-NH-(4-bromo-2-fluorophenyl), and N-[3-(2-piperidinylethoxy)phenyl] substituents) |

TABLE 1-40

| Ex. No. | structural formula |
|---|---|
| 1-235 | (cyclopropyl-pyrido[2,3-d]pyrimidine-2,4,7-trione with N-CH₃, 5-NH-(4-bromo-2-fluorophenyl), and N-[3-(2-diethylaminoethoxy)phenyl] substituents) |
| 1-236 | (cyclopropyl-pyrido[2,3-d]pyrimidine-2,4,7-trione with N-CH₃, 5-NH-(4-bromo-2-fluorophenyl), and N-{3-[3-(4-methylpiperazin-1-yl)propoxy]phenyl} substituents) |
| 1-237 | (cyclopropyl-pyrido[2,3-d]pyrimidine-2,4,7-trione with N-CH₃, N-phenyl, and 5-NH-(4-cyano-3-fluorophenyl) substituents) |

TABLE 1-40-continued

| Ex. No. | structural formula |
|---|---|
| 1-238 | (structure) |
| 1-239 | (structure) |
| 1-240 | (structure) |

TABLE 1-41

| Ex. No. | structural formula |
|---|---|
| 1-241 | (structure) |
| 1-242 | (structure) |
| 1-243 | (structure) |
| 1-244 | (structure) |

TABLE 1-41-continued
| Ex. No. | structural formula |
|---|---|
| 1-245 | 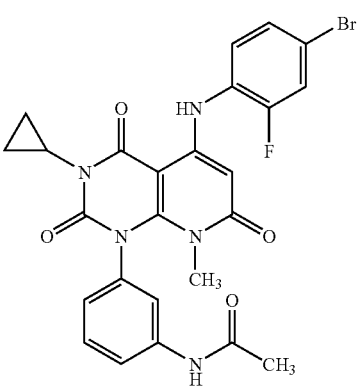 |
| 1-246 | 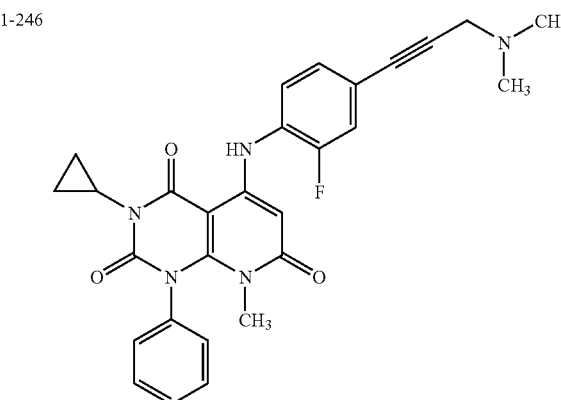 |
TABLE 1-42
| Ex. No. | structural formula |
|---|---|
| 1-247 | 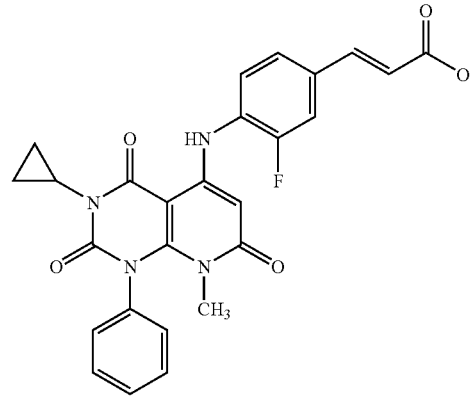 |
TABLE 1-42-continued
| Ex. No. | structural formula |
|---|---|
| 1-248 | 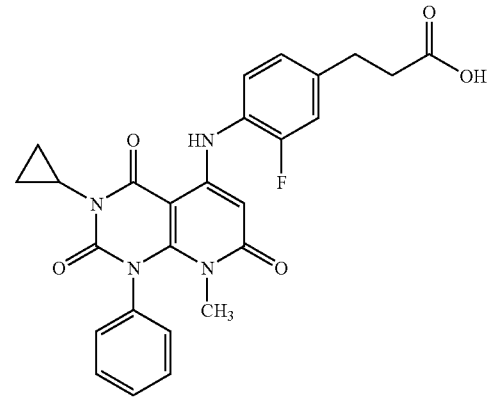 |
| 1-249 | 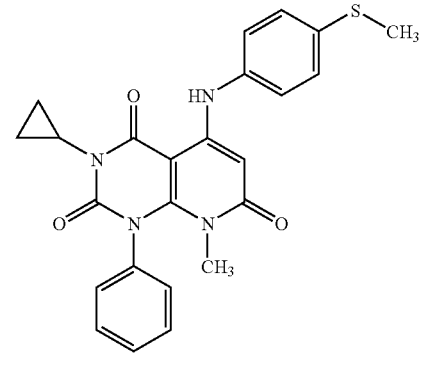 |
| 1-250 | 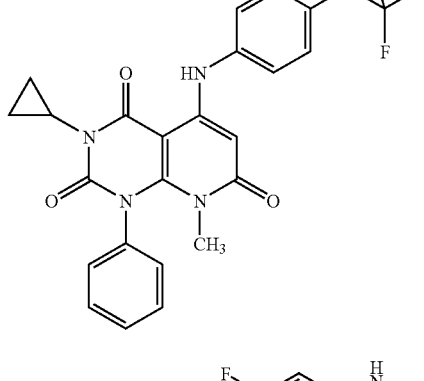 |
| 1-251 | 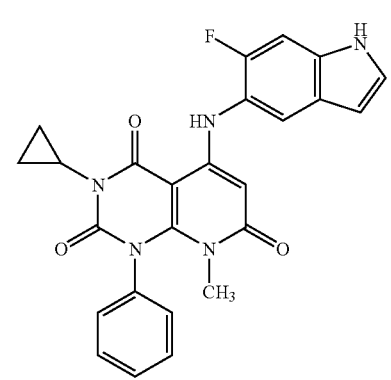 |

TABLE 1-42-continued
| Ex. No. | structural formula |
|---|---|
| 1-252 | 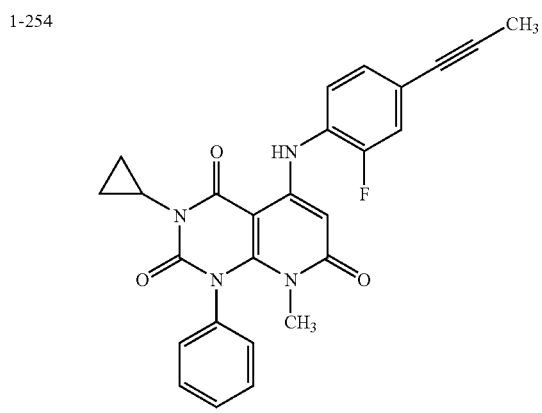 |
TABLE 1-43
| Ex. No. | structural formula |
|---|---|
| 1-253 | |
| 1-254 | |
TABLE 1-43-continued
| Ex. No. | structural formula |
|---|---|
| 1-255 | |
| 1-256 | |
| 1-257 | |
| 1-258 | |

TABLE 1-44
| Ex. No. | structural formula |
|---|---|
| 1-259 | 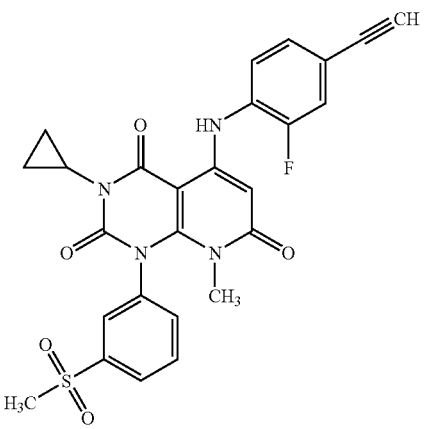 |
| 1-260 | 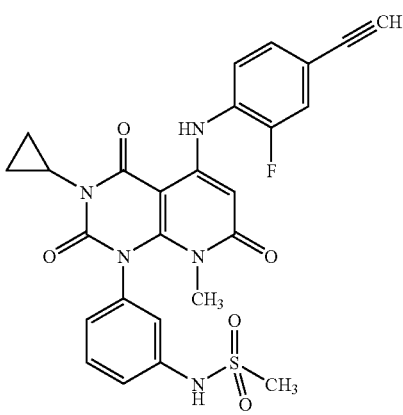 |
| 1-261 | 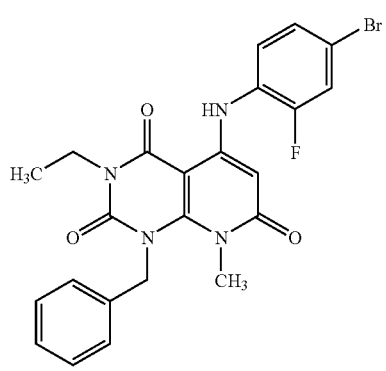 |
TABLE 1-44-continued
| Ex. No. | structural formula |
|---|---|
| 1-262 | 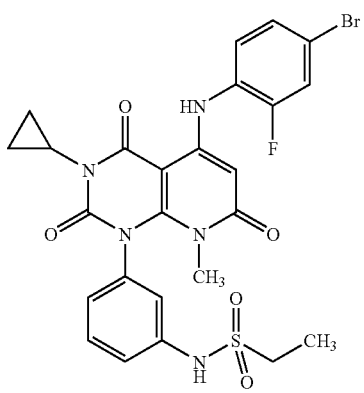 |
| 1-263 | 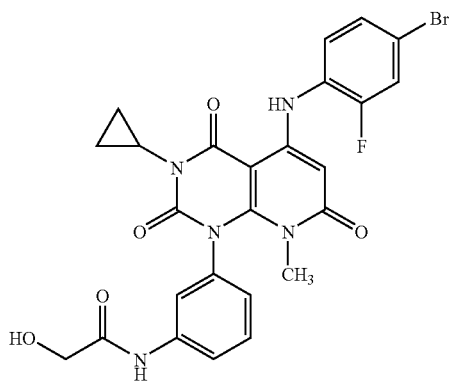 |
| 1-264 | 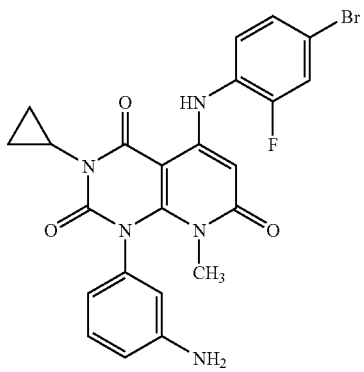 |

TABLE 1-45

| Ex. No. | structural formula |
|---|---|
| 1-265 | (structure) |
| 1-266 | (structure) |
| 1-267 | (structure) |
| 1-268 | (structure) |

TABLE 1-45-continued

| Ex. No. | structural formula |
|---|---|
| 1-269 | (structure) |
| 1-270 | (structure) |

TABLE 1-46

| Ex. No. | structural formula |
|---|---|
| 1-271 | (structure) |

TABLE 1-46-continued
| Ex. No. | structural formula |
|---|---|
| 1-272 | 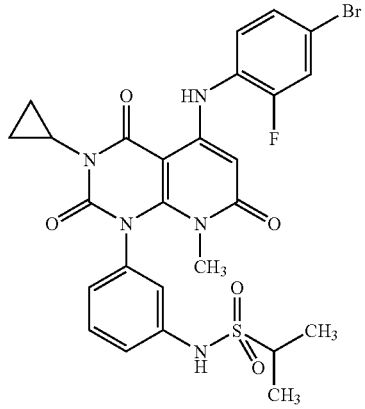 |
| 1-273 | 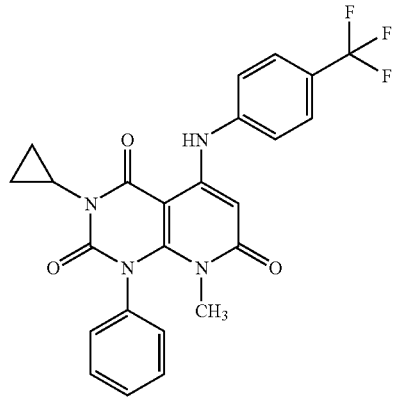 |
| 1-274 | 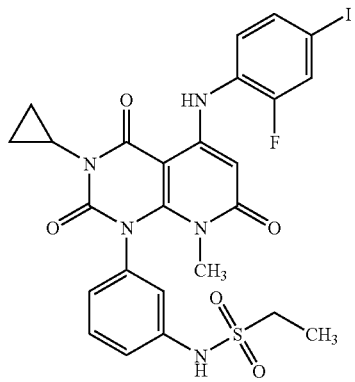 |
TABLE 1-46-continued
| Ex. No. | structural formula |
|---|---|
| 1-275 | 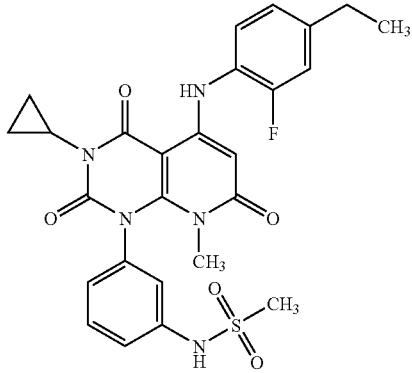 |
| 1-276 | 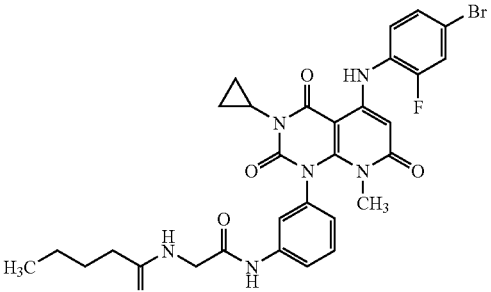 |
TABLE 1-47
| Ex. No. | structural formula |
|---|---|
| 1-277 | 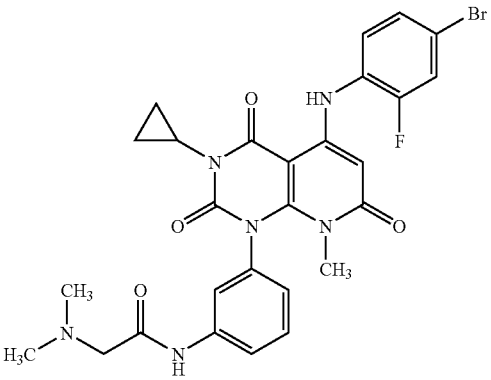 |

TABLE 1-47-continued
| Ex. No. | structural formula |
|---|---|
| 1-278 | 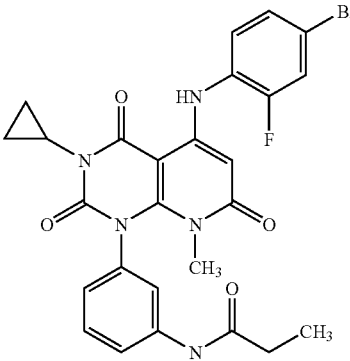 |
| 1-279 | 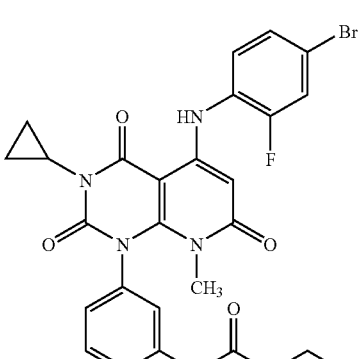 |
| 1-280 | 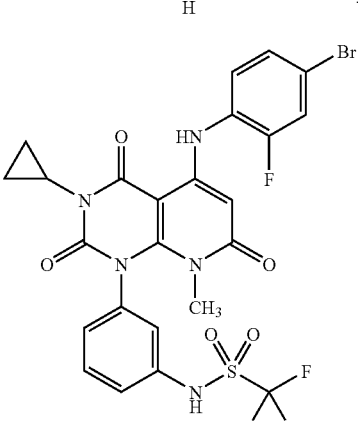 |
| 1-281 | 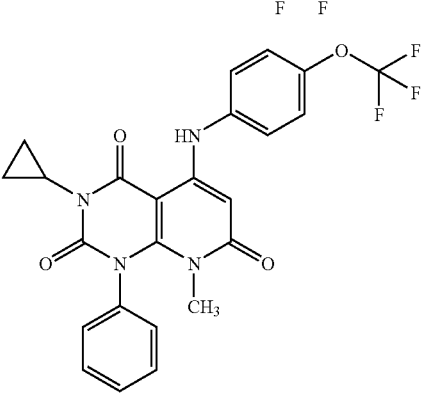 |
TABLE 1-47-continued
| Ex. No. | structural formula |
|---|---|
| 1-282 | 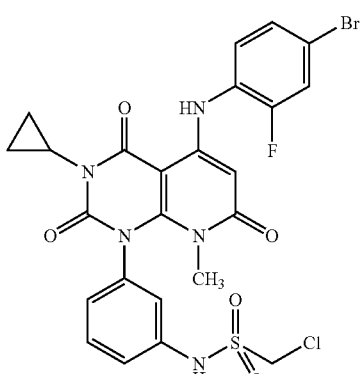 |
TABLE 1-48
| Ex. No. | structural formula |
|---|---|
| 1-283 | 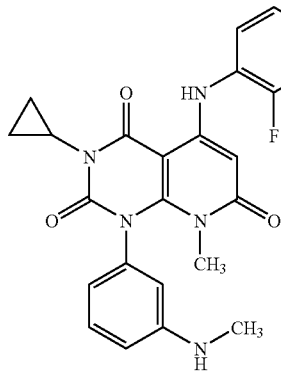 |
| 1-284 | 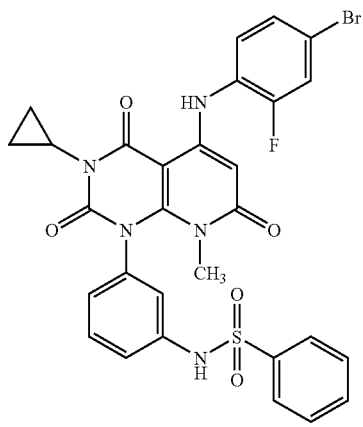 |

TABLE 1-48-continued

| Ex. No. | structural formula |
|---|---|
| 1-285 | |
| 1-286 | |
| 1-287 | |

TABLE 1-48-continued

| Ex. No. | structural formula |
|---|---|
| 1-288 | |

TABLE 1-49

| Ex. No. | structural formula |
|---|---|
| 1-289 | |
| 1-290 | |

TABLE 1-49-continued
| Ex. No. | structural formula |
|---|---|
| 1-291 | 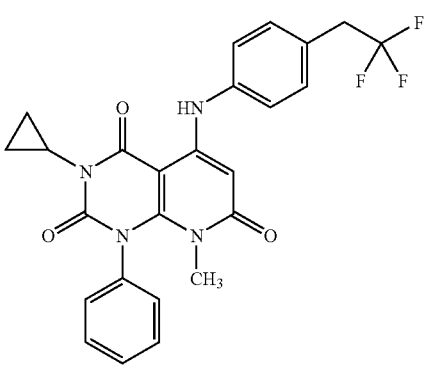 |
| 1-292 | 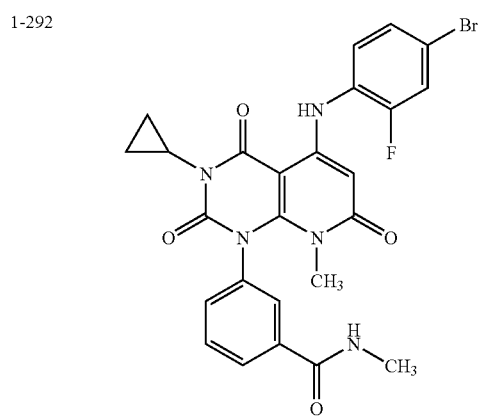 |
| 1-293 | 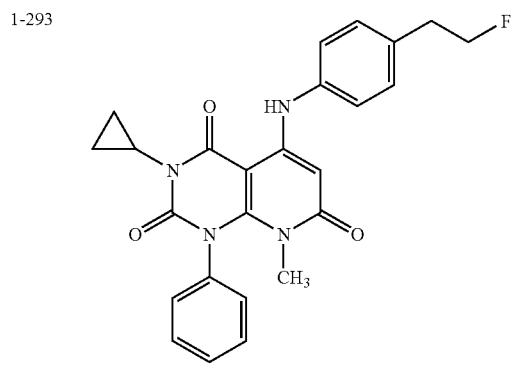 |
TABLE 1-49-continued
| Ex. No. | structural formula |
|---|---|
| 1-294 | 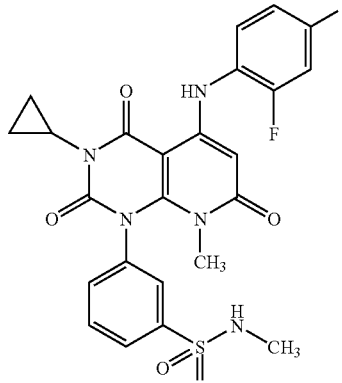 |
TABLE 1-50
| Ex. No. | structural formula |
|---|---|
| 1-295 | 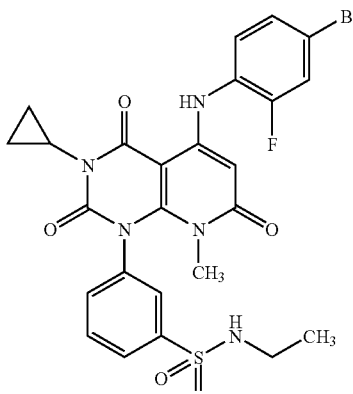 |
| 1-296 | 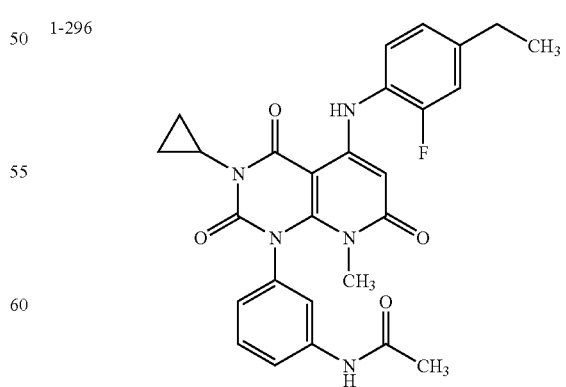 |

TABLE 1-50-continued
| Ex. No. | structural formula |
|---|---|
| 1-297 | 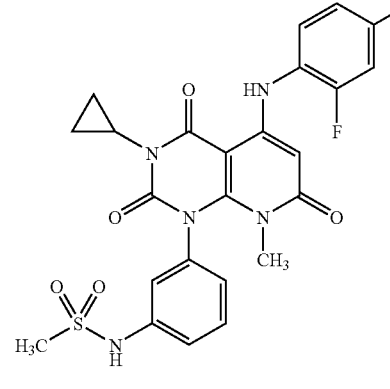 |
| 1-298 | |
| 1-299 | |
| 1-300 | |
TABLE 1-51
| Ex. No. | structural formula |
|---|---|
| 1-301 | 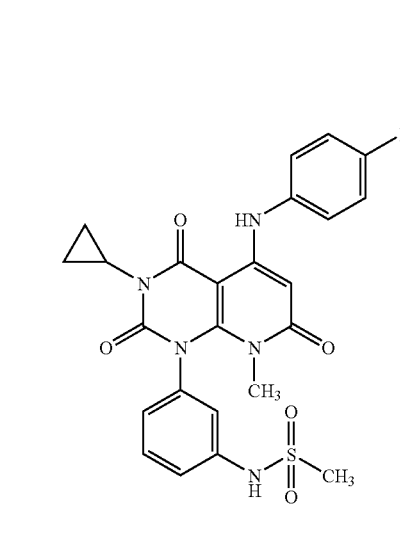 |
| 1-302 | |
| 1-303 | |

TABLE 1-51-continued

| Ex. No. | structural formula |
|---|---|
| 1-304 | (cyclopropyl-pyrido[2,3-d]pyrimidine-2,4,7-trione core with 5-(4-bromophenyl)amino, N8-methyl, N1-(3-methanesulfonamidophenyl)) |
| 1-305 | (cyclopropyl-pyrido[2,3-d]pyrimidine-2,4,7-trione core with 5-(4-bromo-2-fluorophenyl)amino, N8-methyl, N1-(3-(3-hydroxypropanamido)phenyl)) |
| 1-306 | (cyclopropyl-pyrido[2,3-d]pyrimidine-2,4,7-trione core with 5-(4-bromo-2-fluorophenyl)amino, N8-methyl, N1-(3-(3-(dimethylamino)propanamido)phenyl)) |

TABLE 1-52

| Ex. No. | structural formula |
|---|---|
| 1-307 | (cyclopropyl-pyrido[2,3-d]pyrimidine-2,4,7-trione core with 5-(4-bromo-2-fluorophenyl)amino, N8-methyl, N1-(3-(3-ethylureido)phenyl)) |
| 1-308 | (cyclopropyl-pyrido[2,3-d]pyrimidine-2,4,7-trione core with 5-(4-bromo-2-fluorophenyl)amino, N8-methyl, N1-(3-(ethoxycarbonylamino)phenyl)) |
| 1-309 | (cyclopropyl-pyrido[2,3-d]pyrimidine-2,4,7-trione core with 5-(4-bromo-2-fluorophenyl)amino, N8-methyl, N1-(3-(N,N-dimethylsulfamoylamino)phenyl)) |

1-310 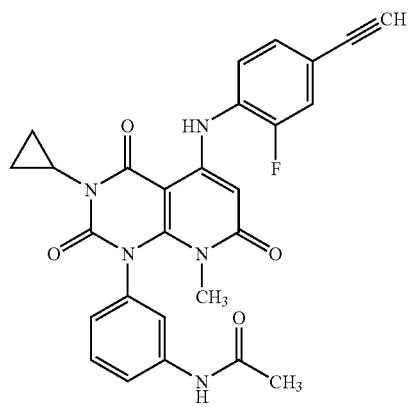
1-311 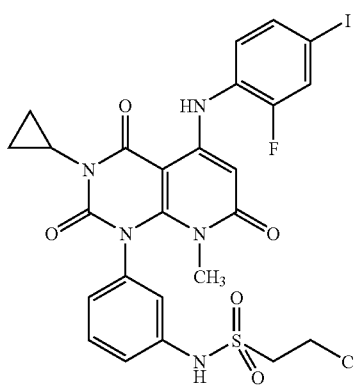
1-312 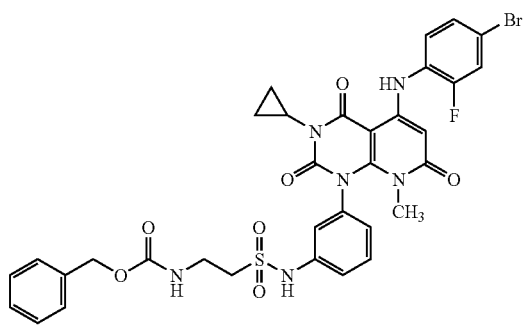
TABLE 1-53
| Ex. No. | structural formula |
|---|---|
| 1-313 | 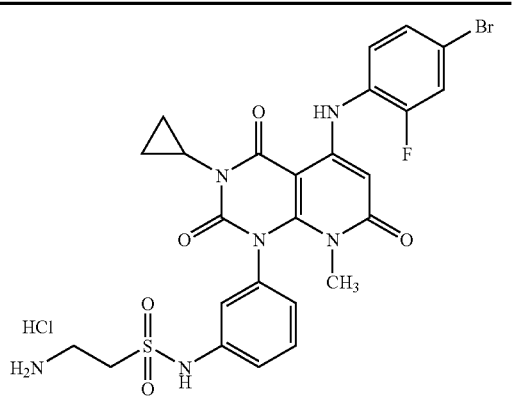 |
TABLE 1-53-continued
| Ex. No. | structural formula |
|---|---|
| 1-314 | 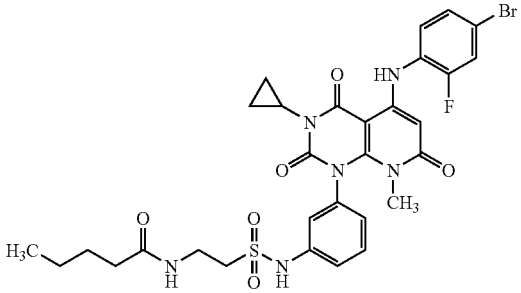 |
| 1-315 | 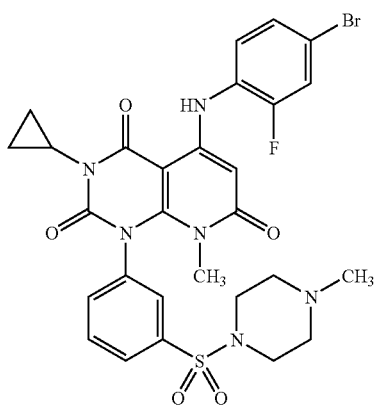 |
| 1-316 | 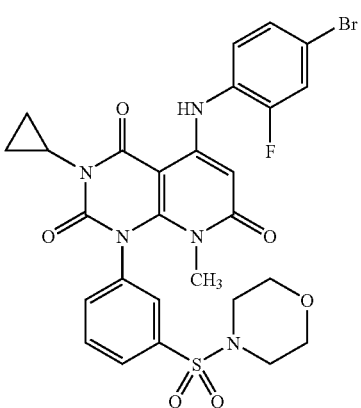 |
| 1-317 | 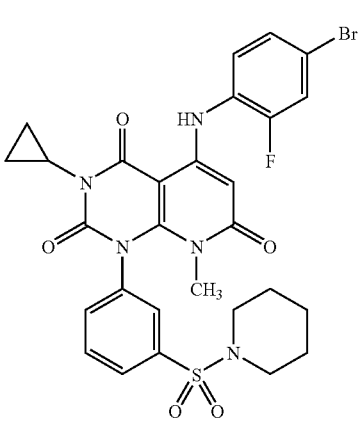 |

TABLE 1-53-continued

| Ex. No. | structural formula |
|---|---|
| 1-318 | (structure: 3-cyclopropyl-5-(4-bromo-2-fluorophenylamino)-8-methyl-1-(3-(pyrrolidin-1-ylsulfonyl)phenyl)pyrido[2,3-d]pyrimidine-2,4,7(1H,3H,8H)-trione) |

TABLE 1-54

| Ex. No. | structural formula |
|---|---|
| 1-319 | (structure: 3-cyclopropyl-5-(4-iodo-2-fluorophenylamino)-8-methyl-1-(3-(isopropylsulfonylamino)phenyl)pyrido[2,3-d]pyrimidine-2,4,7(1H,3H,8H)-trione) |
| 1-320 | (structure: 3-cyclopropyl-5-(4-ethynyl-2-fluorophenylamino)-8-methyl-1-(3-(propylsulfonylamino)phenyl)pyrido[2,3-d]pyrimidine-2,4,7(1H,3H,8H)-trione) |

TABLE 1-54-continued

| Ex. No. | structural formula |
|---|---|
| 1-321 | (structure: 3-cyclopropyl-5-(4-ethynyl-2-fluorophenylamino)-8-methyl-1-(3-(isopropylsulfonylamino)phenyl)pyrido[2,3-d]pyrimidine-2,4,7(1H,3H,8H)-trione) |
| 1-322 | (structure: 3-cyclopropyl-5-(4-iodo-2-chlorophenylamino)-8-methyl-1-(3-(methylsulfonylamino)phenyl)pyrido[2,3-d]pyrimidine-2,4,7(1H,3H,8H)-trione) |

TABLE 1-55

| Ex. No. | structural formula |
|---|---|
| 1-323 | (structure: 3-cyclopropyl-5-(4-bromo-2-fluorophenylamino)-8-methyl-1-(3-(4-(dimethylamino)butanamido)phenyl)pyrido[2,3-d]pyrimidine-2,4,7(1H,3H,8H)-trione) |

TABLE 1-55-continued
| Ex. No. | structural formula |
|---|---|
| 1-324 | 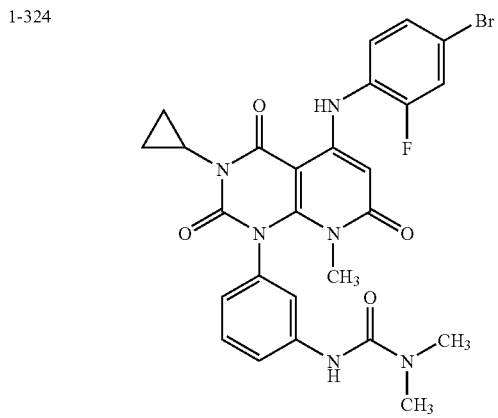 |
| 1-325 | 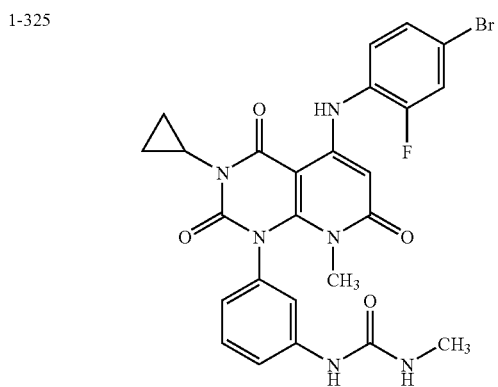 |
| 1-326 | 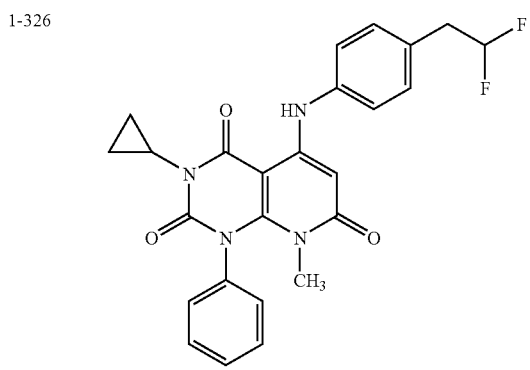 |
| 1-327 | 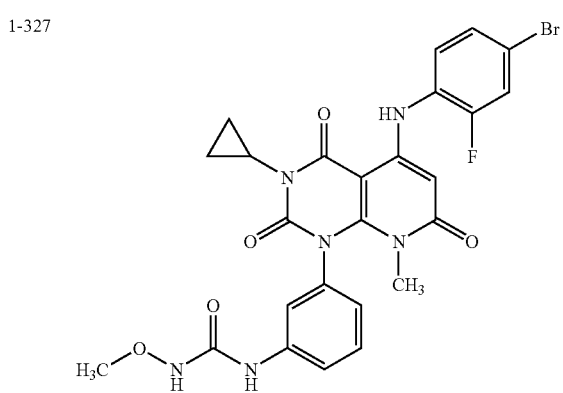 |
TABLE 1-55-continued
| Ex. No. | structural formula |
|---|---|
| 1-328 | 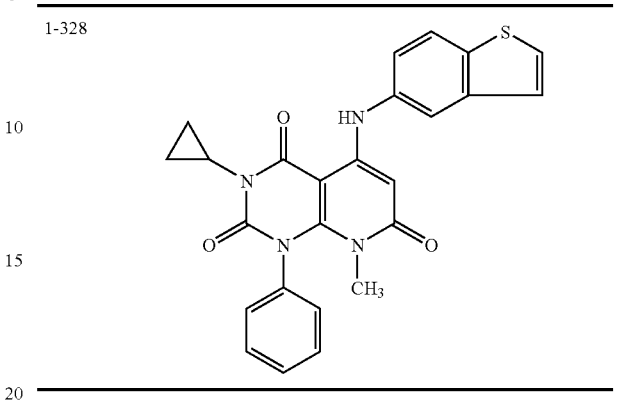 |
TABLE 1-56
| Ex. No. | structural formula |
|---|---|
| 1-329 | 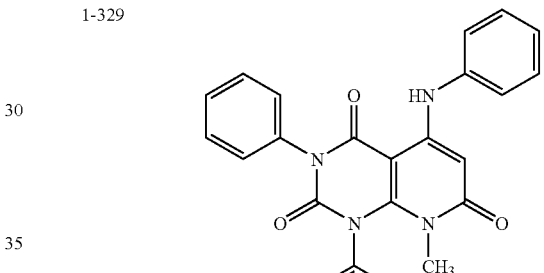 |
| 1-330 | 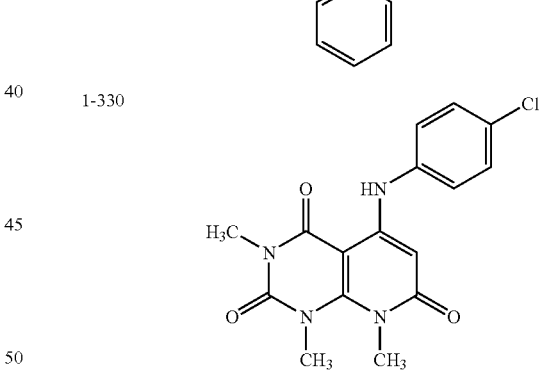 |
| 1-331 | 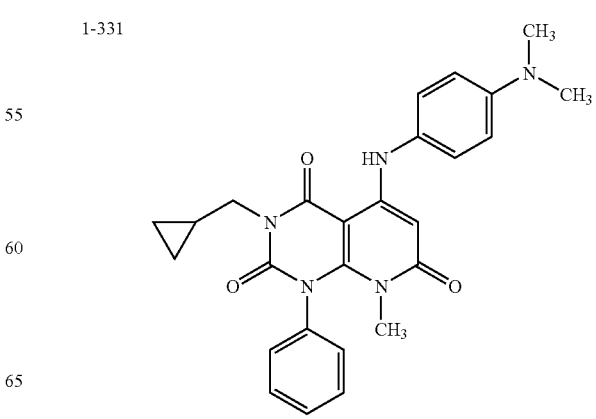 |

TABLE 1-56-continued

| Ex. No. | structural formula |
|---|---|
| 1-332 | |

TABLE 1-57

| Ex. No. | structural formula |
|---|---|
| 1-333 | |
| 1-334 | |

TABLE 1-57-continued

| Ex. No. | structural formula |
|---|---|
| 1-335 | |
| 1-336 | |
| 1-337 | |

TABLE 1-57-continued
| Ex. No. | structural formula |
|---|---|
| 1-338 | 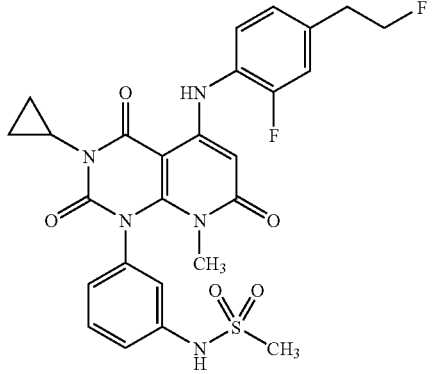 |
TABLE 1-58
| Ex. No. | structural formula |
|---|---|
| 1-339 | 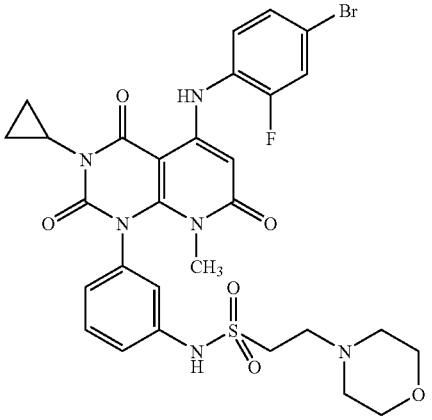 |
| 1-340 | 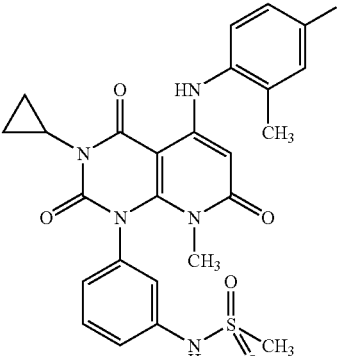 |
TABLE 1-58-continued
| Ex. No. | structural formula |
|---|---|
| 1-341 | 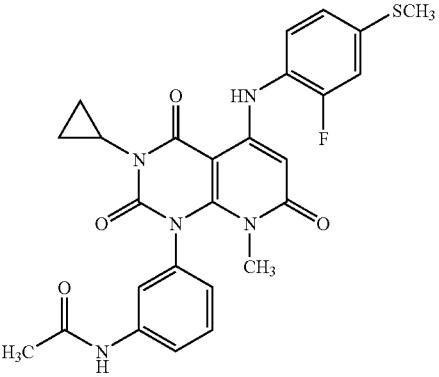 |
| 1-342 | 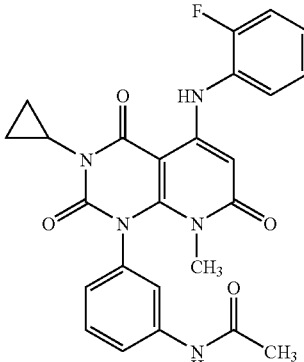 |
| 1-343 | 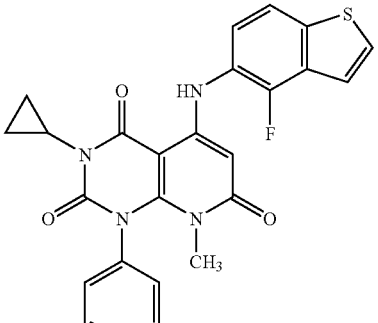 |

Example 2-1

Synthesis of 5-(4-chloro-phenylamino)-8-methyl-1,3-diphenyl-1H,8H-pyrimido[4,5-d]pyrimidine-2,4,7-trione Step 1 Synthesis of 1,3-diphenyl-pyrimidine-2,4,6-trione

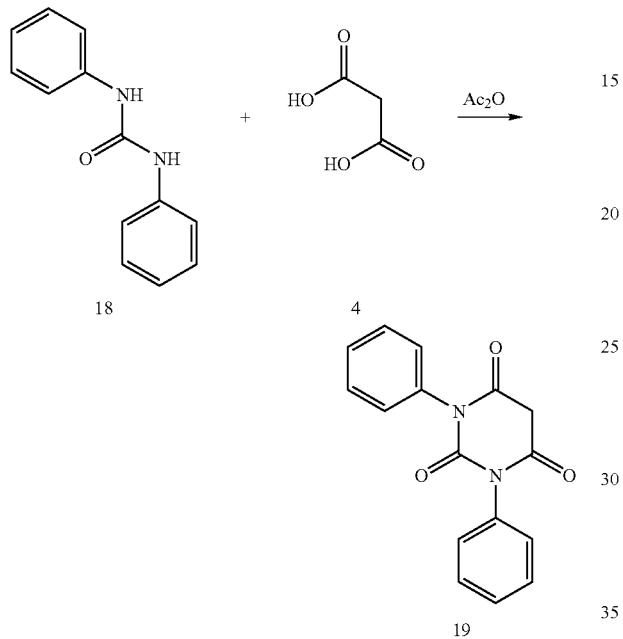

Acetic anhydride (290 ml) was added to 1,3-diphenylurea 18 (148 g), malonic acid 4 (81.6 g) was added under a nitrogen atmosphere, and the mixture was stirred at 90° C. for 3 hrs. The mixture was stirred at 100° C. for 1.5 hrs and allowed to cool to room temperature. The reaction mixture was concentrated under reduced pressure. Ethanol (500 ml) was added to the residue, and the mixture was stirred at 90° C. When the mixture was cooled to 40° C., the crystals were collected by filtration, washed with ethanol and dried to give 1,3-diphenyl-pyrimidine-2,4,6-trione 19 (78.0 g, yield 40%).

Step 2 Synthesis of 6-chloro-1,3-diphenyl-1H-pyrimidine-2,4-dione

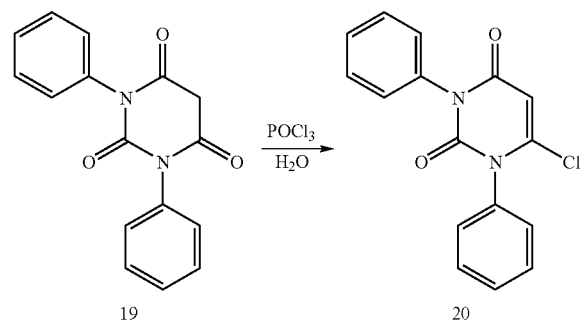

To 1,3-diphenyl-pyrimidine-2,4,6-trione 19 (78.0 g) obtained in Step 1 was added water (16 ml). Phosphorus oxychloride (422 ml) was added dropwise under stirring at room temperature over 50 min. After the completion of the dropwise addition, the mixture was stirred under heating at 110° C. for 3 hrs. After allowing to cool to room temperature, the reaction mixture was added to ice water by small portions and the mixture was stirred at room temperature and extracted with ethyl acetate. The organic layer was washed with brine and saturated aqueous sodium hydrogen carbonate, and dried over anhydrous sodium sulfate. Anhydrous sodium sulfate was filtered off and the filtrate was concentrated under reduced pressure. The residue was purified by column chromatography (hexane:ethyl acetate=2:1→3:2) to give 6-chloro-1,3-diphenyl-1H-pyrimidine-2,4-dione 20 (61.5 g, yield 74%) as pale-yellow crystals.

Step 3 Synthesis of 6-methylamino-1,3-diphenyl-1H-pyrimidine-2,4-dione

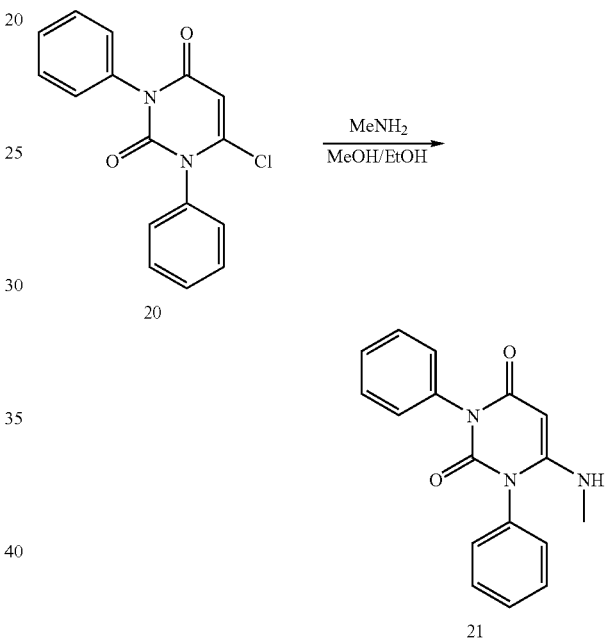

In the same manner as in Step 4 of Example 1-1 and using 6-chloro-1,3-diphenyl-1H-pyrimidine-2,4-dione 20 (5.0 g) obtained in Step 2, ethanol (25 ml), a 40% solution (21.7 ml) of methylamine in methanol, 6-methylamino-1,3-diphenyl-1H-pyrimidine-2,4-dione 21 (4.42 g, yield 90%) was obtained as colorless crystals.

Step 4 Synthesis of ethyl (6-methylamino-2,4-dioxo-1,3-diphenyl-1,2,3,4-tetrahydro-pyrimidine-5-thiocarbonyl)-carbamate

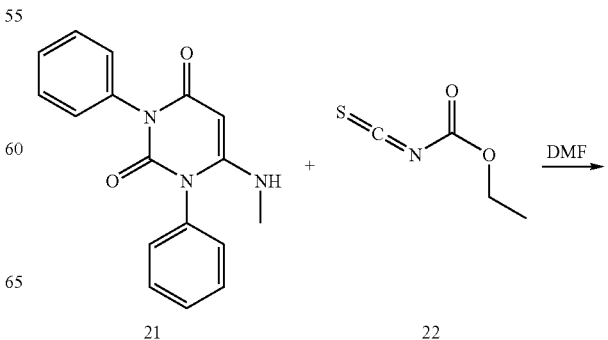

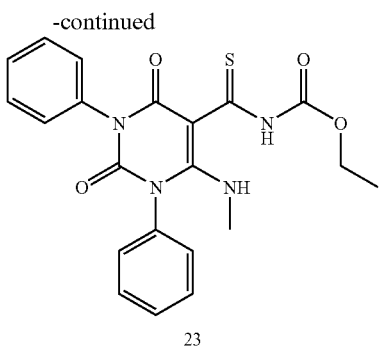

To 6-methylamino-1,3-diphenyl-1H-pyrimidine-2,4-dione 21 (1.18 g) obtained in Step 3 was added N,N-dimethylformamide (5.9 ml), ethyl isothiocyanate formate 22 (0.52 ml) was added under a nitrogen atmosphere, and the mixture was stirred at room temperature for 1 hr. Water (30 ml) was added to the reaction mixture, and the crystals were collected by filtration and washed with water to give crude ethyl (6-methylamino-2,4-dioxo-1,3-diphenyl-1,2,3,4-tetrahydro-pyrimidine-5-thiocarbonyl)-carbamate 23 (1.68 g) as pale-yellow crystals, which were used for the next step without purification.

Step 5 Synthesis of 5-mercapto-8-methyl-1,3-diphenyl-1H,8H-pyrimido[4,5-d]pyrimidine-2,4,7-trione

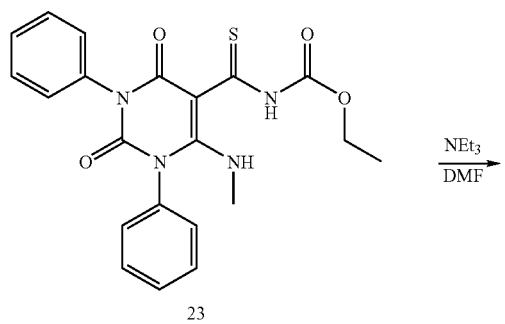

To crude ethyl (6-methylamino-2,4-dioxo-1,3-diphenyl-1,2,3,4-tetrahydro-pyrimidine-5-thiocarbonyl)-carbamate 23 (1.58 g) obtained in Step 4 was added N,N-dimethylformamide (8.4 ml), triethylamine (0.63 ml) was added under a nitrogen atmosphere, and the mixture was stirred at room temperature for 30 min. Water (25 ml) was added, the mixture was stirred, 1N hydrochloric acid (5.0 ml) was added, and the mixture was stirred at room temperature for 1 hr. The crystals were collected by filtration, washed with water and dried to give crude 5-mercapto-8-methyl-1,3-diphenyl-1H,8H-pyrimido[4,5-d]pyrimidine-2,4,7-trione 24 (1.53 g, over weight) as yellow crystals, which were used for the next step without purification.

Step 6 Synthesis of 8-methyl-5-methylsulfanyl-1,3-diphenyl-1H,8H-pyrimido[4,5-d]pyrimidine-2,4,7-trione

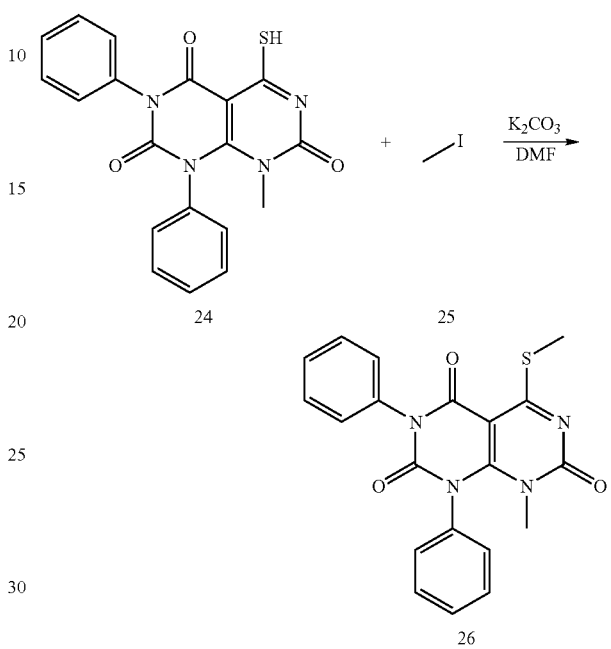

To crude 5-mercapto-8-methyl-1,3-diphenyl-1H,8H-pyrimido[4,5-d]pyrimidine-2,4,7-trione 24 (100 mg) obtained in Step 5 was added N,N-dimethylformamide (0.5 ml). Under a nitrogen atmosphere, potassium carbonate (44 mg) and methyl iodide 25 (20 μl) were successively added, and the mixture was stirred at room temperature for 3 hrs. Water was added, and the mixture was extracted with chloroform. The organic layer was washed with water and brine, and dried over anhydrous sodium sulfate. Anhydrous sodium sulfate was filtered off, and the filtrate was concentrated under reduced pressure. The residue was purified by column chromatography (hexane:ethyl acetate=4:1→3:1) to give 8-methyl-5-methylsulfanyl-1,3-diphenyl-1H,8H-pyrimido[4,5-d]pyrimidine-2,4,7-trione 26 (91 mg, yield 89%) as brown crystals.

Step 7 Synthesis of 5-(4-chloro-phenylamino)-8-methyl-1,3-diphenyl-1H,8H-pyrimido[4,5-d]pyrimidine-2,4,7-trione

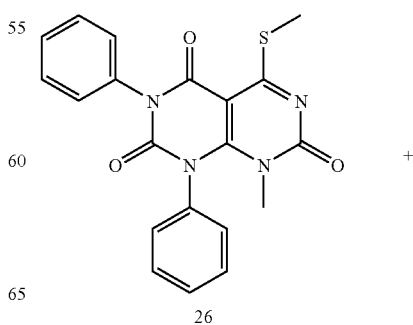

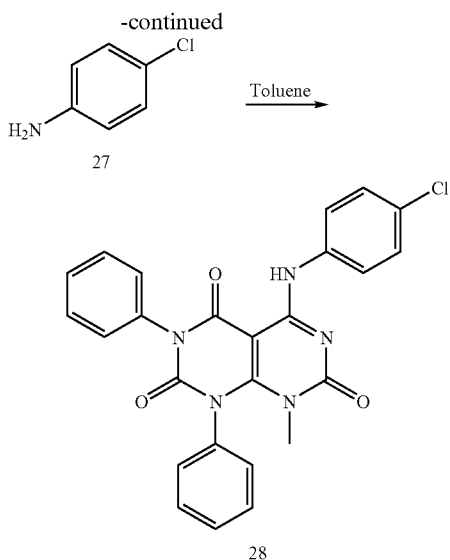

To 8-methyl-5-methylsulfanyl-1,3-diphenyl-1H,8H-pyrimido[4,5-d]pyrimidine-2,4,7-trione 26 (149 mg) obtained in Step 6 was added toluene (2 ml), 4-chloroaniline 27 (97 mg) was added, and the mixture was stirred under reflux for 3.5 hrs. After allowing to cool to room temperature, diethyl ether was added. The crystals were collected by filtration, washed with diethyl ether and dried to give 5-(4-chlorophenylamino)-8-methyl-1,3-diphenyl-1H,8H-pyrimido[4,5-d]pyrimidine-2,4,7-trione 28 (94 mg, yield 53%) as colorless crystals.

MS ESI m/e: 472 (M+H), 470 (M−H).

$^1$H-NMR (DMSO-d$_6$, 400 MHz) δ 2.68 (s, 3H), 7.34-7.39 (m, 2H), 7.41-7.61 (m, 10H), 7.80-7.87 (m, 2H), 11.34 (s, 1H).

Example 2-2

In the same manner as in Example 2-1, the compounds of Example 2-2 were obtained. The structural formulas thereof are shown in Table 2-1 with Example 2-1.

Table 2-1

TABLE 2-1

| Ex. No. | structural formula |
|---|---|
| 2-1 | ![2-1 structure] |

TABLE 2-1-continued

| Ex. No. | structural formula |
|---|---|
| 2-2 | ![2-2 structure] |

Example 3-1

Synthesis of 5-(4-bromo-phenylamino)-3-cyclopropyl-6,8-dimethyl-1-phenylamino-1H,6H-pyrido[4,3-d]pyrimidine-2,4,7-trione Step 1 Synthesis of 1-(4-bromo-phenyl)-3-cyclopropyl-urea

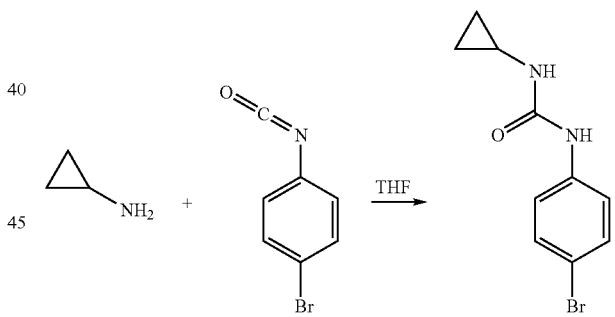

Under a nitrogen atmosphere, tetrahydrofuran (80 ml) was added to 4-bromophenyl isocyanate 30 (10.0 g), and a solution of cyclopropylamine 1 (3.17 g) in tetrahydrofuran (20 ml) was added dropwise with stirring under ice-cooling. After the completion of the dropwise addition, the mixture was stirred at room temperature for 3 hrs, and the reaction mixture was concentrated under reduced pressure. Diethyl ether-hexane [1:1 (volume ratio), 100 ml] was added to the residue and, after stirring, the crystals were collected by filtration and dried to give 1-(4-bromo-phenyl)-3-cyclopropyl-urea 31 (12.9 g, over weight) as colorless crystals, which were used for the next step without purification.

Step 0.2 Synthesis of 1-(4-bromo-phenyl)-3-cyclopropyl-pyrimidine-2,4,6-trione

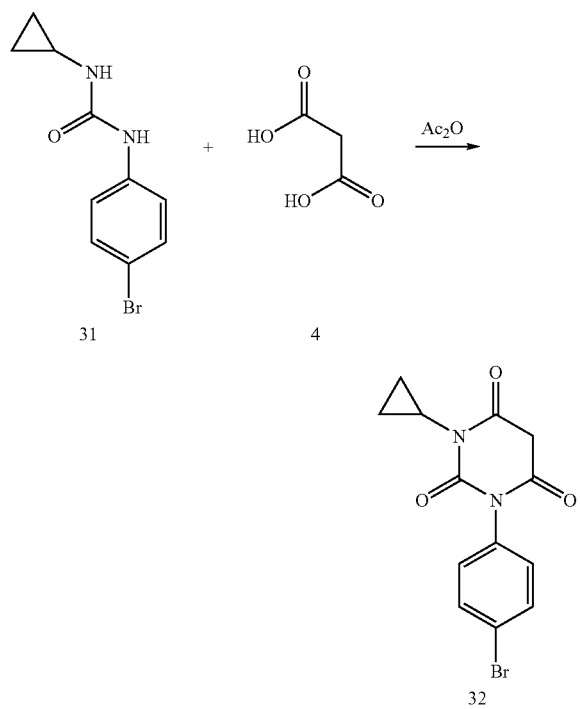

To 1-(4-bromo-phenyl)-3-cyclopropyl-urea 31 (12.9 g) obtained in Step 1 was added acetic anhydride (25.8 ml), malonic acid 4 (5.79 g) was added under a nitrogen atmosphere, and the mixture was stirred at 100° C. for 3 hrs. After allowing to cool to room temperature, the reaction mixture was concentrated under reduced pressure. Diethyl ether-ethanol [4:1 (volume ratio), 100 ml] was added to the residue and, after stirring, the crystals were collected by filtration and dried to give 1-(4-bromo-phenyl)-3-cyclopropyl-pyrimidine-2,4,6-trione 32 (11.9 g, yield 73%) as pale-yellow crystals.

Step 3 Synthesis of 1-(4-bromo-phenyl)-6-chloro-3-cyclopropyl-1H-pyrimidine-2,4-dione

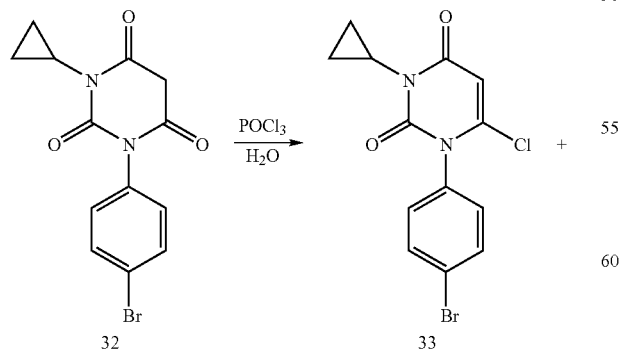

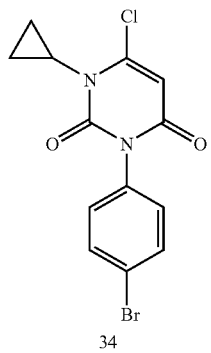

To 1-(4-bromo-phenyl)-3-cyclopropyl-pyrimidine-2,4,6-trione 32 (11.8 g) obtained in Step 2 was added water (1.31 ml) and phosphorus oxychloride (17.0 ml) was added dropwise with stirring at room temperature. After the completion of the dropwise addition, the mixture was stirred at 110° C. for 3 hrs. After allowing to cool to room temperature, the reaction mixture was added to ice water by small portions and the mixture was stirred. The mixture was stirred at room temperature and extracted with chloroform. The organic layer was washed with brine, and dried over anhydrous magnesium sulfate. Anhydrous magnesium sulfate was filtered off, and the filtrate was concentrated under reduced pressure. The residue was purified by column chromatography (hexane:ethyl acetate=2:1→chloroform:acetone=30:1) to give a 1:1.4 mixture (11.6 g, yield 93%) of 1-(4-bromo-phenyl)-6-chloro-3-cyclopropyl-1H-pyrimidine-2,4-dione 33 and 3-(4-bromo-phenyl)-6-chloro-1-cyclopropyl-1H-pyrimidine-2,4-dione 34 as a pale-yellow foamy oil.

Step 4 Synthesis of 1-(4-bromo-phenyl)-3-cyclopropyl-6-methylamino-1H-pyrimidine-2,4-dione

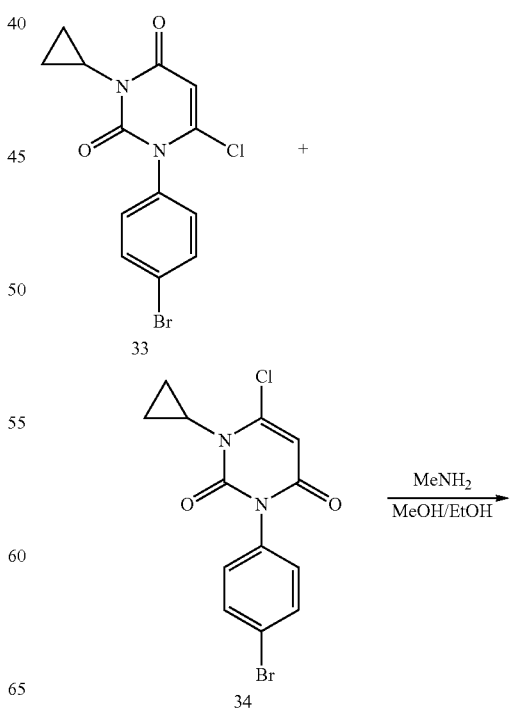

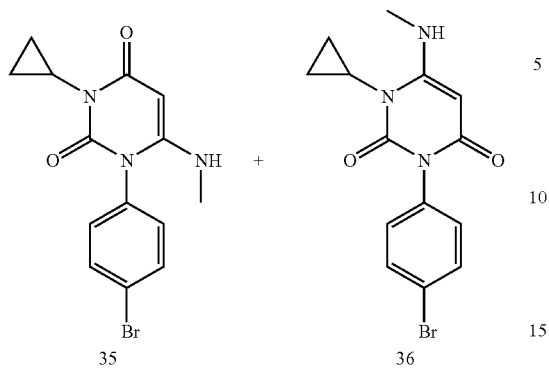

35     36

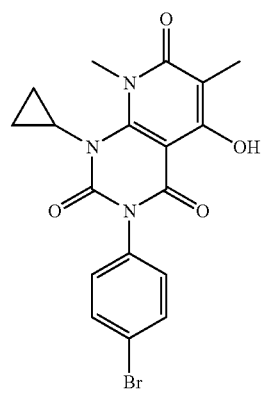

38

A 1:1.3 mixture (5.34 g, yield 78%) of 1-(4-bromophenyl)-3-cyclopropyl-6-methylamino-1H-pyrimidine-2,4-dione 35 and 3-(4-bromo-phenyl)-1-cyclopropyl-6-methylamino-1H-pyrimidine-2,4-dione 36 was obtained as colorless crystals in the same manner as the synthesis of compound 8 and using a 1:1.4 mixture (7.00 g) of 1-(4-bromo-phenyl)-6-chloro-3-cyclopropyl-1H-pyrimidine-2,4-dione 33 and 3-(4-bromo-phenyl)-6-chloro-1-cyclopropyl-1H-pyrimidine-2,4-dione 34 obtained in Step 3, ethanol (20.9 ml) and a 40% solution (10.5 ml) of methylamine in methanol.

Step 5 Synthesis of 1-(4-bromo-phenyl)-3-cyclopropyl-5-hydroxy-6,8-dimethyl-1H,8H-pyrido[2,3-d]pyrimidine-2,4,7-trione 1-(4-Bromo-phenyl)-3-cyclopropyl-5-hydroxy-6,8-dimethyl-1H,8H-pyrido[2,3-d]pyrimidine-2,4,7-trione 38 (0.40 g, yield 32%) was obtained as pale-yellow crystals in the same manner as in Step 5 of Example 1-1 and using a 1:1.3 mixture (1.00 g) of 1-(4-bromo-phenyl)-3-cyclopropyl-6-methylamino-1H-pyrimidine-2,4-dione 35 and 3-(4-bromo-phenyl)-1-cyclopropyl-6-methylamino-1H-pyrimidine-2,4-dione 36 obtained in Step 4, 2-methyl-diethyl malonate 37 (2.56 ml) and diphenyl ether (1.49 g).

Step 6 Synthesis of toluene-4-sulfonic acid 1-(4-bromophenyl)-3-cyclopropyl-6,8-dimethyl-2,4,7-trioxo-1,2,3,4,7,8-hexahydro-pyrido[2,3-d]pyrimidin-5-yl ester

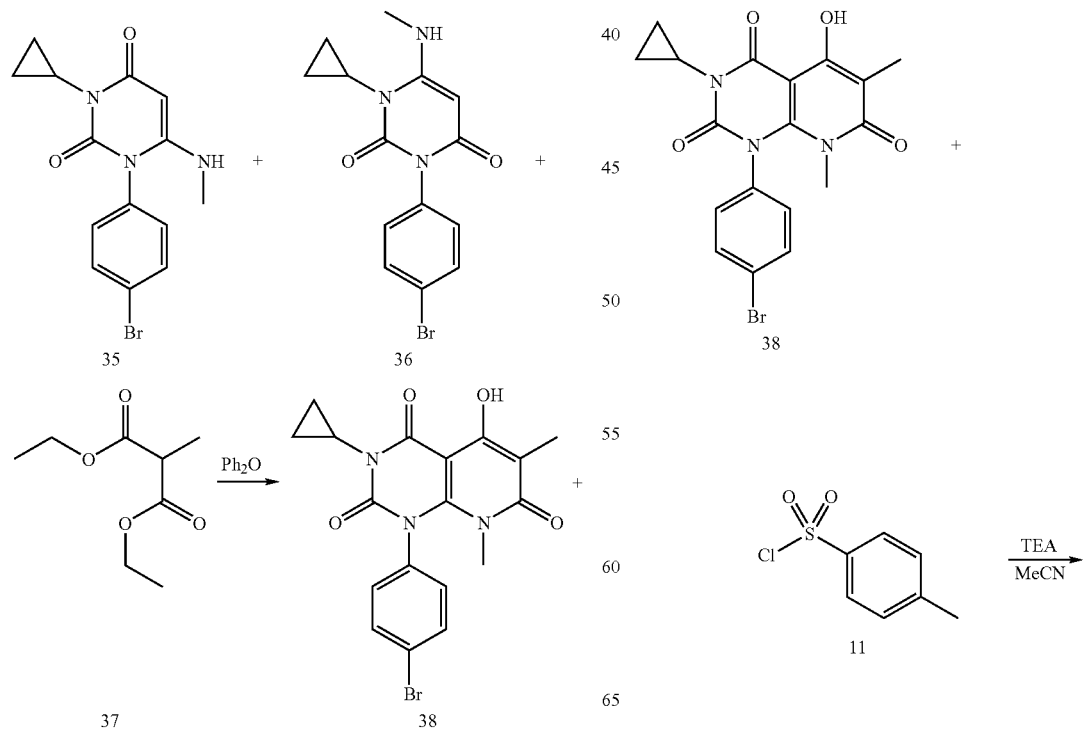

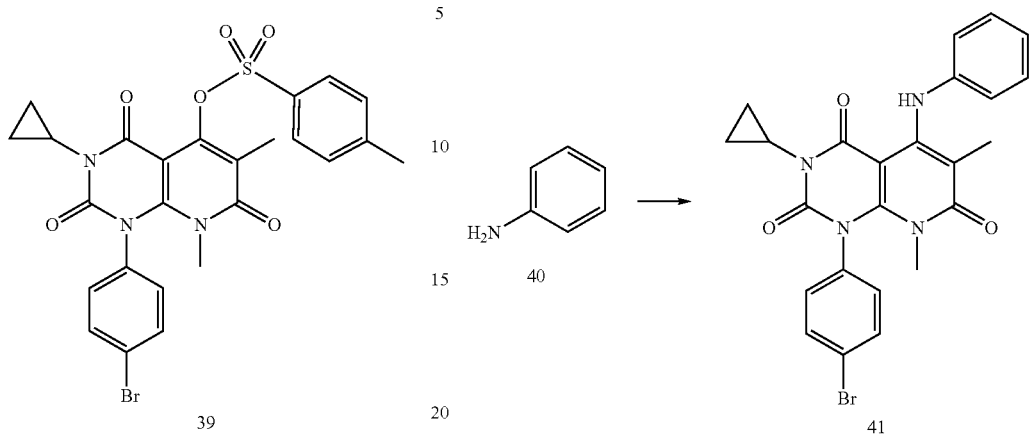

To 1-(4-bromo-phenyl)-3-cyclopropyl-5-hydroxy-6,8-dimethyl-1H,8H-pyrido[2,3-d]pyrimidine-2,4,7-trione 38 (400 mg) obtained in Step 5 was added acetonitrile (8.0 ml), tosyl chloride 11 (458 mg) and triethylamine (0.34 ml) were added under a nitrogen atmosphere, and the mixture was stirred under reflux for 30 hrs. After allowing to cool to room temperature, the mixture was concentrated under reduced pressure. The residue was purified by column chromatography (chloroform:acetone=25:1→20:1) to give toluene-4-sulfonic acid 1-(4-bromo-phenyl)-3-cyclopropyl-6,8-dimethyl-2,4,7-trioxo-1,2,3,4,7,8-hexahydro-pyrido[2,3-d]pyrimidin-5-yl ester 39 (407 mg, yield 74%) as ocher crystals.

Step 7 Synthesis of 1-(4-bromo-phenyl)-3-cyclopropyl-6,8-dimethyl-5-phenylamino-1H,8H-pyrido[2,3-d]pyrimidine-2,4,7-trione To toluene-4-sulfonic acid 1-(4-bromo-phenyl)-3-cyclopropyl-6,8-dimethyl-2,4,7-trioxo-1,2,3,4,7,8-hexahydro-pyrido[2,3-d]pyrimidin-5-yl ester 39 (100 mg) obtained in Step 6 was added aniline 40 (0.64 ml), and the mixture was stirred at 150° C. for 2.5 hrs. After allowing to cool to room temperature, diethyl ether-hexane [1:1 (volume ratio), 30 ml] was added to the reaction mixture, and the crystals were collected by filtration. The obtained crystals were purified by column chromatography (chloroform:acetone=15:1) to give 1-(4-bromo-phenyl)-3-cyclopropyl-6,8-dimethyl-5-phenylamino-1H,8H-pyrido[2,3-d]pyrimidine-2,4,7-trione 41 (81 mg, yield 93%) as pale-yellow crystals.

Step 8 Synthesis of 5-(4-bromo-phenylamino)-3-cyclopropyl-6,8-dimethyl-1-phenylamino-1H,6H-pyrido[4,3-d]pyrimidine-2,4,7-trione

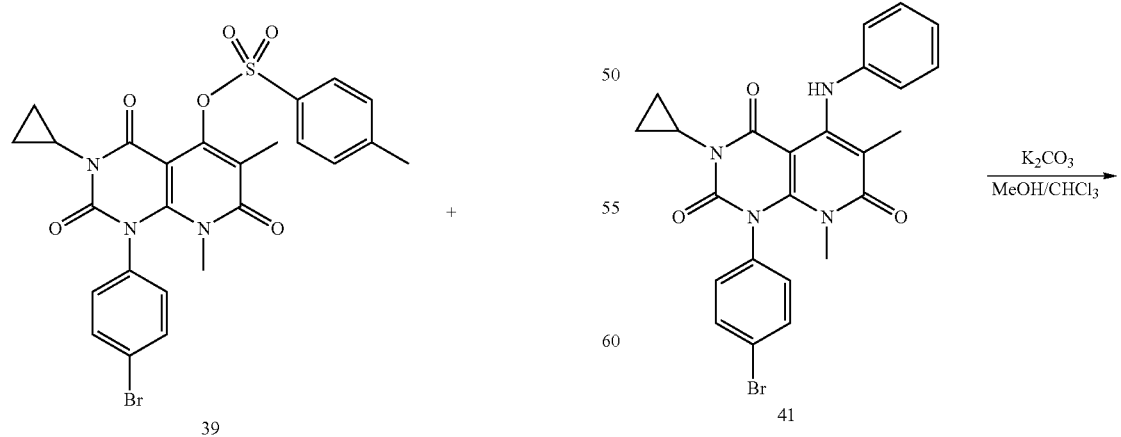

-continued

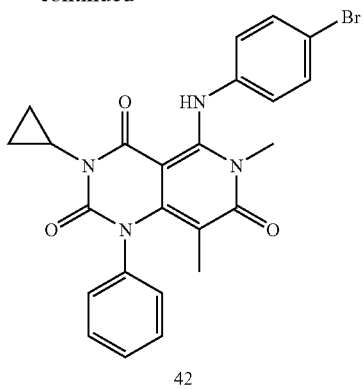

42

To 1-(4-bromo-phenyl)-3-cyclopropyl-6,8-dimethyl-5-phenylamino-1H,8H-pyrido[2,3-d]pyrimidine-2,4,7-trione 41 (78 mg) obtained in Step 7 was added chloroform-methanol [1:1 (volume ratio), 2.0 ml], potassium carbonate (22 mg) was added, and the mixture was stirred at room temperature for 10 hrs. The mixture was further stirred under reflux for 3 hrs, and allowed to cool to room temperature. The mixture was concentrated under reduced pressure and purified by column chromatography (chloroform:acetone=50:1) to give 5-(4-bromo-phenylamino)-3-cyclopropyl-6,8-dimethyl-1-phenylamino-1H,6H-pyrido[4,3-d]pyrimidine-2,4,7-trione 42 (23' mg, yield 26%) as colorless crystals.

MS ESI m/e: 493, 495 (M+H), 491, 493 (M−H).

$^1$H-NMR (CDCl$_3$, 400 MHz) δ 0.77-0.82 (m, 2H), 1.09-1.15 (m, 2H), 1.36 (s, 3H), 2.72-2.74 (m, 1H), 3.20 (s, 3H), 6.86 (d, 2H), 7.28-7.32 (m, 2H), 7.34-7.51 (m, 5H), 11.36 (s, 1H).

Example 3-7

Synthesis of N-{3-[3-cyclopropyl-5-(2-fluoro-4-iodophenylamino)-6,8-dimethyl-2,4,7-trioxo-3,4,6,7-tetrahydro-2H-pyrido[4,3-d]pyrimidin-1-yl]phenyl}methanesulfonamide Step 1 Synthesis of N-{3-[3-cyclopropyl-1-(2-fluoro-4-iodophenyl)-6,8-dimethyl-2,4,7-trioxo-1,2,3,4,7,8-hexahydro-pyrido[2,3-d]pyrimidin-5-ylamino]phenyl}methanesulfonamide

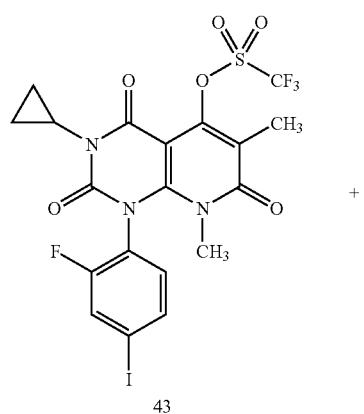

43

-continued

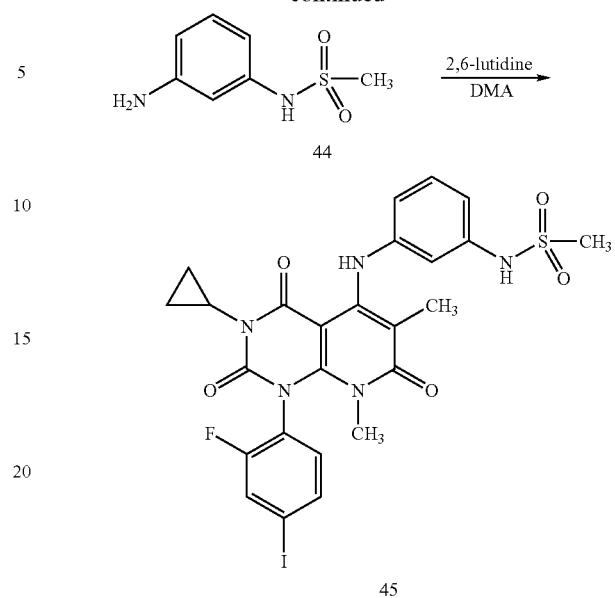

44

45

To trifluoromethanesulfonic acid 3-cyclopropyl-1-(2-fluoro-4-iodophenyl)-6,8-dimethyl-2,4,7-trioxo-1,2,3,4,7,8-hexahydro-pyrido[2,3-d]pyrimidin-5-yl ester 43 (30.0 g) obtained in the same manner in Example 4-2, Step 6 to be mentioned later and N-(3-aminophenyl)methanesulfonamide 44 (10.9 g) were added N,N-dimethylacetamide (60.0 ml) and 2,6-lutidine (6.82 ml), and the mixture was stirred at 130° C. for 3.5 hrs. After allowing to cool to room temperature, methanol (60 ml) was added with stirring and the mixture was stirred for 2 hrs. The crystals were collected by filtration and dried to give N-{3-[3-cyclopropyl-1-(2-fluoro-4-iodophenyl)-6,8-dimethyl-2,4,7-trioxo-1,2,3,4,7,8-hexahydro-pyrido[2,3-d]pyrimidin-5-ylamino]phenyl}methanesulfonamide 45 (30.5 g, yield 96%) as colorless crystals.

Step 2 Synthesis of N-{3-[3-cyclopropyl-5-(2-fluoro-4-iodophenylamino)-6,8-dimethyl-2,4,7-trioxo-3,4,6,7-tetrahydro-2H-pyrido[4,3-d]pyrimidin-1-yl]phenyl}methanesulfonamide

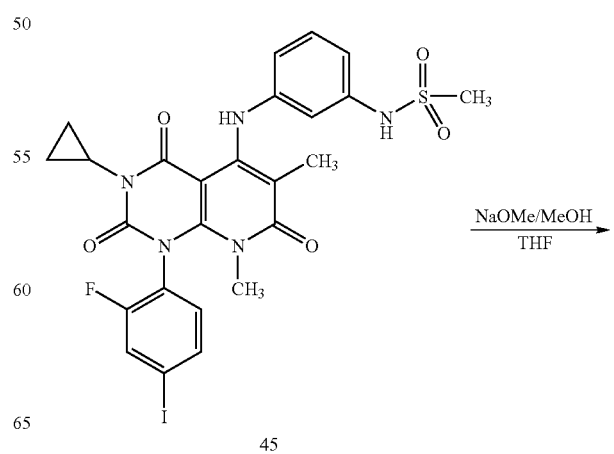

45

-continued

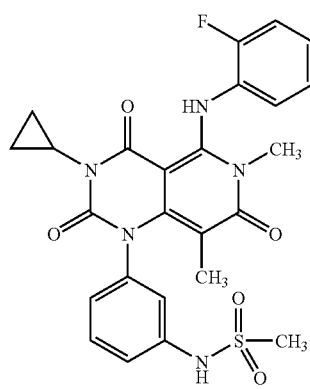

46

Under a nitrogen atmosphere, to a solution (18.5 g) of 28% sodium methoxide in methanol was added tetrahydrofuran (284 ml), N-{3-[3-cyclopropyl-1-(2-fluoro-4-iodophenyl)-6,8-dimethyl-2,4,7-trioxo-1,2,3,4,7,8-hexahydro-pyrido[2,3-d]pyrimidin-5-ylamino]phenyl}methanesulfonamide 45 (28.4 g) obtained in Step 1 was added, and the mixture was stirred at room temperature for 1 hr. Acetic acid (12.5 ml) was added, and the mixture was stirred at room temperature for 1 hr and concentrated under reduced pressure. A 9:1 mixed solvent (426 mL) of 1-butanol and water was added to the obtained solid, and the mixture was stirred with heating under reflux for 3 hrs. The mixture was allowed to return to room temperature and stirred overnight, and the crystals were collected by filtration and dried. A 9:1 mixed solvent (426 mL) of 1-butanol and water was added again to the obtained crystals, and the mixture was stirred with heating under reflux for 3 hrs. The mixture was allowed to return to room temperature and stirred overnight. The crystals were collected by filtration and washed with a 9:1 mixed solvent of methanol and water and dried to give N-{3-[3-cyclopropyl-5-(2-fluoro-4-iodophenylamino)-6,8-dimethyl-2,4,7-trioxo-3,4,6,7-tetrahydro-2H-pyrido[4,3-d]pyrimidin-1-yl]phenyl}methanesulfonamide 46 (26.35 g, yield 93%) as white crystals.

MS ESI m/e: 652 (M+H), 650 (M−H).

$^1$H-NMR(DMSO-d$_6$, 300 MHz)δ 0.62-0.72(m, 2H), 0.91-1.01(m, 2H), 1.25(s, 3H), 2.57-2.67(m, 1H), 3.01(s, 3H), 3.08(s, 3H), 6.92(t, J=9.0 Hz, 1H), 7.09-7.14(m, 1H), 7.20-7.26(m, 2H), 7.37-7.45(m, 1H), 7.52-7.58(m, 1H), 7.79(dd, J=1.8, 9.0 Hz, 1H), 9.89(s, 1H), 11.08(s, 1H).

Example 3-2 to 3-6,3-8 and 3-9

In the same manner as in Examples 3-1 and 3-7, the compounds of Examples 3-2 to 3-6,3-8 and 3-9 were obtained. The structural formulas thereof are shown in Table 3-1 to 3-2 with Examples 3-1 and 3-7.

TABLE 3-1

| Ex. No. | structural formula |
|---|---|
| 3-1 | 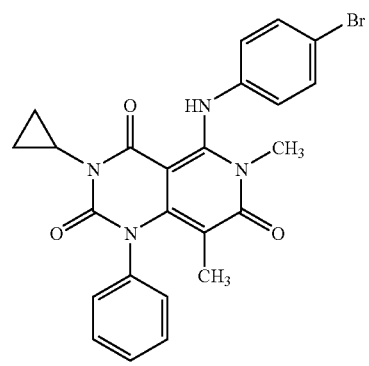 |
| 3-2 | 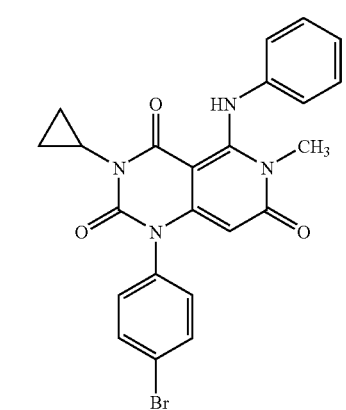 |
| 3-3 | 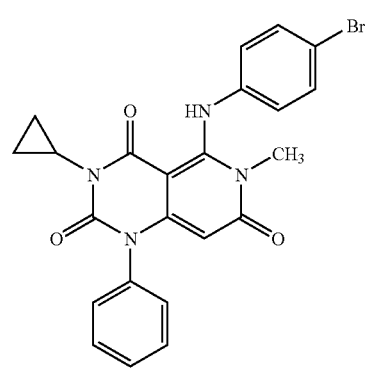 |
| 3-4 | 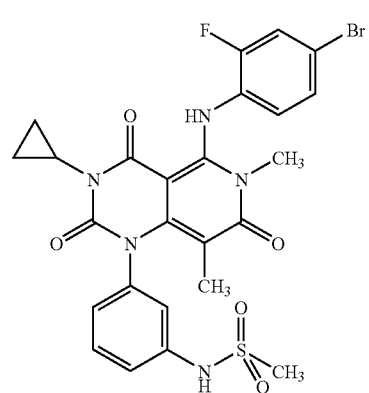 |

TABLE 3-1-continued

| Ex. No. | structural formula |
|---|---|
| 3-5 | (structure) |
| 3-6 | (structure) |

TABLE 3-2

| Ex. No. | structural formula |
|---|---|
| 3-7 | (structure) |
| 3-8 | (structure) |
| 3-9 | (structure) |

Example 3-10

By treating N-{3-[3-cyclopropyl-5-(2-fluoro-4-iodophenylamino)-6,8-dimethyl-2,4,7-trioxo-3,4,6,7-tetrahydro-2H-pyrido[4,3-d]pyrimidin-1-yl]phenyl}methanesulfonamide 46 according to conventional methods, sodium salt and potassium salt thereof were obtained.

N-{3-[3-cyclopropyl-5-(2-fluoro-4-iodophenylamino)-6,8-dimethyl-2,4,7-trioxo-3,4,6,7-tetrahydro-2H-pyrido[4,3-d]pyrimidin-1-yl]phenyl}methanesulfonamide sodium salt:

$^1$H-NMR (DMSO-$d_6$, 300 MHz) δ 0.47(brs, 2H), 0.70-0.90(m, 2H), 1.23(s, 3H), 2.35(brs, 1H), 2.82(s, 3H), 3.22(s, 3H), 6.69(t, J=8.8 Hz, 1H), 6.81(d, J=8.1 Hz, 1H), 6.98(s, 1H), 7.02(d, J=8.8 Hz, 1H), 7.10-7.30(m, 2H), 7.38(d, J=9.2 Hz, 1H), 10.22(brs, 1H).

MS (ESI) m/z 652 [MH]$^+$.

N-{3-[3-cyclopropyl-5-(2-fluoro-4-iodophenylamino)-6,8-dimethyl-2,4,7-trioxo-3,4,6,7-tetrahydro-2H-pyrido[4,3-d]pyrimidin-1-yl]phenyl}methanesulfonamide potassium salt:

Example 4-1

N-{3-[3-cyclopropyl-5-(2-fluoro-4-iodophenylamino)-6,8-dimethyl-2,4,7-trioxo-3,4,6,7-tetrahydro-2H-pyrido[4,3-d]pyrimidin-1-yl]-phenyl}-acetamide Step 1 Synthesis of 1-cyclopropyl-3-(2-fluoro-4-iodo-phenyl)urea

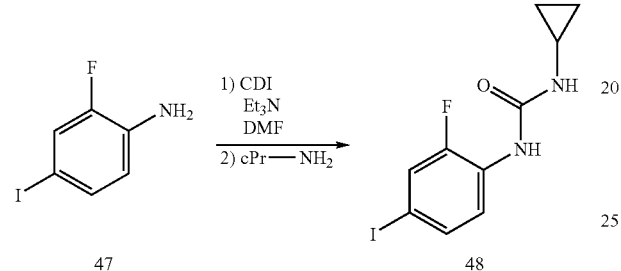

Under a nitrogen atmosphere, to N,N-carbonyldiimidazole (39.9 g) were added N,N-dimethylformamide (200 ml) and triethylamine (34.3 ml) and a solution of 2-fluoro-4-iodoaniline 47 (48.5 g) in N,N-dimethylformamide (50 ml) was added dropwise with stirring under ice-cooling. After the completion of the dropwise addition, the mixture was stirred at room temperature for 18 hrs. The reaction mixture was ice-cooled, and cyclopropylamine (21.3 ml) was added dropwise. The reaction mixture was stirred at room temperature for 1 hr and added dropwise to water-toluene [2:1 (volume ratio), 750 ml] with stirring. The precipitated crystals were collected by filtration and dried to give 1-cyclopropyl-3-(2-fluoro-4-iodophenyl)urea 48 (61.3 g, yield 93.4%) as colorless crystals.

Step 2 Synthesis of 1-cyclopropyl-3-(2-fluoro-4-iodophenyl)pyrimidine-2,4,6-trione

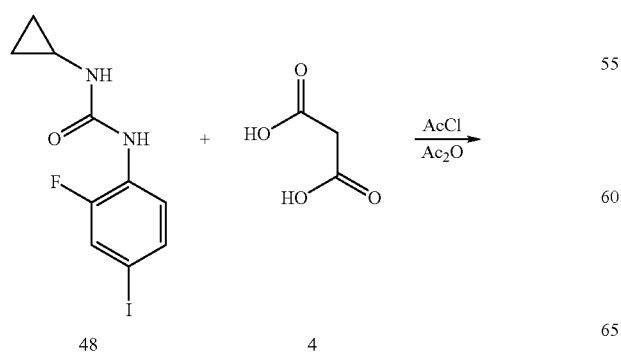

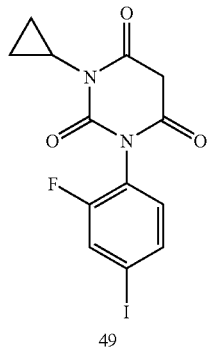

To 1-cyclopropyl-3-(2-fluoro-4-iodophenyl)urea 48 (61.0 g) obtained in Step 1 and malonic acid 4 (19.9 g) were added acetic anhydride (300 ml) and acetyl chloride (27.2 ml), and the mixture was stirred under a nitrogen atmosphere at 60° C. for 3 hrs. After allowing to cool to room temperature, the reaction mixture was added dropwise to water-toluene [2:1 (volume ratio), 900 ml] with stirring. The precipitated crystals were collected by filtration and dried to give 1-cyclopropyl-3-(2-fluoro-4-iodophenyl)pyrimidine-2,4,6-trione 49 (60.9 g, yield 82%) as pale-yellow crystals.

Step 3 Synthesis of 6-chloro-3-cyclopropyl-1-(2-fluoro-4-iodophenyl)-1H-pyrimidine-2,4-dione

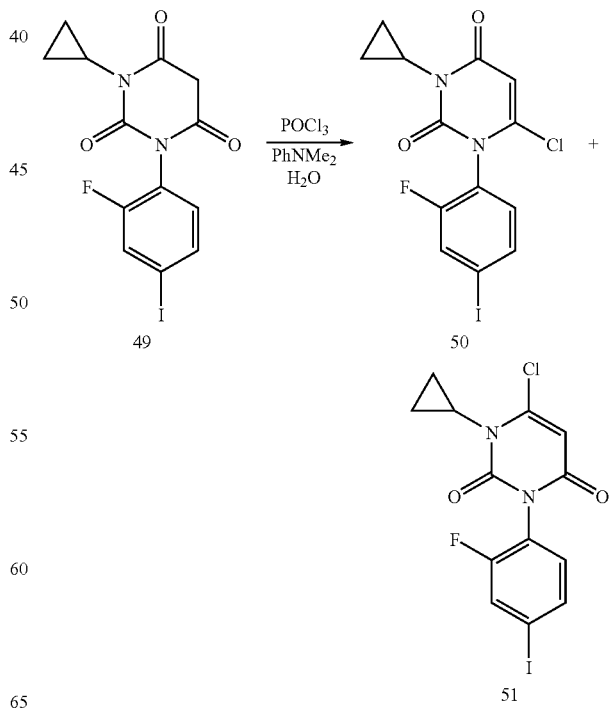

To 1-cyclopropyl-3-(2-fluoro-4-iodophenyl)-pyrimidine-2,4,6-trione 49 (59.0 g) obtained in Step 2 were added phosphorus oxychloride (85.0 ml) and dimethylaniline (29.0 ml), and water (8.3 ml) was added dropwise to the mixture at room temperature with stirring. After the completion of the dropwise addition, the mixture was stirred with heating at 110° C. for 1 hr. After allowing to cool to room temperature, the reaction mixture was added dropwise to ice water-toluene [2:1 (volume ratio), 900 ml] with stirring. The mixture was stirred at room temperature for 1 hr. The organic layer was separated, and washed successively with water (300 ml) and brine (300 ml). Anhydrous magnesium sulfate and activated carbon were added and the mixture was stirred. Anhydrous magnesium sulfate and activated carbon were filtered off, and the filtrate was concentrated under reduced pressure to give a 1:2 mixture (62.9 g) of 6-chloro-3-cyclopropyl-1-(2-fluoro-4-iodophenyl)-1H-pyrimidine-2,4-dione 50 and 6-chloro-1-cyclopropyl-3-(2-fluoro-4-iodophenyl)-1H-pyrimidine-2,4-dione 51 as a yellow foamy oil, which was used for the next step without purification.

Step 4 Synthesis of 3-cyclopropyl-1-(2-fluoro-4-iodophenyl)-6-methylamino-1H-pyrimidine-2,4-dione To a 1:2 mixture (62.9 g) of 6-chloro-3-cyclopropyl-1-(2-fluoro-4-iodophenyl)-1H-pyrimidine-2,4-dione 50 and 6-chloro-1-cyclopropyl-3-(2-fluoro-4-iodophenyl)-1H-pyrimidine-2,4-dione 51 obtained in Step 3 were added methanol (189 ml) and a solution (126 ml) of 40% methylamine in methanol, and the mixture was stirred at room temperature for 2 hrs. The precipitated crystals were filtered off and the filtrate was concentrated under reduced pressure. The residue was extracted with chloroform (200 ml) and water (200 ml), and the organic layer was washed with brine (200 ml) and dried over anhydrous magnesium sulfate. Anhydrous magnesium sulfate was filtered off and the filtrate was concentrated under reduced pressure to give a 2:1 mixture (34.55 g) of 3-cyclopropyl-1-(2-fluoro-4-iodophenyl)-6-methylamino-1H-pyrimidine-2,4-dione 52 and 1-cyclopropyl-3-(2-fluoro-4-iodophenyl)-6-methylamino-1H-pyrimidine-2,4-dione 53 as yellow crystals, which were used for the next step without purification.

Step 5 Synthesis of 3-cyclopropyl-1-(2-fluoro-4-iodophenyl)-5-hydroxy-6,8-dimethyl-1H,8H-pyrido[2,3-d]pyrimidine-2,4,7-trione

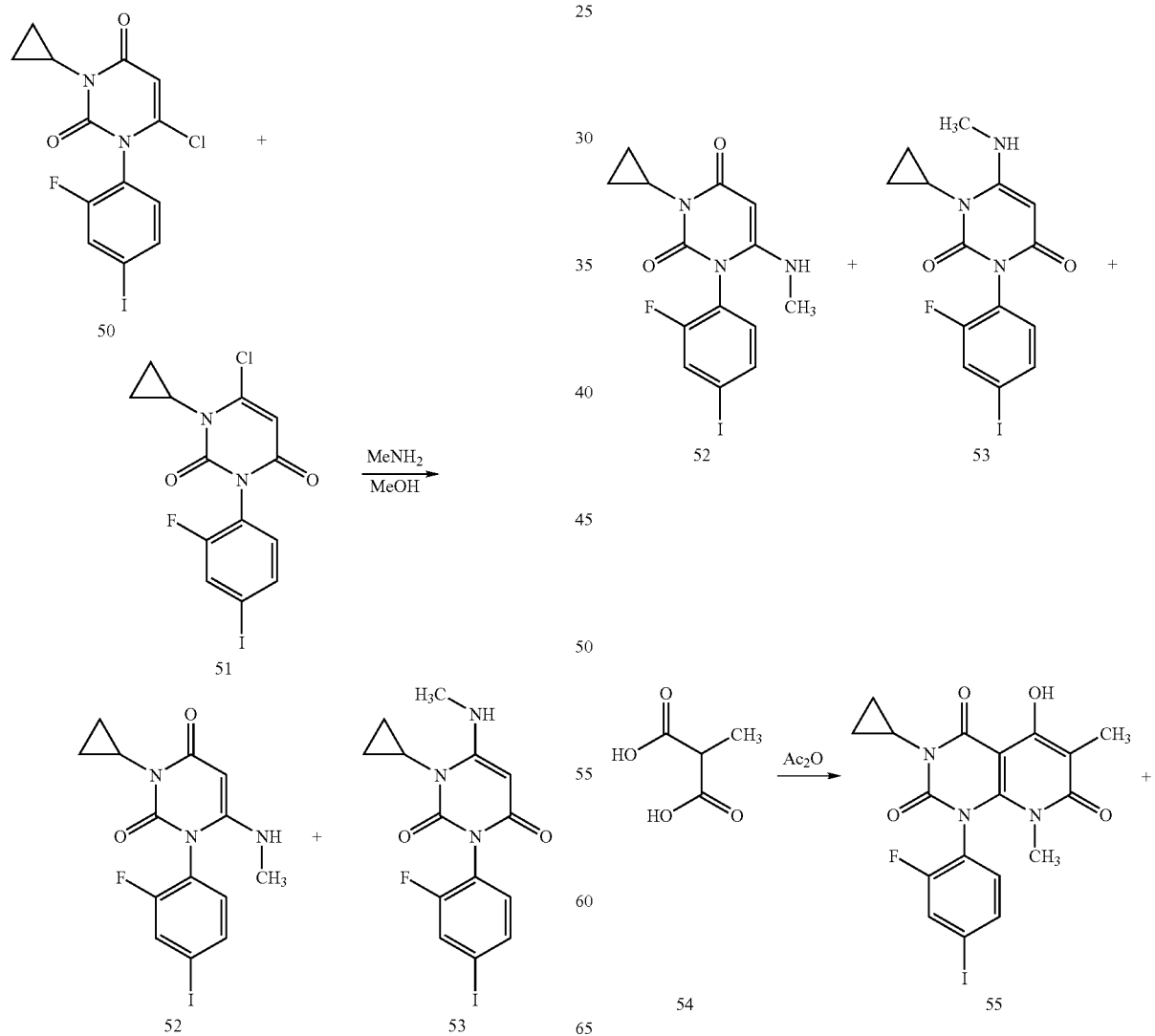

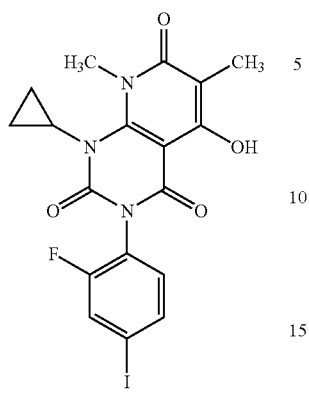

To a 2:1 mixture (34.6 g) of 3-cyclopropyl-1-(2-fluoro-4-iodophenyl)-6-methylamino-1H-pyrimidine-2,4-dione 52 and 1-cyclopropyl-3-(2-fluoro-4-iodo-phenyl)6-methylamino-1H-pyrimidine-2,4-dione 53 obtained in Step 4, and 2-methylmalonic acid 54 (10.2 g) was added acetic anhydride (173 ml), and the mixture was stirred at 100° C. for 2 hrs. After allowing to cool to room temperature, the reaction mixture was concentrated under reduced pressure. Acetone (104 ml) was added to the residue, and the mixture was stirred with heating under reflux for 30 min. After allowing to cool to room temperature, the precipitated crystals were collected by filtration and dried to give 3-cyclopropyl-1-(2-fluoro-4-iodophenyl)-5-hydroxy-6,8-dimethyl-1H,8H-pyrido[2,3-d]pyrimidine-2,4,7-trione 55 (15.1 g, yield from 48, 21%) as colorless crystals.

Step 6 Synthesis of trifluoromethanesulfonic acid 3-cyclopropyl-1-(2-fluoro-4-iodophenyl)-6,8-dimethyl-2,4,7-trioxo-1,2,3,4,7,8-hexahydro-pyrido[2,3-d]pyrimidin-5-yl ester

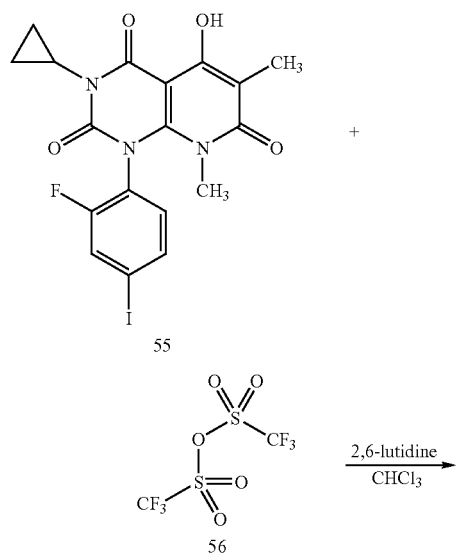

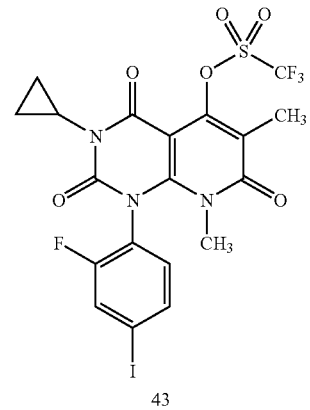

Under a nitrogen atmosphere, to 3-cyclopropyl-1-(2-fluoro-4-iodophenyl)-5-hydroxy-6,8-dimethyl-1H,8H-pyrido[2,3-d]pyrimidine-2,4,7-trione 55 (33.0 g) obtained in Step 5 were added chloroform (165 ml) and 2,6-lutidine (10.4 ml), and trifluoromethanesulfonic anhydride 56 (14.4 ml) was added dropwise under ice-cooling with stirring. After the completion of the dropwise addition, the mixture was stirred at same temperature for 30 min and at room temperature for 2 hrs. The reaction mixture was washed successively with aqueous sodium hydrogen carbonate (165 ml), 1N hydrochloric acid (165 ml) and brine (165 ml) and dried over anhydrous magnesium sulfate. Anhydrous magnesium sulfate was filtered off and the filtrate was concentrated under reduced pressure. 2-Propanol (198 ml) was added to the residue, and the mixture was stirred with heating under reflux, and allowed to return to room temperature. The crystals were collected by filtration and dried to give trifluoromethanesulfonic acid 3-cyclopropyl-1-(2-fluoro-4-iodophenyl)-6,8-dimethyl-2,4,7-trioxo-1,2,3,4,7,8-hexahydro-pyrido[2,3-d]pyrimidin-5-yl ester 43 (31.9 g, yield 93%) as colorless crystals.

Step 7 Synthesis of N-{3-[3-cyclopropyl-1-(2-fluoro-4-iodophenyl)-6,8-dimethyl-2,4,7-trioxo-1,2,3,4,7,8-hexahydro-pyrido[2,3-d]pyrimidin-5-ylamino]phenyl}acetamide

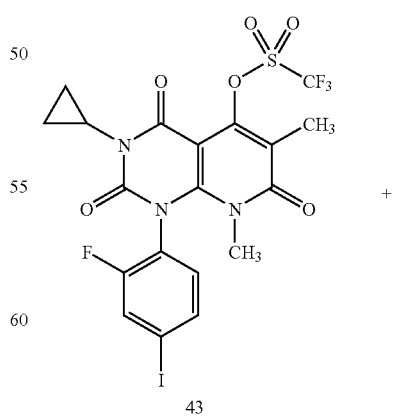

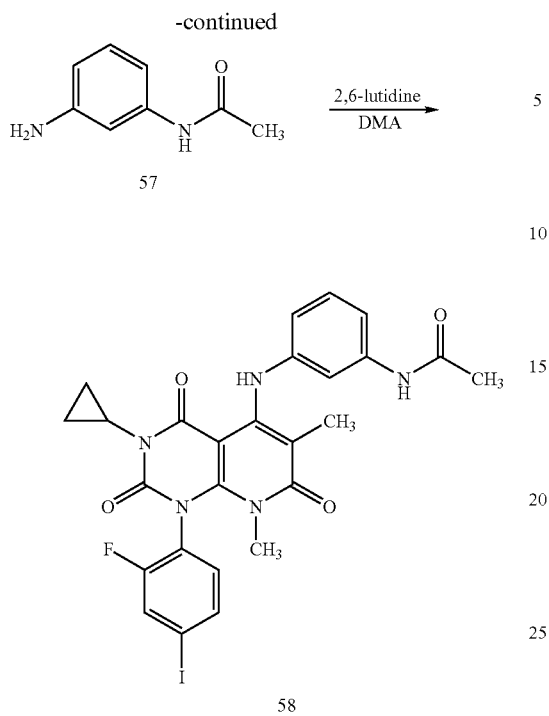

To trifluoromethanesulfonic acid 3-cyclopropyl-1-(2-fluoro-4-iodophenyl)-6,8-dimethyl-2,4,7-trioxo-1,2,3,4,7,8-hexahydro-pyrido[2,3-d]pyrimidin-5-yl ester 43 (25.0 g) obtained in Step 6 and 3'-aminoacetanilide 57 (7.33 g) were added N,N-dimethylacetamide (50.0 ml) and 2,6-lutidine (5.68 ml), and the mixture was stirred at 130° C. for 5 hrs. After allowing to cool to room temperature, methanol-water [1:2 (volume ratio), 150 ml] was added with stirring. The crystals were collected by filtration and dried to give N-{3-[3-cyclopropyl-1-(2-fluoro-4-iodophenyl)-6,8-dimethyl-2,4,7-trioxo-1,2,3,4,7,8-hexahydro-pyrido[2,3-d]pyrimidin-5-ylamino]phenyl}acetamide 58 (24.8 g, yield 99%) as colorless crystals.

Step 8 Synthesis of N-{3-[3-cyclopropyl-5-(2-fluoro-4-iodophenylamino)-6,8-dimethyl-2,4,7-trioxo-3,4,6,7-tetrahydro-2H-pyrido[4,3-d]pyrimidin-1-yl]phenyl}acetamide

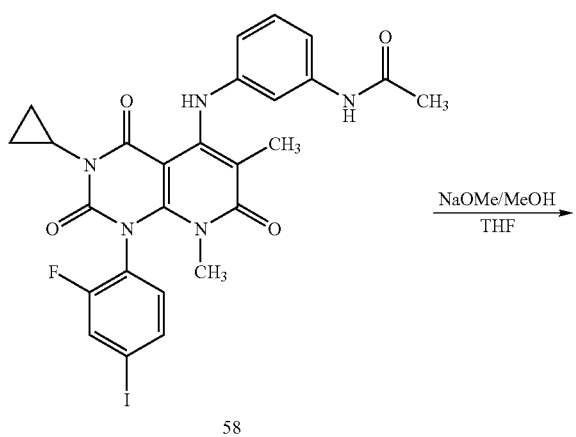

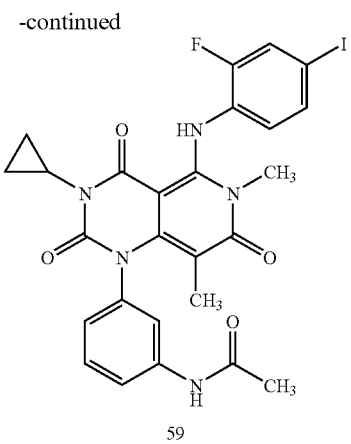

Under a nitrogen atmosphere, to a solution (1.57 g) of 28% sodium methoxide in methanol was added tetrahydrofuran (40 ml), N-{3-[3-cyclopropyl-1-(2-fluoro-4-iodophenyl)-6,8-dimethyl-2,4,7-trioxo-1,2,3,4,7,8-hexahydro-pyrido[2,3-d]pyrimidin-5-ylamino]phenyl}acetamide 58 (5.00 g) obtained in Step 7 was added, and the mixture was stirred at room temperature for 4 hrs. Acetic acid (0.56 ml) was added, and the mixture was stirred at room temperature for 30 min. Water (40 ml) was added and the mixture was further stirred for 1 hr. The crystals were collected by filtration and dried to give N-{3-[3-cyclopropyl-5-(2-fluoro-4-iodophenylamino)-6,8-dimethyl-2,4,7-trioxo-3,4,6,7-tetrahydro-2H-pyrido[4,3-d]pyrimidin-1-yl]phenyl}acetamide 59 (4.75 g, yield 95%) as colorless crystals.

MS ESI m/e: 616 (M+H), 614 (M−H).

$^1$H-NMR(DMSO-$d_6$, 400 MHz) δ 0.63-0.70(m, 2H), 0.91-1.00(m, 2H), 1.25(s, 3H), 2.04(s, 3H), 2.58-2.66(m, 1H), 3.07(s, 3H), 6.92(t, J=8.8 Hz, 1H), 7.00-7.05(m, 1H), 7.36(t, J=8.2 Hz, 1H), 7.52-7.63(m, 3H), 7.79(dd, J=2.0, 10.4 Hz, 1H), 10.10(s, 1H), 11.08(s, 1H).

Example 4-1

Alternative Method

N-{3-[3-cyclopropyl-5-(2-fluoro-4-iodophenylamino)-6,8-dimethyl-2,4,7-trioxo-3,4,6,7-tetrahydro-2H-pyrido[4,3-d]pyrimidin-1-yl]-phenyl}-acetamide Step 1 Synthesis of 1-cyclopropyl-3-(2-fluoro-4-iodo-phenyl)-urea

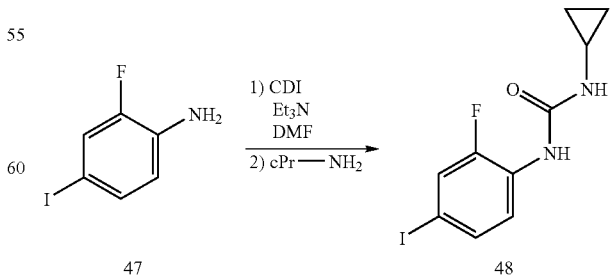

Under a nitrogen atmosphere, to N,N-carbonyldiimidazole (82.1 g) were added N,N-dimethylformamide (400 ml) and triethylamine (70.5 ml), and a solution of 2-fluoro-4-iodoaniline 47 (100 g) in N,N-dimethylformamide (100 ml) was added dropwise under ice-cooling. After the completion of the dropwise addition, the mixture was stirred at room temperature for 5 hrs. The reaction mixture was ice-cooled, and cyclopropylamine (44.0 ml) was added dropwise. The mixture was stirred at room temperature for 1 hr, and the reaction mixture was added dropwise to water-toluene [2:1 (volume ratio), 1500 ml] with stirring. The precipitated crystals were collected by filtration and dried to give 1-cyclopropyl-3-(2-fluoro-4-iodo-phenyl)-urea 48 (129 g, yield 95.5%) as colorless crystals.

Step 2 Synthesis of 1-(2-cyano-acetyl)-1-cyclopropyl-3-(2-fluoro-4-iodo-phenyl)-urea and methanesulfonyl chloride (72.8 ml) was added dropwise with stirring at room temperature. The mixture was stirred at room temperature for 4 hrs. The reaction mixture was cooled with water, and water-isopropanol [2:1 (volume ratio), 1670 ml] was added dropwise. The mixture was stirred under water-cooling for 1 hr, and the precipitated crystals were collected by filtration and dried to give 1-(2-cyano-acetyl)-1-cyclopropyl-3-(2-fluoro-4-iodo-phenyl)-urea 74 (192 g).

Step 3 Synthesis of 6-amino-3-cyclopropyl-1-(2-fluoro-4-iodo-phenyl)-1H-pyrimidine-2,4-dione

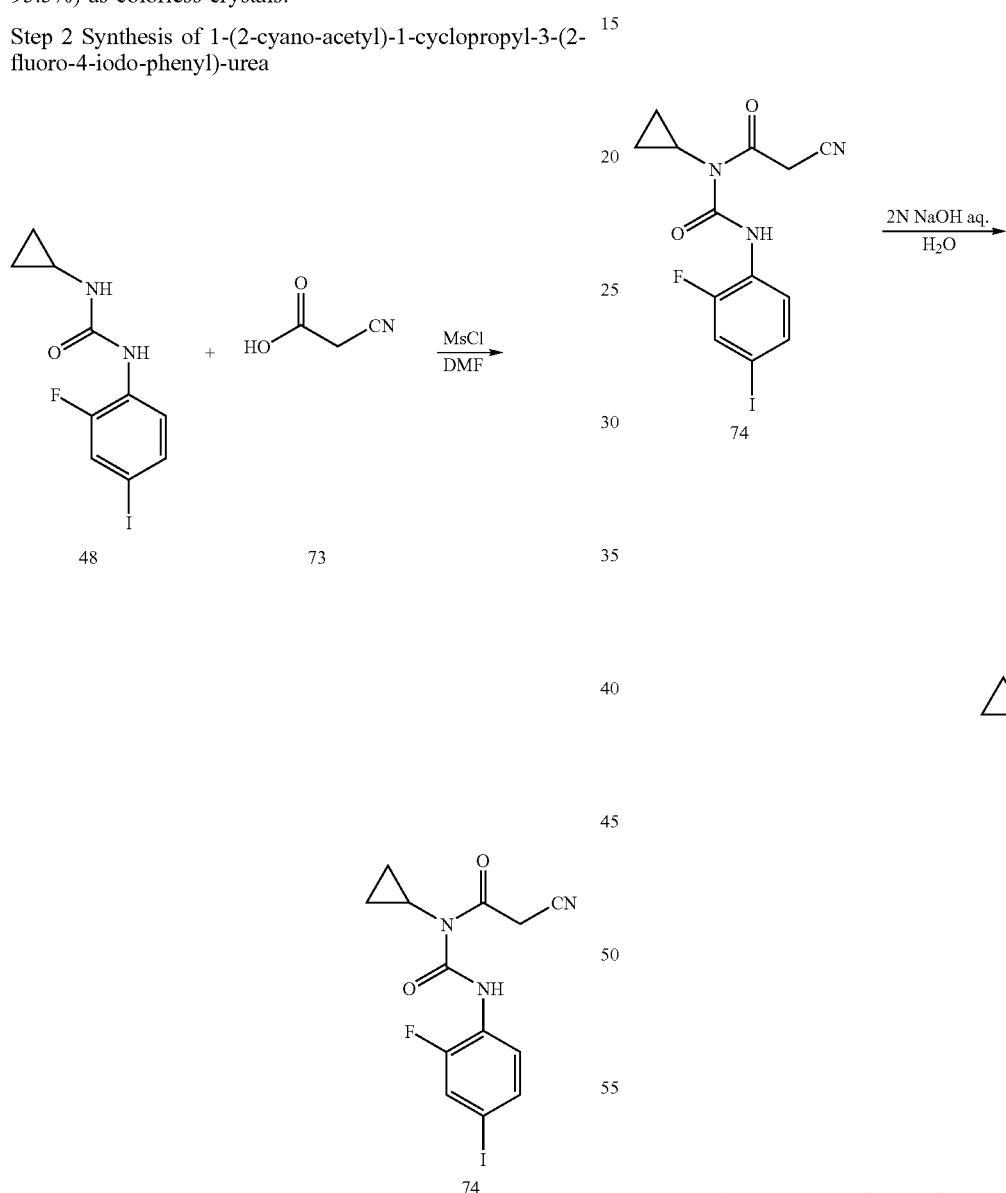

Under a nitrogen atmosphere, to 1-cyclopropyl-3-(2-fluoro-4-iodo-phenyl)-urea 48 (167 g) and cyanoacetic acid 73 (80.0 g), was added N,N-dimethylformamide (836 ml), To 1-(2-cyano-acetyl)-1-cyclopropyl-3-(2-fluoro-4-iodo-phenyl)-urea 74 (192 g) were added water (962 ml) and 2N aqueous sodium hydroxide solution (24.9 ml), and the mixture was stirred with heating at 80° C. for 1 hr. After allowing to cool to room temperature, the crystals were collected by filtration and dried to give 6-amino-3-cyclopropyl-1-(2-fluoro-4-iodo-phenyl)-1H-pyrimidine-2,4-dione 75 (178 g, yield from 48, 88%) as pale-yellow crystals.

Step 4 Synthesis of N'-[1-cyclopropyl-3-(2-fluoro-4-iodo-phenyl)-2,6-dioxo-1,2,3,6-tetrahydro-pyrimidin-4-yl]-N,N-dimethyl-formamidine

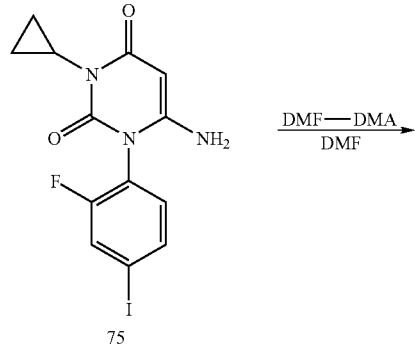

75

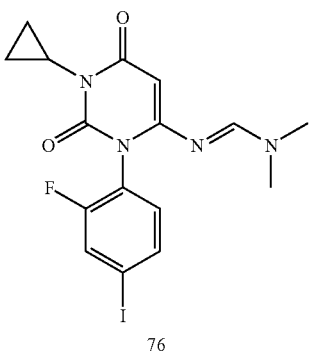

76

Under a nitrogen atmosphere, to 6-amino-3-cyclopropyl-1-(2-fluoro-4-iodo-phenyl)-1H-pyrimidine-2,4-dione 75 (178 g) were added N,N-dimethylformamide (356 ml) and N,N-dimethylformamide dimethylacetal (178 ml), and the mixture was stirred at room temperature for 2 hrs. Isopropanol (178 ml) was added with stirring at room temperature, and water (1068 ml) was added dropwise. The mixture was stirred at room temperature for 2 hrs, and the precipitated crystals were collected by filtration and dried to give N'-[1-cyclopropyl-3-(2-fluoro-4-iodo-phenyl)-2,6-dioxo-1,2,3,6-tetrahydro-pyrimidin-4-yl]-N,N-dimethyl-formamidine 76 (188 g, yield 92%) as yellow crystals.

Step 5 Synthesis of 3-cyclopropyl-1-(2-fluoro-4-iodo-phenyl)-6-methylamino-1H-pyrimidine-2,4-dione

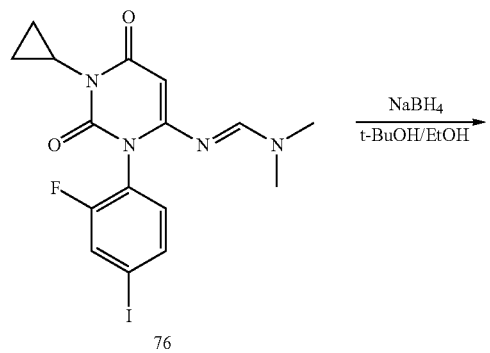

76

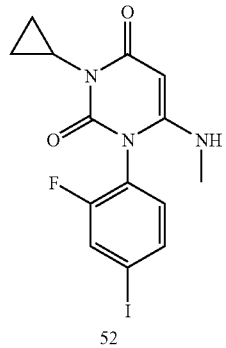

52

Under a nitrogen atmosphere, to t-butanol-ethanol [2:1 (volume ratio), 250 ml] was added sodium borohydride (6.41 g), and the mixture was stirred at room temperature for 1 hr. Under water-cooling, N'-[1-cyclopropyl-3-(2-fluoro-4-iodo-phenyl)-2,6-dioxo-1,2,3,6-tetrahydro-pyrimidin-4-yl]-N,N-dimethyl-formamidine 76 (50.0 g) was added, and the mixture was stirred for 2.5 hrs. Under water-cooling, water (225 ml) and 10% aqueous citric acid solution (175 ml) were successively added dropwise, and the mixture was stirred for 3 hrs. The precipitated crystals were collected by filtration and dried to give crude crystals (34.5 g, LC purity 91%) of 3-cyclopropyl-1-(2-fluoro-4-iodo-phenyl)-6-methylamino-1H-pyrimidine-2,4-dione 52, which were used for the next reaction without purification.

Step 6 Synthesis of 3-cyclopropyl-1-(2-fluoro-4-iodo-phenyl)-5-hydroxy-6,8-dimethyl-1H,8H-pyrido[2,3-d]pyrimidine-2,4,7-trione

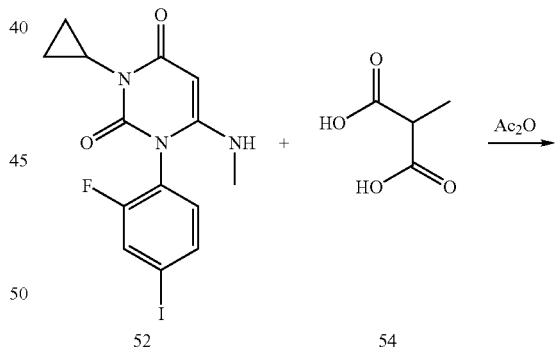

52                    54

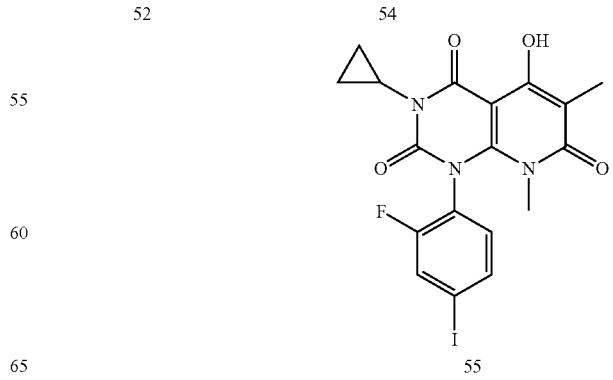

55

Under a nitrogen atmosphere, to 3-cyclopropyl-1-(2-fluoro-4-iodo-phenyl)-6-methylamino-1H-pyrimidine-2,4-dione 52 (34.4 g) and 2-methyl-malonic acid 54 (15.2 g) was added acetic anhydride (34.4 ml), and the mixture was stirred with heating at 100° C. for 3 hrs. After allowing to cool to 50° C., acetone (68.8 ml) was added dropwise, and the mixture was stirred as it was for 30 min. Water (172 ml) was further added dropwise, and the mixture was stirred for 1 hr. After allowing to cool to room temperature with stirring, the precipitated crystals were collected by filtration and dried to give crude crystals (37.7 g, LC purity 91%) of 3-cyclopropyl-1-(2-fluoro-4-iodo-phenyl)-5-hydroxy-6,8-dimethyl-1H,8H-pyrido[2,3-d]pyrimidine-2,4,7-trione 55. Isopropanol (92.0 ml) was added to the obtained crude crystals (30.7 g), and the mixture was stirred at room temperature for 4 hrs. The crystals were collected by filtration and dried to give 3-cyclopropyl-1-(2-fluoro-4-iodo-phenyl)-5-hydroxy-6,8-dimethyl-1H,8H-pyrido[2,3-d]pyrimidine-2,4,7-trione 55 (25.9 g, yield from 76, 58%) as pale-yellow crystals.

Step 7 Synthesis of p-toluenesulfonic acid 3-cyclopropyl-1-(2-fluoro-4-iodo-phenyl)-6,8-dimethyl-2,4,7-trioxo-1,2,3,4,7,8-hexahydro-pyrido[2,3-d]pyrimidin-5-yl ester

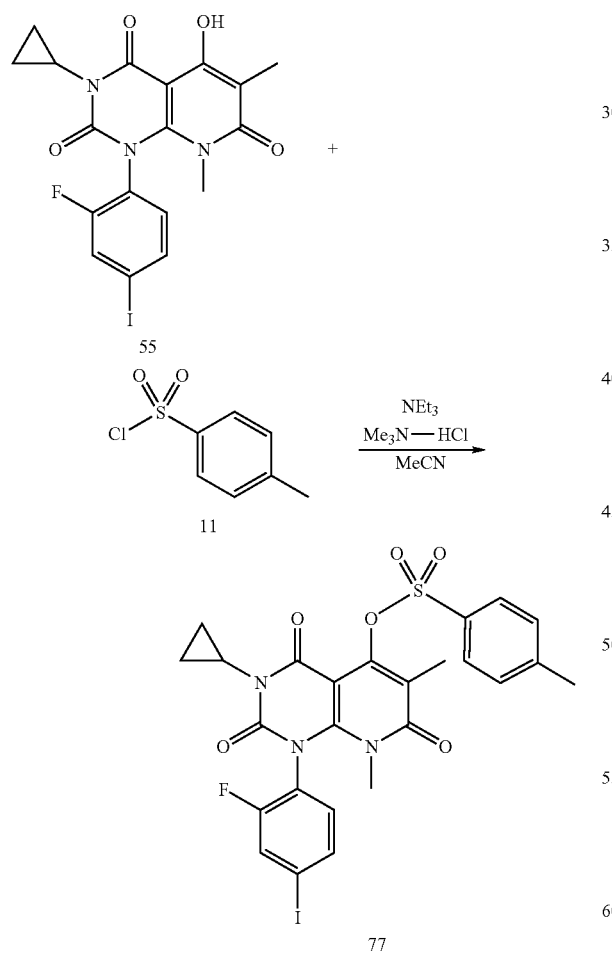

ice-cooling. Triethylamine (11.0 ml) and trimethylamine hydrochloride (2.37 g) were added, and a solution of p-toluenesulfonyl chloride 11 (12.3 g) in acetonitrile (72.0 ml) was added dropwise. The mixture was stirred under ice-cooling for 1 hr, and stirred at room temperature for 3 hrs. Methanol (239 ml) was added, and the mixture was stirred at room temperature for 1 hr. The crystals were collected by filtration and dried to give p-toluenesulfonic acid 3-cyclopropyl-1-(2-fluoro-4-iodo-phenyl)-6,8-dimethyl-2,4,7-trioxo-1,2,3,4,7,8-hexahydro-pyrido[2,3-d]pyrimidin-5-yl ester 77 (28.7 g, yield 91%) as colorless crystals.

Step 8 Synthesis of N-{3-[3-cyclopropyl-1-(2-fluoro-4-iodo-phenyl)-6,8-dimethyl-2,4,7-trioxo-1,2,3,4,7,8-hexahydro-pyrido[2,3-d]pyrimidin-5-ylamino]-phenyl}-acetamide

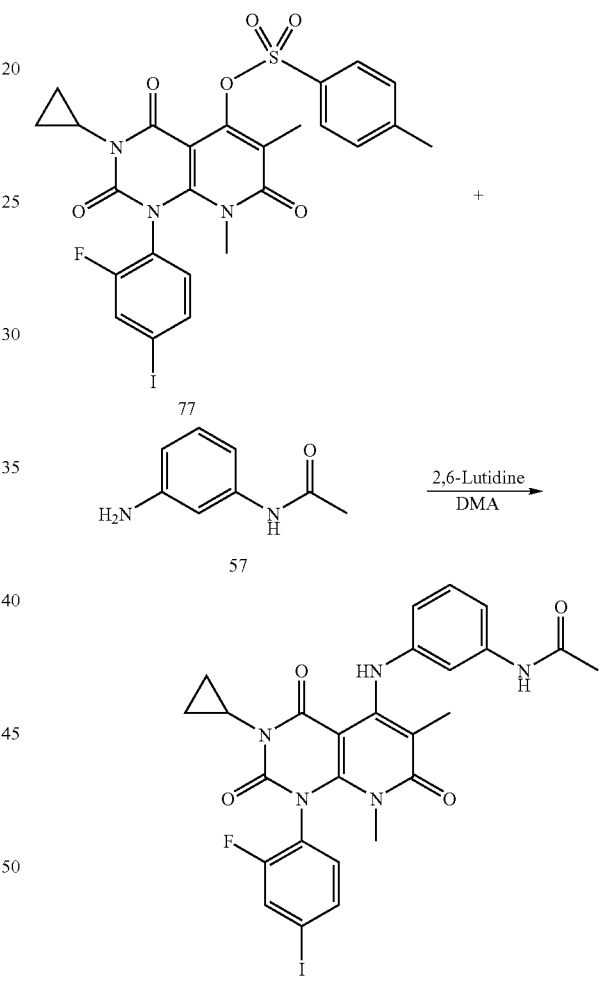

Under a nitrogen atmosphere, to 3-cyclopropyl-1-(2-fluoro-4-iodo-phenyl)-5-hydroxy-6,8-dimethyl-1H,8H-pyrido[2,3-d]pyrimidine-2,4,7-trione 55 (23.9 g) was added acetonitrile (167 ml), and the mixture was stirred under To p-toluenesulfonic acid 3-cyclopropyl-1-(2-fluoro-4-iodo-phenyl)-6,8-dimethyl-2,4,7-trioxo-1,2,3,4,7,8-hexahydro-pyrido[2,3-d]pyrimidin-5-yl ester 77 (28.0 g) and 3'-aminoacetanilide 57 (13.2 g) were added N,N-dimethylacetamide (84.0 ml) and 2,6-lutidine (15.3 ml), and the mixture was stirred at 130° C. for 4 hrs. After allowing to cool with stirring, methanol (196 ml) was added dropwise, and the mixture was stirred at room temperature. The crystals were collected by filtration and dried to give N-{3-[3-cyclopropyl-1-(2-fluoro-4-iodo-phenyl)-6,8-dimethyl-2, 4,7-trioxo-1,2,3,4,7,8-hexahydro-pyrido[2,3-d]pyrimidin-5-ylamino]-phenyl}-acetamide 58 (25.2 g, yield 93%) as colorless crystals.

Step 9 Synthesis of N-{3-[3-cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]-phenyl}-acetamide

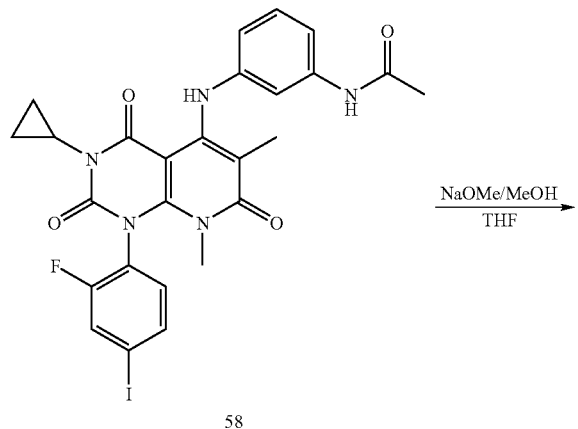

Under a nitrogen atmosphere, to N-{3-[3-cyclopropyl-1-(2-fluoro-4-iodo-phenyl)-6,8-dimethyl-2,4,7-trioxo-1,2,3,4,7,8-hexahydro-pyrido[2,3-d]pyrimidin-5-ylamino]-phenyl}-acetamide 58 (45.7 g) was added tetrahydrofuran (366 ml), and a solution (15.7 g) of 28% sodium methoxide in methanol was added dropwise with stirring at room temperature and the mixture was stirred at room temperature for 4 hrs. Acetic acid (5.61 ml) was added, and the mixture was stirred at room temperature for 30 min. With stirring at 70° C. in an oil bath, water (366 ml) was added dropwise, and the mixture was stirred for 1 hr. After allowing to cool with stirring, the crystals were collected by filtration and dried to give crystal 1 (46.0 g) of N-{3-[3-cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]-phenyl}-acetamide 59.

N,N-Dimethylacetamide (184 ml) was added to crystal 1 (46.0 g), and the mixture was stirred with heating at 130° C. After complete dissolution, the solution was filtered by suction using with paper (5B), and washed with N,N-dimethylacetamide (92.0 ml). The filtrate was stirred under heating at 130° C., 1-butanol (138 ml) and water (96.0 ml) were successively added dropwise, and the mixture was stirred for 30 min. Water (46.0 ml) was further added dropwise, and the mixture was stirred for 30 min allowed to cool with stirring. The crystals were collected by filtration and dried to give crystal 2 (41.7 g) of N-{3-[3-cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]-phenyl}-acetamide 59 as colorless crystals.

To crystal 2 (41.5 g) was added 1-butanol-water [19:1 (volume ratio), 415 ml], and the mixture was stirred at 130° C. for 18 hrs. After allowing to cool with stirring, the crystals were collected by filtration and dried to give N-{3-[3-cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]-phenyl}-acetamide 59 (40.7 g, yield 89%) as colorless crystals.

Example 4-3

N-{3-[3-cyclopropyl-5-(4-ethynyl-2-fluorophenylamino)-6,8-dimethyl-2,4,7-trioxo-3,4,6,7-tetrahydro-2H-pyrido[4,3-d]pyrimidin-1-yl] phenyl}acetamide Step 1 Synthesis of N-{3-[3-cyclopropyl-5-(2-fluoro-4-trimethylsilanylethynylphenylamino)-6,8-dimethyl-2,4,7-trioxo-3,4,6,7-tetrahydro-2H-pyrido[4,3-d]pyrimidin-1-yl] phenyl}acetamide

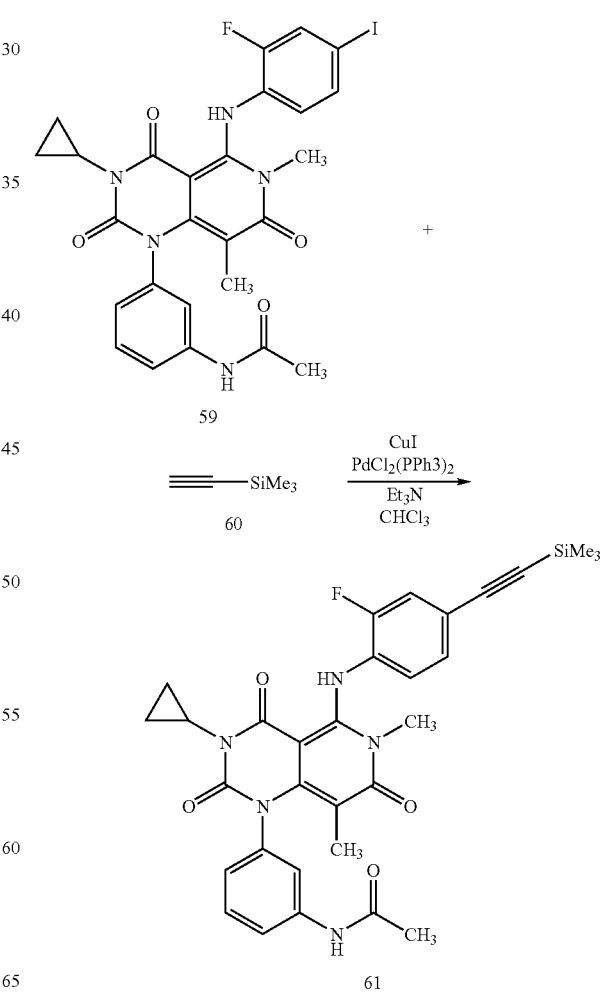

Under a nitrogen atmosphere, to N-{3-[3-cyclopropyl-5-(2-fluoro-4-iodophenylamino)-6,8-dimethyl-2,4,7-trioxo-3,4,6,7-tetrahydro-2H-pyrido[4,3-d]pyrimidin-1-yl]phenyl}acetamide 59 (14.5 g) obtained in Example 4-1 were added chloroform (145 ml), trimethylsilylacetylene 60 (4.99 ml) and triethylamine (13.1 ml). Copper(I) iodide (22 mg) and bis(triphenylphosphine)palladium(II)chloride (83 mg) were added, and the mixture was stirred at room temperature for 20 hrs. The mixture was concentrated under reduced pressure, activated carbon (435 mg) and methanol (435 ml) were added to the residue, and the mixture was stirred with heating at reflux for 2 hrs. Activated carbon was filtered off while it was hot, and the filtrate was concentrated under reduced pressure. The residue was purified by column chromatography (chloroform:acetone=10:1→4:1) and toluene-acetone [5:1 (volume ratio), 87 ml] was added to the obtained crystals. The mixture was stirred at 80° C. for 1 hr. After allowing to cool to room temperature, the crystals were collected by filtration and dried to give N-{3-[3-cyclopropyl-5-(2-fluoro-4-trimethylsilanylethynylphenylamino)-6,8-dimethyl-2,4,7-trioxo-3,4,6,7-tetrahydro-2H-pyrido[4,3-d]pyrimidin-1-yl]phenyl}acetamide 61 (12.9 g, yield 93%) as pale-yellow crystals.

Step 2 Synthesis of N-{3-[3-cyclopropyl-5-(4-ethynyl-2-fluorophenylamino)-6,8-dimethyl-2,4,7-trioxo-3,4,6,7-tetrahydro-2H-pyrido[4,3-d]pyrimidin-1-yl]phenyl}acetamide

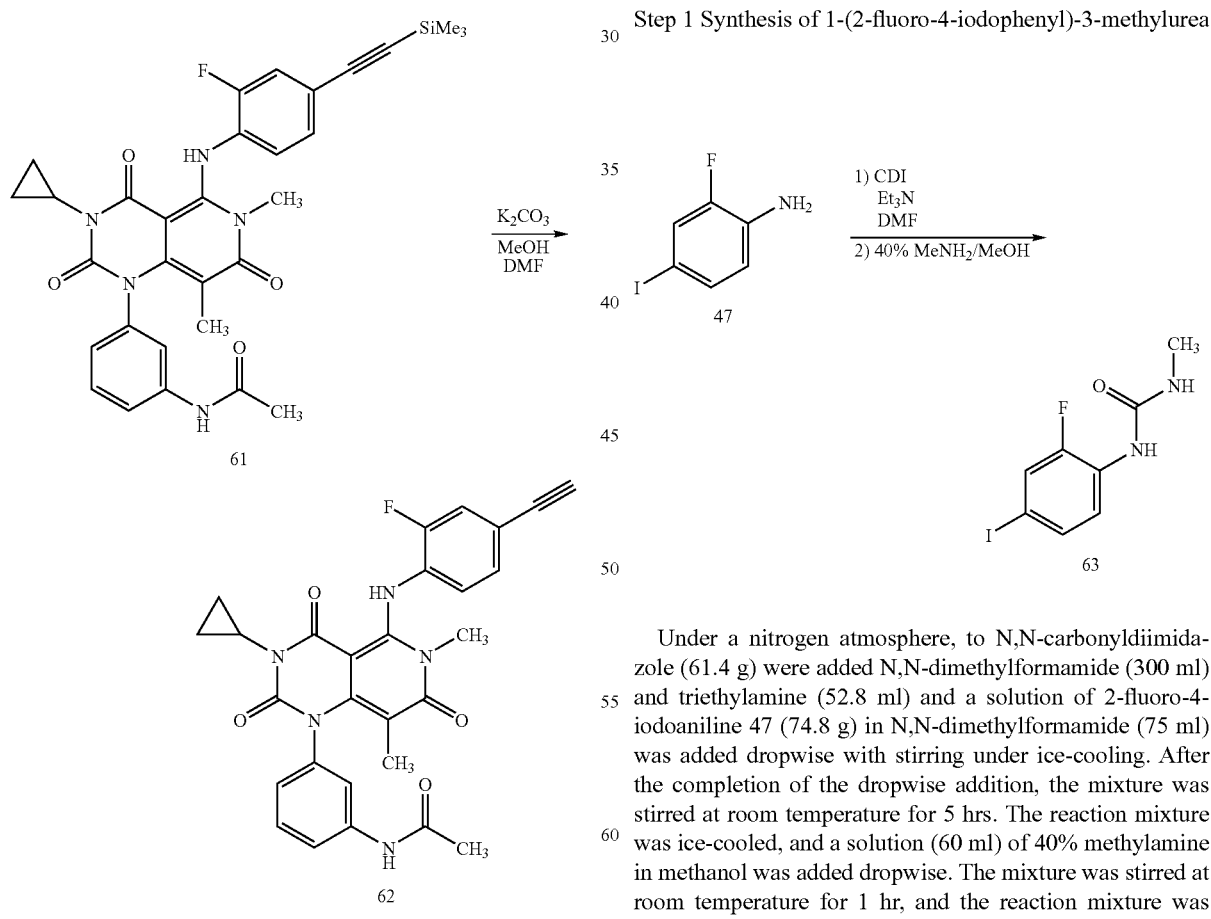

61 (1.00 g) obtained in Step 2 and potassium carbonate (236 mg) was added methanol/N,N-dimethylformamide [1:1 (volume ratio), 10.0 ml], and the mixture was stirred at room temperature for 20 hrs. The mixture was neutralized with 2N hydrochloric acid, water (10.0 ml) was added, and the mixture was stirred at room temperature for 1 hr. The crystals were collected by filtration and dried to give N-{3-[3-cyclopropyl-5-(4-ethynyl-2-fluorophenylamino)-6,8-dimethyl-2,4,7-trioxo-3,4,6,7-tetrahydro-2H-pyrido[4,3-d]pyrimidin-1-yl]phenyl}acetamide 62 (815 mg, yield 93%) as pale-yellow crystals.

MS ESI m/e: 514 (M+H), 512 (M−H).

$^1$H-NMR(DMSO-$d_6$, 400 MHz) δ 0.63-0.70(m, 2H), 0.91-0.99(m, 2H), 1.26(s, 3H), 2.04(s, 3H), 2.58-2.66(m, 1H), 3.10(s, 3H), 4.30(s, 3H), 7.01-7.06(m, 1H), 7.09(t, J=8.4 Hz, 1H), 7.31(dd, J=1.6, 8.4 Hz, 1H), 7.36(t, J=7.8 Hz, 1H), 7.52(dd, J=1.6, 11.6 Hz, 1H), 7.57-7.63(m, 2H), 10.10 (s, 1H), 11.10(s, 1H).

Example 4-16

N-{3-[5-(2-fluoro-4-iodophenylamino)-3,6,8-trimethyl-2,4,7-trioxo-3,4,6,7-tetrahydro-2H-pyrido[4,3-d]pyrimidin-1-yl]phenyl}methanesulfonamide Step 1 Synthesis of 1-(2-fluoro-4-iodophenyl)-3-methylurea Under a nitrogen atmosphere, to N,N-carbonyldiimidazole (61.4 g) were added N,N-dimethylformamide (300 ml) and triethylamine (52.8 ml) and a solution of 2-fluoro-4-iodoaniline 47 (74.8 g) in N,N-dimethylformamide (75 ml) was added dropwise with stirring under ice-cooling. After the completion of the dropwise addition, the mixture was stirred at room temperature for 5 hrs. The reaction mixture was ice-cooled, and a solution (60 ml) of 40% methylamine in methanol was added dropwise. The mixture was stirred at room temperature for 1 hr, and the reaction mixture was added dropwise to water-toluene [2:1 (volume ratio), 1125 ml] under stirring. The precipitated crystals were collected by filtration and dried to give 1-(2-fluoro-4-iodophenyl)-3-methylurea 63 (87.9 g, yield 94.8%) as colorless crystals.

To N-{3-[3-cyclopropyl-5-(2-fluoro-4-trimethylsilanylethynylphenylamino)-6,8-dimethyl-2,4,7-trioxo-3,4,6,7-tetrahydro-2H-pyrido[4,3-d]pyrimidin-1-yl]phenyl}acetamide Step 2 Synthesis of 1-(2-fluoro-4-iodophenyl)-3-methylpyrimidine-2,4,6-trione

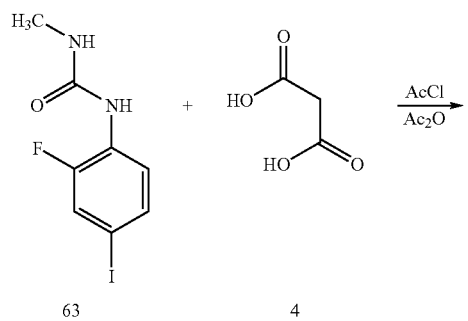

63        4

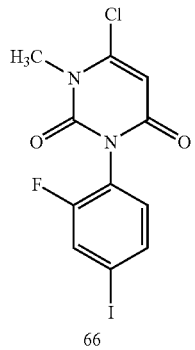

66

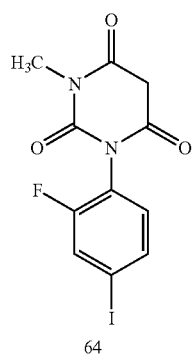

64

Under a nitrogen atmosphere, to 1-(2-fluoro-4-iodophenyl)-3-methylurea 63 (87.9 g) obtained in Step 1 and malonic acid 4 (31.1 g) were added acetic anhydride (264 ml) and acetyl chloride (42.5 ml), and the mixture was stirred at 65° C. for 3 hrs. After allowing to cool to room temperature, the reaction mixture was added dropwise to water-toluene [2:1 (volume ratio), 800 ml] with stirring, and hexane (132 ml) was successively added. The precipitated crystals were collected by filtration and dried to give 1-(2-fluoro-4-iodophenyl)-3-methylpyrimidine-2,4,6-trione 64 (75.3 g, yield 69.5%) as pale-yellow crystals.

Step 3 Synthesis of 6-chloro-1-(2-fluoro-4-iodophenyl)-3-methyl-1H-pyrimidine-2,4-dione Under a nitrogen atmosphere, to 1-(2-fluoro-4-iodophenyl)-3-methylpyrimidine-2,4,6-trione 64 (75.3 g) were added phosphorus oxychloride (116.3 ml) and dimethylaniline (39.5 ml) and water (11.6 ml) was added dropwise with stirring under room temperature. After the completion of the dropwise addition, the mixture was stirred at 125° C. for 1 hr. After allowing to cool to room temperature, the reaction mixture was added dropwise with stirring to ice water (500 ml)/chloroform (150 ml). The mixture was stirred at room temperature for 1 hr, and chloroform (150 ml) was added. The organic layer was separated, washed successively with water (300 ml) and brine (300 ml), and dried over anhydrous sodium sulfate.

Anhydrous sodium sulfate was filtered off, and the filtrate was concentrated under reduced pressure. To a solution of the residue in chloroform (250 ml), silica gel (200 ml) was added and the mixture was stirred. Silica gel was filtered off and washed with chloroform/ethyl acetate [10:1 (volume ratio), 1l]. The filtrate was concentrated under reduced pressure to give a 6:5 mixture (75.7 g, yield 95.6%) of 6-chloro-1-(2-fluoro-4-iodophenyl)-3-methyl-1H-pyrimidine-2,4-dione 65 and 6-chloro-3-(2-fluoro-4-iodophenyl)-1-methyl-1H-pyrimidine-2,4-dione 66 as pale-yellow crystals.

Step 4 Synthesis of 1-(2-fluoro-4-iodophenyl)-3-methyl-6-methylamino-1H-pyrimidine-2,4-dione

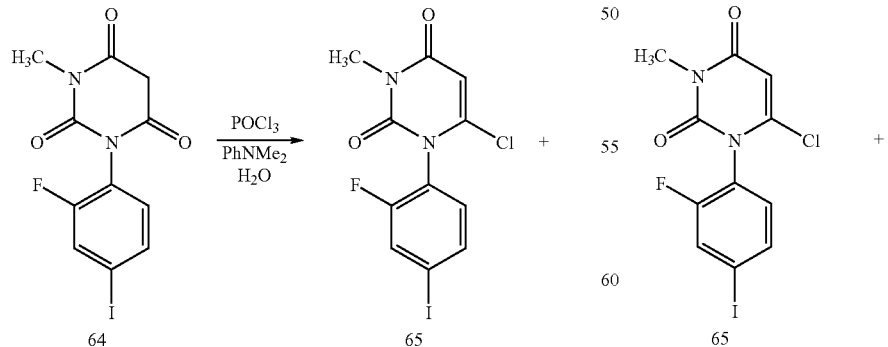

64        65        65

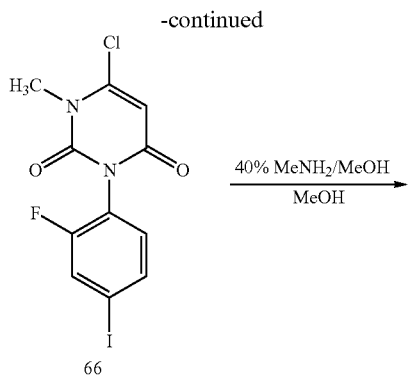

66

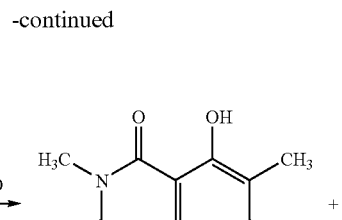

54

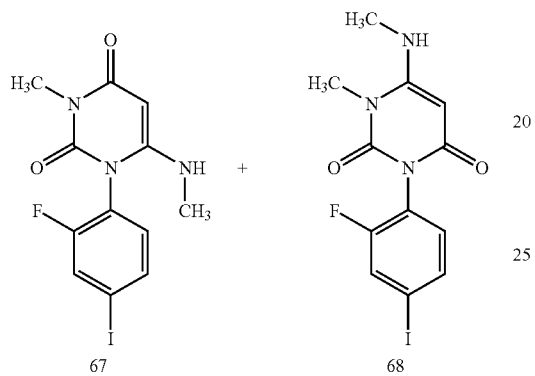

67          68

To a 6:5 mixture (75.7 g) of 6-chloro-1-(2-fluoro-4-iodophenyl)-3-methyl-1H-pyrimidine-2,4-dione 65 and 6-chloro-3-(2-fluoro-4-iodophenyl)-1-methyl-1H-pyrimidine-2,4-dione 66 obtained in Step 3 were added methanol (227 ml) and 40% solution (152 ml) of methylamine in methanol, and the mixture was stirred at room temperature for 2.5 hrs. The reaction mixture was concentrated under reduced pressure, and toluene(150 ml) and water (150 ml) were added to the residue, and the mixture was stirred under heating at reflux for 30 min. After allowing to return to room temperature, the crystals were collected by filtration and dried to give a 6:5 mixture (59.6 g, yield 79.9%) of 1-(2-fluoro-4-iodophenyl)-3-methyl-6-methylamino-1H-pyrimidine-2,4-dione 67 and 3-(2-fluoro-4-iodophenyl)-1-methyl-6-methylamino-1H-pyrimidine-2,4-dione 68 as pale-yellow crystals.

Step 5 Synthesis of 1-(2-fluoro-4-iodophenyl)-5-hydroxy-3,6,8-trimethyl-1H,8H-pyrido[2,3-d]pyrimidine-2,4,7-trione

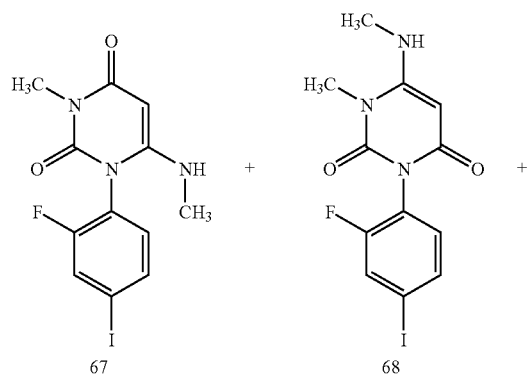

67          68

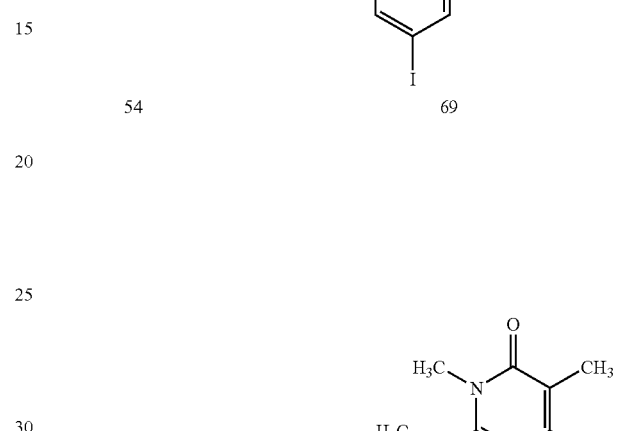

69

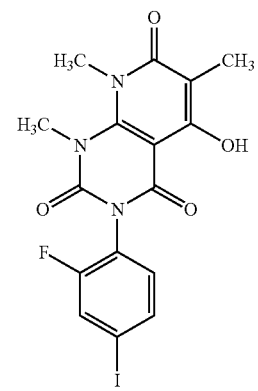

To a 6:5 mixture (59.6 g) of 1-(2-fluoro-4-iodophenyl)-3-methyl-6-methylamino-1H-pyrimidine-2,4-dione 67 and 3-(2-fluoro-4-iodophenyl)-1-methyl-6-methylamino-1H-pyrimidine-2,4-dione 68 obtained in Step 4 and 2-methylmalonic acid 54 (20.7 g) was added acetic anhydride (180 ml), and the mixture was stirred with heating at 95° C. for 1 hr. After allowing to cool to room temperature, the mixture was concentrated under reduced pressure. Tetrahydrofuran (350 ml) was added to the residue, and the mixture was stirred with heating under reflux for 1 hr. After allowing to cool to room temperature, the crystals were filtered off. The filtrate was concentrated under reduced pressure and the residue was purified by column chromatography (chloroform:tetrahydrofuran=18:1). Toluene (150 ml) was added to the obtained solid, and the mixture was stirred with heating under reflux for 30 min. After allowing to return to room temperature, the crystals were collected by filtration and dried to give 1-(2-fluoro-4-iodophenyl)-5-hydroxy-3,6,8-trimethyl-1H,8H-pyrido[2,3-d]pyrimidine-2,4,7-trione 69 (27.0 g, yield 37%) as colorless crystals.

Step 6 Synthesis of trifluoromethanesulfonic acid 1-(2-fluoro-4-iodophenyl)-3,6,8-trimethyl-2,4,7-trioxo-1,2,3,4,7,8-hexahydro-pyrido[2,3-d]pyrimidin-5-yl ester Step 7 Synthesis of N-{3-[1-(2-fluoro-4-iodophenyl)-3,6,8-trimethyl-2,4,7-trioxo-1,2,3,4,7,8-hexahydro-pyrido[2,3-d]pyrimidin-5-ylamino]phenyl}methanesulfonamide

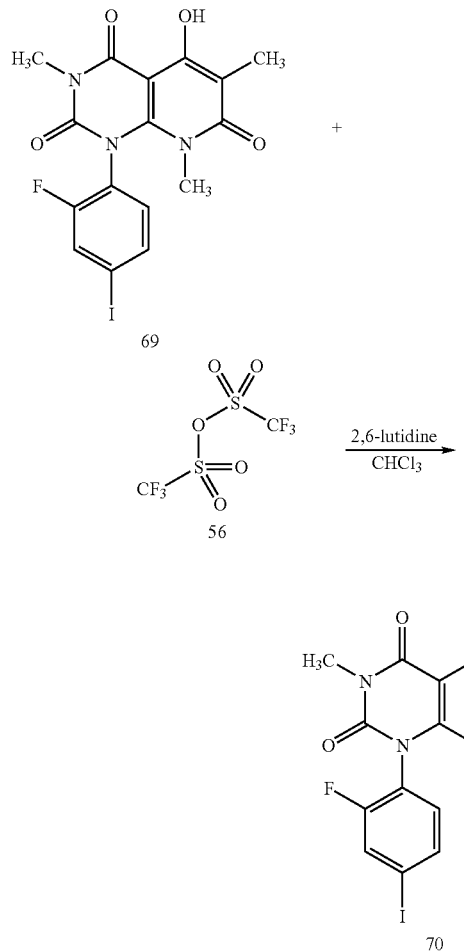

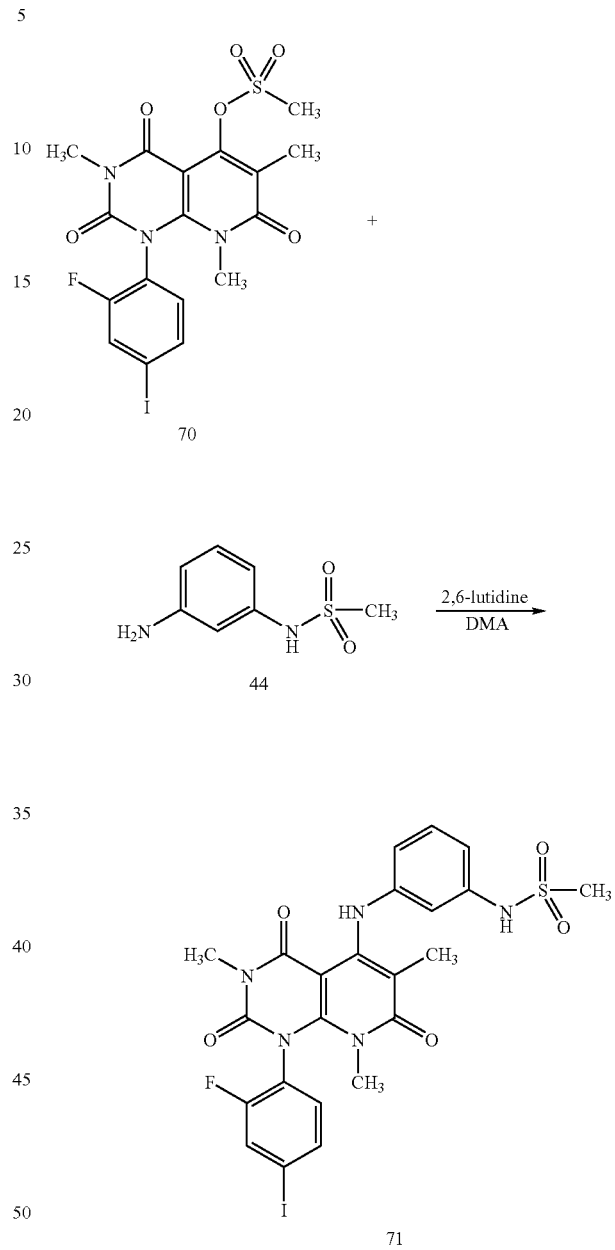

Under a nitrogen atmosphere, to 1-(2-fluoro-4-iodophenyl)-5-hydroxy-3,6,8-trimethyl-1H,8H-pyrido[2,3-d]pyrimidine-2,4,7-trione 69 (27.0 g) obtained in Step 5 were added chloroform (200 ml) and 2,6-lutidine (11.1 ml) and trifluoromethanesulfonic anhydride 56 (14.9 ml) was added dropwise under ice-cooling with stirring. After the completion of the dropwise addition, the mixture was stirred at the same temperature for 30 min, and at room temperature for 3 hrs. With stirring under ice-cooling, water (200 ml) was added to the reaction mixture. The organic layer was separated, washed successively with water (300 ml) and brine (300 ml), and dried over anhydrous magnesium sulfate. Anhydrous magnesium sulfate was filtered off, and the filtrate was concentrated under reduced pressure. 2-Propanol (150 ml) was added to the residue, and seed crystals were added at room temperature to allow precipitation of the crystals. The mixture was stirred with heating under reflux for 30 min, and allowed to cool to room temperature. The crystals were collected by filtration and dried to give trifluoromethanesulfonic acid 1-(2-fluoro-4-iodophenyl)-3,6,8-trimethyl-2,4,7-trioxo-1,2,3,4,7,8-hexahydro-pyrido[2,3-d]pyrimidin-5-yl ester 70 (22.9 g, yield 66%) as colorless crystals.

To trifluoromethanesulfonic acid 1-(2-fluoro-4-iodophenyl)-3,6,8-trimethyl-2,4,7-trioxo-1,2,3,4,7,8-hexahydro-pyrido[2,3-d]pyrimidin-5-yl ester 70 (3.00 g) obtained in Step 6 and N-(3-aminophenyl)methanesulfonamide 44 (1.14 g) were added N,N-dimethylacetamide (6.00 ml) and 2,6-lutidine (0.712 ml), and the mixture was stirred at 130° C. for 4 hrs. After allowing to cool to room temperature, methanol/water [1:2 (volume ratio), 18.0 ml] was added under stirring. The crystals were collected by filtration and dried to give N-{3-[1-(2-fluoro-4-iodophenyl)-3,6,8-trimethyl-2,4,7-trioxo-1,2,3,4,7,8-hexahydro-pyrido[2,3-d]pyrimidin-5-ylamino]phenyl}methanesulfonamide 71 (3.13 g, yield 98%) as a pale-gray solid.

Step 8 Synthesis of N-{3-[5-(2-fluoro-4-iodophenylamino)-3,6,8-trimethyl-2,4,7-trioxo-3,4,6,7-tetrahydro-2H-pyrido[4,3-d]pyrimidin-1-yl]phenyl}methanesulfonamide

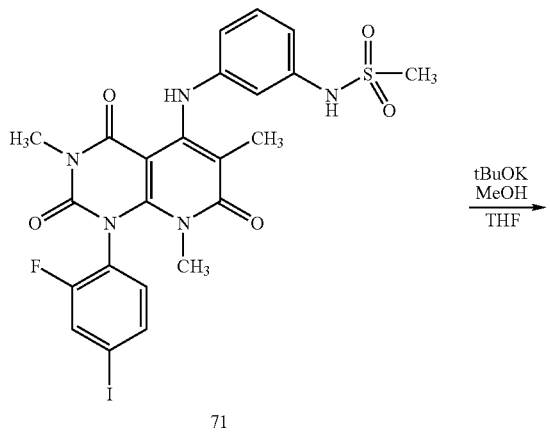

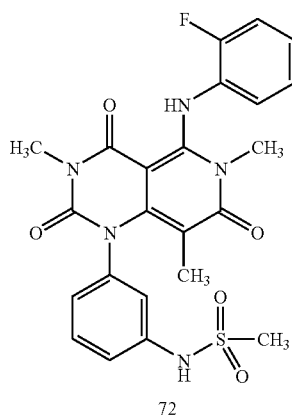

Under ice-cooling, to a suspension of N-{3-[1-(2-fluoro-4-iodophenyl)-3,6,8-trimethyl-2,4,7-trioxo-1,2,3,4,7,8-hexahydro-pyrido[2,3-d]pyrimidin-5-ylamino]phenyl}methanesulfonamide 71 (3.10 g) obtained in Step 7 in tetrahydrofuran (31.0 ml) was added dropwise a mixture of potassium t-butoxide (1.33 g), methanol (0.482 ml) and tetrahydrofuran (15.5 ml), and the mixture was stirred under ice-cooling for 2 hrs. Acetic acid (1.36 ml) was added, the mixture was allowed to warm to room temperature and stirred for 1 hr. The reaction mixture was concentrated, methanol/water [1:2 (volume ratio), 45.0 ml] was added, and the mixture was further stirred at room temperature for 1 hr. The crystals were collected by filtration and dried to give N-{3-[5-(2-fluoro-4-iodophenylamino)-3,6,8-trimethyl-2,4,7-trioxo-3,4,6,7-tetrahydro-2H-pyrido[4,3-d]pyrimidin-1-yl]phenyl}methanesulfonamide 72 (3.01 g, yield 97%) as a pale-gray solid.

MS ESI m/e: 626(M+H), 624 (M−H).

$^1$H-NMR(DMSO-d$_6$, 300 MHz)δ 1.26(s, 3H), 3.01(s, 3H), 3.09(s, 3H), 3.21(s, 3H), 6.93(t, J=8.3 Hz, 1H), 7.11-7.15(m, 1H), 7.20-7.28(m, 2H), 7.42(t, J=8.3 Hz, 1H), 7.52-7.57(m, 1H), 7.76-7.81(m, 1H), 9.94(brs, 1H), 11.21 (brs, 1H).

Example 4-144

N-{3-[5-(2-Fluoro-4-iodophenylamino)-3-(4-hydroxybutyl)-6,8-dimethyl-2,4,7-trioxo-3,4,6,7-tetrahydro-2H-pyrido[4,3-d]pyrimidin-1-yl]-phenyl}-acetamide Step 1 Synthesis of (2-fluoro-4-iodophenyl)-urea

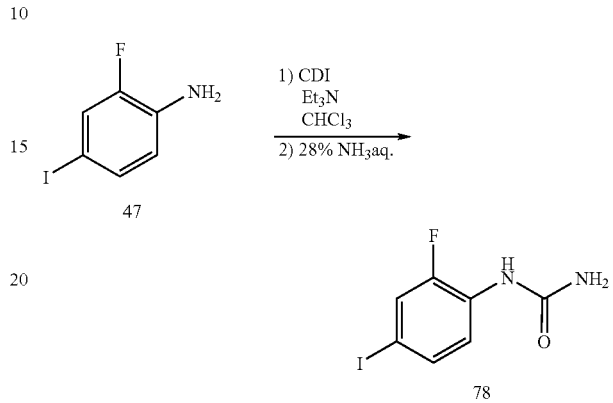

Under argon atmosphere, to a solution of 2-fluoro-4-iodoaniline 47 (20.0 g) and triethylamine (23.6 ml) in chloroform (200 ml) was added N,N-carbonyldiimidazole (27.4 g) with stirring under ice-cooling. After the completion of the addition, the mixture was stirred under ice-cooling for 15 min and at room temperature for 4 hrs. The reaction mixture was ice-cooled, and 28% aqueous ammonia (100 ml) was added dropwise. The mixture was stirred at room temperature for 1.5 hrs. The precipitated crystals were collected by filtration, washed with water and dried to give (2-fluoro-4-iodophenyl)-urea 78 (23.5 g, yield 98.8%) as pale-pink crystals.

Step 2 Synthesis of 1-(2-cyanoacetyl)-3-(2-fluoro-4-iodophenyl)-urea

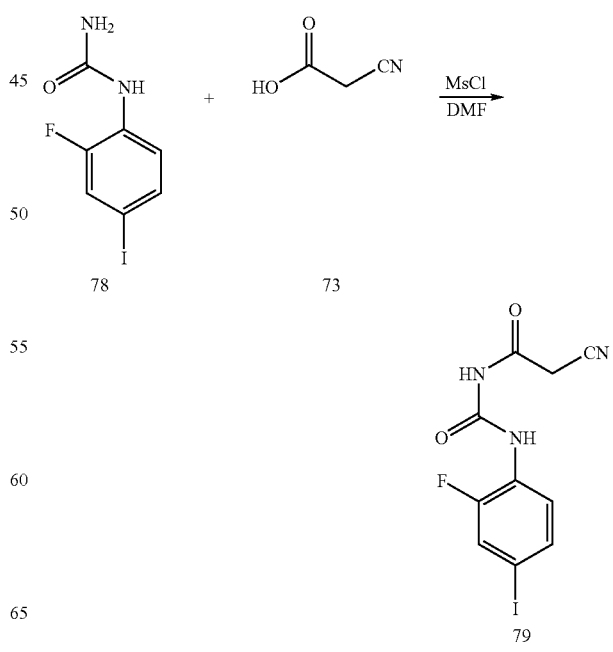

To a mixture of (2-fluoro-4-iodophenyl)-urea 78 (21.7 g) and cyanoacetic acid 73 (7.88 g) in N,N-dimethylformamide (108 ml) was added, and methanesulfonyl chloride (7.17 ml) was added dropwise with stirring at room temperature. The mixture was stirred at room temperature for 2 hrs, and water-isopropyl alcohol [1:2 (volume ratio), 210 ml] was added dropwise. The mixture was stirred at room temperature for 1 hr. The precipitated crystals were collected by filtration and washed with water to give 1-(2-cyanoacetyl)-3-(2-fluoro-4-iodophenyl)-urea 79 (wet crystals), which was used for the next reaction in the form of wet crystals.

Step 3 Synthesis of 6-amino-1-(2-fluoro-4-iodophenyl)-1H-pyrimidine-2,4-dione

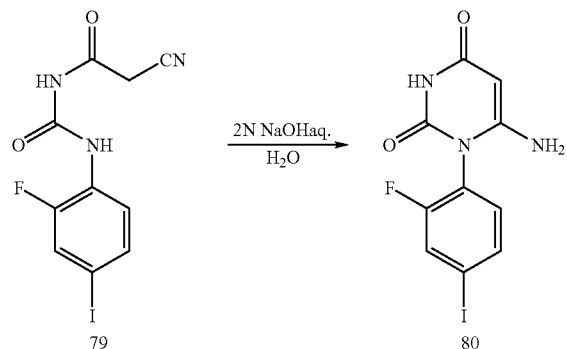

To a suspension of 1-(2-cyanoacetyl)-3-(2-fluoro-4-iodophenyl)-urea 79 (wet crystals) in water (110 ml) was added 2N aqueous sodium hydroxide solution (3.96 ml), and the mixture was stirred with heating at 85° C. for 1 hr. After allowing to cool to room temperature, 2N hydrochloric acid (3.96 ml) and isopropyl alcohol (44.0 ml) were successively added dropwise. The mixture was stirred at room temperature for 1.5 hrs, the precipitated crystals were collected by filtration, washed with isopropyl alcohol, and dried to give a mixture of 6-amino-1-(2-fluoro-4-iodophenyl)-1H-pyrimidine-2,4-dione 80 and 78 (21.8 g) as colorless crystals, which were used for the next reaction without purification.

Step 4 Synthesis of N'-[3-(2-fluoro-4-iodophenyl)-2,6-dioxo-1,2,3,6-tetrahydropyrimidin-4-yl]-N,N-dimethylformamidine

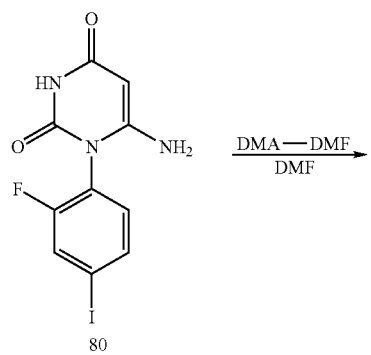

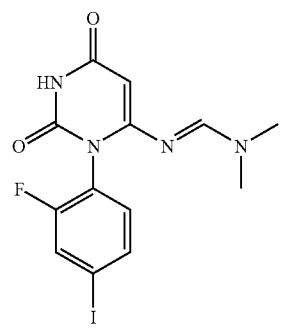

To a mixture (21.8 g) of 6-amino-1-(2-fluoro-4-iodophenyl)-1H-pyrimidine-2,4-dione 80 and 78 was added N,N-dimethylformamide (42.0 ml) and N,N-dimethylformamidedimethylacetal (21.0 ml) and the mixture was stirred at room temperature for 4.5 hrs. With stirring at room temperature, isopropyl alcohol (20.0 ml) was added, and water (100 ml) was added dropwise. The mixture was stirred at room temperature for 45 min, and the precipitated crystals were collected by filtration, washed with water and dried to give N'-[3-(2-fluoro-4-iodophenyl)-2,6-dioxo-1,2,3,6-tetrahydropyrimidin-4-yl]-N,N-dimethylformamidine 81 (21.7 g, yield 67.7% from 78) as colorless crystals.

Step 5 Synthesis of N'-[3-(2-fluoro-4-iodophenyl)-1-(4-methoxybenzyl)-2,6-dioxo-1,2,3,6-tetrahydropyrimidin-4-yl]-N,N-dimethylformamidine

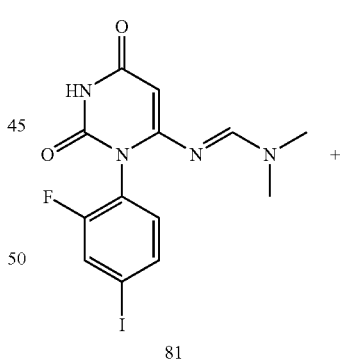

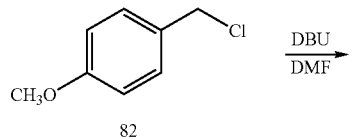

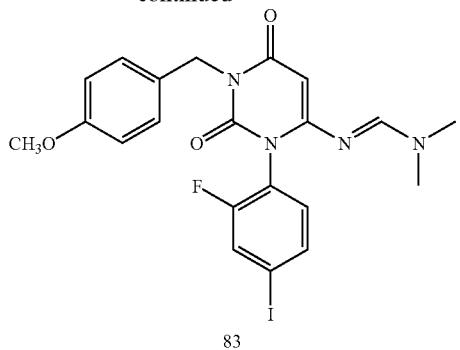

83

To a solution of N'-[3-(2-fluoro-4-iodophenyl)-2,6-dioxo-1,2,3,6-tetrahydropyrimidin-4-yl]-N,N-dimethylformamidine 81 (20.0 g) in N,N-dimethylformamide (150 ml) was added 1,8-diazabicyclo[5.4.0]undec-7-en (14.9 ml) and 4-methoxybenzyl chloride 82 (10.1 ml) at room temperature. The mixture was stirred with heating at 75° C. for 2.5 hrs, 1,8-diazabicyclo[5.4.0]undec-7-en (7.50 ml) and 4-methoxybenzyl chloride (4.00 ml) were added, and the mixture was stirred with heating at the same temperature for 2.5 hrs. After allowing to cool to room temperature, isopropyl alcohol (150 ml) and water (300 ml) were successively added dropwise. The mixture was stirred overnight at room temperature, and the precipitated crystals were collected by filtration and dried to give N'-[3-(2-fluoro-4-iodophenyl)-1-(4-methoxybenzyl)-2,6-dioxo-1,2,3,6-tetrahydropyrimidin-4-yl]-N,N-dimethylformamidine 83 (20.2 g, yield 77.8%) as yellow crystals.

Step 6 Synthesis of 1-(2-fluoro-4-iodophenyl)-3-(4-methoxybenzyl)-6-methylamino-1H-pyrimidine-2,4-dione

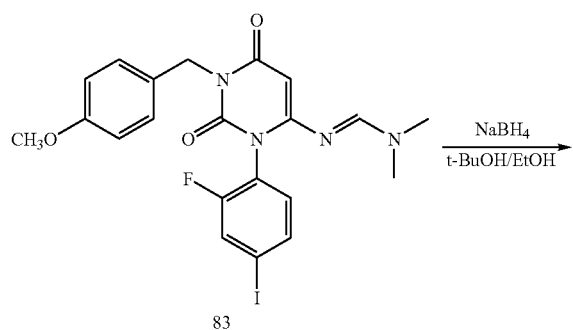

83

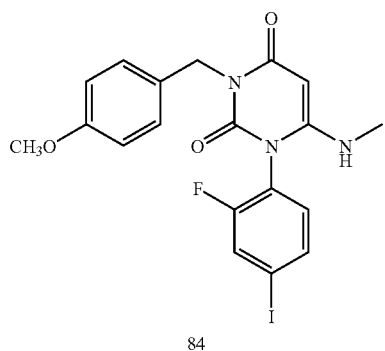

84

To a suspension of sodium borohydride (326 mg) in t-butanol/ethanol [2:1 (volume ratio), 18.0 ml] was added N'-[3-(2-fluoro-4-iodophenyl)-1-(4-methoxybenzyl)-2,6-dioxo-1,2,3,6-tetrahydropyrimidin-4-yl]-N,N-dimethylformamidine 83 (3.00 g) with stirring at room temperature. The mixture was stirred at room temperature for 1 hr, and at 65° C. for 2 hrs. With stirring at the same temperature, water (30.0 ml) and ammonium chloride (461 mg) were successively added, and the mixture was stirred to allow to cool to room temperature. The reaction solution was extracted twice with ethyl acetate. The organic layers were combined, washed successively with saturated aqueous hydrogen carbonate solution and brine, dried over anhydrous sodium sulfate, and concentrated under reduced pressure. The obtained crude product was purified by column chromatography to give 1-(2-fluoro-4-iodophenyl)-3-(4-methoxybenzyl)-6-methylamino-1H-pyrimidine-2,4-dione 84 (2.57 g, yield 93.1%) as a pale-yellow solid.

Step 7 Synthesis of 1-(2-fluoro-4-iodophenyl)-5-hydroxy-3-(4-methoxybenzyl)-6,8-dimethyl-1H,8H-pyrido[2,3-d]pyrimidine-2,4,7-trione

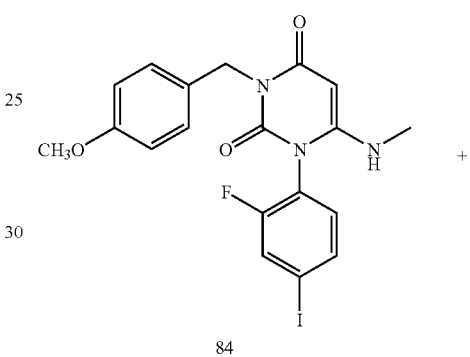

84

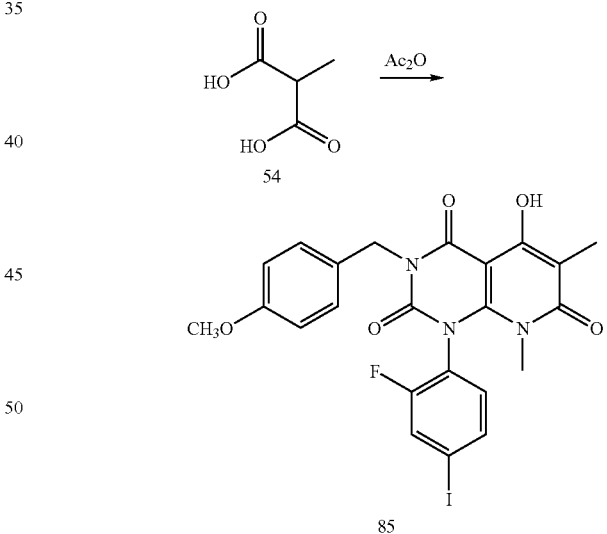

85

To a suspension of 1-(2-fluoro-4-iodophenyl)-3-(4-methoxybenzyl)-6-methylamino-1H-pyrimidine-2,4-dione 84 (13.3 g) in acetic anhydride (13.0 ml) was added 2-methylmalonic acid 54 (4.90 g), and the mixture was stirred with heating at 90° C. for 3 hrs and at 100° C. for 1 hr. After allowing to cool to about 50° C., acetone (13.3 ml) was added dropwise, and water (75.0 ml) was further added. After seeding with compound 85, acetone (30.0 ml) was added, and the mixture was stirred for 1.5 hrs. Water (30.0 ml) as added and the mixture was stirred for 45 min, and allowed to cool to room temperature. The precipitated crystals were collected by filtration, washed with water and dried to give 1-(2-fluoro-4-iodophenyl)-5-hydroxy-3-(4-methoxybenzyl)-6,8-dimethyl-1H,8H-pyrido[2,3-d]pyrimidine-2,4,7-trione 85 (14.1 g, yield 90.7%) as pale-ocher crystals.

Step 8 Synthesis of trifluoromethanesulfonic acid 1-(2-fluoro-4-iodophenyl)-3-(4-methoxybenzyl)-6,8-dimethyl-2,4,7-trioxo-1,2,3,4,7,8-hexahydropyrido[2,3-d]pyrimidin-5-yl ester

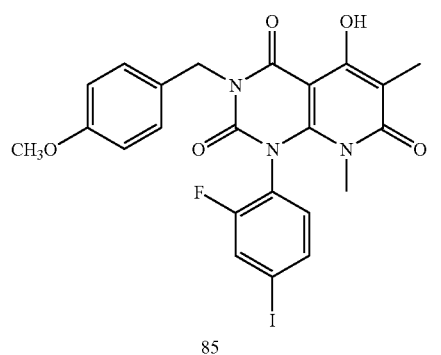

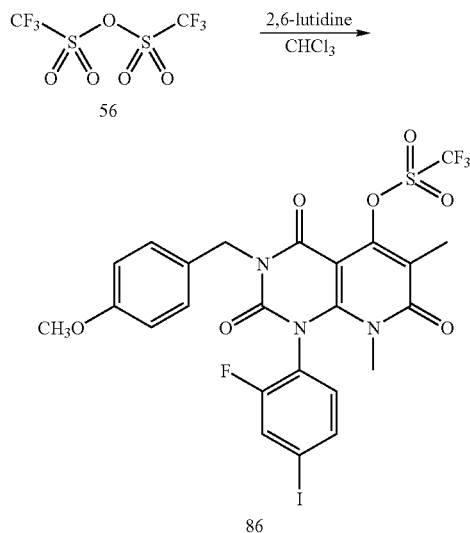

Under argon atmosphere, to a solution of 1-(2-fluoro-4-iodophenyl)-5-hydroxy-3-(4-methoxybenzyl)-6,8-dimethyl-1H,8H-pyrido[2,3-d]pyrimidine-2,4,7-trione 85 (14.1 g) in chloroform (70.0 ml) was added 2,6-lutidine(3.79 ml) and trifluoromethanesulfonic anhydride 56 (5.47 ml) under ice-cooling, and the mixture was stirred under ice-cooling for 1 hr, and at room temperature for 1.5 hrs. To the reaction mixture was added saturated aqueous sodium hydrogen carbonate solution and chloroform to allow partitioning. The organic layer was washed once with saturated aqueous sodium hydrogen carbonate solution, twice with 1N hydrochloric acid, once with saturated aqueous sodium chloride solution, and dried over anhydrous sodium sulfate. After filtration, the filtrate was concentrated under reduced pressure. To the obtained crude product was added isopropyl alcohol (35.0 ml), and the mixture was stirred with heating at an outer temperature of 95° C. for 30 min. After allowing to cool with stirring to room temperature, isopropyl alcohol (35.0 ml) was added, and the mixture was stirred for 1 hr.

The precipitated crystals were collected by filtration, washed with isopropyl alcohol and dried to give trifluoromethanesulfonic acid 1-(2-fluoro-4-iodophenyl)-3-(4-methoxybenzyl)-6,8-dimethyl-2,4,7-trioxo-1,2,3,4,7,8-hexahydropyrido[2,3-d]pyrimidin-5-yl ester 86 (14.4 g, yield 82.8%) as brown crystals.

Step 9 Synthesis of N-{3-[1-(2-fluoro-4-iodophenyl)-3-(4-methoxybenzyl)-6,8-dimethyl-2,4,7-trioxo-1,2,3,4,7,8-hexahydropyrido[2,3-d]pyrimidin-5-ylamino]-phenyl}-acetamide

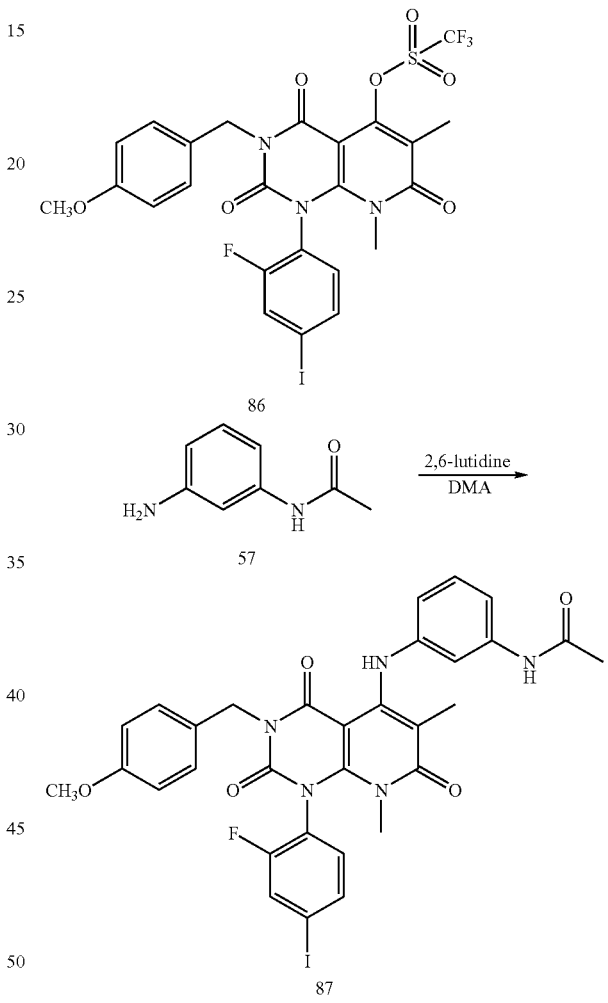

To trifluoromethanesulfonic acid 1-(2-fluoro-4-iodophenyl)-3-(4-methoxybenzyl)-6,8-dimethyl-2,4,7-trioxo-1,2,3,4,7,8-hexahydropyrido[2,3-d]pyrimidin-5-yl ester 86 (1.10 g) and 3'-aminoacetanilide 57 (285 mg) were added, N,N-dimethylacetamide (2.20 ml) and 2,6-lutidine (221 µl), and the mixture was stirred at 130° C. for 2 hrs. After allowing to return to room temperature, methanol (12.0 ml) was added dropwise with stirring. The precipitated crystals were collected by filtration, washed with methanol and dried to give N-{3-[1-(2-fluoro-4-iodophenyl)-3-(4-methoxybenzyl)-6,8-dimethyl-2,4,7-trioxo-1,2,3,4,7,8-hexahydropyrido[2,3-d]pyrimidin-5-ylamino]-phenyl}-acetamide 87 (1.04 g, yield 94.6%) as colorless crystals.

Step 10 Synthesis of N-{3-[5-(2-fluoro-4-iodophenylamino)-3-(4-methoxybenzyl)-6,8-dimethyl-2,4,7-trioxo-3,4,6,7-tetrahydro-2H-pyrido[4,3-d]pyrimidin-1-yl]-phenyl}-acetamide

Step 11 Synthesis of N-{3-[5-(2-fluoro-4-iodophenylamino)-6,8-dimethyl-2,4,7-trioxo-3,4,6,7-tetrahydro-2H-pyrido[4,3-d]pyrimidin-1-yl]-phenyl}-acetamide

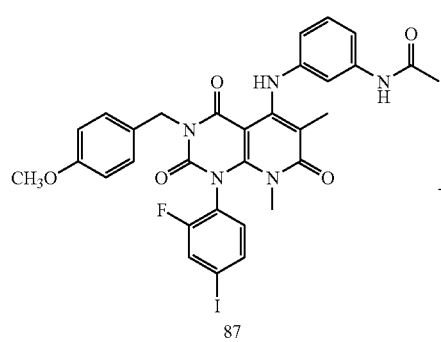

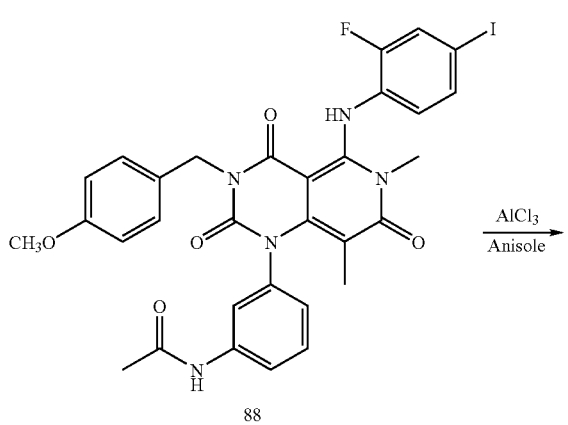

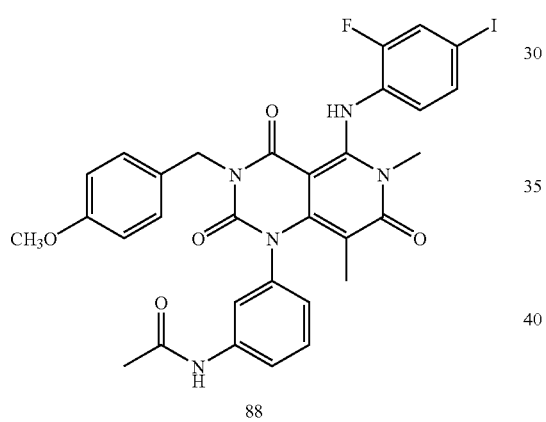

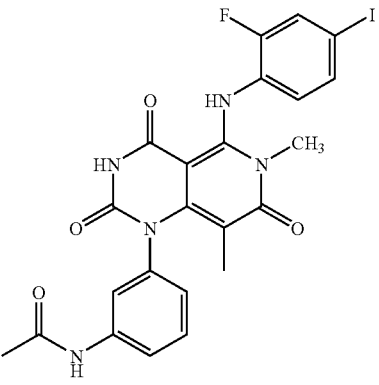

To a solution (305 mg) of 28% sodium methoxide in methanol were added tetrahydrofuran (4.00 ml) and N-{3-[1-(2-fluoro-4-iodophenyl)-3-(4-methoxybenzyl)-6,8-dimethyl-2,4,7-trioxo-1,2,3,4,7,8-hexahydropyrido[2,3-d]pyrimidin-5-ylamino]-phenyl}-acetamide 87 (1.00 g). The wall was washed with tetrahydrofuran (4.00 ml). The mixture was stirred at room temperature for 1.5 hrs., 2N hydrochloric acid (900 µl) was added, and the mixture was concentrated under reduced pressure. To the residue was added isopropyl alcohol, methanol and water, and after refluxing, the mixture was allowed to cool to room temperature with stirring. The precipitated crystals were collected by filtration, washed with methanol, and dried to give N-{3-[5-(2-fluoro-4-iodophenylamino)-3-(4-methoxybenzyl)-6,8-dimethyl-2,4,7-trioxo-3,4,6,7-tetrahydro-2H-pyrido[4,3-d]pyrimidin-1-yl]-phenyl}-acetamide 88 (974 mg, yield 97.2%) as colorless crystals.

To a suspension of N-{3-[5-(2-fluoro-4-iodophenylamino)-3-(4-methoxybenzyl)-6,8-dimethyl-2,4,7-trioxo-3,4,6,7-tetrahydro-2H-pyrido[4,3-d]pyrimidin-1-yl]-phenyl}-acetamide 88 (960 mg) in anisole (10.0 ml) was added aluminum chloride (1.94 g) with stirring in a water bath. The mixture was stirred at room temperature for 37 hrs, methanol (12.0 ml) was added dropwise, and the mixture was concentrated under reduced pressure. The obtained residue was dissolved in methanol (12.0 ml), and 2N hydrochloric acid (20.0 ml) was added dropwise with stirring in a water bath. The mixture was stirred at room temperature for 1 hr, hexane (10.0 ml) was added, and the mixture was stirred for 1 hr. The precipitated crystals were collected by filtration, washed with hexane, water and methanol, and dried to give N-{3-[5-(2-fluoro-4-iodophenylamino)-6,8-dimethyl-2,4,7-trioxo-3,4,6,7-tetrahydro-2H-pyrido[4,3-d]pyrimidin-1-yl]-phenyl}-acetamide 89 (620 mg, yield 78.1%) as colorless crystals.

Step 12 Synthesis of N-{3-[3-(4-benzyloxybutyl)-5-(2-fluoro-4-iodophenylamino)-6,8-dimethyl-2,4,7-trioxo-3,4,6,7-tetrahydro-2H-pyrido[4,3-d]pyrimidin-1-yl]-phenyl}-acetamide

Step 13 Synthesis of N-{3-[5-(2-fluoro-4-iodophenylamino)-3-(4-hydroxybutyl)-6,8-dimethyl-2,4,7-trioxo-3,4,6,7-tetrahydro-2H-pyrido[4,3-d]pyrimidin-1-yl]-phenyl}-acetamide

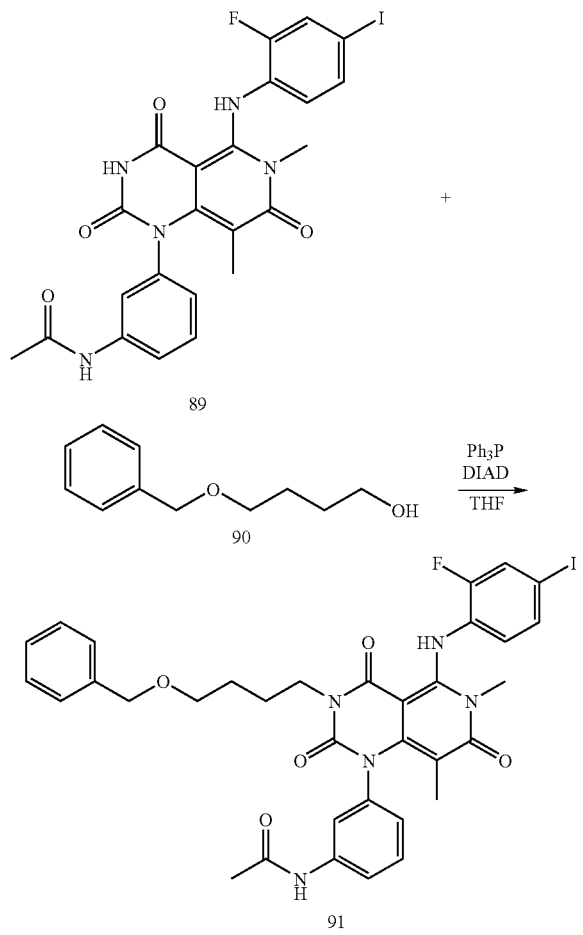

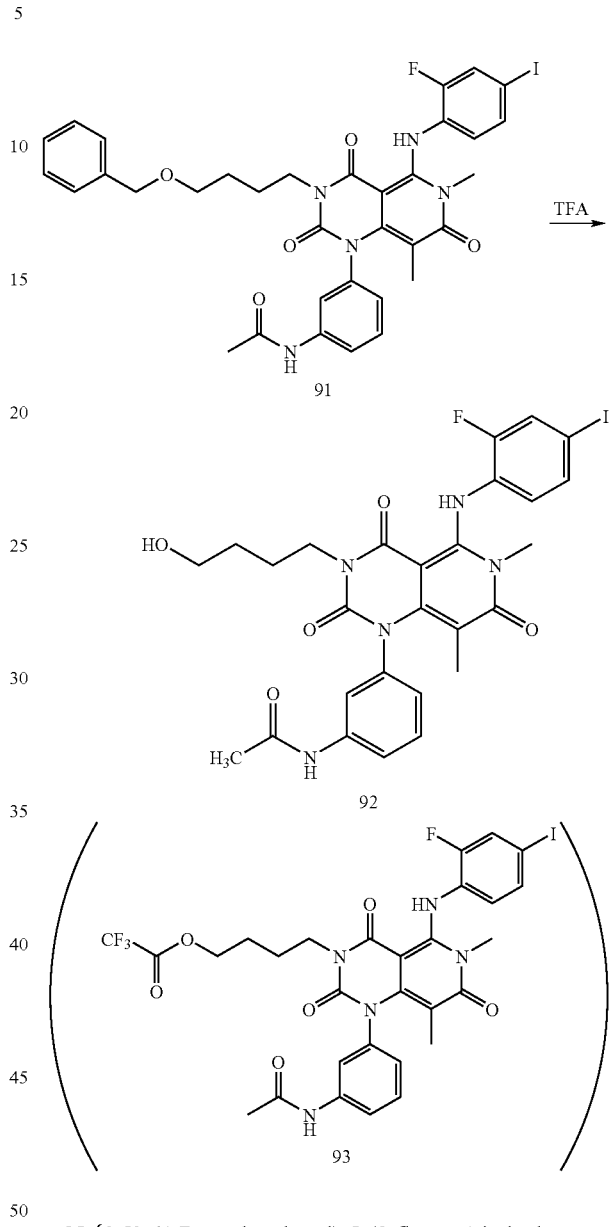

Under argon atmosphere, to a suspension of N-{3-[5-(2-fluoro-4-iodophenylamino)-6,8-dimethyl-2,4,7-trioxo-3,4,6,7-tetrahydro-2H-pyrido[4,3-d]pyrimidin-1-yl]-phenyl}-acetamide 89 (75.0 mg), 4-benzyloxybutyl alcohol 90 (25.0 μl) and triphenylphosphine (37.0 mg) in tetrahydrofuran (1.00 ml) was added diisopropyl azodicarboxylate (28.0 μl) with stirring under ice cooling. The mixture was stirred at the same temperature for 2 hrs, and 4-benzyloxybutyl alcohol (13.0 μl), triphenylphosphine (19.0 mg) and diisopropyl azodicarboxylate (14.0 μl) were added. The mixture was stirred at the same temperature for 1 hr, and water and ethyl acetate were added to allow partitioning. The organic layer was washed with saturated aqueous sodium chloride solution, dried over anhydrous sodium sulfate and concentrated under reduced pressure. The residue was purified by column chromatography (chloroform:ethyl acetate=2:1→1:1) and thin layer chromatography (hexane:acetone=1:1) for further purification to give N-{3-[3-(4-benzyloxybutyl)-5-(2-fluoro-4-iodophenylamino)-6,8-dimethyl-2,4,7-trioxo-3,4,6,7-tetrahydro-2H-pyrido[4,3-d]pyrimidin-1-yl]-phenyl}-acetamide 91 (74 mg, yield 77%) as a pale-yellow amorphous form.

N-{3-[3-(4-Benzyloxybutyl)-5-(2-fluoro-4-iodophenylamino)-6,8-dimethyl-2,4,7-trioxo-3,4,6,7-tetrahydro-2H-pyrido[4,3-d]pyrimidin-1-yl]-phenyl}-acetamide 91 (74 mg) was stirred under reflux for 5.5 hrs in trifluoroacetic acid (1.00 ml). The reaction mixture was concentrated under reduced pressure, and ethyl acetate and saturated aqueous sodium hydrogen carbonate solution were added to the residue to allow partitioning. The organic layer was washed successively with saturated aqueous sodium hydrogen carbonate solution, water and brine, dried over anhydrous sodium sulfate and concentrated under reduced pressure. To the residue was added diisopropyl ether (1.00 ml), and the mixture was stirred at 60° C. to allow cooling to room temperature with stirring. The crystals were collected by filtration, washed with diisopropyl ether, and dried to give compound 93 (26 mg) as colorless crystals. Compound 93 was stirred in a mixed solution of saturated aqueous sodium hydrogen carbonate solution (300 μl), methanol (300 μl) and ethyl acetate (300 μl) at room temperature for 1 hr, and extracted with ethyl acetate. The organic layer was washed with brine, dried over anhydrous sodium sulfate and concentrated under reduced pressure. To the residue were added ethyl acetate, hexane and diethyl ether, and the mixture was stirred at room temperature for 1 hr. The precipitated crystals were collected by filtration, washed with hexane and dried to give N-{3-[5-(2-fluoro-4-iodophenylamino)-3-(4-hydroxybutyl)-6,8-dimethyl-2,4,7-trioxo-3,4,6,7-tetrahydro-2H-pyrido[4,3-d]pyrimidin-1-yl]-phenyl}-acetamide 92 (5 mg, yield 8%) as colorless crystals.

Examples 4-2, 4-4-15, 4-17-143 and 4-145-148

In the same manner as in Examples 4-1, 4-3 and 4-16, the compounds of Examples 4-2, 4-4-15, 4-17-133 and 4-138-4-140 were obtained. In addition, in the same manner as in Example 4-144, the compounds of Examples 4-83-86, Examples 4-134-137, 4-141-143 and 4-145-148 were obtained. The structural formulas thereof are shown in Table 4-1 to 4-25 with Examples 4-1, 4-3, 4-16 and 4-144.

TABLE 4-1

| Ex. No. | structural formula |
|---|---|
| 4-1 | |
| 4-2 | |

TABLE 4-1-continued

| Ex. No. | structural formula |
|---|---|
| 4-3 | |
| 4-4 | |
| 4-5 | |

TABLE 4-1-continued
| Ex. No. | structural formula |
|---|---|
| 4-6 | |
TABLE 4-2
| Ex. No. | structural formula |
|---|---|
| 4-7 | |
| 4-8 | 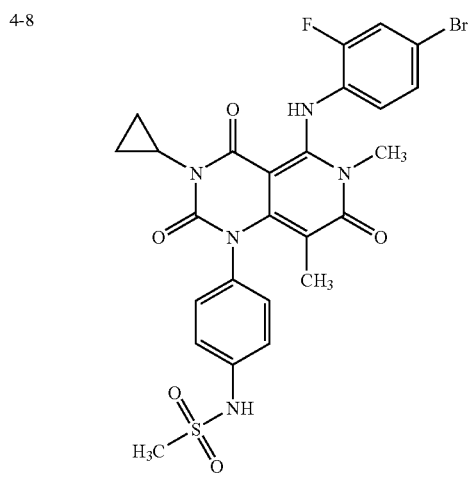 |
TABLE 4-2-continued
| Ex. No. | structural formula |
|---|---|
| 4-9 | |
| 4-10 | 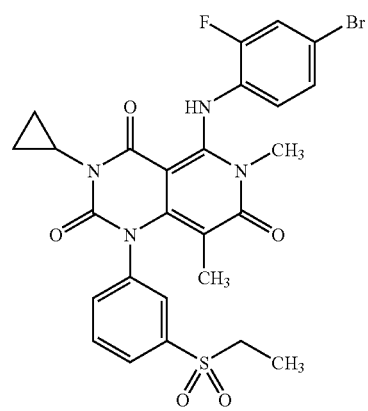 |
| 4-11 | 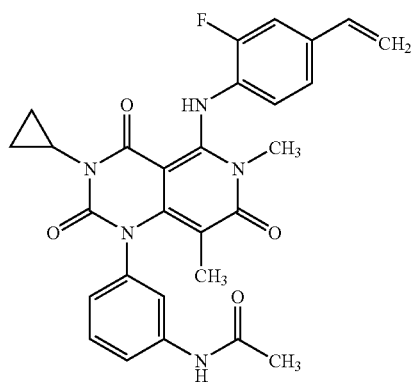 |

TABLE 4-2-continued

| Ex. No. | structural formula |
|---|---|
| 4-12 | |

TABLE 4-3

| Ex. No. | structural formula |
|---|---|
| 4-13 | |
| 4-14 | |

TABLE 4-3-continued

| Ex. No. | structural formula |
|---|---|
| 4-15 | |
| 4-16 | |
| 4-17 | |
| 4-18 | |

TABLE 4-4

| Ex. No. | structural formula |
|---|---|
| 4-19 | (structure) |
| 4-20 | (structure) |
| 4-21 | (structure) |
| 4-22 | (structure) |

TABLE 4-4-continued

| Ex. No. | structural formula |
|---|---|
| 4-23 | (structure) |
| 4-24 | (structure) |

TABLE 4-5

| Ex. No. | structural formula |
|---|---|
| 4-25 | (structure) |

TABLE 4-5-continued
| Ex. No. | structural formula |
|---|---|
| 4-26 | 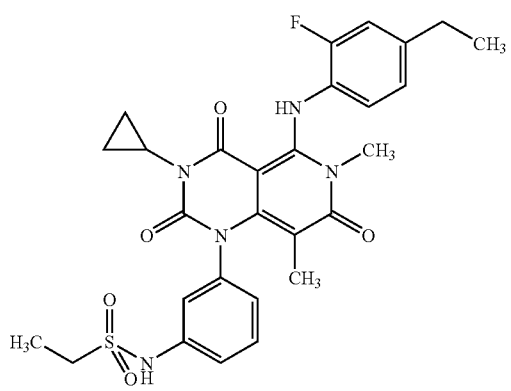 |
| 4-27 | 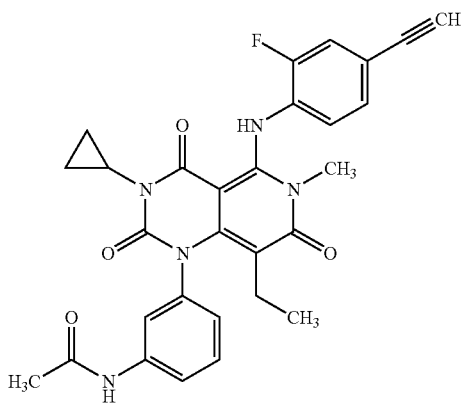 |
| 4-28 | 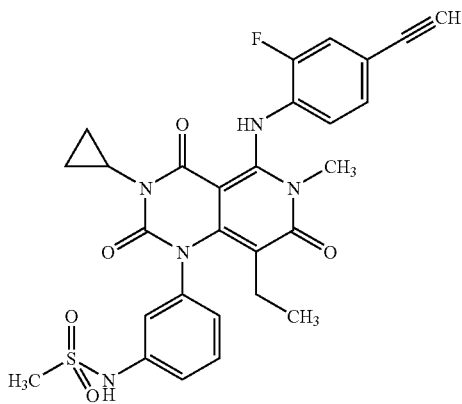 |
TABLE 4-5-continued
| Ex. No. | structural formula |
|---|---|
| 4-29 | 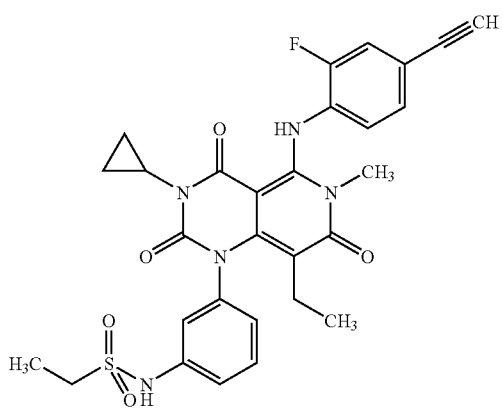 |
| 4-30 | 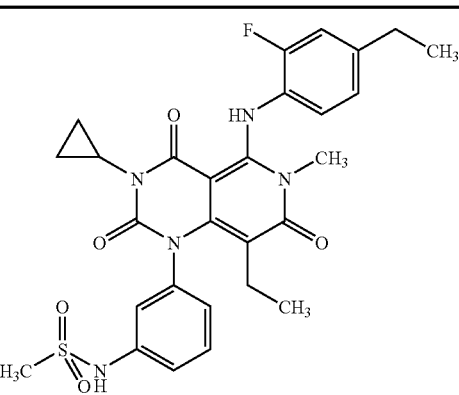 |
TABLE 4-6
| Ex. No. | structural formula |
|---|---|
| 4-31 | |

TABLE 4-6-continued
| Ex. No. | structural formula |
|---|---|
| 4-32 | 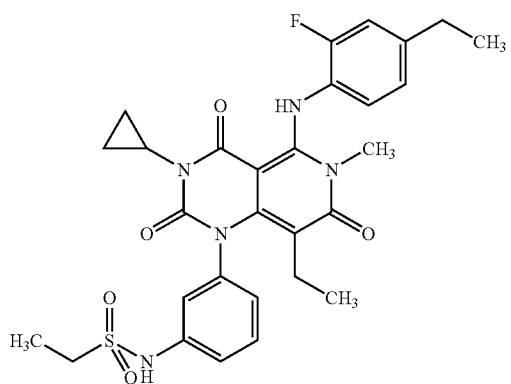 |
| 4-33 | 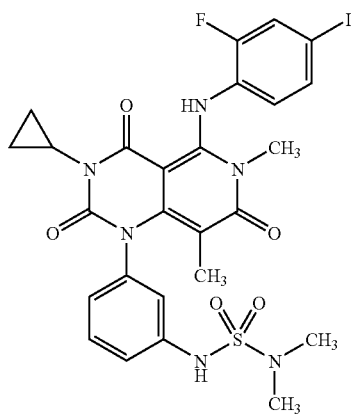 |
| 4-34 | 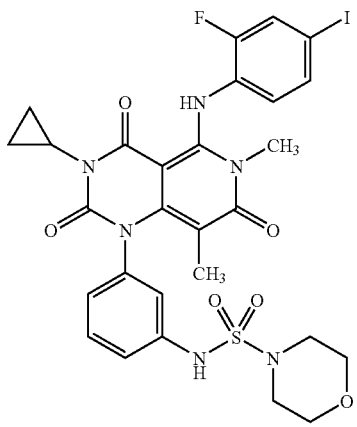 |
TABLE 4-6-continued
| Ex. No. | structural formula |
|---|---|
| 4-35 | 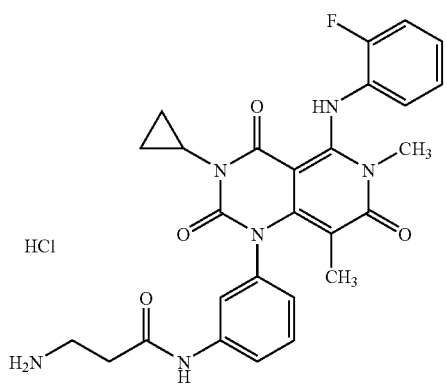 |
| 4-36 | 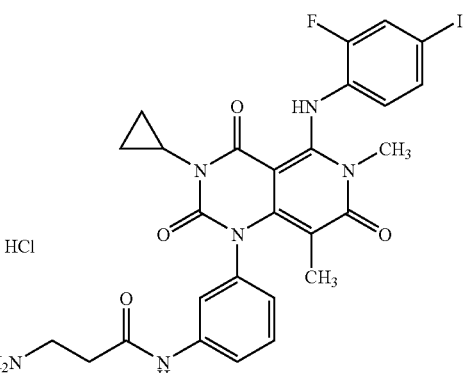 |
TABLE 4-7
| Ex. No. | structural formula |
|---|---|
| 4-37 | 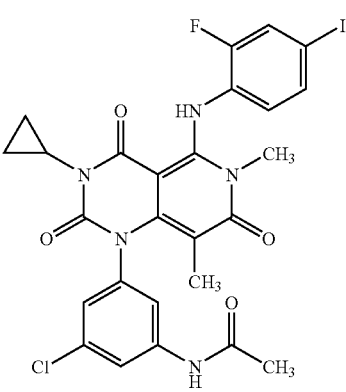 |

TABLE 4-7-continued
| Ex. No. | structural formula |
|---|---|
| 4-38 | 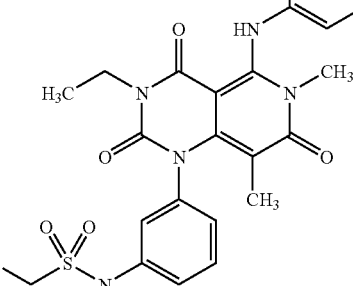 |
| 4-39 | |
| 4-40 | |
TABLE 4-7-continued
| Ex. No. | structural formula |
|---|---|
| 4-41 | 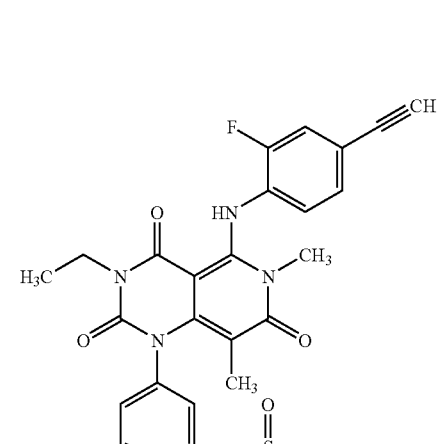 |
| 4-42 | |
TABLE 4-8
| Ex. No. | structural formula |
|---|---|
| 4-43 | 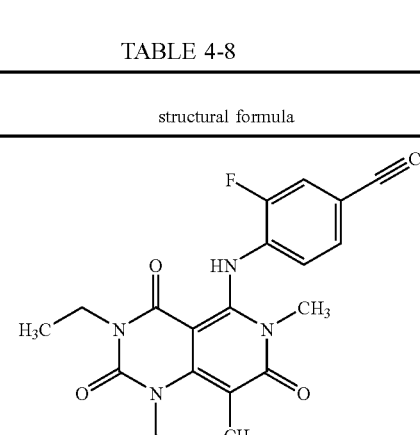 |

TABLE 4-8-continued

| Ex. No. | structural formula |
|---|---|
| 4-44 | (structure) |
| 4-45 | (structure) |
| 4-46 | (structure) |
| 4-47 | (structure) |
| 4-48 | (structure) |

TABLE 4-9

| Ex. No. | structural formula |
|---|---|
| 4-49 | (structure) |
| 4-50 | (structure) |

TABLE 4-9-continued
| Ex. No. | structural formula |
|---|---|
| 4-51 | 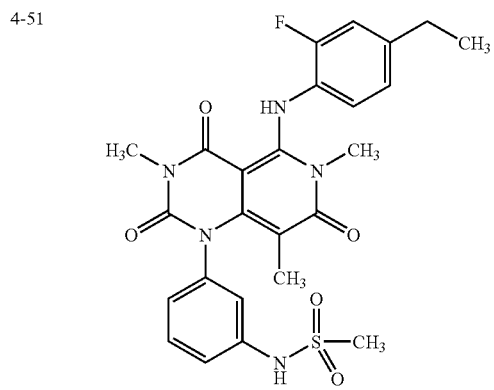 |
| 4-52 | 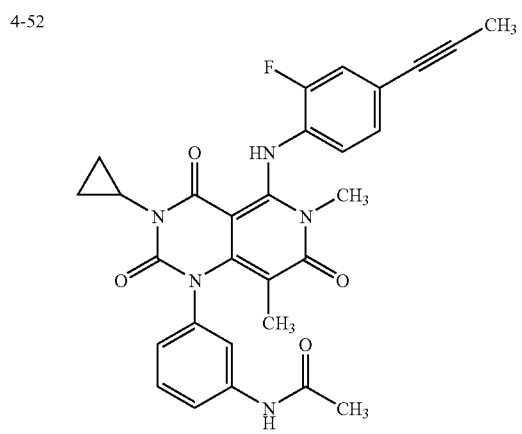 |
| 4-53 | 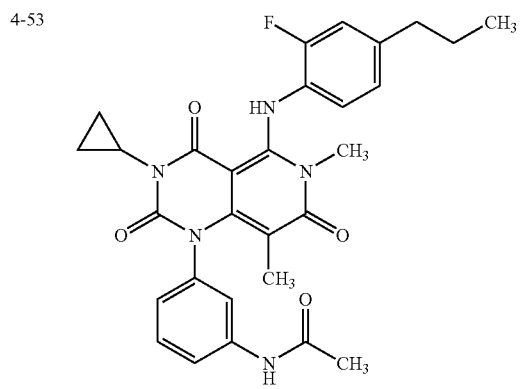 |
TABLE 4-9-continued
| Ex. No. | structural formula |
|---|---|
| 4-54 | 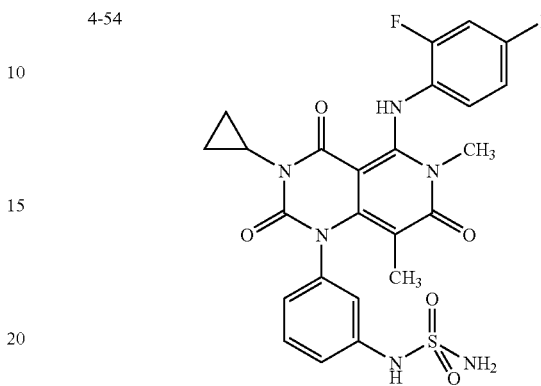 |
TABLE 4-10
| Ex. No. | structural formula |
|---|---|
| 4-55 | 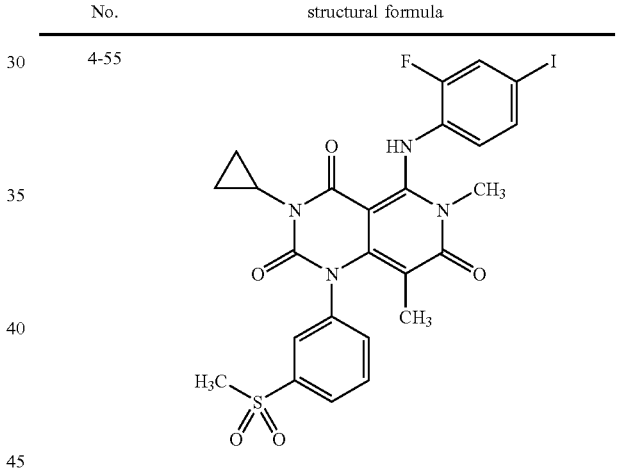 |
| 4-56 | 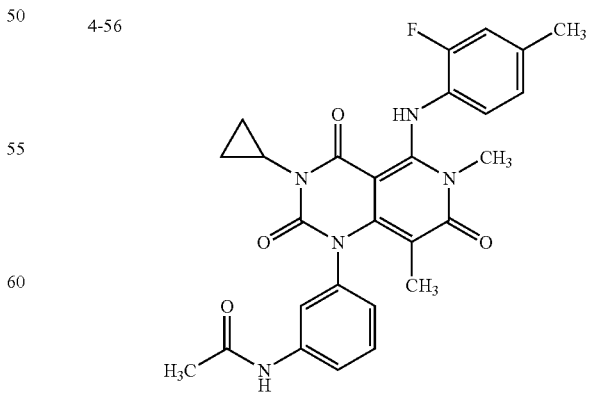 |

TABLE 4-10-continued
| Ex. No. | structural formula |
|---|---|
| 4-57 | 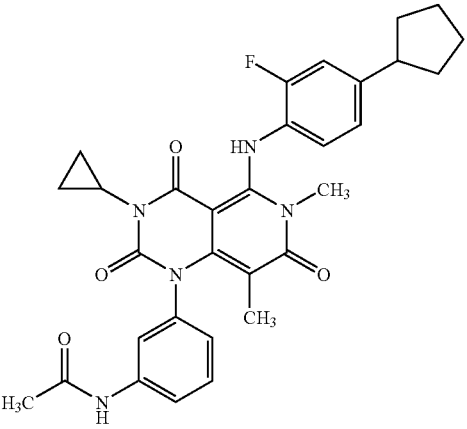 |
| 4-58 | 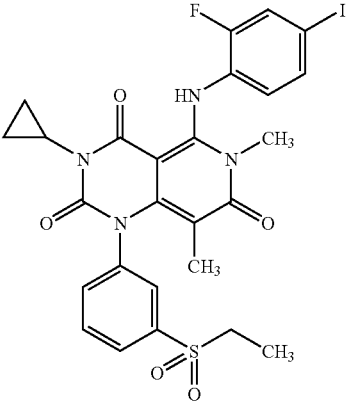 |
| 4-59 | 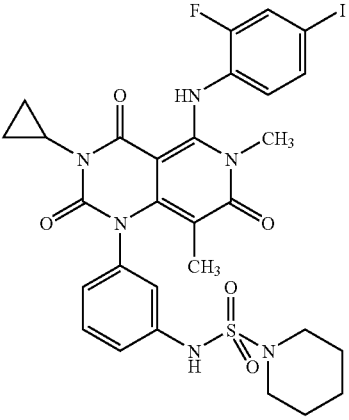 |
TABLE 4-10-continued
| Ex. No. | structural formula |
|---|---|
| 4-60 | 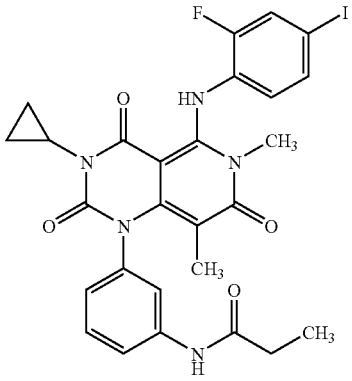 |
TABLE 4-11
| Ex. No. | structural formula |
|---|---|
| 4-61 | 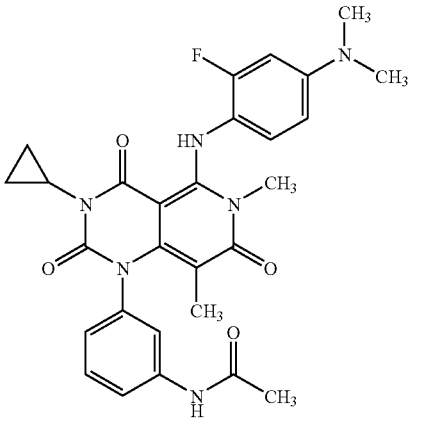 |
| 4-62 | 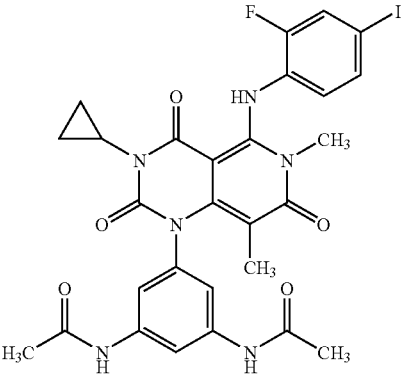 |

TABLE 4-11-continued

| Ex. No. | structural formula |
|---|---|
| 4-63 | (structure) |
| 4-64 | (structure) |
| 4-65 | (structure) |
| 4-66 | (structure) |

TABLE 4-12

| Ex. No. | structural formula |
|---|---|
| 4-67 | (structure) |
| 4-68 | (structure) |

TABLE 4-12-continued
| Ex. No. | structural formula |
|---|---|
| 4-69 | 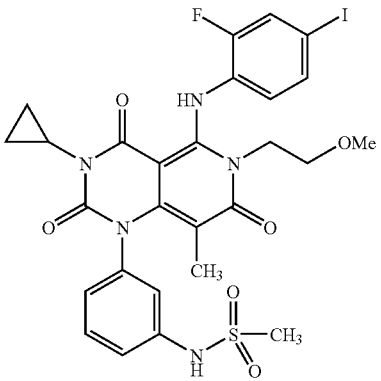 |
| 4-70 | 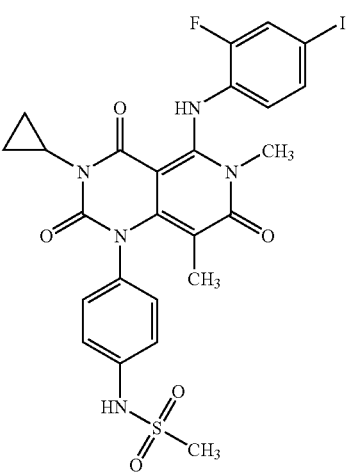 |
| 4-71 | 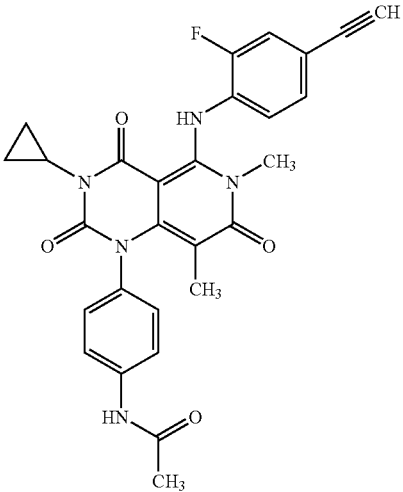 |
TABLE 4-12-continued
| Ex. No. | structural formula |
|---|---|
| 4-72 | 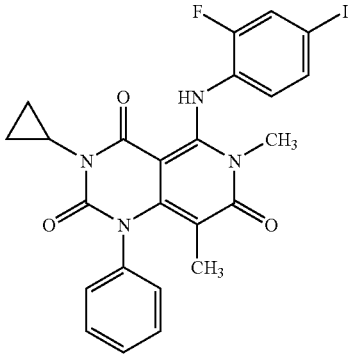 |
TABLE 4-13
| Ex. No. | structural formula |
|---|---|
| 4-73 | 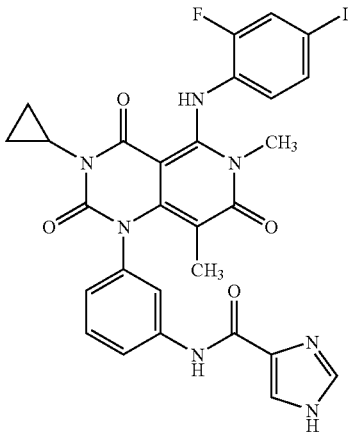 |
| 4-74 | |

TABLE 4-13-continued
| Ex. No. | structural formula |
|---|---|
| 4-75 | 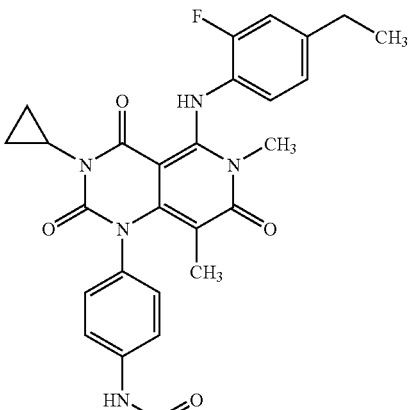 |
| 4-76 | 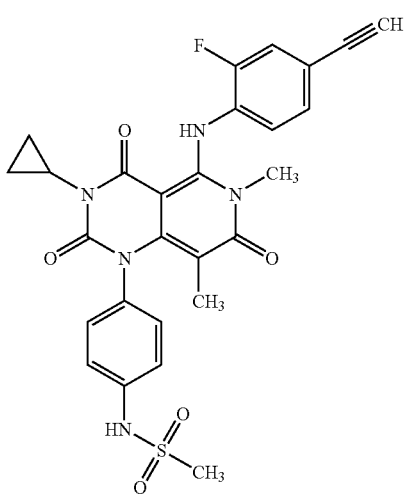 |
| 4-77 | 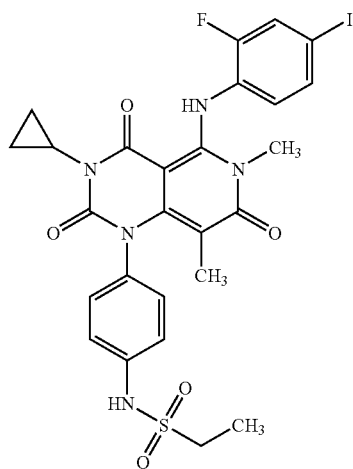 |
TABLE 4-13-continued
| Ex. No. | structural formula |
|---|---|
| 4-78 | 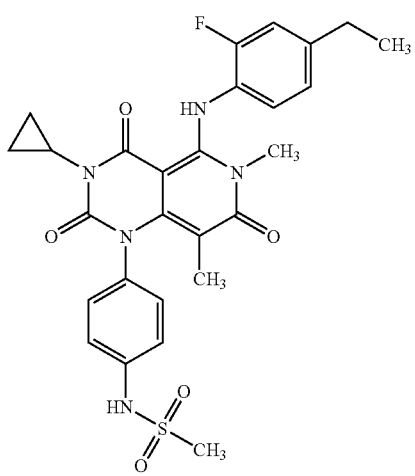 |
TABLE 4-14
| Ex. No. | structural formula |
|---|---|
| 4-79 | 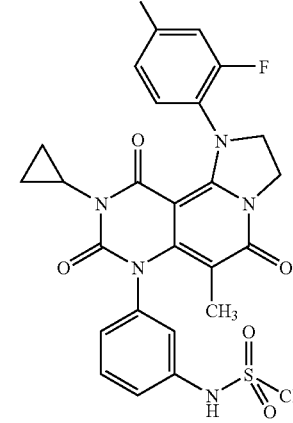 |
| 4-80 | 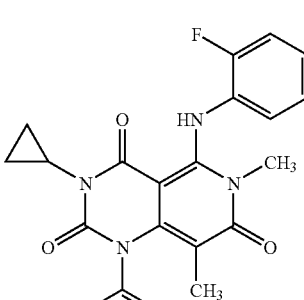 |

TABLE 4-14-continued
| Ex. No. | structural formula |
|---|---|
| 4-81 | 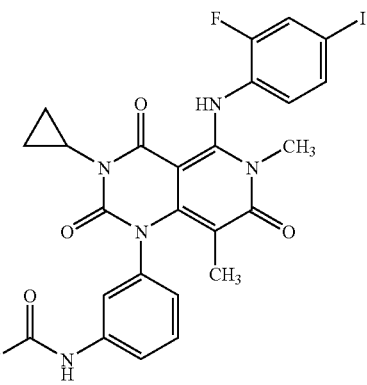 |
| 4-82 | 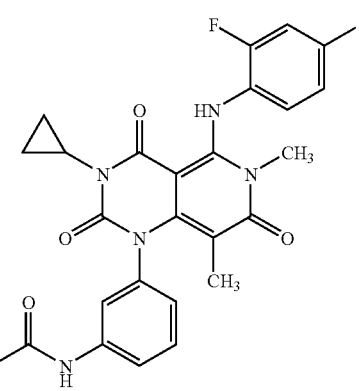 |
| 4-83 | 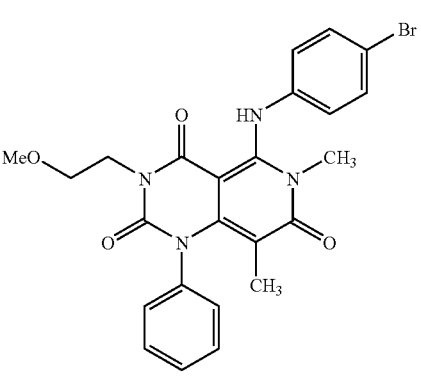 |
| 4-84 | 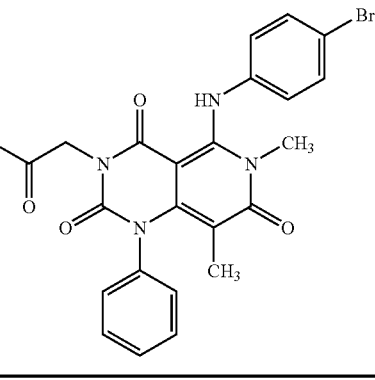 |
TABLE 4-15
| Ex. No. | structural formula |
|---|---|
| 4-85 | 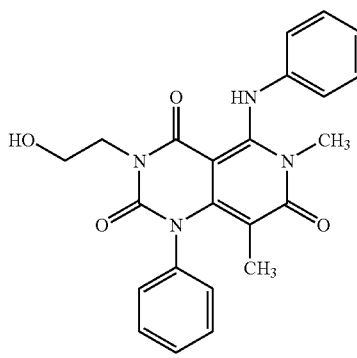 |
| 4-86 | 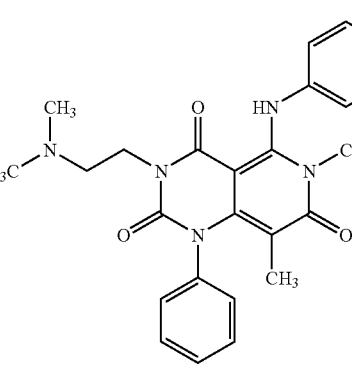 |
| 4-87 | 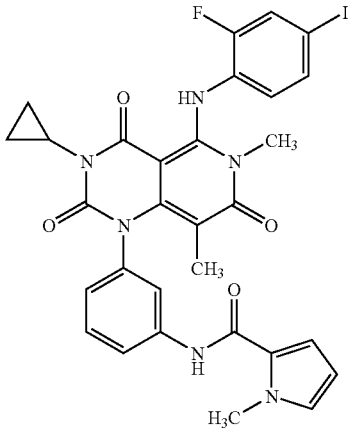 |

TABLE 4-15-continued

| Ex. No. | structural formula |
|---|---|
| 4-88 | |
| 4-89 | |
| 4-90 | |

TABLE 4-16

| Ex. No. | structural formula |
|---|---|
| 4-91 | |
| 4-92 | |
| 4-93 | |

TABLE 4-16-continued
| Ex. No. | structural formula |
|---|---|
| 4-94 | 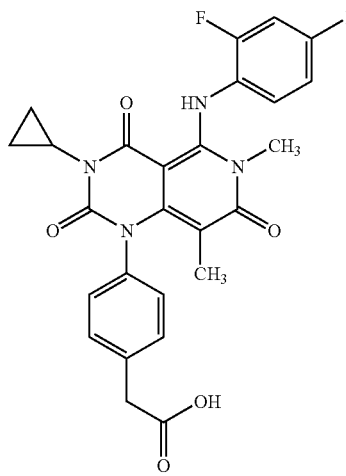 |
| 4-95 | 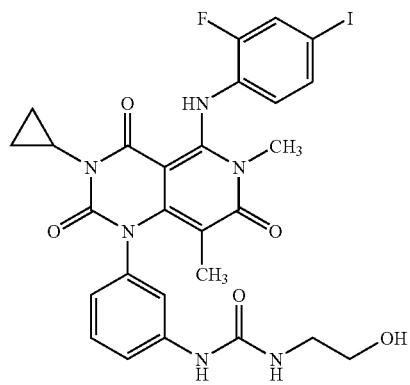 |
| 4-96 | 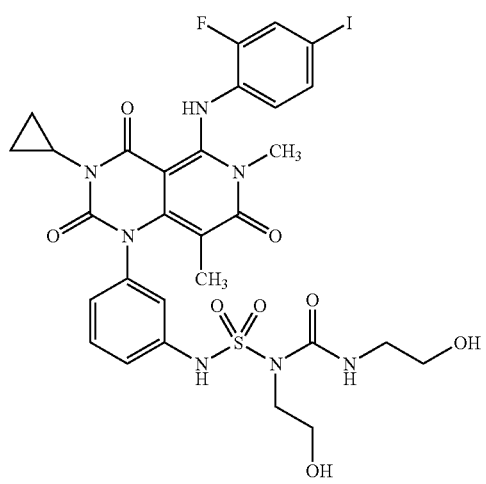 |
TABLE 4-17
| Ex. No. | structural formula |
|---|---|
| 4-97 | 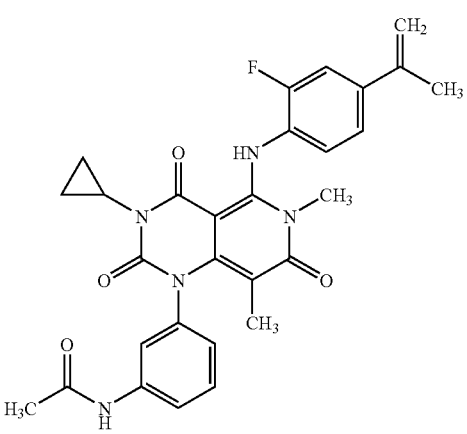 |
| 4-98 | 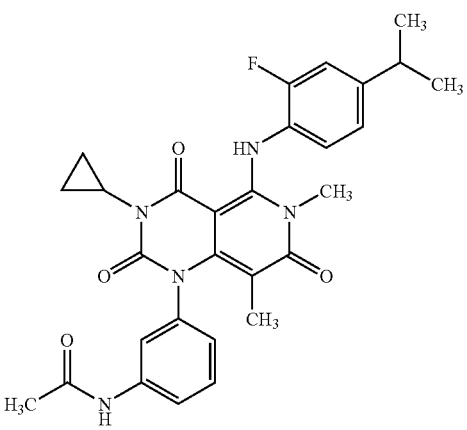 |
| 4-99 | 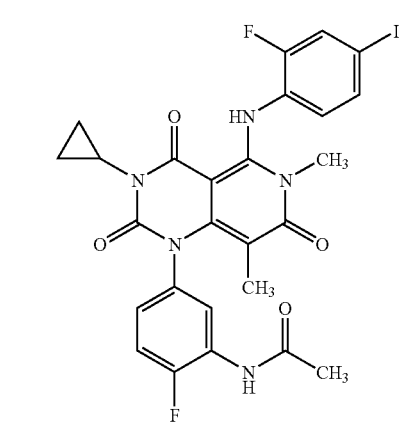 |

TABLE 4-17-continued
| Ex. No. | structural formula |
|---|---|
| 4-100 | 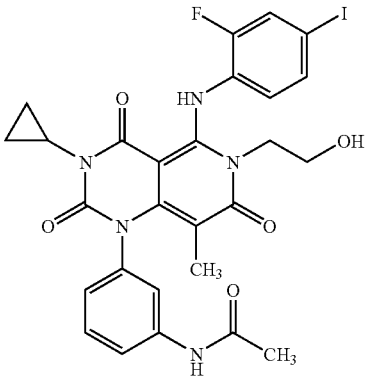 |
| 4-101 | 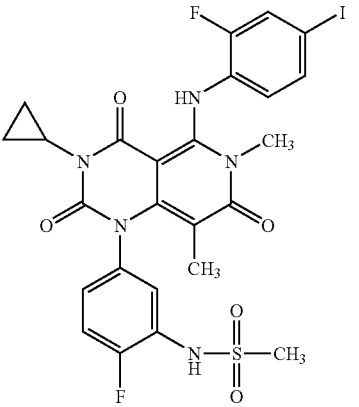 |
| 4-102 | 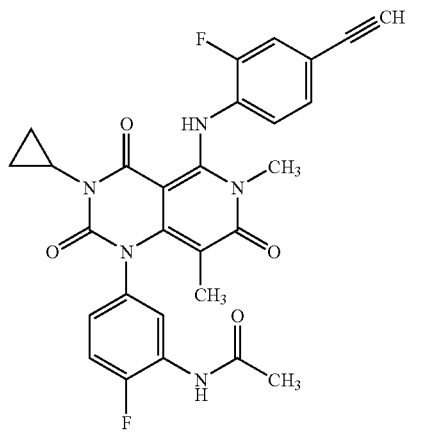 |
TABLE 4-18
| Ex. No. | structural formula |
|---|---|
| 4-103 | 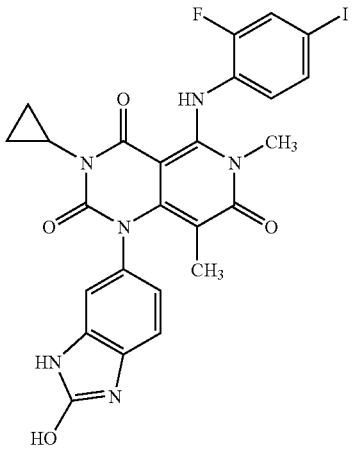 |
| 4-104 | 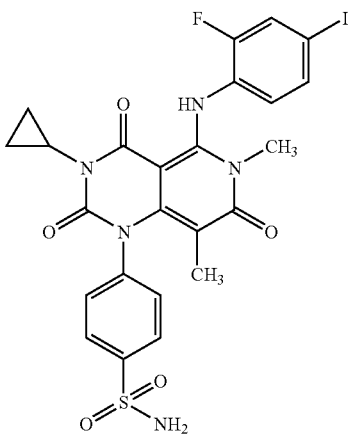 |
| 4-105 | 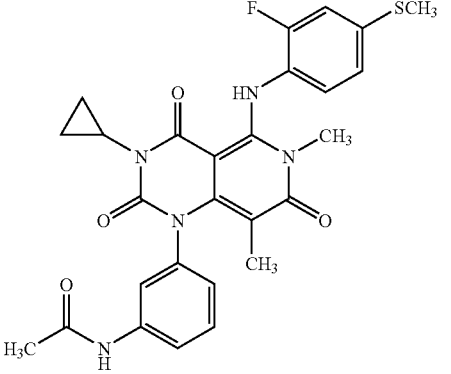 |

TABLE 4-18-continued

| Ex. No. | structural formula |
|---|---|
| 4-106 | |
| 4-107 | |
| 4-108 | |

TABLE 4-19

| Ex. No. | structural formula |
|---|---|
| 4-109 | |
| 4-110 | |
| 4-111 | |

TABLE 4-19-continued
| Ex. No. | structural formula |
|---|---|
| 4-112 | 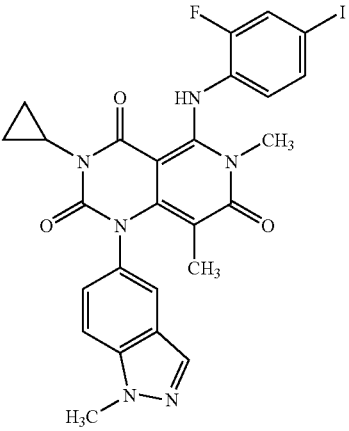 |
| 4-113 | 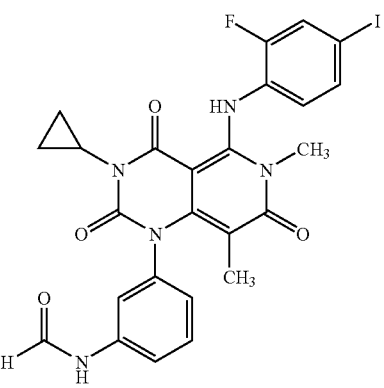 |
| 4-114 | 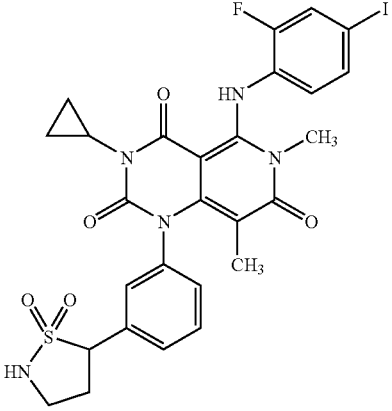 |
TABLE 4-20
| Ex. No. | structural formula |
|---|---|
| 4-115 | 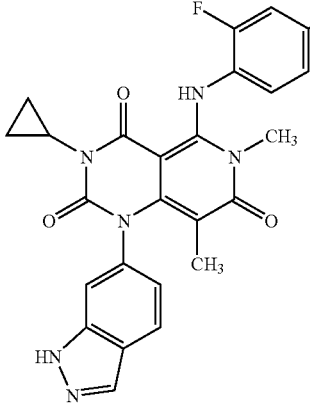 |
| 4-116 | 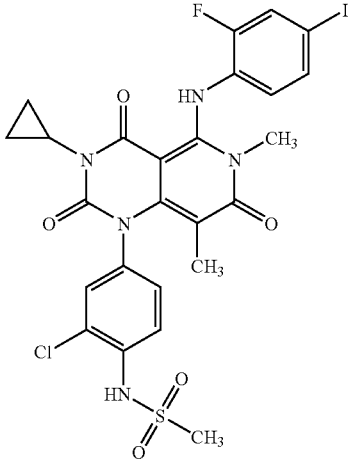 |
| 4-117 | 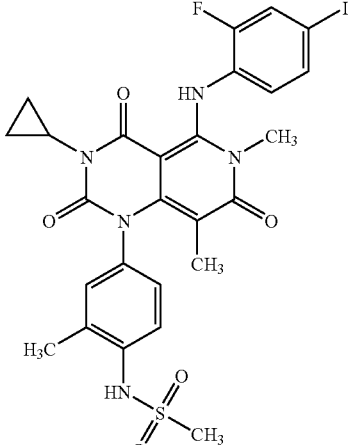 |

TABLE 4-20-continued
| Ex. No. | structural formula |
|---|---|
| 4-118 | 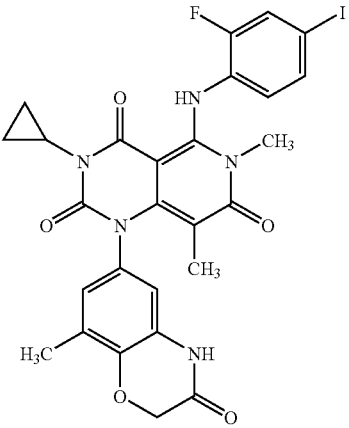 |
| 4-119 | 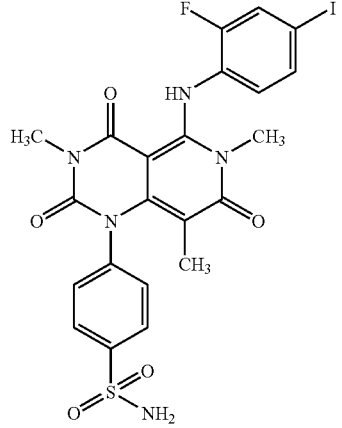 |
| 4-120 | 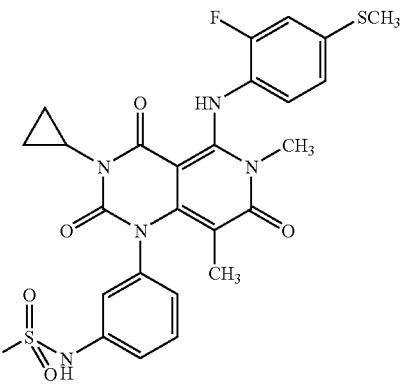 |
TABLE 4-21
| Ex. No. | structural formula |
|---|---|
| 4-121 | 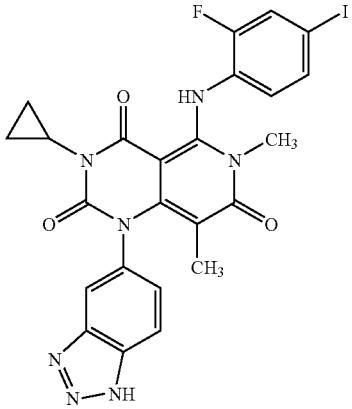 |
| 4-122 | 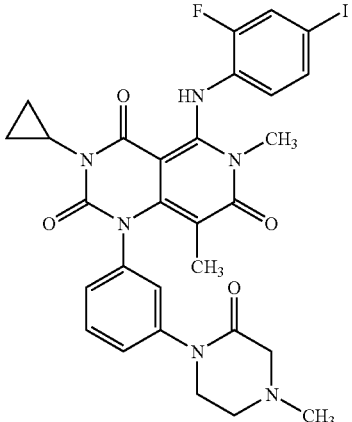 |
| 4-123 | 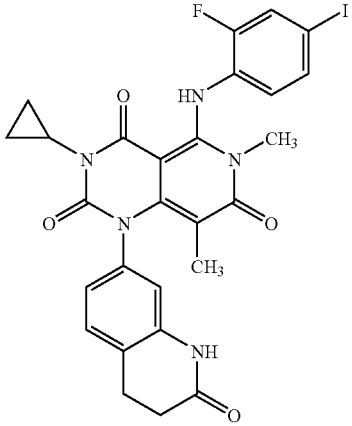 |

TABLE 4-21-continued
| Ex. No. | structural formula |
|---|---|
| 4-124 | 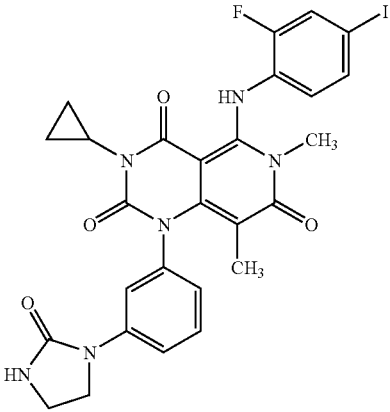 |
| 4-125 | 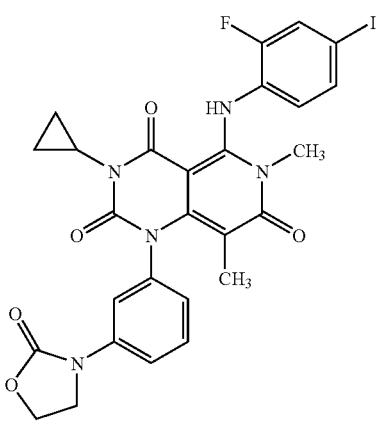 |
| 4-126 | 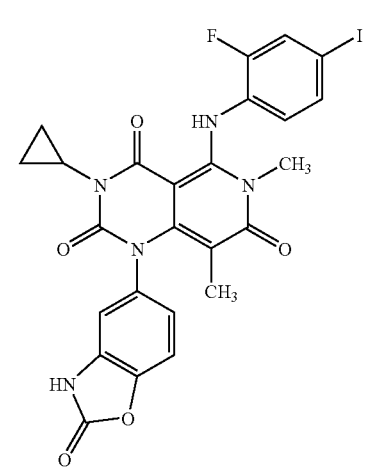 |
TABLE 4-22
| Ex. No. | structural formula |
|---|---|
| 4-127 | 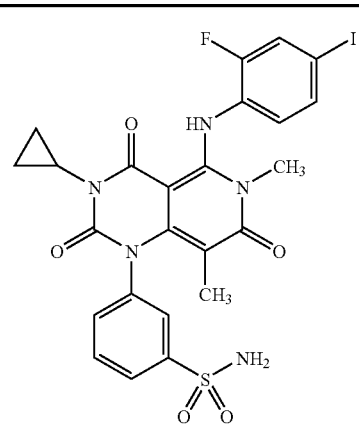 |
| 4-128 | 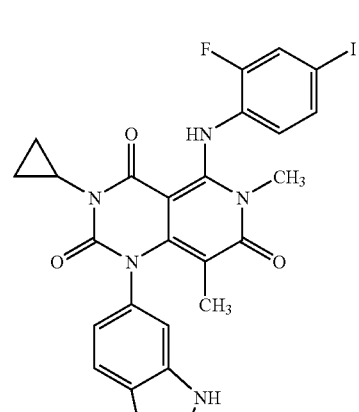 |
| 4-129 | 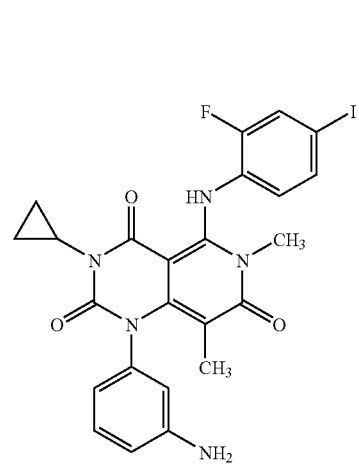 |

TABLE 4-22-continued
| Ex. No. | structural formula |
|---|---|
| 4-130 | 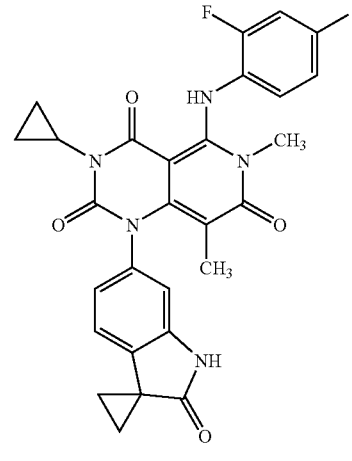 |
| 4-131 | |
TABLE 4-23
| Ex. No. | structural formula |
|---|---|
| 4-132 | 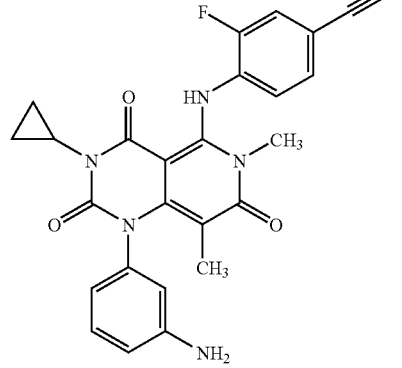 |
TABLE 4-23-continued
| Ex. No. | structural formula |
|---|---|
| 4-133 | 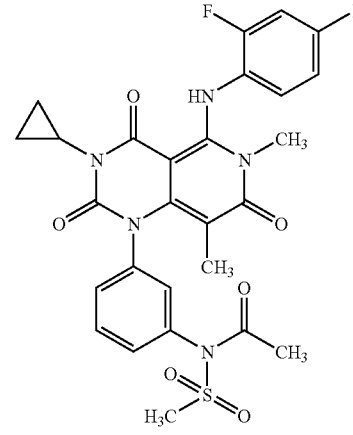 |
| 4-134 | |
| 4-135 | 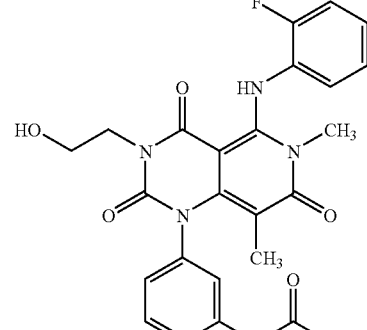 |

TABLE 4-23-continued
| Ex. No. | structural formula |
|---|---|
| 4-136 | 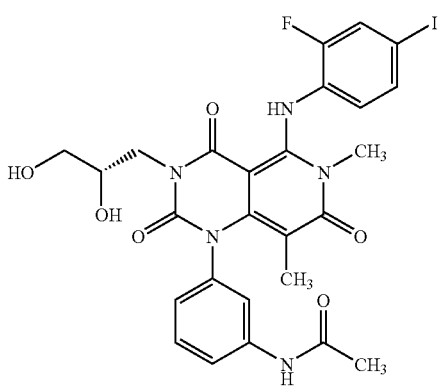 |
| 4-137 | 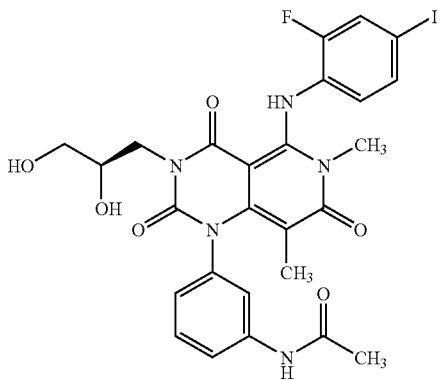 |
TABLE 4-24
| Ex. No. | structural formula |
|---|---|
| 4-138 | 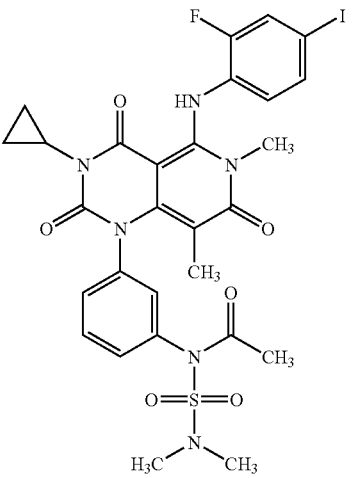 |
TABLE 4-24-continued
| Ex. No. | structural formula |
|---|---|
| 4-139 | 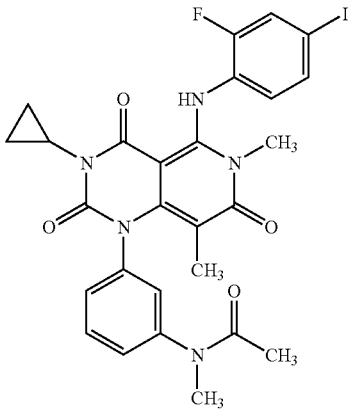 |
| 4-140 | 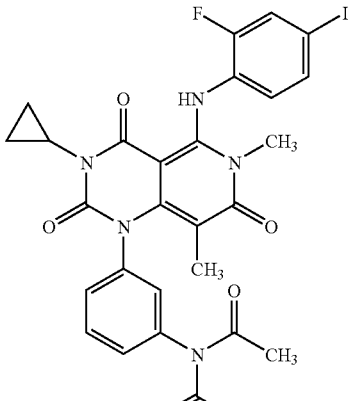 |
| 4-141 | 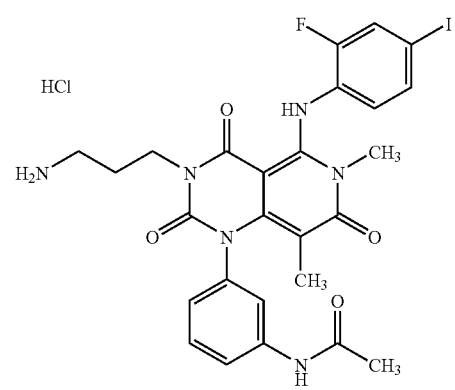 |

TABLE 4-24-continued

| Ex. No. | structural formula |
|---|---|
| 4-142 | (structure) |
| 4-143 | (structure) |

TABLE 4-25

| Ex. No. | structural formula |
|---|---|
| 4-144 | (structure) |
| 4-145 | (structure) |
| 4-146 | (structure) |
| 4-147 | (structure) |

TABLE 4-25-continued

| Ex. No. | structural formula |
| --- | --- |
| 4-148 | (structure shown) |

Example 4-149

By treating N-{3-[3-Cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]-phenyl}-acetamide 59 by a conventional method, sodium salt, hydrate, acetic acid solvate, dimethylsulfoxide solvate, ethanol solvate, nitromethane solvate, chlorobenzene solvate, 1-pentanol solvate, isopropyl alcohol solvate, ethylene glycol solvate and 3-methylbutanol solvate thereof were obtained.

N-{3-[3-Cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]-phenyl}-acetamide sodium salt:
$^1$H-NMR (DMSO-d$_6$, 400 MHz) δ 0.35-0.41 (m, 2H), 0.71-0.77 (m, 2H), 1.16 (s, 3H), 2.02 (s, 3H), 2.18-2.24 (m, 1H), 3.32 (s, 3H), 6.59 (t, J=8.8 Hz, 1H), 6.94 (d, J=8.6 Hz, 1H), 7.04 (d, J=10.2 Hz, 1H), 7.19 (d, J=11.1 Hz, 1H), 7.27 (t, J=8.0 Hz, 1H), 7.34 (s, 1H), 7.64 (d, J=8.3 Hz, 1H), 10.00 (s, 1H).
MS (ESI) m/z 616 [MH]$^+$.

N-{3-[3-Cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]-phenyl}-acetamide hydrate:
$^1$H-NMR (DMSO-d$_6$, 400 MHz) δ 0.63-0.70 (m, 2H), 0.91-1.00 (m, 2H), 1.25 (s, 3H), 2.04 (s, 3H), 2.58-2.66 (m, 1H), 3.08 (s, 3H), 6.92 (t, J=8.8 Hz, 1H), 7.00-7.05 (m, 1H), 7.36 (t, J=8.2 Hz, 1H), 7.52-7.63 (m, 3H), 7.79 (dd, J=2.0, 10.4 Hz, 1H), 10.09 (s, 1H), 11.08 (s, 1H).
MS (ESI) m/z 616 [MH]$^+$.

N-{3-[3-Cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]-phenyl}-acetamide acetic acid solvate:
$^1$H-NMR (DMSO-d$_6$, 400 MHz) δ 0.63-0.70 (m, 2H), 0.92-0.98 (m, 2H), 1.25 (s, 3H), 1.91 (s, 3H), 2.04 (s, 3H), 2.59-2.65 (m, 1H), 3.08 (s, 3H), 6.92 (t, J=8.6 Hz, 1H), 7.00-7.05 (m, 1H), 7.36 (t, J=7.6 Hz, 1H), 7.53-7.62 (m, 3H), 7.79(dd, J=10.4 Hz, 1H), 10.08(s, 1H), 11.07(s, 1H), 11.94(s, 1H).
MS (ESI) m/z 616 [MH]$^+$.

N-{3-[3-Cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]-phenyl}-acetamide dimethyl sulfoxide solvate:
$^1$H-NMR (CDCl$_3$, 400 MHz) δ 0.76-0.82 (m, 2H), 1.09-1.15 (m, 2H), 1.41 (s, 3H), 2.14 (s, 3H), 2.62 (s, 6H), 2.71-2.77 (m, 1H), 3.20 (s, 3H), 6.70 (t, J=8.4 Hz, 1H), 7.00 (brs, 1H), 7.32 (brs, 2H), 7.43-7.47 (m, 1H), 7.52 (dd, J=2.0, 9.6 Hz, 1H), 7.71 (brs, 2H), 11.30 (s, 1H).
MS (ESI) m/z 616 [MH]$^+$.

N-{3-[3-Cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]-phenyl}-acetamide ethanol solvate:
$^1$H-NMR (DMSO-d$_6$, 300 MHz) δ 0.63-0.70 (m, 2H), 0.91-1.00 (m, 2H), 1.06 (t, J=7.1 Hz, 3H), 1.25 (s, 3H), 2.04 (s, 3H), 2.58-2.66 (m, 1H), 3.07 (s, 3H), 3.40-3.49 (m, 2H), 4.33 (t, J=5.1 Hz, 1H), 6.92 (t, J=8.8 Hz, 1H), 7.00-7.05 (m, 1H), 7.36 (t, J=8.2 Hz, 1H), 7.52-7.63 (m, 3H), 7.79 (dd, J=2.0, 10.4 Hz, 1H), 10.08 (s, 1H), 11.07 (s, 1H).
MS (ESI) m/z 616 [MH]$^+$.

N-{3-[3-Cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]-phenyl}-acetamide nitromethane solvate:
$^1$H-NMR (DMSO-d$_6$, 300 MHz) δ 0.63-0.70 (m, 2H), 0.91-1.00 (m, 2H), 1.25 (s, 3H), 2.04 (s, 3H), 2.58-2.66 (m, 1H), 3.07 (s, 3H), 4.42 (s, 2H), 6.92 (t, J=8.8 Hz, 1H), 7.00-7.05 (m, 1H), 7.36 (t, J=8.2 Hz, 1H), 7.52-7.63 (m, 3H), 7.79 (dd, J=2.0, 10.4 Hz, 1H), 10.08 (s, 1H), 11.07 (s, 1H).

N-{3-[3-Cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]-phenyl}-acetamide chlorobenzene solvate:
$^1$H-NMR (DMSO-d$_6$, 300 MHz) δ 0.63-0.70 (m, 2H), 0.91-1.00 (m, 2H), 1.25 (s, 3H), 2.04 (s, 3H), 2.58-2.66 (m, 1H), 3.07 (s, 3H), 6.92 (t, J=8.8 Hz, 1H), 7.00-7.05 (m, 1H), 7.29-7.45 (m, 5H), 7.50-7.63 (m, 3H), 7.79 (dd, J=2.0, 10.4 Hz, 1H), 10.08 (s, 1H), 11.07 (s, 1H).

N-{3-[3-Cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]-phenyl}-acetamide 1-pentanol solvate
$^1$H-NMR (DMSO-d$_6$, 300 MHz) δ 0.62-0.70 (m, 2H), 0.86 (t, J=7.0 Hz, 1.5H), 0.90-0.99 (m, 2H), 1.22-1.30 (m, 5H), 1.35-1.44 (m, 1H), 2.04 (s, 3H), 2.56-2.67 (m, 1H), 3.08 (s, 3H), 3.33-3.41 (m, 1H), 4.30 (t, J=5.1 Hz, 0.5H), 6.91 (t, J=8.5 Hz, 1H), 7.00-7.06 (m, 1H), 7.36 (t, J=8.3 Hz, 1H), 7.52-7.62 (m, 3H), 7.74-7.81 (m, 1H), 10.08 (s, 1H), 11.07 (s, 1H).

N-{3-[3-Cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]-phenyl}-acetamide isopropyl alcohol solvate:
$^1$H-NMR (DMSO-d$_6$, 400 MHz) δ 0.63-0.69(m, 2H), 0.91-0.98 (m, 2H), 1.04 (d, J=6.0 Hz, 6H), 1.25 (s, 3H), 2.04 (s, 3H), 2.58-2.66 (m, 1H), 3.07 (s, 3H), 3.73-3.81 (m, 1H), 4.34 (d, J=4.2 Hz, 1H), 6.92 (t, J=8.7 Hz, 1H), 7.00-7.05 (m, 1H), 7.36 (t, J=8.3 Hz, 1H), 7.52-7.62 (m, 3H), 7.79 (dd, J=1.8, 10.2 Hz, 1H), 10.10 (s, 1H), 11.08 (s, 1H).

N-{3-[3-Cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]-phenyl}-acetamide ethylene glycol solvate:
$^1$H-NMR (DMSO-d$_6$, 300 MHz) δ 0.63-0.70 (m, 2H), 0.91-1.00 (m, 2H), 1.24 (s, 3H), 2.04 (s, 3H), 2.58-2.66 (m, 1H), 3.07 (s, 3H), 3.36-3.41 (m, 4H), 4.37-4.44 (m, 1H), 6.92 (t, J=8.8 Hz, 1H), 7.00-7.05 (m, 1H), 7.36 (t, J=8.2 Hz, 1H), 7.52-7.63 (m, 3H), 7.79 (dd, J=2.0, 10.4 Hz, 1H), 10.10 (s, 1H), 11.08 (s, 1H).

N-{3-[3-Cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]-phenyl}-acetamide 3-methyl-1-butanol solvate:

$^1$H-NMR (DMSO-d$_6$, 400 MHz) δ 0.64-0.69 (m, 2H), 0.85 (d, J=6.7 Hz, 6H), 0.92-0.98 (m, 2H), 1.25 (s, 3H), 1.31 (q, J=6.7 Hz, 2H), 1.60-1.70 (m, 1H), 2.04 (s, 3H), 2.59-2.66 (m, 1H), 3.08 (s, 3H), 3.38-3.44 (m, 2H), 4.26 (t, J=5.1 Hz, 1H), 6.92 (t, J=8.7 Hz, 1H), 7.01-7.05 (m, 1H), 7.35 (t, J=8.0 Hz, 1H), 7.52-7.62 (m, 3H), 7.78 (dd, J=1.9, 10.2 Hz, 1H), 10.08 (s, 1H), 11.07 (s, 1H).

Example 4-150

By treating N-{3-[3-cyclopropyl-5-(4-ethynyl-2-fluorophenylamino)-6,8-dimethyl-2,4,7-trioxo-3,4,6,7-tetrahydro-2H-pyrido[4,3-d]pyrimidin-1-yl]phenyl}acetamide 62 according to a conventional method, acetic acid solvate was obtained.

N-{3-[3-cyclopropyl-5-(4-ethynyl-2-fluorophenylamino)-6,8-dimethyl-2,4,7-trioxo-3,4,6,7-tetrahydro-2H-pyrido[4,3-d]pyrimidin-1-yl]phenyl}acetamide acetic acid solvate:

$^1$H-NMR (DMSO-d$_6$, 400 MHz) δ 0.60-0.70(m, 2H), 0.90-1.00(m, 2H), 1.26(s, 3H), 1.91(s, 3H), 2.04(s, 3H), 2.59-2.66(m, 1H), 3.10(s, 3H), 4.29(s, 1H), 7.01-7.05(m, 1H), 7.08(t, J=8.6 Hz, 1H), 7.31(dd, J=1.6, 8.3 Hz, 1H), 7.36(t, J=8.1 Hz, 1H), 7.52(dd, J=1.6, 11.3 Hz, 1H), 7.57-7.62(m, 2H), 10.09(s, 1H), 11.09(s, 1H), 11.94(s, 1H).

MS (ESI) m/z 514 [MH]$^+$.

Example 4-151

By treating N-{3-[5-(2-fluoro-4-iodophenylamino)-3,6,8-trimethyl-2,4,7-trioxo-3,4,6,7-tetrahydro-2H-pyrido[4,3-d]pyrimidin-1-yl]phenyl}methanesulfonamide 72 according to a conventional method, a sodium salt was obtained.

N-{3-[5-(2-fluoro-4-iodophenylamino)-3,6,8-trimethyl-2,4,7-trioxo-3,4,6,7-tetrahydro-2H-pyrido[4,3-d]pyrimidin-1-yl]phenyl}methanesulfonamide sodium salt:

$^1$H-NMR (DMSO-d$_6$, 300 MHz) δ 1.25(s, 3H), 2.78(s, 3H), 2.97(s, 3H), 3.24(s, 3H), 6.68(t, J=8.7 Hz, 1H), 6.77(d, J=7.5 Hz, 1H), 6.90-7.00(m, 2H), 7.10-7.30(m, 2H), 7.37(d, J=10.0 Hz, 1H), 10.30(brs, 1H).

MS (ESI) m/z 626 [MH]$^+$.

Example 1001-6010

The compounds shown in Tables 11-1 to 11-6 can be obtained in the same manner as in Examples 1-1 to 1-148 or by other conventional method employed as necessary.

TABLE 11-1

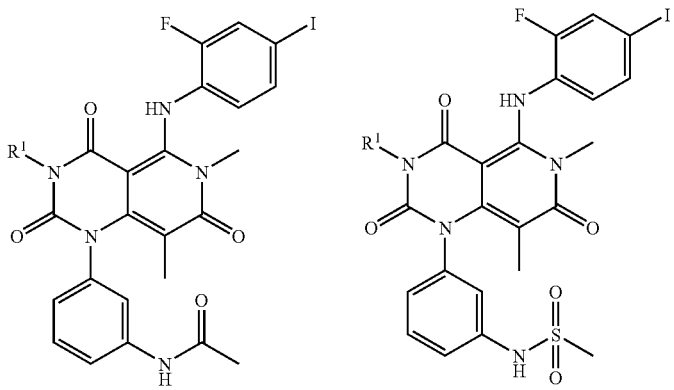

| Example No. | R$^1$ | Example No. | R$^1$ |
|---|---|---|---|
| 1001 | 2-F—Ph— | 1002 | 2-F—Ph— |
| 1003 | 3-F—Ph— | 1004 | 3-F—Ph— |
| 1005 | 4-F—Ph— | 1006 | 4-F—Ph— |
| 1007 | 2-Me—Ph— | 1008 | 2-Me—Ph— |
| 1009 | 3-Me—Ph— | 1010 | 3-Me—Ph— |
| 1011 | 4-Me—Ph— | 1012 | 4-Me—Ph— |
| 1013 | 2-MeO—Ph— | 1014 | 2-MeO—Ph— |
| 1015 | 3-MeO—Ph— | 1016 | 3-MeO—Ph— |
| 1017 | 4-MeO—Ph— | 1018 | 4-MeO—Ph— |
| 1019 | 2-Py— | 1020 | 2-Py— |
| 1021 | 3-Py— | 1022 | 3-Py— |
| 1023 | 4-Py— | 1024 | 4-Py— |
| 1025 | 2-MeS(CH2)2— | 1026 | 2-MeS(CH2)2— |
| 1027 | 2-HS(CH2)2— | 1028 | 2-HS(CH2)2— |
| 1029 | 4-(Me)2N—Bzl— | 1030 | 4-(Me)2N—Bzl— |
| 1031 | 3-(Me)2N—Bzl— | 1032 | 3-(Me)2N—Bzl— |
| 1033 | 2-(Me)2N—Bzl— | 1034 | 2-(Me)2N—Bzl— |
| 1035 | 4-(Me)2N—Phenethyl- | 1036 | 4-(Me)2N—Phenethyl- |
| 1037 | 4-HO—Phenethyl- | 1038 | 4-HO—Phenethyl- |
| 1039 | 4-HO—Bzl— | 1040 | 4-HO—Bzl— |
| 1041 | 3-HO—Bzl— | 1042 | 3-HO—Bzl— |
| 1043 | 2-HO—Bzl— | 1044 | 2-HO—Bzl— |
| 1045 | 4-MeO—Bzl— | 1046 | 4-MeO—Bzl— |
| 1047 | 4-Py—(CH2)2— | 1048 | 4-Py—(CH2)2— |

TABLE 11-1-continued
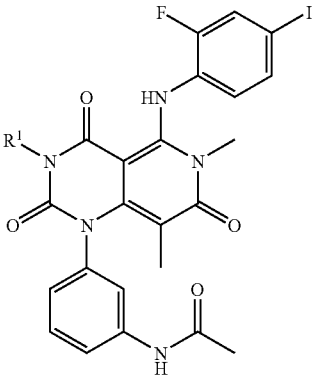 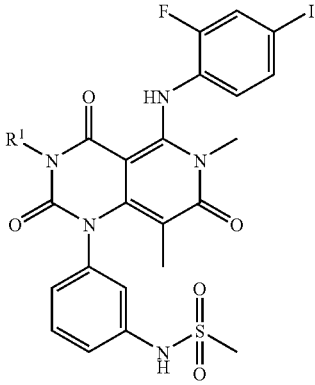
| Example No. | R¹ | Example No. | R¹ |
|---|---|---|---|
| 1049 | 3-Py—(CH2)2— | 1050 | 3-Py—(CH2)2— |
| 1051 | 2-Py—(CH2)2— | 1052 | 2-Py—(CH2)2— |
| 1053 | 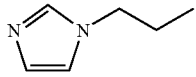 | 1054 | 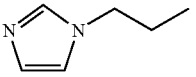 |
| 1055 | 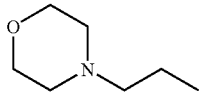 | 1056 | 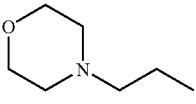 |
| 1057 | Allyl- | 1058 | Allyl- |
| 1059 | CF3CH2— | 1060 | CF3CH2— |
| 1061 | n-Propyl- | 1062 | n-Propyl- |
| 1063 | Cyclopropylmethyl- | 1064 | Cyclopropylmethyl- |
| 1065 | HO— | 1066 | HO— |
| 1067 | HO—(CH2)2—O— | 1068 | HO—(CH2)2—O— |
| 1069 | HO—(CH2)3—O— | 1070 | HO—(CH2)3—O— |
| 1071 | 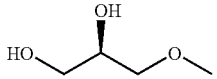 | 1072 | 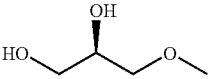 |
| 1073 | 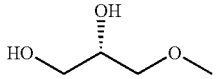 | 1074 | 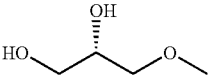 |
| 1075 | 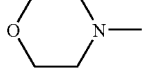 | 1076 | 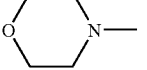 |
| 1077 | 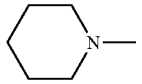 | 1078 | 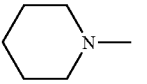 |
| 1079 | 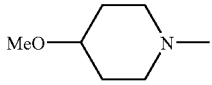 | 1080 | 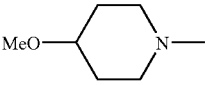 |
| 1081 | 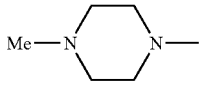 | 1082 | 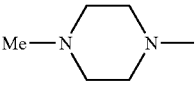 |

TABLE 11-1-continued
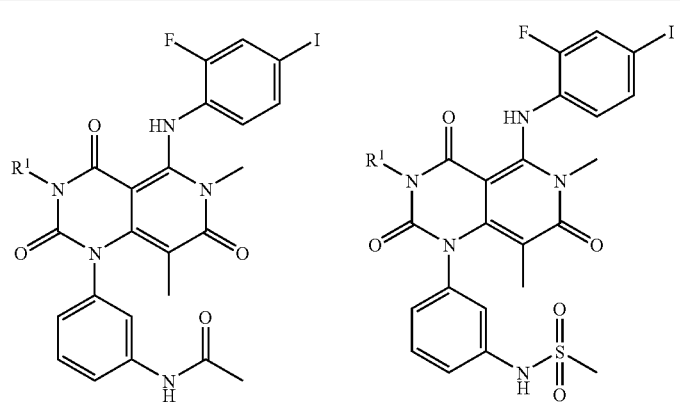
| Example No. | R¹ | Example No. | R¹ |
|---|---|---|---|
| 1083 | 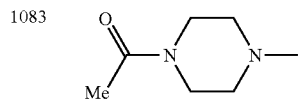 | 1084 | 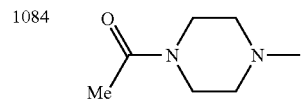 |
Py: Pyridyl,
Ph: Phenyl
Bzl: Benzyl
TABLE 11-2
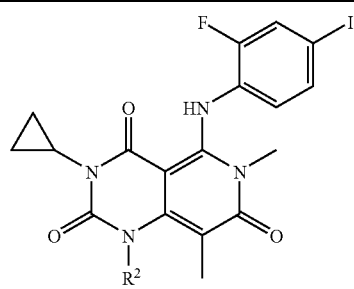
| Example No. | R1 | Example No. | R1 |
|---|---|---|---|
| 2001 | 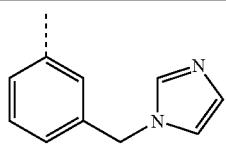 | 2002 | 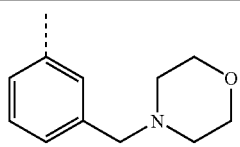 |
| 2003 | 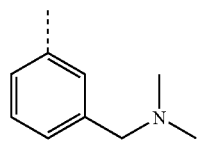 | 2004 | 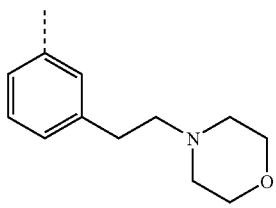 |
| 2005 | 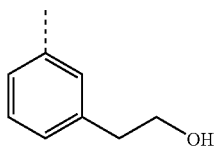 | 2006 | 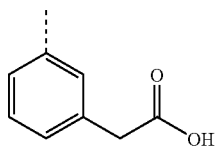 |

TABLE 11-2-continued

| Example No. | R1 | Example No. | R1 |
|---|---|---|---|
| 2007 | 3-(2-methoxyethyl)phenyl | 2008 | 3-(2-(dimethylamino)ethyl)phenyl |
| 2009 | 3-(2-(imidazol-1-yl)ethoxy)phenyl | 2010 | 3-(2-(4-methylpiperazin-1-yl)ethoxy)phenyl |
| 2011 | 3-(2-(piperidin-1-yl)ethoxy)phenyl | 2012 | 3-(2-(dimethylamino)ethoxy)phenyl |
| 2013 | 3-(2-hydroxyethoxy)phenyl | 2014 | 3-(2-carboxyethoxy)phenyl |
| 2015 | 3-(2-(imidazol-1-yl)ethylamino)phenyl | 2016 | 3-(2-(morpholin-4-yl)ethylamino)phenyl |
| 2017 | 3-(N-acetyl-N-(2-(dimethylamino)ethyl)amino)phenyl | 2018 | 3-((2-methoxyethyl)amino)phenyl |
| 2019 | 3-(N-methyl-N-(2-methoxyethyl)amino)phenyl | 2020 | 3-((3-methoxy-3-oxopropyl)amino)phenyl |

TABLE 11-3
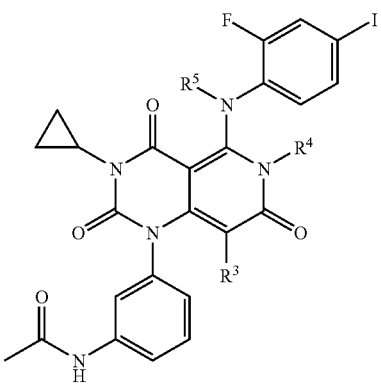
| Example No. | R³ | R⁴ | R⁵ |
|---|---|---|---|
| 3001 | Allyl— | Me— | H |
| 3002 | n-Propyl— | Me— | H |
| 3003 | CF3CH2— | Me— | H |
| 3004 | MeO(CH2)2— | Me— | H |
| 3005 | (Me)2N—(CH2)2— | Me— | H |
| 3006 | Ph— | Me— | H |
| 3007 | 3-Py | Me— | H |
| 3008 | Me— | Allyl— | H |
| 3009 | Me— | MeO— | H |
| 3010 | Me— | Cyclopropyl | H |
| 3011 | Me— | Me— | HO— |
| 3012 | Me— | Me— | MeO— |
TABLE 11-4
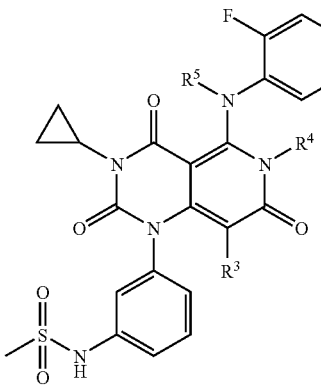
| Example No. | R³ | R⁴ | R⁵ |
|---|---|---|---|
| 4001 | Allyl— | Me— | H |
| 4002 | n-Propyl— | Me— | H |
| 4003 | CF3CH2— | Me— | H |
| 4004 | MeO(CH2)2— | Me— | H |
| 4005 | (Me)2N—(CH2)2— | Me— | H |
| 4006 | Ph— | Me— | H |
| 4007 | 3-Py | Me— | H |
| 4008 | Me— | Allyl— | H |
| 4009 | Me— | MeO— | H |
| 4010 | Me— | Cyclopropyl | H |
| 4011 | Me— | Me— | HO— |
| 4012 | Me— | Me— | MeO— |
TABLE 11-5
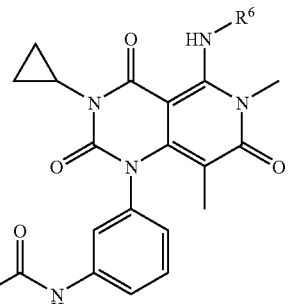
| Example No. | R⁶ | Example No. | R⁶ |
|---|---|---|---|
| 5001 | 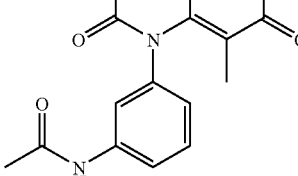 | 5002 | 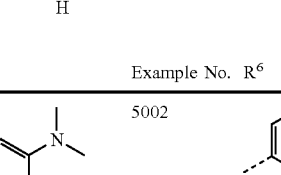 |
| 5003 | 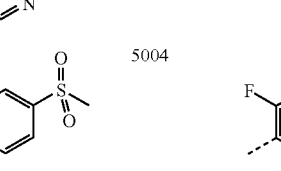 | 5004 | 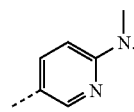 |
| 5005 | 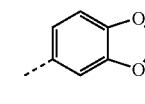 | 5006 | 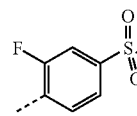 |
| 5007 | 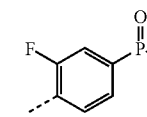 | 5008 | 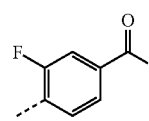 |
| 5009 | 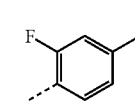 | 5010 | 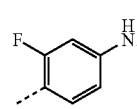 |
TABLE 11-6
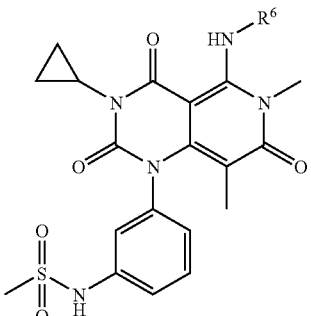
| Example No. | R⁶ | Example No. | R⁶ |
|---|---|---|---|
| 6001 |  | 6002 |  |

TABLE 11-6-continued

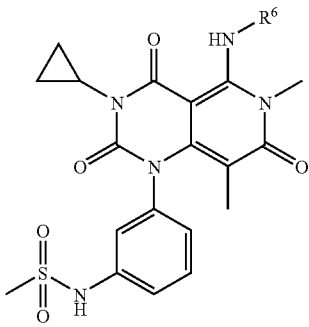

| Example No. | R⁶ | Example No. | R⁶ |
|---|---|---|---|
| 6003 | F-phenyl-SO₂-methyl | 6004 | F-phenyl-P(O)(methyl)₂ |
| 6005 | F-phenyl-C(O)O-methyl | 6006 | F-phenyl-CN |
| 6007 | F-phenyl-NH-S(O)₂-methyl | 6008 | biphenyl |
| 6009 | phenyl-N-morpholine | 6010 | F-phenyl-CH₂-CF₃ |

Example 5

Evaluation of Growth Inhibitory Effect Against Cancer Cell Lines

Renal cancer cell line ACHN cell or colorectal cancer cell line HT-29 cells were cultured in a 96 well plate at $1.0 \times 10^4$ cells/90 μL/well for 24 hrs, then a test substance dissolved in DMSO (dimethyl sulfoxide) was added. After 18 hrs, $^3$H-thymidine (0.25 μCi/well) was added and the cells were cultured for 6 hrs. Using a cell harvester, the cells were recovered on a UniFilter-96 GF/B glass filter and the $^3$H radioactivity uptaken by the cells was measured by Top-Count (Packard). As a control, DMSO was used and the activity of the test substance was expressed in the concentration ($IC_{50}$) necessary for inhibiting $^3$H radioactivity uptaken by the cell to 50% of that of the control group. The measurements were made in triplicate.

The results are shown in Tables 5-1 to 5-8 according to the following.

A: not less than 0.1 μM and less than 1 μM
B: not less than 0.01 μM and less than 0.1 μM
C: less than 0.01 μM

TABLE 5-1

| | IC₅₀ | |
|---|---|---|
| Example No. | ACHN cell | HT-29 cell |
| 1-1 | B | C |
| 1-2 | | A |
| 1-7 | | A |
| 1-11 | | A |
| 1-55 | | A |
| 1-88 | A | A |
| 1-89 | A | B |
| 1-95 | | A |
| 1-96 | | A |
| 1-97 | | A |
| 1-99 | | A |
| 1-100 | | A |
| 1-106 | A | A |
| 1-111 | | A |
| 1-112 | A | B |
| 1-113 | A | A |
| 1-114 | A | A |
| 1-116 | | A |
| 1-117 | | A |
| 1-126 | | A |
| 1-127 | | A |
| 1-129 | | A |
| 1-132 | | A |
| 1-133 | | A |
| 1-136 | | A |
| 1-138 | | A |
| 1-140 | | A |
| 1-142 | | A |
| 1-143 | | A |
| 1-151 | | A |
| 1-152 | A | B |
| 1-153 | | A |
| 1-156 | | A |
| 1-159 | | A |
| 1-163 | | A |
| 1-164 | | B |

TABLE 5-2

| | IC₅₀ | |
|---|---|---|
| Example No. | ACHN cell | HT-29 cell |
| 1-165 | | A |
| 1-166 | | B |
| 1-168 | | B |
| 1-171 | | B |
| 1-175 | | A |
| 1-176 | A | B |
| 1-183 | | A |
| 1-185 | A | B |
| 1-186 | | B |
| 1-188 | A | B |
| 1-189 | | A |
| 1-190 | | A |
| 1-191 | A | B |
| 1-192 | A | B |
| 1-193 | A | C |
| 1-199 | A | B |
| 1-200 | A | B |
| 1-201 | | A |
| 1-205 | A | C |
| 1-206 | | A |
| 1-207 | B | C |
| 1-208 | B | C |
| 1-211 | | A |
| 1-212 | A | C |
| 1-213 | A | B |
| 1-214 | | B |
| 1-215 | | A |

TABLE 5-2-continued

| Example No. | IC$_{50}$ ACHN cell | IC$_{50}$ HT-29 cell |
|---|---|---|
| 1-216 |   | A |
| 1-217 |   | A |
| 1-218 |   | B |
| 1-219 | A | B |
| 1-221 | B | C |
| 1-222 | A | B |
| 1-223 | A | B |
| 1-224 | A | C |
| 1-225 |   | A |

TABLE 5-3

| Example No. | IC$_{50}$ ACHN cell | IC$_{50}$ HT-29 cell |
|---|---|---|
| 1-226 | A | B |
| 1-227 |   | B |
| 1-228 | A | B |
| 1-229 |   | A |
| 1-230 |   | A |
| 1-232 | A | B |
| 1-233 |   | A |
| 1-234 |   | A |
| 1-235 |   | A |
| 1-236 |   | A |
| 1-240 | B | B |
| 1-242 | A | B |
| 1-243 | A | B |
| 1-244 |   | A |
| 1-245 | B | C |
| 1-246 | A | B |
| 1-249 | A | B |
| 1-252 |   | B |
| 1-253 | A | B |
| 1-255 |   | A |
| 1-257 | C | C |
| 1-258 |   | A |
| 1-259 | A | C |
| 1-260 | C | C |
| 1-262 | B | C |
| 1-263 | A | C |
| 1-264 | A | B |
| 1-265 | A | B |
| 1-266 | A | C |
| 1-267 | A | B |
| 1-268 | B | B |
| 1-270 | A | B |
| 1-271 | B | C |
| 1-272 | B | B |
| 1-273 |   | A |
| 3-1 | A | A |

TABLE 5-4

| Example No. | IC$_{50}$ ACHN cell | IC$_{50}$ HT-29 cell |
|---|---|---|
| 1-274 | C | C |
| 1-275 | B | C |
| 1-276 | A | B |
| 1-277 |   | B |
| 1-278 | A | B |
| 1-279 | A | B |
| 1-282 | A | B |
| 1-283 | A | B |

TABLE 5-4-continued

| Example No. | IC$_{50}$ ACHN cell | IC$_{50}$ HT-29 cell |
|---|---|---|
| 1-284 | A | B |
| 1-285 | B | B |
| 1-286 | B | C |
| 1-287 | A | B |
| 1-288 |   | B |
| 1-289 | C | C |
| 1-290 | B | C |
| 1-292 |   | B |
| 1-293 | A | A |
| 1-294 | B |   |
| 1-295 | A | B |
| 1-296 | A | C |
| 1-297 | B | C |
| 1-298 | B | C |
| 1-299 | A | B |
| 1-301 | A | B |
| 1-302 | B | C |
| 1-303 | A | B |
| 1-304 | A | B |
| 1-305 |   | B |
| 1-307 | A | B |
| 1-308 | A | B |
| 1-309 | B | C |
| 1-310 | B | C |
| 1-311 | C | C |
| 1-313 |   | B |
| 1-313 |   | B |
| 1-315 | A | B |

TABLE 5-5

| Example No. | IC$_{50}$ ACHN cell | IC$_{50}$ HT-29 cell |
|---|---|---|
| 1-316 | A | B |
| 1-317 | A | B |
| 1-318 | A | C |
| 1-319 | C | C |
| 1-320 | B | C |
| 1-321 | B | C |
| 1-322 | B | C |
| 1-324 |   | B |
| 1-325 | A | B |
| 1-326 |   | A |
| 1-327 | A | B |
| 1-328 | A | B |
| 1-333 | B | C |
| 1-334 |   | A |
| 1-335 | A | B |
| 1-336 | B | C |
| 1-337 | B | C |
| 1-338 | B | C |
| 1-339 | A |   |
| 1-340 | B | C |
| 1-341 | B | C |
| 1-342 | A | C |
| 1-343 | A | B |
| 3-4 | B | C |
| 3-5 | B | C |
| 3-6 | A | C |
| 3-7 | C | C |
| 3-8 | B | C |
| 4-1 | C | C |
| 4-2 | C | C |
| 4-3 | B | C |
| 4-4 |   | A |
| 4-5 | A | B |
| 4-6 | B | C |

TABLE 5-5-continued

| Example No. | IC$_{50}$ ACHN cell | IC$_{50}$ HT-29 cell |
|---|---|---|
| 4-7 | | A |
| 4-9 | B | C |

TABLE 5-6

| Example No. | IC$_{50}$ ACHN cell | IC$_{50}$ HT-29 cell |
|---|---|---|
| 4-10 | A | B |
| 4-11 | B | C |
| 4-12 | B | C |
| 4-13 | | A |
| 4-15 | B | C |
| 4-16 | C | C |
| 4-19 | B | C |
| 4-20 | B | C |
| 4-21 | B | C |
| 4-25 | B | C |
| 4-26 | B | C |
| 4-27 | A | |
| 4-33 | C | C |
| 4-34 | C | C |
| 4-37 | A | B |
| 4-39 | A | |
| 4-40 | B | C |
| 4-41 | B | B |
| 4-42 | B | C |
| 4-43 | A | B |
| 4-44 | A | B |
| 4-45 | A | B |
| 4-46 | A | B |
| 4-47 | A | |
| 4-48 | B | C |
| 4-49 | B | C |
| 4-50 | A | B |
| 4-51 | B | C |
| 4-52 | A | A |
| 4-53 | A | B |
| 4-54 | C | C |
| 4-55 | B | C |
| 4-56 | A | B |
| 4-57 | | A |
| 4-58 | B | C |
| 4-59 | B | C |

TABLE 5-7

| Example No. | IC$_{50}$ ACHN cell | IC$_{50}$ HT-29 cell |
|---|---|---|
| 4-60 | B | C |
| 4-61 | B | B |
| 4-63 | | B |
| 4-64 | A | B |
| 4-66 | A | B |
| 4-67 | B | C |
| 4-70 | B | C |
| 4-71 | A | B |
| 4-72 | B | C |
| 4-73 | B | C |
| 4-74 | B | C |
| 4-75 | | B |
| 4-76 | B | C |
| 4-77 | B | C |
| 4-78 | A | B |

TABLE 5-7-continued

| Example No. | IC$_{50}$ ACHN cell | IC$_{50}$ HT-29 cell |
|---|---|---|
| 4-80 | B | C |
| 4-81 | B | C |
| 4-82 | B | C |
| 4-85 | | A |
| 4-87 | A | B |
| 4-88 | C | C |
| 4-89 | A | B |
| 4-90 | A | B |
| 4-91 | B | C |
| 4-92 | B | C |
| 4-93 | B | C |
| 4-94 | A | B |
| 4-95 | A | B |
| 4-96 | A | B |
| 4-97 | B | C |
| 4-98 | B | C |
| 4-99 | A | C |
| 4-101 | B | C |
| 4-102 | A | B |
| 4-103 | A | C |
| 4-104 | C | C |

TABLE 5-8

| Example No. | IC$_{50}$ ACHN cell | IC$_{50}$ HT-29 cell |
|---|---|---|
| 4-105 | B | C |
| 4-106 | B | C |
| 4-107 | B | C |
| 4-108 | B | C |
| 4-109 | B | C |
| 4-110 | B | C |
| 4-111 | A | B |
| 4-112 | A | C |
| 4-113 | C | C |
| 4-114 | B | C |
| 4-115 | B | C |
| 4-116 | A | C |
| 4-117 | A | C |
| 4-118 | B | C |
| 4-119 | B | C |
| 4-120 | B | C |
| 4-121 | B | C |
| 4-122 | B | C |
| 4-123 | A | C |
| 4-124 | B | C |
| 4-125 | C | C |
| 4-126 | C | C |
| 4-127 | B | C |
| 4-128 | B | C |
| 4-133 | | A |
| 4-135 | | A |
| 4-138 | | A |
| 4-140 | | A |
| 4-145 | | A |
| 4-146 | | A |
| 4-147 | | A |
| 4-148 | | A |

Example 6

Evaluation of p15 Induction Activity

ACHN cells or HT-29 cells were cultured in a 6 well plate at 2.5×10$^5$ cells/1.8 mL/well for 24 hrs, then a test substance (0.1 μM) dissolved in DMSO was added. After 24 hrs, cells were detached using trypsin-EDTA (ethylene diamine tetraacetic acid) and solubilized with NuPAGE LDS sample buffer (Invitrogen). Using an RC DC protein assay kit (BIO-RAD), the protein concentration of the sample was quantitated, and a sample in an amount corresponding to 10 µg of BSA (bovine serum albumin) was analyzed by Western blotting using an anti-p15 antibody. The density of the band stained with the anti-p15 antibody was measured by a densitometer to quantify the amount of p15 protein. As a control, DMSO was used and the test was performed with n=2 and the average protein amount was determined.

The results are shown in Tables 6-1 to 6-6 according to the following.

+: As compared to DMSO, not less than 1.5-fold induction of p15 protein

TABLE 6-1

| Example No. | Induction of p15 protein |
|---|---|
| 1-1 | + |
| 1-4 | + |
| 1-6 | + |
| 1-7 | + |
| 1-8 | + |
| 1-9 | + |
| 1-11 | + |
| 1-12 | + |
| 1-16 | + |
| 1-17 | + |
| 1-26 | + |
| 1-33 | + |
| 1-34 | + |
| 1-35 | + |
| 1-36 | + |
| 1-37 | + |
| 1-38 | + |
| 1-40 | + |
| 1-43 | + |
| 1-46 | + |
| 1-49 | + |
| 1-51 | + |
| 1-53 | + |
| 1-55 | + |
| 1-65 | + |
| 1-77 | + |
| 1-78 | + |
| 1-79 | + |
| 1-80 | + |
| 1-81 | + |
| 1-84 | + |
| 1-85 | + |
| 1-86 | + |
| 1-88 | + |
| 1-89 | + |
| 1-92 | + |

TABLE 6-2

| Example No. | Induction of p15 protein |
|---|---|
| 1-93 | + |
| 1-94 | + |
| 1-95 | + |
| 1-96 | + |
| 1-97 | + |
| 1-99 | + |
| 1-100 | + |
| 1-102 | + |
| 1-103 | + |
| 1-104 | + |
| 1-106 | + |
| 1-107 | + |
| 1-108 | + |

TABLE 6-2-continued

| Example No. | Induction of p15 protein |
|---|---|
| 1-109 | + |
| 1-110 | + |
| 1-111 | + |
| 1-112 | + |
| 1-113 | + |
| 1-114 | + |
| 1-116 | + |
| 1-117 | + |
| 1-126 | + |
| 1-127 | + |
| 1-131 | + |
| 1-132 | + |
| 1-133 | + |
| 1-136 | + |
| 1-137 | + |
| 1-138 | + |
| 1-142 | + |
| 1-143 | + |
| 1-146 | + |
| 1-151 | + |
| 1-152 | + |
| 1-153 | + |
| 1-154 | + |

TABLE 6-3

| Example No. | Induction of p15 protein |
|---|---|
| 1-156 | + |
| 1-157 | + |
| 1-162 | + |
| 1-163 | + |
| 1-165 | + |
| 1-166 | + |
| 1-167 | + |
| 1-168 | + |
| 1-172 | + |
| 1-173 | + |
| 1-175 | + |
| 1-176 | + |
| 1-183 | + |
| 1-185 | + |
| 1-186 | + |
| 1-188 | + |
| 1-191 | + |
| 1-192 | + |
| 1-193 | + |
| 1-199 | + |
| 1-200 | + |
| 1-205 | + |
| 1-207 | + |
| 1-208 | + |
| 1-212 | + |
| 1-213 | + |
| 1-218 | + |
| 1-219 | + |
| 1-221 | + |
| 1-222 | + |
| 1-223 | + |
| 1-224 | + |
| 1-226 | + |
| 1-240 | + |
| 1-242 | + |
| 1-243 | + |
| 1-245 | + |
| 1-246 | + |

TABLE 6-4

| Example No. | Induction of p15 protein |
|---|---|
| 1-264 | + |
| 1-265 | + |
| 1-266 | + |
| 1-268 | + |
| 1-271 | + |
| 1-272 | + |
| 1-282 | + |
| 1-283 | + |
| 1-284 | + |
| 1-285 | + |
| 1-286 | + |
| 1-287 | + |
| 1-289 | + |
| 1-290 | + |
| 1-293 | + |
| 1-295 | + |
| 1-296 | + |
| 1-297 | + |
| 1-298 | + |
| 1-301 | + |
| 1-317 | + |
| 1-318 | + |
| 1-319 | + |
| 1-320 | + |
| 1-321 | + |
| 1-322 | + |
| 1-325 | + |
| 1-327 | + |
| 1-328 | + |
| 1-333 | + |
| 1-336 | + |
| 1-337 | + |
| 1-338 | + |
| 1-340 | + |
| 1-341 | + |
| 1-342 | + |
| 3-4 | + |
| 3-6 | + |

TABLE 6-5

| Example No. | Induction of p15 protein |
|---|---|
| 3-7 | + |
| 3-8 | + |
| 4-1 | + |
| 4-2 | + |
| 4-3 | + |
| 4-6 | + |
| 4-9 | + |
| 4-10 | + |
| 4-11 | + |
| 4-12 | + |
| 4-15 | + |
| 4-16 | + |
| 4-21 | + |
| 4-43 | + |
| 4-45 | + |
| 4-48 | + |
| 4-49 | + |
| 4-50 | + |
| 4-51 | + |
| 4-53 | + |
| 4-54 | + |
| 4-55 | + |
| 4-56 | + |
| 4-58 | + |
| 4-59 | + |
| 4-60 | + |
| 4-61 | + |
| 4-64 | + |
| 4-66 | + |
| 4-67 | + |
| 4-70 | + |
| 4-71 | + |
| 4-72 | + |
| 4-73 | + |
| 4-74 | + |
| 4-76 | + |
| 4-77 | + |
| 4-78 | + |

TABLE 6-6

| Example No. | Induction of p15 protein |
|---|---|
| 4-80 | + |
| 4-81 | + |
| 4-82 | + |
| 4-88 | + |
| 4-89 | + |
| 4-90 | + |
| 4-91 | + |
| 4-92 | + |
| 4-93 | + |
| 4-97 | + |
| 4-98 | + |
| 4-101 | + |
| 4-102 | + |
| 4-103 | + |
| 4-104 | + |
| 4-105 | + |
| 4-106 | + |
| 4-107 | + |
| 4-108 | + |
| 4-109 | + |
| 4-110 | + |
| 4-111 | + |
| 4-112 | + |
| 4-113 | + |
| 4-114 | + |
| 4-115 | + |
| 4-116 | + |
| 4-117 | + |
| 4-118 | + |
| 4-119 | + |
| 4-120 | + |
| 4-121 | + |
| 4-122 | + |
| 4-123 | + |
| 4-124 | + |
| 4-125 | + |
| 4-126 | + |
| 4-127 | + |
| 4-128 | + |

Example 7

Cell Cycle Analysis

ACHN cells or HT-29 cells were cultured in a 6 well plate at $2.5 \times 10^5$ cells/1.8 mL/well for 24 hrs, then a test substance (less than 10 μM) dissolved in DMSO was added. After 24 hrs, cells were detached using trypsin-EDTA and the DNA content of single cell was analyzed by flow cytometry method using a CycleTEST PLUS (BECKTON DICKINSON) kit, and the proportion of the cells in the G0/G1 phase·S phase·G2/M phase was calculated. As a control, DMSO was used and the test was performed with n=2.

The results are shown in Tables 7-1 and 7-2 according to the following.
G1: the ratio of the cells in the G0/G1 phase was not less than 1.2-fold as compared to that of DMSO.

TABLE 7-1

| Example No. | CELL RATIO OF G0/G1 PHASE |
| --- | --- |
| 1-2 | G1 |
| 1-4 | G1 |
| 1-6 | G1 |
| 1-7 | G1 |
| 1-9 | G1 |
| 1-11 | G1 |
| 1-21 | G1 |
| 1-25 | G1 |
| 1-26 | G1 |
| 1-33 | G1 |
| 1-34 | G1 |
| 1-38 | G1 |
| 1-43 | G1 |
| 1-49 | G1 |
| 1-50 | G1 |
| 1-51 | G1 |
| 1-55 | G1 |
| 1-69 | G1 |
| 1-77 | G1 |
| 1-78 | G1 |
| 1-84 | G1 |
| 1-85 | G1 |
| 1-86 | G1 |
| 1-88 | G1 |
| 1-89 | G1 |
| 1-90 | G1 |
| 1-91 | G1 |
| 1-92 | G1 |
| 1-93 | G1 |
| 1-94 | G1 |
| 1-95 | G1 |
| 1-97 | G1 |
| 1-99 | G1 |
| 1-100 | G1 |
| 1-101 | G1 |
| 1-102 | G1 |
| 1-103 | G1 |
| 1-104 | G1 |

TABLE 7-2

| Example No. | CELL RATIO OF G0/G1 PHASE |
| --- | --- |
| 3-7 | G1 |
| 4-1 | G1 |
| 4-3 | G1 |
| 4-16 | G1 |
| 4-70 | G1 |
| 4-82 | G1 |
| 4-104 | G1 |
| 4-126 | G1 |

Example 8

Evaluation on the Nude-Mouse Xenograft Model

HT-29 cells ($5.0 \times 10^6$ cells/100 μL/head, suspended in HBSS (Hanks' solution)) in the logarithmic growth phase were implanted in a mouse (Balb/c-nu/nu) at the right lateral abdomen under ether anesthesia. After 5 days of implantation, the long diameter and short diameter of the tumor were measured, and the mice were divided into groups such that each group has an equivalent average tumor volume. For grouping, a grouping soft (general grouping system (Visions) was used. From the next day of the grouping, a test substance suspended in 0.5% MC (methyl cellulose) was repeatedly orally administered twice a day for 10 days(30 mg/kg). The tumor volume was measured twice a week and used as an index of antitumor activity. As a control, 0.5% MC was used and the test was performed with n=6-8.

The index (T/C (%)) of the antitumor activity was calculated according to the following formula.

$$T/C(\%) = (\text{The average tumor volume of the group treated with a test substance})/(\text{The average tumor volume of the Vehicle group}) \times 100$$

The tumor volume was calculated according to the following formula.

$$\text{Tumor volume (mm}^3) = L \times W \times W/2 \text{ (L: long diameter (mm) of tumor, W: short diameter (mm) of tumor)}$$

TABLE 8

| Example No. | T/C (%) |
| --- | --- |
| 1-257 | 26 |
| 3-8 | 27 |
| 4-1 | 3 |
| 4-15 | 31 |
| 4-16 | 10 |
| 4-49 | 35 |
| 4-54 | 11 |
| 4-70 | 31 |

Example 9 p27 Protein Induction Test

ACHN cells or HT-29 cells were cultured in a 6 well plate at $2.5 \times 10^5$ cells/1.8 mL/well for 24 hrs, a test substance (0.1 μM) dissolved in DMSO was added. After 24 hrs, cells were detached using trypsin-EDTA (ethylene diamine tetraacetic acid) and solubilized with NuPAGE LDS sample buffer (Invitrogen). Using an RC DC protein assay kit (BIO-RAD), the protein concentration of the sample was quantitated, and a sample in an amount corresponding to 10 μg of BSA (bovine serum albumin) was analyzed by Western blotting using an anti-p27 antibody. The density of the band stained with the anti-p27 antibody was measured by a densitometer to quantify the amount of p27 protein. As a control, DMSO was used and the test was performed with n=2 and the average protein amount was determined.

The results are shown in Tables 9-1 to 9-4 according to the following.
+: As compared to DMSO, not less than 1.5-fold induction of p27 protein

TABLE 9-1

| Example No. | Induction of p27 protein |
| --- | --- |
| 1-1 | + |
| 1-89 | + |
| 1-112 | + |
| 1-114 | + |
| 1-142 | + |
| 1-152 | + |
| 1-175 | + |
| 1-182 | + |
| 1-185 | + |
| 1-186 | + |

TABLE 9-1-continued

| Example No. | Induction of p27 protein |
|---|---|
| 1-218 | + |
| 1-219 | + |
| 1-221 | + |
| 1-222 | + |
| 1-224 | + |
| 1-226 | + |
| 1-228 | + |
| 1-240 | + |
| 1-242 | + |
| 1-243 | + |
| 1-245 | + |
| 1-249 | + |
| 1-253 | + |
| 1-257 | + |
| 1-259 | + |
| 1-260 | + |
| 1-262 | + |
| 1-263 | + |
| 1-264 | + |
| 1-265 | + |
| 1-266 | + |
| 1-268 | + |
| 1-271 | + |
| 1-272 | + |
| 1-274 | + |
| 1-275 | + |
| 1-279 | + |
| 1-282 | + |

TABLE 9-2

| Example No. | Induction of p27 protein |
|---|---|
| 1-283 | + |
| 1-284 | + |
| 1-285 | + |
| 1-286 | + |
| 1-287 | + |
| 1-289 | + |
| 1-290 | + |
| 1-293 | + |
| 1-295 | + |
| 1-296 | + |
| 1-297 | + |
| 1-298 | + |
| 1-299 | + |
| 1-301 | + |
| 1-302 | + |
| 1-303 | + |
| 1-307 | + |
| 1-309 | + |
| 1-310 | + |
| 1-311 | + |
| 1-315 | + |
| 1-316 | + |
| 1-317 | + |
| 1-318 | + |
| 1-319 | + |
| 1-320 | + |
| 1-322 | + |
| 1-325 | + |
| 1-327 | + |
| 1-328 | + |
| 1-336 | + |
| 1-337 | + |
| 1-338 | + |
| 1-340 | + |
| 1-341 | + |
| 1-342 | + |
| 3-4 | + |
| 3-5 | + |

TABLE 9-3

| Example No. | Induction of p27 protein |
|---|---|
| 3-6 | + |
| 3-7 | + |
| 3-8 | + |
| 4-1 | + |
| 4-2 | + |
| 4-3 | + |
| 4-6 | + |
| 4-9 | + |
| 4-10 | + |
| 4-11 | + |
| 4-12 | + |
| 4-15 | + |
| 4-16 | + |
| 4-21 | + |
| 4-43 | + |
| 4-45 | + |
| 4-48 | + |
| 4-49 | + |
| 4-50 | + |
| 4-51 | + |
| 4-53 | + |
| 4-54 | + |
| 4-55 | + |
| 4-56 | + |
| 4-58 | + |
| 4-59 | + |
| 4-60 | + |
| 4-61 | + |
| 4-64 | + |
| 4-66 | + |
| 4-67 | + |
| 4-70 | + |
| 4-71 | + |
| 4-72 | + |
| 4-73 | + |
| 4-74 | + |
| 4-76 | + |
| 4-77 | + |

TABLE 9-4

| Example No. | Induction of p27 protein |
|---|---|
| 4-78 | + |
| 4-80 | + |
| 4-81 | + |
| 4-82 | + |
| 4-88 | + |
| 4-89 | + |
| 4-90 | + |
| 4-91 | + |
| 4-92 | + |
| 4-93 | + |
| 4-97 | + |
| 4-98 | + |
| 4-99 | + |
| 4-101 | + |
| 4-102 | + |
| 4-103 | + |
| 4-104 | + |
| 4-105 | + |
| 4-106 | + |
| 4-107 | + |
| 4-108 | + |
| 4-109 | + |
| 4-110 | + |
| 4-113 | + |
| 4-114 | + |
| 4-115 | + |
| 4-116 | + |
| 4-117 | + |
| 4-118 | + |

TABLE 9-4-continued

| Example No. | Induction of p27 protein |
|---|---|
| 4-119 | + |
| 4-120 | + |
| 4-121 | + |
| 4-122 | + |
| 4-123 | + |
| 4-124 | + |
| 4-125 | + |
| 4-126 | + |
| 4-127 | + |
| 4-128 | + |

Example 10

Evaluation of MEK Enzyme Inhibitory Activity

To an evaluation system where Raf (B-Raf or c-Raf) and MEK (MEK1 or MEK2) were mixed, or MEK (MEK1 or MEK2) and ERK2 were mixed was added a test substance dissolved in DMSO, and an ATP solution containing [γ-32P]-ATP was added to start the enzyme reaction. After reacting at 30° C. for 20 min, the reaction mixture was subjected to SDS-PAGE (sodium dodecylsulfate-polyacrylamide gel electrophoresis) and radioactivity of phosphorylated MEK or ERK2 was measured by Bio Imaging Analyzer (BAS2000, Fuji photo film).

With the radioactivity of the solvent added control as 100%, inhibitory rate (%) by the test substance was determined, and $IC_{50}$ value was calculated.

The test was performed with n=1 and the average values of two or three times of testing are shown. The results are summarized in Table 10.

TABLE 10

| $IC_{50}$ of various enzyme reaction system (μM) | | |
|---|---|---|
| enzyme | Example 1-257 | Example 4-1 |
| B-Raf MEK1 | 0.0060 | 0.0067 |
| B-Raf MEK2 | 0.0188 | 0.0128 |
| c-Raf MEK1 | — | — |
| c-Raf MEK2 | 0.0078 | 0.0130 |
| MEK1 ERK2 | 1.3 | 0.290 |
| MEK2 ERK2 | 1.6 | 0.190 |

Example 11

Evaluation on the Mouse Collagen Arthritis Model

Bovine type II collagen (100 μg) was resuspended with Freund's complete adjuvant and intracutaneously administered (initial immunization) to the tail head of mouse (DBA/1). Three weeks later, the same collagen was given to the tail head as boost, whereby multiple arthritis was induced. The test substance was oral administered forcibly once a day for 38 days from immediately before the initial immunization, and arthritis score after boost was calculated twice a week to examine the arthritis onset suppressing effect. For arthritis scores, the level of swelling of each of the four limbs of the mice was scored in 4 levels, and the average of the scores of four limbs was taken as the arthritis score of each individual. The test was performed with n=16.

The arthritis score at 17 days after boost (after consecutive administration for 38 days) was 2.2 for the medium administration group, and 0.57 ($p<0.001$, wilcoxson test) for the 1 mg/kg acetic acid solvate of compound of Example 4-1 administration group, thus showing a significant suppressive effect on the arthritis onset.

Example 12

Evaluation on Inflammatory Cytokine Production

The compounds of Example 4-1 and Example 4-16 suppressed production of TNF-α or IL-6 upon stimulation of human peripheral blood-derived nomonuclear cell (PBMC) with LPS.

The MS and NMR data of the Example compounds shown in the above-mentioned Table 1-1 to Table 4-25 are shown below.

Example 1-1

MS ESI m/e: 590, 592 (M+H), 588, 590 (M−H).
$^1$H-NMR (DMSO-$d_6$, 300 MHz) δ 0.71-0.79 (m, 2H), 0.99-1.08 (m, 2H), 2.64-2.70 (m, 4H), 3.02 (s, 3H), 5.36 (s, 1H), 7.13 (d, J=9.0 Hz, 1H), 7.24-7.30 (m, 2H), 7.43-7.54 (m, 3H), 7.74 (d, J=9.0 Hz, 1H), 10.00 (brs, 1H), 10.53 (brs, 1H).

Example 1-2

Example 1-3

Example 1-4

MS ESI m/e: 470, 471(M+H), 473, 474, 469 (M−H), 470, 471.
$^1$H-NMR (DMSO-$d_6$, 300 MHz) δ 2.68 (s, 3H), 5.47 (s, 1H), 7.24-7.63 (m, 14H), 10.63 (brs, 1H).

Example 1-5

MS ESI m/e: 470, 471(M+H), 473, 474, 469 (M−H), 470, 471.
$^1$H-NMR (DMSO-$d_6$, 300 MHz) δ 2.68 (s, 3H), 5.60 (s, 1H), 7.25-7.57 (m, 14H), 10.52 (brs, 1H).

Example 1-6

MS ESI m/e: 451 (M+H), 449 (M−H).
$^1$H-NMR (CDCl$_3$, 400 MHz) δ 2.34 (s, 3H), 2.88 (s, 3H), 5.79 (s, 1H), 7.08-7.18 (m, 4H), 7.27-7.32 (m, 2H), 7.37-7.54 (m, 8H), 10.24 (s, 1H).

Example 1-7

MS ESI m/e: 480 (M+H).
$^1$H-NMR (CDCl$_3$, 400 MHz) δ 2.87 (s, 3H), 2.95 (s, 6H), 5.66 (s, 1H), 6.67-6.73 (m, 2H), 7.05-7.11 (m, 2H), 7.27-7.32 (m, 2H), 7.37-7.55 (m, 8H), 10.24 (s, 1H).

Example 1-8

MS ESI m/e: 455 (M+H), 453 (M−H).
$^1$H-NMR (CDCl$_3$, 400 MHz) δ 2.88 (s, 3H), 5.69 (s, 1H), 7.03-7.10 (m, 2H), 7.17-7.23 (m, 2H), 7.27-7.32 (m, 2H), 7.37-7.55 (m, 8H), 10.24 (s, 1H).

Example 1-9

MS ESI m/e: 467 (M+H), 465 (M−H).
$^1$H-NMR (CDCl$_3$, 300 MHz) δ 2.88 (s, 3H), 3.81 (s, 3H), 5.67 (s, 1H), 6.86-6.95 (m, 2H), 7.12-7.20 (m, 2H), 7.28-7.34 (m, 2H), 7.37-7.58 (m, 8H), 10.14 (s, 1H).

Example 1-10

MS ESI m/e: 485 (M+H), 483 (M−H).
$^1$H-NMR (CDCl$_3$, 400 MHz) δ 2.86 (s, 3H), 4.32 (d, J=4.0 Hz, 2H), 5.39 (s, 1H), 7.23-7.31 (m, 6H), 7.34-7.38 (m, 2H), 7.39-7.52 (m, 6H), 9.03 (t, J=6.0 Hz, 1H).

Example 1-11

MS ESI m/e: 515, 517 (M+H), 513, 515 (M−H).
$^1$H-NMR (DMSO-d$_6$, 400 MHz) δ 2.67 (s, 3H), 5.56 (s, 1H), 7.25-7.29 (m, 2H), 7.34-7.38 (m, 2H), 7.41-7.55 (m, 8H), 7.57-7.61 (m, 2H), 10.48 (s, 1H).

Example 1-12

Example 1-13

Example 1-14

MS ESI m/e: 485 (M+H).
$^1$H-NMR (DMSO-d$_6$, 400 MHz) δ 2.74 (s, 3H), 3.22 (s, 3H), 6.03 (s, 1H), 6.99-7.05 (m, 4H), 7.21-7.25 (m, 2H), 7.32-7.40 (m, 3H), 7.44-7.54 (m, 5H).

Example 1-15

MS ESI m/e: 443 (M+H).
$^1$H-NMR (DMSO-d$_6$, 300 MHz) δ 1.17-1.95 (m, 11H), 2.63 (s, 3H), 5.28 (s, 1H), 7.31-7.55 (m, 10H), 8.76 (d, J=6.0 Hz, 1H).

Example 1-16

MS ESI m/e: 481 (M+H), 479 (M−H).
$^1$H-NMR (CDCl$_3$, 300 MHz) δ 2.88 (s, 3H), 5.69 (s, 1H), 5.99 (s, 2H), 6.85-6.82 (m, 3H), 7.28-7.34 (m, 2H), 7.37-7.58 (m, 8H), 10.12 (s, 1H).

Example 1-17

MS ESI m/e: 505, 507 (M+H), 503, 505 (M−H).
$^1$H-NMR (CDCl$_3$, 400 MHz) δ 2.90 (s, 3H), 5.87 (s, 1H), 7.07-7.11 (m, 1H), 7.26-7.31 (m, 2H), 7.35-7.56 (m, 10H), 10.45 (s, 1H).

Example 1-18

MS ESI m/e: 499 (M+H), 497 (M−H).
$^1$H-NMR (DMSO-d$_6$, 300 MHz) δ 0.56 (t, J=7.5 Hz, 3H), 1.05-1.12 (m, 2H), 3.30-3.40 (m, 2H), 5.54 (s, 1H), 7.31-7.56 (m, 14H), 10.52 (s, 1H).

Example 1-19

MS ESI m/e: 513 (M+H), 511 (M−H).
$^1$H-NMR (DMSO-d$_6$, 300 MHz) δ 0.62 (s, 3H), 0.64 (s, 3H), 1.04 (d, J=6.0 Hz, 1H), 1.94-2.06 (m, 1H), 3.13 (brs, 1H), 5.56 (s, 1H), 7.32-7.60 (m, 14H), 10.58 (s, 1H).

Example 1-20

MS ESI m/e: 515 (M+H), 513 (M−H).
$^1$H-NMR (DMSO-d$_6$, 300 MHz) δ 3.04 (t, J=6.0 Hz, 2H), 3.09 (s, 3H), 3.61 (t, J=4.5 Hz, 2H), 5.53 (s, 1H), 7.32-7.60 (m, 14H), 10.52 (s, 1H).

Example 1-21

MS ESI m/e: 465 (M+H), 463 (M−H).
$^1$H-NMR (DMSO-d$_6$, 400 MHz) δ 1.19 (t, J=8.0 Hz, 3H), 2.61 (q, J=8.0 Hz, 2H), 2.66 (s, 3H), 5.46 (s, 1H), 7.17-7.21 (m, 2H), 7.25-7.29 (m, 2H), 7.34-7.38 (m, 2H), 7.41-7.55 (m, 8H), 10.37 (s, 1H).

Example 1-22

MS ESI m/e: 451 (M+H), 449 (M−H).
$^1$H-NMR (DMSO-d$_6$, 400 MHz) δ 2.21 (s, 3H), 2.66 (s, 3H), 5.12 (s, 1H), 7.18-7.55 (m, 14H), 10.22 (s, 1H).

Example 1-23

MS ESI m/e: 513 (M+H), 511 (M−H).
$^1$H-NMR (DMSO-d$_6$, 400 MHz) δ 2.68 (s, 3H), 5.65 (s, 1H), 7.33-7.56 (m, 15H), 7.66-7.74 (m, 4H), 10.56 (s, 1H).

Example 1-24

MS ESI m/e: 467 (M+H), 465 (M−H).
$^1$H-NMR (CDCl$_3$, 400 MHz) δ 2.89 (s, 3H), 3.82 (s, 3H), 5.83 (s, 1H), 6.91-6.98 (m, 2H), 7.13-7.19 (m, 1H), 7.27-7.33 (m, 2H), 7.37-7.54 (m, 9H), 10.21 (s, 1H).

Example 1-25

MS ESI m/e: 479 (M+H), 477 (M−H).
$^1$H-NMR (CDCl$_3$, 400 MHz) δ 1.25 (d, J=6.7 Hz, 6H), 2.85-2.95 (m, 1H), 2.88 (s, 3H), 5.80 (s, 1H), 7.12-7.17 (m, 2H), 7.19-7.24 (m, 2H), 7.27-7.32 (m, 2H), 7.37-7.55 (m, 8H), 10.24 (s, 1H).

Example 1-26

MS ESI m/e: 505, 507 (M+H), 503, 505 (M−H).
$^1$H-NMR (CDCl$_3$, 400 MHz) δ 2.89 (s, 3H), 5.70 (s, 1H), 7.22-7.32 (m, 3H), 7.37-7.55 (m, 10H), 10.39 (s, 1H).

Example 1-27

MS ESI m/e: 520 (M+H).
$^1$H-NMR (CDCl$_3$, 400 MHz) δ 1.54-1.62 (m, 4H), 1.67-1.75 (m, 4H), 2.87 (s, 3H), 3.14 (t, J=5.6 Hz, 2H), 5.70 (s, 1H), 6.87-6.93 (m, 2H), 7.06-7.11 (m, 2H), 7.27-7.32 (m, 2H), 7.37-7.54 (m, 8H), 10.09 (s, 1H).

Example 1-28

MS ESI m/e: 508 (M+H), 506 (M−H).
$^1$H-NMR (CDCl$_3$, 400 MHz) δ 1.16 (t, J=7.1 Hz, 6H), 2.87 (s, 3H), 3.34 (q, J=7.1 Hz, 4H), 5.65 (s, 1H), 6.60-6.65 (m, 2H), 7.00-7.06 (m, 2H), 7.27-7.31 (m, 2H), 7.36-7.54 (m, 8H), 9.98 (s, 1H).

Example 1-29

MS ESI m/e: 527 (M+H), 525 (M−H).
$^1$H-NMR (CDCl$_3$, 300 MHz) δ 2.88 (s, 3H), 3.97 (s, 2H), 5.83 (s, 1H), 7.12-7.58 (m, 19H), 10.29 (s, 1H).

Example 1-30

MS ESI m/e: 522 (M+H), 520 (M−H).
$^1$H-NMR (DMSO-d$_6$, 300 MHz) δ 2.66 (s, 3H), 3.10-3.13 (m, 4H), 3.73-3.76 (m, 4H), 5.32 (s, 1H), 7.01 (d, J=9.0 Hz, 2H), 7.15 (d, J=9.0 Hz, 2H), 7.35-7.57 (m, 10H), 10.20 (brs, 1H).

Example 1-31

MS ESI m/e: 493 (M+H), 491 (M−H).
$^1$H-NMR (DMSO-d$_6$, 400 MHz) δ 0.90 (t, J=8.0 Hz, 3H), 1.26-1.36 (m, 2H), 1.52-1.60 (m, 2H), 2.58 (t, J=8.0 Hz, 2H), 2.66 (s, 3H), 5.46 (s, 1H), 7.18 (d, J=8.0 Hz, 2H), 7.25 (d, J=8.0 Hz, 2H), 7.35-7.37 (m, 2H), 7.41-7.54 (m, 8H), 10.36 (brs, 1H).

Example 1-32

MS ESI m/e: 409 (M+H), 407 (M−H).
$^1$H-NMR (DMSO-d$_6$, 300 MHz) δ 3.46 (s, 3H), 3.48 (s, 3H), 5.49 (s, 1H), 7.28-7.34 (m, 4H), 7.41-7.53 (m, 5H), 10.44 (brs, 1H).

Example 1-33

MS ESI m/e: 505 (M+H), 503 (M−H).
$^1$H-NMR (DMSO-d$_6$, 400 MHz) δ 2.67 (s, 3H), 5.78 (s, 1H), 7.34 (d, J=8.0 Hz, 2H), 7.40-7.53 (m, 10H), 7.73 (d, J=8.0 Hz, 2H), 10.75 (brs, 1H).

Example 1-34

MS ESI m/e: 485 (M+H), 483 (M−H).
$^1$H-NMR (DMSO-d$_6$, 300 MHz) δ 2.32 (s, 3H), 2.67 (s, 3H), 5.35 (s, 1H), 7.23-7.56 (m, 13H), 10.48 (brs, 1H).

Example 1-35

MS ESI m/e: 409 (M+H), 407 (M−H).
$^1$H-NMR (DMSO-d$_6$, 300 MHz) δ 2.61 (s, 3H), 3.26 (s, 3H), 5.50 (s, 1H), 7.35 (d, J=6.0 Hz, 2H), 7.44-7.54 (m, 5H), 7.49 (d, J=6.0 Hz, 2H), 10.62 (brs, 1H).

Example 1-36

MS ESI m/e: 431 (M+H).
$^1$H-NMR (CDCl$_3$, 400 MHz) δ 1.00 (s, 9H), 2.86 (s, 3H), 2.92 (d, J=8.0 Hz, 2H), 5.43 (s, 1H), 7.24-7.29 (m, 2H), 7.34-7.53 (m, 8H), 8.78 (t, J=6.0 Hz, 1H).

Example 1-37

MS ESI m/e: 481 (M+H), 479 (M−H).
$^1$H-NMR (DMSO-d$_6$, 300 MHz) δ 2.70 (s, 3H), 5.85 (s, 1H), 7.36-7.54 (m, 10H), 7.43 (d, J=9.0 Hz, 2H), 7.97 (d, J=9.0 Hz, 2H), 10.81 (brs, 1H).

Example 1-38

MS ESI m/e: 465 (M+H), 463 (M−H).
$^1$H-NMR (CDCl$_3$, 300 MHz) δ 1.18 (t, J=7.5 Hz, 3H), 2.63 (q, J=7.5 Hz, 2H), 2.88 (s, 3H), 5.43 (s, 1H), 7.20-7.36 (m, 6H), 7.39-7.57 (m, 8H), 10.07 (s, 1H).

Example 1-39

MS ESI m/e: 507 (M+H), 505 (M−H).
$^1$H-NMR (CDCl$_3$, 300 MHz) δ 0.78 (t, J=7.3 Hz, 6H), 1.44-1.77 (m, 4H), 2.25-2.38 (m, 1H), 2.89 (s, 3H), 5.85 (s, 1H), 7.10-7.19 (m, 4H), 7.28-7.34 (m, 2H), 7.38-7.57 (m, 8H), 10.28 (s, 1H).

Example 1-40

MS ESI m/e: 535 (M+H), 533 (M−H).
$^1$H-NMR (CDCl$_3$, 300 MHz) δ 0.85 (t, J=7.4 Hz, 6H), 1.08-1.24 (m, 4H), 1.45-1.64 (m, 4H), 2.45-2.58 (m, 1H), 2.89 (s, 3H), 5.84 (s, 1H), 7.10-7.18 (m, 4H), 7.28-7.34 (m, 2H), 7.38-7.57 (m, 8H), 10.27 (s, 1H).

Example 1-41

MS ESI m/e: 497 (M+H), 495 (M−H).
$^1$H-NMR (CDCl$_3$, 400 MHz) δ 0.79-1.00 (m, 4H), 1.70-1.78 (m, 1H), 5.73 (s, 1H), 7.12-7.18 (m, 2H), 7.26-7.34 (m, 4H), 7.35-7.55 (m, 8H), 10.35 (s, 1H).

Example 1-42

MS ESI m/e: 539, 541 (M+H), 537, 539 (M−H).
$^1$H-NMR (CDCl$_3$, 400 MHz) δ 2.92 (s, 3H), 5.80 (s, 1H), 7.14-7.19 (m, 2H), 7.19-7.24 (m, 2H), 7.30-7.36 (m, 4H), 7.45-7.51 (m, 4H), 10.24 (s, 1H).

Example 1-43

MS ESI m/e: 485 (M+H), 483 (M−H).
$^1$H-NMR (DMSO-d$_6$, 300 MHz) δ 1.57 (s, 3H), 2.76 (s, 3H), 6.93 (d, J=9.0 Hz, 2H), 7.31-7.54 (m, 12H), 10.07 (brs, 1H).

Example 1-44

MS ESI m/e: 477 (M+H), 475 (M−H).
$^1$H-NMR (DMSO-d$_6$, 300 MHz) δ 1.07-1.85 (m, 11H), 2.60 (s, 3H), 4.65-4.65 (m, 1H), 5.49 (s, 1H), 7.35-7.54 (m, 5H), 10.63 (brs, 1H).

Example 1-45

MS ESI m/e: 485 (M+H), 483 (M−H).
$^1$H-NMR (DMSO-d$_6$, 300 MHz) δ 2.63 (s, 3H), 5.10 (brs, 2H), 5.51 (s, 1H), 7.24-7.56 (m, 14H), 10.57 (s, 1H).

Example 1-46

MS ESI m/e: 452 (M+H).
$^1$H-NMR (DMSO-$d_6$, 300 MHz) δ 2.67 (s, 3H), 5.47 (s, 1H), 7.19 (d, J=9.0 Hz, 2H), 7.29 (d, J=6.0 Hz, 2H), 7.35-7.40 (m, 2H), 7.41-7.57 (m, 8H), 10.40 (s, 1H).

Example 1-47

MS ESI m/e: 421 (M+H), 419 (M−H).
$^1$H-NMR (CDCl$_3$, 300 MHz) δ 2.19-2.30 (m, 2H), 4.09-4.20 (m, 4H), 5.73 (s, 1H), 7.11-7.19 (m, 2H), 7.23-7.36 (m, 4H), 7.45-7.60 (m, 3H), 10.49 (s, 1H).

Example 1-48

MS ESI m/e: 453(M+H), 451 (M−H).
$^1$H-NMR (DMSO-$d_6$, 300 MHz) δ 2.65 (s, 3H), 5.08 (s, 1H), 6.07 (brs, 2H), 6.52 (d, J=9.0 Hz, 1H), 7.29-7.57 (m, 11H), 7.80 (d, J=3.0 Hz, 1H), 9.94 (brs, 1H).

Example 1-49

MS ESI m/e: 466(M+H).
$^1$H-NMR (DMSO-$d_6$, 300 MHz) δ 2.67 (s, 3H), 2.86 (s, 3H), 5.50 (s, 1H), 7.33-7.57 (m, 14H), 10.44 (brs, 1H).

Example 1-50

MS ESI m/e: 479 (M+H), 477 (M−H).
$^1$H-NMR (CDCl$_3$, 300 MHz) δ 0.90 (t, J=7.3 Hz, 3H), 1.51-1.66 (m, 2H), 2.57 (t, J=7.5 Hz, 2H), 2.88 (s, 3H), 5.43 (s, 1H), 7.17-7.30 (m, 4H), 7.30-7.37 (m, 2H), 7.39-7.58 (m, 8H), 10.07 (s, 1H).

Example 1-51

MS ESI m/e: 493 (M+H), 491 (M−H).
$^1$H-NMR (CDCl$_3$, 300 MHz) δ 0.88 (t, J=6.0 Hz, 3H), 1.26-1.38 (m, 2H), 1.49-1.61 (m, 2H), 2.55-2.61 (m, 2H), 2.88 (s, 3H), 5.43 (s, 1H), 7.14-7.34 (m, 6H), 7.39-7.56 (m, 8H), 10.07 (brs, 1H).

Example 1-52

MS ESI m/e: 528 (M+H), 526 (M−H).
$^1$H-NMR (CDCl$_3$, 400 MHz) δ 2.15 (s, 6H), 2.12-2.22 (m, 2H), 3.72 (t, J=6.5 Hz, 2H), 5.81 (s, 1H), 7.15-7.21 (m, 2H), 7.26-7.35 (m, 4H), 7.40-7.56 (m, 8H), 10.35 (s, 1H).

Example 1-53

MS ESI m/e: 485 (M+H), 483 (M−H).
$^1$H-NMR (CDCl$_3$, 400 MHz) δ 2.24 (s, 3H), 2.88 (s, 3H), 5.39 (s, 1H), 7.17-7.20 (m, 2H), 7.28-7.33 (m, 2H), 7.37-7.55 (m, 9H), 10.04 (s, 1H).

Example 1-54

MS ESI m/e: 472 (M+H), 470 (M−H).
$^1$H-NMR (DMSO-$d_6$, 400 MHz) δ 2.68 (s, 3H), 5.50 (s, 1H), 7.34-7.38 (m, 2H), 7.41-7.57 (m, 9H), 7.87 (dd, J=4.0, 8.0 Hz, 1H), 8.37 (d, J=4.0 Hz, 1H), 10.49 (s, 1H).

Example 1-55

MS ESI m/e: 494 (M+H), 492 (M−H).
$^1$H-NMR (DMSO-$d_6$, 300 MHz) δ 2.15 (s, 3H), 2.64 (s, 3H), 2.90 (s, 6H), 4.92 (s, 1H), 6.63 (dd, J=3.0, 9.0 Hz, 1H), 6.69 (d, J=3.0 Hz, 1H), 7.03 (d, J=9.0 Hz, 1H), 7.36-7.57 (m, 10H), 9.89(s, 1H).

Example 1-56

MS ESI m/e: 497 (M+H), 495 (M−H).
$^1$H-NMR (CDCl$_3$, 400 MHz) δ 4.24 (d, J=4.2 Hz, 2H), 4.87 (d, J=16.9 Hz, 1H), 5.02 (d, J=10.4 Hz, 1H), 5.40-5.51 (m, 1H), 5.83 (s, 1H), 7.16-7.21 (m, 2H), 7.26-7.30 (m, 2H), 7.31-7.36 (m, 2H), 7.36-7.41 (m, 2H), 7.43-7.55 (m, 6H), 10.40 (s, 1H).

Example 1-57

MS ESI m/e: 482 (M+H), 480 (M−H).
$^1$H-NMR (CDCl$_3$, 300 MHz) δ 2.93 (s, 3H), 6.20 (s, 1H), 7.28-7.33 (m, 2H), 7.35-7.44 (m, 4H), 7.46-7.59 (m, 6H), 8.20-8.27 (m, 2H), 10.95 (s, 1H).

Example 1-58

MS ESI m/e: 451(M+H), 449(M−H).
$^1$H-NMR (DMSO-$d_6$, 300 MHz) δ 0.83 (d, J=9.0 Hz, 6H), 1.90-2.04 (m, 1H), 3.45 (s, 3H), 3.98 (d, J=9.0 Hz, 2H), 5.50 (s, 1H), 7.28-7.34 (m, 4H), 7.43-7.55 (m, 5H), 10.30 (brs, 1H).

Example 1-59

MS ESI m/e: 444 (M+H), 442 (M−H).
$^1$H-NMR (CDCl$_3$, 300 MHz) δ 3.14 (s, 3H), 5.22 (s, 1H), 6.96-7.03 (m, 2H), 7.17-7.41 (m, 5H), 7.41-7.55 (m, 3H), 7.60 (d, J=3.7 Hz, 1H), 7.89 (d, J=3.7 Hz, 1H), 11.57 (s, 1H).

Example 1-60

MS ESI m/e: 457 (M+H), 455 (M−H).
$^1$H-NMR (CDCl$_3$, 300 MHz) δ 5.70 (s, 1H), 7.14-7.12 (m, 2H), 7.30-7.43 (m, 6H), 7.43-7.65 (m, 6H), 10.48 (s, 1H).

Example 1-61

MS ESI m/e: 466 (M+H), 464 (M−H).
$^1$H-NMR (CDCl$_3$, 300 MHz) δ 2.95 (s, 3H), 5.56 (s, 1H), 6.65-6.75 (m, 2H), 7.02-7.14 (m, 2H), 7.29-7.67 (m, 10H), 10.18 (s, 1H).

Example 1-62

MS ESI m/e: 506 (M+H), 504 (M−H).
$^1$H-NMR (CDCl$_3$, 300 MHz) δ 2.96 (6H, s), 4.23 (d, J=4.7 Hz, 2H), 4.88 (d, J=17.3 Hz, 1H), 5.02 (d, J=10.6 Hz, 1H), 5.40-5.55 (m, 1H), 5.69 (s, 1H), 6.68-6.75 (m, 2H), 7.07-7.14 (m, 2H), 7.27-7.33 (m, 2H), 7.37-7.56 (m, 8H), 10.10 (s, 1H).

Example 1-63

MS ESI m/e: 472 (M+H).
$^1$H-NMR (DMSO-$d_6$, 300 MHz) δ 2.72 (s, 3H), 7.16 (d, J=9.0 Hz, 1H), 7.34-7.42 (m, 2H), 7.43-7.60 (m, 10H), 7.82 (dd, J=3.0, 6.0 Hz, 1H), 8.42 (d, J=3.0 Hz, 1H), 11.68 (s, 1H).

Example 1-64

MS ESI m/e: 487 (M+H).
$^1$H-NMR (CDCl$_3$, 400 MHz) δ 2.94 (s, 3H), 3.12 (s, 6H), 7.26-7.32 (m, 2H), 7.34-7.54 (m, 8H), 7.68 (s, 1H), 9.00 (d, J=4.8 Hz, 1H), 10.26 (d, J=5.8 Hz, 1H).

Example 1-65

MS ESI m/e: 480 (M+H), 478 (M–H).
$^1$H-NMR (DMSO-$d_6$, 300 MHz) δ 1.24 (t, J=7.3 Hz, 3H), 2.68 (s, 3H), 3.27 (q, J=7.3 Hz, 2H), 5.53 (s, 1H), 7.29-7.60 (m, 16H), 10.46 (s, 1H).

Example 1-66

MS ESI m/e: 478 (M+H), 477 (M–H).
$^1$H-NMR (DMSO-$d_6$, 300 MHz) δ 1.16 (d, J=6.8 Hz, 6H), 2.65 (s, 3H), 3.05-3.15 (m, 1H), 5.00 (s, 1H), 7.27-7.54 (m, 14H), 10.19 (brs, 1H).

Example 1-67

MS ESI m/e: 485 (M+H), 483 (M–H).
$^1$H-NMR (DMSO-$d_6$, 300 MHz) δ 0.56 (t, J=7.0 Hz, 3H), 3.55 (q, 2H, J=7.0 Hz), 5.53 (s, 1H), 7.10-7.13 (m, 2H), 7.32-7.56 (m, 12H), 10.49 (brs, 1H).

Example 1-68

MS ESI m/e: 528 (M+H), 526 (M–H).
$^1$H-NMR (CDCl$_3$, 400 MHz) δ 2.15 (s, 6H), 2.88 (s, 3H), 3.31 (s, 2H), 5.65 (s, 1H), 7.21-7.54 (m, 13H), 10.50 (s, 1H).

Example 1-69

MS ESI m/e: 493 (M+H), 491 (M–H).
$^1$H-NMR (DMSO-$d_6$, 300 MHz) δ 0.84 (d, J=6.6 Hz, 6H), 1.78-1.88 (m, 1H), 2.45 (d, J=7.2 Hz, 2H), 2.67 (s, 3H), 5.15 (s, 1H), 7.20-7.53 (m, 14H), 10.24 (brs, 1H).

Example 1-70

MS ESI m/e: 499, 501 (M+H), 497, 499 (M–H).
$^1$H-NMR (DMSO-$d_6$, 300 MHz) δ 2.37 (s, 3H), 2.38 (s, 3H), 2.70 (s, 3H), 5.54 (s, 1H), 7.21-7.50 (m, 12H), 10.51 (brs, 1H).

Example 1-71

MS ESI m/e: 507, 508 (M+H), 505, 506 (M–H).
$^1$H-NMR (DMSO-$d_6$, 300 MHz) δ 0.85 (d, J=6.5 Hz, 6H), 1.37-1.42 (m, 2H), 1.49-1.53 (m, 1H), 2.50-2.58 (m, 2H), 2.67 (s, 3H), 5.12 (s, 1H), 7.24-7.55 (m, 14H), 10.23 (brs, 1H).

Example 1-72

MS ESI m/e: 499 (M+H), 497 (M–H).
$^1$H-NMR (CDCl$_3$, 300 MHz) δ 2.12-2.44 (m, 6H), 2.84 (s, 3H), 5.83 (brs, 1H), 7.05-7.48 (m, 12H), 10.47-10.57 (m, 1H).

Example 1-73

MS ESI m/e: 522 (M+H), 520 (M–H).
$^1$H-NMR (CDCl$_3$, 300 MHz) δ 0.91 (t, J=7.3 Hz, 3H), 1.49-1.66 (m, 2H), 2.50 (t, J=7.7 Hz, 2H), 2.87 (s, 3H), 2.95 (s, 6H), 5.33 (s, 1H), 6.54-6.63 (m, 2H), 7.01-7.08 (m, 1H), 7.30-7.37 (m, 2H), 7.38-7.58 (m, 8H), 9.80 (s, 1H).

Example 1-74

MS ESI m/e: 506 (M+H), 504 (M–H).
$^1$H-NMR (CDCl$_3$, 300 MHz) δ 1.91-2.03 (m, 2H), 2.73 (t, J=6.4 Hz, 2H), 2.87 (s, 3H), 2.88 (s, 3H), 3.22 (t, J=5.7 Hz, 2H), 5.68 (s, 1H), 6.54 (d, J=8.4 Hz, 1H), 6.79-6.85 (m, 1H), 6.87-6.93 (m, 1H), 7.28-7.34 (m, 2H), 7.36-7.58 (m, 8H), 10.00 (s, 1H).

Example 1-75

MS ESI m/e: 531, 533 (M+H), 529, 531 (M–H).
$^1$H-NMR (DMSO-$d_6$, 300 MHz) δ 2.63 (s, 3H), 3.72 (s, 3H), 3.73 (s, 3H), 5.45 (s, 1H), 6.97 (t, J=9.1 Hz, 4H), 7.16-7.42 (m, 8H), 10.46 (brs, 1H).

Example 1-76

MS ESI m/e: 499, 501 (M+H), 497, 499 (M–H).
$^1$H-NMR (DMSO-$d_6$, 300 MHz) δ 2.26 (s. 3H), 2.27 (s, 3H), 2.63 (s, 3H), 5.46 (s, 1H), 7.09-7.42 (m, 12H), 10.42 (brs, 1H).

Example 1-77

MS ESI m/e: 483, 485 (M+H), 481, 483 (M–H).
$^1$H-NMR (DMSO-$d_6$, 300 MHz) δ 2.68 (s, 3H), 5.45 (s, 1H), 7.00-7.64 (m, 10H), 10.35 (brs, 1H).

Example 1-78

MS ESI m/e: 423 (M+H), 421 (M–H).
$^1$H-NMR (CDCl$_3$, 400 MHz) δ 1.30 (t, J=6.9 Hz, 3H), 2.82 (s, 3H), 4.08 (q, J=7.0 Hz, 2H), 5.77 (s, 1H), 7.19-7.25 (m, 2H), 7.31-7.39 (m, 4H), 7.41-7.54 (m, 3H), 10.53 (s, 1H).

Example 1-79

MS ESI m/e: 507, 508 (M+H), 505, 503 (M–H).
$^1$H-NMR (DMSO-$d_6$, 300 MHz) δ 2.64 (s, 3H), 5.46 (s, 1H), 7.23-7.51 (m, 12H), 10.37 (brs, 1H).

Example 1-80

MS ESI m/e: 463 (M+H), 461 (M–H).
$^1$H-NMR (CDCl$_3$, 300 MHz) δ 1.52-1.67 (m, 2H), 1.82-2.02 (m, 4H), 2.04-2.20 (m, 2H), 2.80 (s, 3H), 5.21-5.37 (m, 1H), 5.75 (s, 1H), 7.18-7.28 (m, 2H), 7.30-7.56 (m, 7H), 10.54 (s, 1H).

Example 1-81

MS ESI m/e: 437 (M+H), 435 (M−H).
$^1$H-NMR (CDCl$_3$, 300 MHz) δ 1.51 (d, J=7.0 Hz, 6H), 2.81 (s, 3H), 5.09-5.23 (m, 1H), 5.75 (s, 1H), 7.18-7.28 (m, 2H), 7.29-7.55 (m, 7H), 10.53 (s, 1H).

Example 1-82

MS ESI m/e: 437 (M+H), 435 (M−H).
$^1$H-NMR (CDCl$_3$, 400 MHz) δ 0.98 (t, J=7.4 Hz, 3H), 1.66-1.79 (m, 2H), 2.82 (s, 3H), 3.96 (t, J=7.6 Hz, 2H), 5.77 (s, 1H), 7.20-7.25 (m, 2H), 7.32-7.40 (m, 4H), 7.41-7.54 (m, 3H), 10.54 (s, 1H).

Example 1-83

MS ESI m/e: 451 (M+H), 449 (M−H).
$^1$H-NMR (CDCl$_3$, 400 MHz) δ 0.96 (t, J=7.4 Hz, 3H), 1.34-1.47 (m, 2H), 1.62-1.73 (m, 2H), 2.81 (s, 3H), 3.99 (t, J=7.6 Hz, 2H), 5.76 (s, 1H), 7.18-7.24 (m, 2H), 7.31-7.39 (m, 4H), 7.41-7.52 (m, 3H), 10.53 (s, 1H).

Example 1-84

MS ESI m/e: 435 (M+H), 433 (M−H).
$^1$H-NMR (CDCl$_3$, 400 MHz) δ 0.81-0.90 (m, 2H), 1.14-1.24 (m, 2H), 2.71-2.81 (m, 1H), 2.81 (s, 3H), 5.77 (s, 1H), 7.17-7.24 (m, 2H), 7.27-7.39 (m, 4H), 7.39-7.52 (m, 3H), 10.38 (s, 1H).

Example 1-85

MS ESI m/e: 423 (M+H), 421 (M−H).
$^1$H-NMR (DMSO-d$_6$, 300 MHz) δ 2.25-2.30 (m, 3H), 2.51-2.57 (m, 3H), 3.26-3.31 (m, 3H), 5.48-5.52 (m, 1H), 7.24-7.55 (m, 8H), 10.74 (s, 1H).

Example 1-86

MS ESI m/e: 423 (M+H), 421 (M−H).
$^1$H-NMR (DMSO-d$_6$, 300 MHz) δ 2.35 (s, 3H), 2.65 (s, 3H), 3.26 (s, 3H), 5.51 (s, 1H), 7.23-7.32 (m, 3H), 7.32-7.45 (m, 3H), 7.46-7.54 (m, 2H), 10.64 (s, 1H).

Example 1-87

MS ESI m/e: 423 (M+H), 421 (M−H).
$^1$H-NMR (DMSO-d$_6$, 300 MHz) δ 2.37 (s, 3H), 2.63 (s, 3H), 3.26 (s, 3H), 5.50 (s, 1H), 7.29-7.39 (m, 6H), 7.46-7.53 (m, 2H), 10.64 (s, 1H).

Example 1-88

MS ESI m/e: 444 (M+H), 442 (M−H).
$^1$H-NMR (CDCl$_3$, 300 MHz) δ 0.82-0.91 (m, 2H), 1.13-1.23 (m, 2H), 2.71-2.80 (m, 1H), 2.80 (s, 3H), 2.97 (s, 6H), 5.62 (s, 1H), 6.69-6.77 (m, 2H), 7.08-7.16 (m, 2H), 7.29-7.35 (m, 2H), 7.38-7.52 (m, 3H), 10.07 (s, 1H).

Example 1-89

MS ESI m/e: 479, 481 (M+H), 477, 479 (M−H).
$^1$H-NMR (CDCl$_3$, 300 MHz) δ 0.81-0.91 (m, 2H), 1.15-1.26 (m, 2H), 2.71-2.82 (m, 1H), 2.82 (s, 3H), 5.80 (s, 1H), 7.13-7.21 (m, 2H), 7.28-7.36 (m, 2H), 7.39-7.56 (m, 5H), 10.41 (s, 1H).

Example 1-90

MS ESI m/e: 477 (M+H), 475 (M−H).
$^1$H-NMR (CDCl$_3$, 300 MHz) δ 2.84 (s, 3H), 4.75 (q, J=8.4 Hz, 2H), 5.76 (s, 1H), 7.19-7.28 (m, 2H), 7.31-7.42 (m, 4H), 7.43-7.57 (m, 3H), 10.20 (s, 1H).

Example 1-91

MS ESI m/e: 513 (M+H), 511 (M−H).
$^1$H-NMR (DMSO-d$_6$, 300 MHz) δ 0.64 (t, J=6.0 Hz, 3H), 1.21-1.41 (m, 2H), 2.15 (t, J=7.5 Hz, 2H), 2.76 (s, 3H), 6.93-7.07 (m, 2H), 7.27-7.37 (m, 4H), 7.39-7.64 (m, 8H), 9.92 (s, 1H).

Example 1-92

MS ESI m/e: 521, 523 (M+H), 519, 521 (M−H).
$^1$H-NMR (CDCl$_3$, 300 MHz) δ 2.85 (s, 3H), 4.75 (q, J=8.4 Hz, 2H), 5.78 (s, 1H), 7.14-7.22 (m, 2H), 7.32-7.40 (m, 2H), 7.44-7.58 (m, 5H), 10.20 (s, 1H).

Example 1-93

MS ESI m/e: 486 (M+H), 484 (M−H).
$^1$H-NMR (CDCl$_3$, 300 MHz) δ 2.83 (s, 3H), 2.97 (s, 6H), 4.75 (q, J=8.4 Hz, 2H), 5.61 (s, 1H), 6.67-6.81 (m, 2H), 7.08-7.18 (m, 2H), 7.32-7.40 (m, 2H), 7.41-7.56 (m, 3H), 9.92 (s, 1H).

Example 1-94

MS ESI m/e: 457 (M+H), 455 (M−H).
$^1$H-NMR (DMSO-d$_6$, 300 MHz) δ 1.18 (t, J=6.7 Hz, 3H), 2.66 (s, 3H), 3.93 (q, J=6.7 Hz, 2H), 5.50 (s, 1H), 7.36 (d, J=9.0 Hz, 2H), 7.46-7.56 (m, 4H), 7.57-7.66 (m, 2H), 10.62 (s, 1H).

Example 1-95

MS ESI m/e: 467, 469 (M+H), 465, 467 (M−H).
$^1$H-NMR (DMSO-d$_6$, 400 MHz) δ 2.28 (s, 3H), 2.53 (s, 3H), 3.28 (s, 3H), 5.51 (s, 1H), 7.23-7.35 (m, 4H), 7.38-7.44 (m, 2H), 7.58-7.65 (m, 2H), 10.72 (s, 1H).

Example 1-96

MS ESI m/e: 467, 469 (M+H), 465, 467 (M−H).
$^1$H-NMR (CDCl$_3$, 400 MHz) δ 1.29 (t, J=7.1 Hz, 3H), 2.81 (s, 3H), 4.07 (q, J=7.1 Hz, 2H), 5.78 (s, 1H), 7.14-7.19 (m, 2H), 7.31-7.36 (m, 2H), 7.40-7.53 (m, 5H), 10.53 (s, 1H).

Example 1-97

MS ESI m/e: 432 (M+H).
$^1$H-NMR (CDCl$_3$, 400 MHz) δ 1.29 (t, J=7.1 Hz, 3H), 2.80 (s, 3H), 2.96 (s, 6H), 4.07 (q, J=7.0 Hz, 2H), 5.59 (s, 1H), 6.69-6.75 (m, 2H), 7.08-7.14 (m, 2H), 7.31-7.36 (m, 2H), 7.38-7.50 (m, 3H), 10.19 (s, 1H).

Example 1-98

MS ESI m/e: 435 (M+H), 433 (M−H).
$^1$H-NMR (CDCl$_3$, 300 MHz) δ 0.80-0.91 (m, 2H), 1.25-1.35 (m, 2H), 3.38-3.49 (m, 1H), 3.74 (s, 3H), 5.76 (s, 1H), 7.09-7.18 (m, 2H), 7.20-7.37 (m, 4H), 7.44-7.60 (m, 3H), 10.23 (s, 1H).

Example 1-99

MS ESI m/e: 432 (M+H).
$^1$H-NMR (DMSO-d$_6$, 300 MHz) δ 2.27 (s, 3H), 2.51 (s, 3H), 2.92 (s, 6H), 3.27 (s, 3H), 5.21 (s, 1H), 6.76-6.84 (m, 2H), 7.06-7.14 (m, 2H), 7.23-7.38 (m, 2H), 7.38-7.44 (m, 2H), 10.35 (s, 1H).

Example 1-100

MS ESI m/e: 453 (M+H), 451 (M−H).
$^1$H-NMR (CDCl$_3$, 300 MHz) δ 0.83-0.92 (m, 2H), 1.14-1.24 (m, 2H), 2.74-2.83 (m, 1H), 2.86 (s, 3H), 5.76 (s, 1H), 7.18-7.33 (m, 5H), 7.33-7.40 (m, 2H), 7.45-7.55 (m, 1H), 10.41 (s, 1H).

Example 1-101

MS ESI m/e: 503 (M+H), 501 (M−H).
$^1$H-NMR (CDCl$_3$, 300 MHz) δ 0.78-0.91 (m, 2H), 1.14-1.26 (m, 2H), 2.73-2.86 (m, 1H), 2.82 (s, 3H), 5.76 (s, 1H), 7.19-7.29 (m, 2H), 7.32-7.41 (m, 2H), 7.42-7.50 (m, 1H), 7.61-7.79 (m, 2H), 7.80-7.89 (m, 1H), 10.50 (s, 1H).

Example 1-102

MS ESI m/e: 449 (M+H), 447 (M−H).
$^1$H-NMR (CDCl$_3$, 300 MHz) δ 0.74-0.96 (m, 2H), 1.11-1.31 (m, 2H), 2.30 (s, 3H), 2.74 (s, 3H), 2.76-2.85 (m, 1H), 5.76 (s, 1H), 7.04-7.12 (m, 1H), 7.18-7.43 (m, 7H), 10.53 (s, 1H).

Example 1-103

MS ESI m/e: 463 (M+H), 461 (M−H).
$^1$H-NMR (CDCl$_3$, 300 MHz) δ 0.76-0.90 (m, 2H), 1.11-1.27 (m, 2H), 1.26 (t, J=70.5 Hz, 3H), 2.40-2.67 (m, 2H), 2.71-2.84 (m, 1H), 2.75 (s, 3H), 5.76 (s, 1H), 7.08-7.14 (m, 1H), 7.18-7.47 (m, 7H), 10.54 (s, 1H).

Example 1-104

MS ESI m/e: 465 (M+H), 463 (M−H).
$^1$H-NMR (CDCl$_3$, 300 MHz) δ 0.79-0.94 (m, 2H), 1.11-1.28 (m, 2H), 2.71-2.83 (m, 1H), 2.84 (s, 3H), 3.84 (s, 3H), 5.76 (s, 1H), 7.00-7.13 (m, 2H), 7.19-7.30 (m, 3H), 7.32-7.40 (m, 2H), 7.41-7.52 (m, 1H), 10.52 (s, 1H).

Example 1-105

MS ESI m/e: 445 (M+H), 443 (M−H).
$^1$H-NMR (CDCl$_3$, 300 MHz) δ 0.92 (t, J=7.5 Hz, 3H), 1.36 (sext, J=7.5 Hz, 2H), 1.59 (quint, J=7.5 Hz, 2H), 2.33 (s, 3H), 2.62 (t, J=7.5 Hz, 2H), 2.75 (s, 3H), 3.45 (s, 3H), 5.43 (s, 1H), 7.08-7.45 (m, 8H), 10.37 (s, 1H).

Example 1-106

MS ESI m/e: 458 (M+H).
$^1$H-NMR (CDCl$_3$, 300 MHz) δ 0.77-0.92 (m, 2H), 1.14-1.27 (m, 2H), 2.30 (s, 3H), 2.72 (s, 3H), 2.74-2.85 (m, 1H), 2.96 (s, 6H), 5.60 (s, 1H), 6.69-6.79 (m, 2H), 7.03-7.18 (m, 3H), 7.22-7.42 (m, 3H), 10.20 (s, 1H).

Example 1-107

MS ESI m/e: 493, 495 (M+H), 491, 493 (M−H).
$^1$H-NMR (DMSO-d$_6$, 300 MHz) δ 1.68-1.79 (m, 2H), 2.19-2.32 (m, 2H), 2.59 (s, 3H), 2.60-2.75 (m, 2H), 4.88-4.98 (m, 1H), 5.49 (s, 1H), 7.29 (d, J=8.7 Hz, 2H), 7.41-7.53 (m, 5H), 7.60 (d, J=8.6 Hz, 2H), 10.52 (brs, 1H).

Example 1-108

MS ESI m/e: 535, 537 (M+H), 533, 535 (M−H).
$^1$H-NMR (DMSO-d$_6$, 300 MHz) δ 2.27 (s, 3H), 2.54 (s, 3H), 4.62-4.88 (m, 2H), 5.49 (s, 1H), 7.28-7.30 (m, 4H), 7.41-7.42 (m, 2H), 7.62 (d, J=9.0 Hz, 2H), 10.40 (brs, 1H).

Example 1-109

MS ESI m/e: 437 (M+H), 435 (M−H).
$^1$H-NMR (CDCl$_3$, 300 MHz) δ 1.30 (t, J=6.0 Hz, 3H), 2.30 (s, 3H), 2.75 (s, 3H), 4.09 (q, J=6.0 Hz, 2H), 5.75 (s, 1H), 7.12 (d, J=6.0 Hz, 1H), 7.19-7.43 (m, 7H), 10.65 (s, 1H).

Example 1-110

MS ESI m/e: 446 (M+H), 444 (M−H).
$^1$H-NMR (CDCl$_3$, 300 MHz) δ 1.30 (t, J=7.1 Hz, 3H), 2.30 (s, 3H), 2.73 (s, 3H), 2.96 (s, 6H), 4.09 (q, J=2.3 Hz, 2H), 4.84 (q, J=149.0 Hz, 2H), 6.68-6.77 (m, 2H), 7.08-7.17 (m, 3H), 7.25-7.32 (m, 1H), 7.33-7.38 (m, 2H), 10.31 (brs, 1H).

Example 1-111

MS ESI m/e: 481, 483 (M+H), 479, 481 (M−H).
$^1$H-NMR (CDCl$_3$, 300 MHz) δ 1.30 (t, J=6.0 Hz, 3H), 2.30 (s, 1H), 2.75 (s, 1H), 4.09 (q, J=7.0 Hz, 2H), 5.77 (s, 1H), 7.08-7.22 (m, 3H), 7.26-7.42 (m, 3H), 7.49-7.56 (m, 2H), 10.66 (brs, 1H).

Example 1-112

MS ESI m/e: 458 (M+H), 456 (M−H).
$^1$H-NMR (CDCl$_3$, 300 MHz) δ 0.83-0.93 (m, 2H), 1.14-1.24 (m, 2H), 2.23 (s, 3H), 2.71-2.82 (m, 1H), 2.79 (s, 3H), 2.95 (s, 6H), 5.29 (s, 1H), 6.55-6.64 (m, 2H), 7.02-7.10 (m, 1H), 7.29-7.36 (m, 2H), 7.38-7.53 (m, 3H), 9.86 (s, 1H).

Example 1-113

MS ESI m/e: 497, 499 (M+H), 495, 497 (M−H).
$^1$H-NMR (CDCl$_3$, 300 MHz) δ 0.82-0.92 (m, 2H), 1.14-1.24 (m, 2H), 2.73-2.83 (m, 1H), 2.86 (s, 3H), 5.78 (s, 1H), 7.12-7.21 (m, 2H), 7.21-7.34 (m, 3H), 7.45-7.55 (m, 3H), 10.41 (s, 1H).

Example 1-114

MS ESI m/e: 462 (M+H), 460 (M−H).
$^1$H-NMR (CDCl$_3$, 300 MHz) δ 0.83-0.93 (m, 2H), 1.13-1.25 (m, 2H), 2.72-2.84 (m, 1H), 2.84 (s, 3H), 2.96 (s, 6H), 5.60 (s, 1H), 6.69-6.77 (m, 2H), 7.08-7.15 (m, 2H), 7.17-7.31 (m, 3H), 7.43-7.53 (m, 1H), 10.09 (s, 1H).

Example 1-115

MS ESI m/e: 441 (M+H), 439 (M−H).
$^1$H-NMR (CDCl$_3$, 300 MHz) δ 1.31 (t, J=7.0 Hz, 3H), 2.86 (s, 3H), 4.08 (q, J=7.0 Hz, 2H), 5.75 (s, 1H), 7.18-7.40 (m, 7H), 7.46-7.56 (m, 1H), 10.54 (s, 1H).

Example 1-116

MS ESI m/e: 485, 487 (M+H), 483, 485 (M−H).
$^1$H-NMR (CDCl$_3$, 300 MHz) δ 1.31 (t, J=7.0 Hz, 3H), 2.86 (s, 3H), 4.08 (q, J=7.0 Hz, 2H), 5.77 (s, 1H), 7.13-7.21 (m, 2H), 7.24-7.34 (m, 3H), 7.46-7.56 (m, 3H), 10.55 (s, 1H).

Example 1-117

MS ESI m/e: 450 (M+H), 448 (M−H).
$^1$H-NMR (CDCl$_3$, 300 MHz) δ 1.31 (t, J=7.0 Hz, 3H), 2.85 (s, 3H), 2.96 (s, 6H), 4.08 (q, J=7.1 Hz, 2H), 5.59 (s, 1H), 6.69-6.77 (m, 2H), 7.08-7.17 (m, 2H), 7.22-7.34 (m, 3H), 7.43-7.54 (m, 1H), 10.21 (s, 1H).

Example 1-118

MS ESI m/e: 472 (M+H).
$^1$H-NMR (CDCl$_3$, 300 MHz) δ 0.79-0.89 (m, 2H), 1.14-1.25 (m, 2H), 2.16 (s, 6H), 2.71 (s, 3H), 2.77-2.87 (m, 1H), 2.96 (s, 6H), 5.59 (s, 1H), 6.68-6.77 (m, 2H), 7.08-7.19 (m, 4H), 7.23-7.31 (m, 1H), 10.31 (s, 1H).

Example 1-119

MS ESI m/e: 480 (M+H).
$^1$H-NMR (DMSO-d$_6$, 300 MHz) δ 0.71-0.79 (m, 2H), 0.99-1.10 (m, 2H), 2.68-2.79 (m, 1H), 2.71 (s, 1H), 5.21 (s, 1H), 6.79 (d, J=9.0 Hz, 2H), 7.12 (d, J=9.0 Hz, 2H), 7.39 (t, J=9.0 Hz, 2H), 7.65-7.75 (m, 1H), 10.11 (brs, 1H).

Example 1-120

MS ESI m/e: 515, 517 (M+H), 513, 515 (M−H).
$^1$H-NMR (DMSO-d$_6$, 300 MHz) δ 0.71-0.79 (m, 2H), 1.00-1.10 (m, 2H), 2.71-2.80 (m, 1H), 2.74 (s, 3H), 5.51 (s, 1H), 7.32 (d, J=9.0 Hz, 2H), 7.41 (t, J=7.5 Hz, 2H), 7.62 (d, J=6.0 Hz, 2H), 7.64-7.76 (m, 1H), 10.47 (brs, 1H).

Example 1-121

MS ESI m/e: 471 (M+H), 469 (M−H).
$^1$H-NMR (DMSO-d$_6$, 300 MHz) δ 0.71-0.79 (m, 2H), 1.03-1.07 (m, 2H), 2.70-2.80 (m, 1H), 2.74 (s, 3H), 5.49 (s, 1H), 7.36-7.43 (m, 4H), 7.50 (d, J=9.0 Hz, 2H), 7.65-7.76 (m, 1H), 10.47 (brs, H).

Example 1-122

MS ESI m/e: 460 (M+H), 458 (M−H).
$^1$H-NMR (DMSO-d$_6$, 300 MHz) δ 1.16 (t, J=7.5 Hz, 3H), 1.18 (t, J=6.0 Hz, 3H), 2.52 (q, J=4.0 Hz, 2H), 2.50 (s, 3H), 2.92 (s, 6H), 3.94 (q, J=5.0 Hz, 2H), 5.20 (s, 1H), 6.79 (d, J=9.0 Hz, 2H), 7.12 (d, J=9.0 Hz, 2H), 7.33 (d, J=3.0 Hz, 2H), 7.47 (s, 2H), 10.35 (brs, H).

Example 1-123

MS ESI m/e: 495, 497 (M+H), 493, 495 (M−H).
$^1$H-NMR (DMSO-d$_6$, 300 MHz) δ 1.16 (t, J=7.5 Hz, 3H), 1.18 (t, J=6.0 Hz, 3H), 2.50-2.56 (m, 2H), 2.53 (s, 3H), 3.96 (q, J=7.0 Hz, 2H), 5.51 (s, 1H), 7.29-7.34 (m, 4H), 7.46-7.48 (m, 2H), 7.62 (d, J=6.0 Hz, 2H), 10.74 (brs, H).

Example 1-124

MS ESI m/e: 451 (M+H), 499 (M−H).
$^1$H-NMR (DMSO-d$_6$, 300 MHz) δ 1.16 (t, J=6.0 Hz, 3H), 1.18 (t, J=6.0 Hz, 3H), 2.50-2.55 (m, 2H), 2.56 (s, 3H), 3.95 (q, J=8.0 Hz, 2H), 5.49 (s, 1H), 7.33-7.38 (m, 4H), 7.48-7.51 (m, 4H), 10.73 (brs, H).

Example 1-125

MS ESI m/e: 463 (M+H), 461 (M−H).
$^1$H-NMR (CDCl$_3$, 300 MHz) δ 0.78-0.88 (m, 2H), 1.16-1.29 (m, 2H), 2.15 (s, 6H), 2.72 (s, 3H), 2.77-2.88 (m, 1H), 5.74 (s, 1H), 7.11-7.40 (m, 7H), 10.64 (s, 1H).

Example 1-126

MS ESI m/e: 458 (M+H).
$^1$H-NMR (CDCl$_3$, 300 MHz) δ 0.83-0.90 (m, 2H), 1.13-1.23 (m, 2H), 2.39 (s, 3H), 2.71-2.78 (m, 1H), 2.81 (s, 3H), 2.96 (s, 6H), 5.60 (s, 1H), 6.68-6.78 (m, 2H), 7.07-7.32 (m, 6H), 10.08 (brs, 1H).

Example 1-127

MS ESI m/e: 458 (M+H).
$^1$H-NMR (CDCl$_3$, 300 MHz) δ 0.81-0.93 (m, 2H), 1.13-1.23 (m, 2H), 2.39 (s, 3H), 2.71-2.81 (m, 1H), 2.83 (s, 3H), 2.96 (s, 6H), 5.62 (s, 1H), 6.70-6.76 (m, 2H), 7.08-7.16 (m, 4H), 7.20-7.25 (m, 1H), 7.31-7.39 (m, 1H), 10.08 (brs, 1H).

Example 1-128

MS ESI m/e: 472 (M+H).
$^1$H-NMR (CDCl$_3$, 300 MHz) δ 0.82-0.92 (m, 2H), 1.14-1.25 (m, 2H), 1.18 (t, J=7.0 Hz, 6H), 2.71-2.82 (m, 1H), 2.80 (s, 3H), 3.36 (q, J=7.0 Hz, 4H), 5.62 (s, 1H), 6.63-6.71 (m, 2H), 7.03-7.13 (m, 2H), 7.28-7.36 (m, 2H), 7.37-7.53 (m, 3H), 10.03 (s, 1H).

Example 1-129

MS ESI m/e: 431 (M+H), 429 (M−H).
$^1$H-NMR (CDCl$_3$, 400 MHz) δ 0.84-0.90 (m, 2H), 1.15-1.23 (m, 2H), 2.72-2.80 (m, 1H), 2.80 (s, 3H), 3.82 (s, 3H), 5.61 (s, 1H), 6.88-6.94 (m, 2H), 7.14-7.21 (m, 2H), 7.28-7.33 (m, 2H), 7.38-7.50 (m, 3H), 10.15 (s, 1H).

Example 1-130

MS ESI m/e: 408 (M+H).
$^1$H-NMR (DMSO-d$_6$, 300 MHz) δ 0.68-0.73 (m, 4H), 0.96-1.02 (m, 2H), 1.05-1.12 (m, 2H), 2.54-2.63 (m, 1H), 2.91 (s, 6H), 3.30-3.40 (m, 1H), 3.48 (s, 3H), 5.14 (s, 1H), 6.77 (d, J=9.0 Hz, 2H), 7.06 (d, J=9.0 Hz, 2H), 10.04 (brs, H).

Example 1-131

MS ESI m/e: 468, 470 (M+H), 466, 468 (M−H).
$^1$H-NMR (DMSO-d$_6$, 300 MHz) δ 1.20 (t, J=7.5 Hz, 3H), 2.62 (s, 3H), 3.95 (q, J=7.0 Hz, 2H), 5.53 (s, 1H), 7.32 (d, J=9.0 Hz, 2H), 7.52-7.64 (m, 3H), 7.97 (d, J=9.0 Hz, 1H), 8.67 (d, J=15 Hz, 1H), 8.68 (d, J=15 Hz, 1H), 10.62 (brs, H).

Example 1-132

MS ESI m/e: 462 (M+H), 460 (M−H).
$^1$H-NMR (CDCl$_3$, 400 MHz) δ 0.82-0.89 (m, 2H), 1.15-1.22 (m, 2H), 2.72-2.79 (m, 1H), 2.82 (s, 3H), 2.96 (s, 6H), 5.60 (s, 1H), 6.69-6.75 (m, 2H), 7.07-7.21 (m, 4H), 7.27-7.33 (m, 2H), 10.03 (s, 1H).

Example 1-133

MS ESI m/e: 462 (M+H), 460 (M−H).
$^1$H-NMR (CDCl$_3$, 400 MHz) δ 0.83-0.89 (m, 2H), 1.15-1.23 (m, 2H), 2.72-2.80 (m, 1H), 2.85 (s, 3H), 2.96 (s, 6H), 5.61 (s, 1H), 6.69-6.75 (m, 2H), 7.03-7.19 (m, 5H), 7.39-7.46 (m, 1H), 10.01 (s, 1H).

Example 1-134

MS ESI m/e: 444 (M+H), 442 (M−H).
$^1$H-NMR (CDCl$_3$, 300 MHz) δ 0.82-0.93 (m, 2H), 1.13-1.24 (m, 2H), 2.72-2.82 (m, 1H), 2.82 (s, 3H), 2.96 (s, 6H), 5.90 (s, 1H), 6.55-6.62 (m, 2H), 6.63-6.69 (m, 1H), 7.19-7.24 (m, 1H), 7.30-7.35 (m, 2H), 7.38-7.53 (m, 3H), 10.31 (s, 1H).

Example 1-135

MS ESI m/e: 416 (M+H).
$^1$H-NMR (DMSO-d$_6$, 300 MHz) δ 0.70-0.82 (m, 2H), 0.99-1.09 (m, 2H), 2.60 (s, 3H), 2.63-2.74 (m, 1H), 5.52 (s, 1H), 7.36-7.57 (m, 9H), 10.61 (s, 1H).

Example 1-136

MS ESI m/e: 430 (M+H).
$^1$H-NMR (DMSO-d$_6$, 300 MHz) δ 0.71-0.80 (m, 2H), 0.98-1.08 (m, 2H), 2.60 (s, 3H), 2.63-2.72 (m, 1H), 2.89 (s, 3H), 5.51 (d, J=2.9 Hz, 1H), 7.38-7.56 (m, 9H), 10.59 (brs, 1H).

Example 1-137

MS ESI m/e: 444 (M+H), 442 (M−H).
$^1$H-NMR (DMSO-d$_6$, 300 MHz) δ 0.71-0.80 (m, 2H), 0.98-1.08 (m, 2H), 1.27 (t, J=7.5 Hz, 3H), 2.61 (s, 3H), 2.64-2.72 (m, 1H), 3.31 (q, J=7.0 Hz, 2H), 5.54 (s, 1H), 7.07-7.19 (m, 2H), 7.38-7.57 (m, 9H), 10.62 (brs, 1H).

Example 1-138

MS ESI m/e: 454 (M+H).
$^1$H-NMR (DMSO-d$_6$, 300 MHz) δ 0.71-0.80 (m, 2H), 0.99-1.08 (m, 2H), 2.57 (s, 3H), 2.62-2.75 (m, 1H), 3.81 (s, 3H), 5.26 (s, 1H), 6.44 (d, J=3.0 Hz, 1H), 7.06 (dd, J=3.0, 3.0 Hz, 1H), 7.37-7.52 (m, 8H), 10.37 (brs, H).

Example 1-139

MS ESI m/e: 444 (M+H).
$^1$H-NMR (DMSO-d$_6$, 300 MHz) δ 2.59 (s, 3H), 2.92 (s, 6H), 4.49 (d, J=3.0 Hz, 2H), 5.15 (d, J=9.0 Hz, 1H), 5.22 (dd, J=3.0, 9.0 Hz, 2H), 6.78 (d, J=6.0 Hz, 2H), 7.10 (d, J=6.0 Hz, 2H), 7.48-7.50 (m, 5H), 10.19 (brs, H).

Example 1-140

MS ESI m/e: 444 (M+H), 442 (M−H).
$^1$H-NMR (DMSO-d$_6$, 300 MHz) δ 2.60 (s, 3H), 3.03 (s, 6H), 4.50 (d, J=3.0 Hz, 2H), 5.17 (dd, J=21.0, 24.0 Hz, 2H), 5.38 (s, 1H), 5.79-5.92 (m, 1H), 7.19-7.38 (m, 4H), 7.41-7.55 (m, 5H), 10.42 (brs, H).

Example 1-141

MS ESI m/e: 456 (M+H), 454 (M−H).
$^1$H-NMR (DMSO-d$_6$, 300 MHz) δ 0.70-0.79 (m, 2H), 0.99-1.08 (m, 2H), 2.55 (s, 3H), 2.61-2.68 (m, 1H), 2.71 (s, 3H), 2.89 (t, J=9.0 Hz, 2H), 3.28 (t, J=7.5 Hz, 2H), 5.18 (s, 1H), 6.54 (d, J=9.0 Hz, 1H), 6.90 (d, J=6.0 Hz, 1H), 6.96 (s, 1H), 7.39-7.50 (m, 5H), 10.13 (brs, H).

Example 1-142

MS ESI m/e: 476 (M+H).
$^1$H-NMR (CDCl$_3$, 300 MHz) δ 0.85-0.93 (m, 2H), 1.14-1.24 (m, 2H), 2.23 (s, 3H), 2.74-2.83 (m, 1H), 2.83 (s, 3H), 2.95 (s, 6H), 5.27 (s, 1H), 6.55-6.65 (m, 2H), 7.02-7.09 (m, 1H), 7.18-7.32 (m, 3H), 7.43-7.54 (m, 1H), 9.89 (s, 1H).

Example 1-143

MS ESI m/e: 462 (M+H), 460 (M−H).
$^1$H-NMR (CDCl$_3$, 300 MHz) δ 0.81-0.92 (m, 2H), 1.14-1.25 (m, 2H), 2.71-2.81 (m, 1H), 2.81 (s, 1H), 2.87 (s, 6H), 5.71 (s, 1H), 6.86-7.02 (m, 3H), 7.27-7.35 (m, 2H), 7.41-7.54 (m, 3H), 10.22 (brs, 1H).

Example 1-144

MS ESI m/e: 454 (M+H), 452 (M−H).
$^1$H-NMR (DMSO-d$_6$, 300 MHz) δ 0.72-0.80 (m, 2H), 1.00-1.09 (m, 2H), 2.58 (s, 3H), 2.64-2.71 (m, 1H), 3.78 (s, 3H), 5.40 (s, 1H), 6.45 (d, J=3.0 Hz, 1H), 6.97 (d, J=6.0 Hz, 1H), 7.34-7.51 (m, 7H), 7.60 (d, J=9.0 Hz, 1H), 8.30 (brs, H).

Example 1-145

MS ESI m/e: 479 (M+H), 477 (M−H).
$^1$H-NMR (CDCl$_3$, 300 MHz) δ 0.82-0.91 (m, 2H), 1.15-1.26 (m, 2H), 2.73-2.83 (m, 1H), 2.85 (s, 3H), 3.08 (s, 3H), 6.08 (s, 1H), 7.29-7.37 (m, 2H), 7.41-7.56 (m, 5H), 7.92-8.00 (m, 2H), 10.87 (s, 1H).

Example 1-146

MS ESI m/e: 461 (M+H), 459 (M−H).

$^1$H-NMR (CDCl$_3$, 300 MHz) δ 0.82-0.92 (m, 2H), 1.13-1.24 (m, 2H), 2.72-2.83 (m, 1H), 2.80 (s, 3H), 3.83 (s, 3H), 3.84 (s, 3H), 5.60 (s, 1H), 6.45-6.58 (m, 2H), 7.19-7.26 (m, 1H), 7.28-7.35 (m, 2H), 7.38-7.52 (m, 3H), 10.01 (s, 1H).

Example 1-147

MS ESI m/e: 458 (M+H), 456 (M−H).

$^1$H-NMR (CDCl$_3$, 300 MHz) δ 0.81-0.91 (m, 2H), 1.13-1.23 (m, 2H), 2.32 (s, 3H), 2.67-2.84 (m, 1H), 2.71 (s, 6H), 2.81 (s, 3H), 5.72 (s, 1H), 6.99-7.10 (m, 3H), 7.28-7.36 (m, 2H), 7.38-7.53 (m, 3H), 10.19 (s, 1H).

Example 1-148

MS ESI m/e: 512 (M+H), 510 (M−H).

$^1$H-NMR (CDCl$_3$, 400 MHz) δ 0.84-0.90 (m, 2H), 1.16-1.24 (m, 2H), 2.73-2.79 (m, 1H), 2.75 (s, 6H), 2.81 (s, 3H), 5.66 (s, 1H), 7.29-7.37 (m, 3H), 7.39-7.52 (m, 5H), 10.33 (brs, 1H).

Example 1-149

MS ESI m/e: 472 (M+H), 470 (M−H).

$^1$H-NMR (CDCl$_3$, 400 MHz) δ 0.84-0.91 (m, 2H), 1.17-1.25 (m, 2H), 1.91 (s, 3H), 2.74-2.81 (m, 1H), 2.83 (s, 3H), 3.28 (s, 3H), 5.84 (s, 1H), 7.18-7.24 (m, 2H), 7.29-7.35 (m, 4H), 7.40-7.52 (m, 3H), 10.47 (s, 1H).

Example 1-150

MS ESI m/e: 493, 495 (M+H), 491, 493 (M−H).

$^1$H-NMR (CDCl$_3$, 300 MHz) δ 0.39-0.57 (m, 4H), 1.24-1.36 (m, 1H), 2.83 (s, 3H), 3.91 (d, J=7.0 Hz, 2H), 5.80 (s, 1H), 7.15-7.21 (m, 2H), 7.33-7.39 (m, 2H), 7.42-7.55 (m, 5H), 10.57 (s, 1H).

Example 1-151

MS ESI m/e: 497, 499 (M+H), 495, 497 (M−H).

$^1$H-NMR (DMSO-d$_6$, 300 MHz) δ 0.73-0.79 (m, 2H), 1.01-1.09 (m, 2H), 2.61 (s, 3H), 2.68-2.71 (m, 1H), 5.65 (s, 1H), 7.19 (d, J=9.0 Hz, 1H), 7.40-7.52 (m, 6H), 7.73 (t, J=9.0 Hz, 1H), 10.67 (brs, H).

Example 1-152

MS ESI m/e: 497, 499 (M+H), 495, 497 (M−H).

$^1$H-NMR (DMSO-d$_6$, 300 MHz) δ 0.72-0.79 (m, 2H), 1.01-1.09 (m, 2H), 2.60 (s, 3H), 2.62-2.72 (m, 1H), 5.37 (s, 1H), 7.42-7.52 (m, 7H), 7.73 (d, J=12.0 Hz, 1H), 10.55 (brs, H).

Example 1-153

MS ESI m/e: 493, 495 (M+H), 491, 493 (M−H).

H-NMR (DMSO-d$_6$, 300 MHz) δ 0.81-1.17 (m, 6H), 2.29-2.35 (m, 1H), 2.58 (s, 3H), 5.50 (s, 1H), 7.29 (d, J=6.0 Hz, 2H), 7.39-7.52 (m, 5H), 7.61 (d, J=9.0 Hz, 2H), 10.56 (brs, H).

Example 1-154

MS ESI m/e: 445 (M+H), 443 (M−H).

$^1$H-NMR (CDCl$_3$, 300 MHz) δ 0.84-0.93 (m, 2H), 1.16-1.24 (m, 2H), 2.26 (s, 3H), 2.74-2.80 (m, 1H), 2.80 (s, 3H), 3.81 (s, 3H), 5.27 (s, 1H), 6.73-6.84 (m, 2H), 7.14 (d, J=9.0 Hz, 1H), 7.30-7.35 (m, 2H), 7.39-7.52 (m, 3H), 9.94 (brs, 1H).

Example 1-155

MS ESI m/e: 444 (M+H), 442 (M−H).

$^1$H-NMR (DMSO-d$_6$, 300 MHz) δ 0.71-0.79 (m, 2H), 1.00-1.10 (m, 2H), 2.60 (s, 3H), 2.64-2.76 (m, 1H), 2.76 (brs, 6H), 5.51 (brs, 1H), 7.09-7.58 (m, 8H), 10.46 (brs, 1H).

Example 1-156

MS ESI m/e: 493, 495 (M+H), 491, 495 (M−H).

$^1$H-NMR (CDCl$_3$, 300 MHz) δ 0.82-0.92 (m, 2H), 1.15-1.25 (m, 2H), 2.29 (s, 3H), 2.73-2.85 (m, 1H), 2.81 (s, 3H), 5.41 (s, 1H), 7.16 (d, J=8.4 Hz, 1H), 7.30-7.39 (m, 3H), 7.40-7.53 (m, 4H), 10.13 (s, 1H).

Example 1-157

MS ESI m/e: 493, 495 (M+H), 491, 495 (M−H).

$^1$H-NMR (CDCl$_3$, 300 MHz) δ 0.82-0.91 (m, 2H), 1.14-1.24 (m, 2H), 2.40 (s, 3H), 2.71-2.82 (m, 1H), 2.82 (s, 3H), 5.81 (s, 1H), 6.99 (dd, J=2.6, 8.4 Hz, 1H), 7.17 (d, J=2.6 Hz, 1H), 7.28-7.36 (m, 2H), 7.39-7.57 (m, 4H), 10.37 (s, 1H).

Example 1-158

MS ESI m/e: 454 (M+H), 452 (M−H).

$^1$H-NMR (DMSO-d$_6$, 300 MHz) δ 0.72-0.80 (m, 2H), 1.01-1.09 (m, 2H), 2.55 (s, 3H), 2.63-2.72 (m, 1H), 3.85 (s, 3H), 4.71 (s, 1H), 6.48 (d, J=3.0 Hz, 1H), 6.97 (d, J=15.0 Hz, 1H), 7.06 (t, J=9.0 Hz, 1H), 7.29 (d, J=3.0 Hz, 1H), 7.41-7.56 (m, 6H), 10.37 (brs, H).

Example 1-159

MS ESI m/e: 509, 511 (M+H), 507, 509 (M−H).

$^1$H-NMR (DMSO-d$_6$, 300 MHz) δ 0.61-0.79 (m, 2H), 0.96-1.08 (m, 2H), 2.61 (s, 3H), 2.61-2.74 (m, 1H), 3.77 (s, 3H), 5.49 (s, 1H), 7.07 (t, J=6.0 Hz, 1H), 7.20 (d, J=12.0 Hz, 1H), 7.29 (d, J=9.0 Hz, 2H), 7.38 (d, J=6.0 Hz, 1H), 7.48 (t, J=9.0 Hz, 1H), 7.60 (d, J=9.0 Hz, 2H), 10.60 (brs, H).

Example 1-160

MS ESI m/e: 455 (M+H), 453 (M−H).

$^1$H-NMR (CDCl$_3$, 300 MHz) δ 0.85-0.93 (m, 2H), 1.15-1.26 (m, 2H), 2.74-2.84 (m, 1H), 2.81 (s, 3H), 3.88 (s, 3H), 5.65 (s, 1H), 7.22-7.29 (m, 1H), 7.30-7.37 (m, 2H), 7.37-7.54 (m, 4H), 7.70 (d, J=1.8 Hz, 1H), 7.90 (s, 1H), 10.36 (s, 1H).

Example 1-161

MS ESI m/e: 455 (M+H), 453 (M−H).

$^1$H-NMR (CDCl$_3$, 300 MHz) δ 0.85-0.94 (m, 2H), 1.15-1.26 (m, 2H), 2.74-2.84 (m, 1H), 2.82 (s, 3H), 4.10 (s, 3H), 5.65 (s, 1H), 7.28-7.37 (m, 3H), 7.39-7.54 (m, 4H), 7.60-7.64 (m, 1H), 7.95-7.98 (m, 1H), 10.36 (s, 1H).

Example 1-162

MS ESI m/e: 437 (M+H), 435 (M−H).

$^1$H-NMR (CDCl$_3$, 400 MHz) δ 0.83-0.91 (m, 2H), 1.15-1.24 (m, 2H), 2.73-2.81 (m, 1H), 2.81 (s, 3H), 5.49 (s, 1H), 6.88-6.98 (m, 2H), 7.28-7.38 (m, 3H), 7.39-7.52 (m, 3H), 10.15 (s, 1H).

Example 1-163

MS ESI m/e: 469, 471 (M+H), 467, 469 (M−H).

$^1$H-NMR (CDCl$_3$, 400 MHz) δ 0.83-0.90 (m, 2H), 1.16-1.24 (m, 2H), 2.74-2.81 (m, 1H), 2.82 (s, 3H), 5.70 (s, 1H), 7.24-7.34 (m, 3H), 7.39-7.52 (m, 5H), 10.50 (s, 1H).

Example 1-164

MS ESI m/e: 485, 487 (M+H), 483, 485 (M−H).

$^1$H-NMR (CDCl$_3$, 400 MHz) δ 1.30 (t, J=7.1 Hz, 3H), 2.82 (s, 3H), 4.08 (q, J=7.0 Hz, 2H), 5.66 (s, 1H), 7.28-7.39 (m, 5H), 7.41-7.53 (m, 3H), 10.48 (s, 1H).

Example 1-165

MS ESI m/e: 440 (M+H), 438 (M−H).

$^1$H-NMR (DMSO-d$_6$, 300 MHz) δ 0.71-0.81 (m, 2H), 1.00-1.10 (m, 2H), 2.58 (s, 3H), 2.62-2.78 (m, 1H), 5.28 (s, 1H), 6.46 (s, 1H), 7.01 (d, J=9.0 Hz, 1H), 7.40-7.68 (m, 8H), 10.37 (brs, H), 11.22 (brs, H).

Example 1-166

MS ESI m/e: 527, 529 (M+H), 525, 527 (M−H).

$^1$H-NMR (DMSO-d$_6$, 300 MHz) δ 0.62-0.81 (m, 2H), 0.99-1.09 (m, 2H), 2.63 (s, 3H), 2.66-2.75 (m, 1H), 3.79 (s, 3H), 5.34 (s, 1H), 7.09 (t, J=7.5 Hz, 1H), 7.23 (d, J=9.0 Hz, 1H), 7.40 (d, J=6.0 Hz, 1H), 7.43-7.54 (m, 3H), 7.73 (d, J=9.0 Hz, 1H), 10.58 (brs, H).

Example 1-167

MS ESI m/e: 468 (M+H), 466 (M−H).

$^1$H-NMR (CDCl$_3$, 300 MHz) δ 0.82-0.94 (m, 2H), 1.14-1.26 (m, 2H), 1.49 (t, J=7.4 Hz, 3H), 2.72-2.84 (m, 1H), 2.81 (s, 3H), 4.19 (q, J=7.3 Hz, 2H), 5.68 (s, 1H), 6.47 (d, J=3.0 Hz, 1H), 7.10 (dd, J=1.9, 8.6 Hz, 1H), 7.16 (d, J=3.0 Hz, 1H), 7.29-7.38 (m, 3H), 7.38-7.55 (m, 4H), 10.27 (brs, 1H).

Example 1-168

MS ESI m/e: 433 (M+H), 431 (M−H).

$^1$H-NMR (CDCl$_3$, 300 MHz) δ 0.75-0.90 (m, 2H), 1.10-1.25 (m, 2H), 2.37 (s, 3H), 2.77 (m, 1H), 2.81 (s, 3H), 5.59 (s, 1H), 6.90-7.05 (m, 2H), 7.25 (t, J=8.3 Hz, 1H), 7.30-7.35 (m, 2H), 7.40-7.50 (m, 3H), 10.16 (s, 1H).

Example 1-169

MS ESI m/e: 438 (M+H), 436 (M−H).

$^1$H-NMR (CDCl$_3$, 300 MHz) δ 0.75-0.85 (m, 2H), 1.10-1.25 (m, 2H), 2.50-2.55 (m, 4H), 2.65-2.80 (m, 3H), 2.80 (s, 3H), 3.26 (q, J=5.8 Hz, 2H), 3.70-3.80 (m, 4H), 5.37 (s, 1H), 7.25-7.35 (m, 2H), 7.35-7.50 (m, 3H), 8.90 (brs, 1H).

Example 1-170

MS ESI m/e: 477 (M+H), 475 (M−H).

$^1$H-NMR (CDCl$_3$, 300 MHz) δ 0.82-0.92 (m, 2H), 1.15-1.26 (m, 2H), 1.76 (d, J=12.8 Hz, 6H), 2.72-2.82 (m, 1H), 2.84 (s, 3H), 5.99 (s, 1H), 7.29-7.36 (m, 2H), 7.39-7.56 (m, 5H), 7.70-7.82 (m, 2H), 10.67 (s, 1H).

Example 1-171

MS ESI m/e: 453 (M+H), 451 (M−H).

$^1$H-NMR (DMSO-d$_6$, 300 MHz) δ 0.68-0.79 (m, 2H), 0.98-1.09 (m, 2H), 2.58 (s, 3H), 2.61-2.71 (m, 1H), 5.32 (s, 1H), 7.34-7.63 (m, 8H), 10.52 (brs, H).

Example 1-172

MS ESI m/e: 417 (M+H), 415 (M−H).

$^1$H-NMR (DMSO-d$_6$, 300 MHz) δ 0.68-0.78 (m, 2H), 0.97-1.06 (m, 2H), 2.55 (s, 3H), 2.61-2.69 (m, 1H), 5.19 (s, 1H), 6.82 (d, J=9.0 Hz, 2H), 7.08 (d, J=6.0 Hz, 2H), 7.39-7.50 (m, 5H), 9.53 (brs, H), 10.18 (brs, H).

Example 1-173

MS ESI m/e: 419 (M+H), 417 (M−H).

$^1$H-NMR (DMSO-d$_6$, 300 MHz) δ 2.71-2.80 (m, 2H), 1.01-1.09 (m, 2H), 2.60 (s, 3H), 2.64-2.72 (m, 1H), 5.34 (s, 1H), 7.28-7.54 (m, 9H), 10.53 (brs, H).

Example 1-174

MS ESI m/e: 437 (M+H), 435 (M−H).

$^1$H-NMR (DMSO-d$_6$, 300 MHz) δ 0.69-0.78 (m, 2H), 0.96-1.08 (m, 2H), 2.57 (s, 3H), 2.61-2.72 (m, 1H), 4.84 (s, 1H), 7.24-7.52 (m, 8H), 10.15 (brs, H).

Example 1-175

MS ESI m/e: 449 (M+H), 447 (M−H).

$^1$H-NMR (CDCl$_3$, 400 MHz) δ 0.83-0.92 (m, 2H), 1.15-1.24 (m, 2H), 2.72-2.81 (m, 1H), 2.81 (s, 3H), 3.82 (s, 3H), 5.46 (d, J=1.6 Hz, 1H), 6.69-6.79 (m, 2H), 7.19-7.29 (m, 1H), 7.29-7.36 (m, 2H), 7.39-7.54 (m, 3H), 10.01 (brs, 1H).

Example 1-176

MS ESI m/e: 513, 515 (M+H), 511, 513 (M−H).

$^1$H-NMR (CDCl$_3$, 300 MHz) δ 0.83-0.91 (m, 2H), 1.16-1.24 (m, 2H), 2.75-2.82 (m, 1H), 2.82 (s, 3H), 5.73 (s, 1H), 7.30-7.36 (m, 2H), 7.38-7.53 (m, 4H), 7.41 (d, J=1.8 Hz, 1H), 7.66 (d, J=1.8 Hz, 1H), 10.53 (brs, 1H).

Example 1-177

MS ESI m/e: 507, 509 (M+H), 505, 507 (M−H).

$^1$H-NMR (CDCl$_3$, 400 MHz) δ 0.85-0.89 (m, 2H), 1.17-1.22 (m, 2H), 1.23 (t, J=7.5 Hz, 3H), 2.63 (q, J=7.5 Hz, 2H), 2.74-2.79 (m, 1H), 2.80 (s, 3H), 5.40 (s, 1H), 7.15 (d, J=8.4 Hz, 1H), 7.29-7.36 (m, 3H), 7.40-7.51 (m, 4H), 10.11 (brs, 1H).

Example 1-178

MS ESI m/e: 459 (M+H), 457 (M–H).

$^1$H-NMR (DMSO-d$_6$, 300 MHz) δ 0.73-0.79 (m, 2H), 1.00-1.09 (m, 2H), 2.63 (s, 3H), 2.65-2.72 (m, 1H), 3.86 (s, 3H), 5.84 (s, 1H), 7.42-7.56 (m, 6H), 7.99-8.03 (m, 2H), 10.96 (brs, 1H).

Example 1-179

MS ESI m/e: 383 (M+H).

$^1$H-NMR (CDCl$_3$, 300 MHz) δ 0.79-0.87 (m, 2H), 1.12-1.21 (m, 2H), 2.69-2.76 (m, 1H), 2.80 (s, 3H), 3.36 (q, J=5.4 Hz, 2H), 3.44 (s, 3H), 3.66 (t, J=5.4 Hz, 2H), 5.39 (s, 1H), 7.23-7.31 (m, 2H), 7.37-7.51 (m, 3H), 8.80-8.88 (m, 1H).

Example 1-180

MS ESI m/e: 422 (M+H).

$^1$H-NMR (DMSO-d$_6$, 300 MHz) δ 0.65-0.74 (m, 2H), 0.95-1.05 (m, 2H), 1.42-1.56 (m, 2H), 1.88-1.98 (m, 2H), 2.10-2.21 (m, 2H), 2.18 (s, 3H), 2.55 (s, 3H), 2.58-2.70 (m, 3H), 3.33-3.44 (m, 1H), 5.23 (s, 1H), 7.34-7.41 (m, 2H), 7.42-7.53 (m, 3H), 8.77-8.84 (m, 1H).

Example 1-181

MS ESI m/e: 365 (M+H).

$^1$H-NMR (CDCl$_3$, 300 MHz) δ 0.59-0.67 (m, 2H), 0.77-0.89 (m, 4H), 1.11-1.21 (m, 2H), 2.42-2.50 (m, 1H), 2.66-2.76 (m, 1H), 2.81 (s, 3H), 5.81 (s, 1H), 7.24-7.28 (m, 1H), 7.29-7.31 (m, 1H), 7.37-7.51 (m, 3H), 8.68 (brs, 1H).

Example 1-182

MS ESI m/e: 450 (M+H).

$^1$H-NMR (CDCl$_3$, 300 MHz) δ 0.77-0.86 (m, 2H), 1.01-1.12 (m, 6H), 1.12-1.21 (m, 2H), 1.54-1.74 (m, 2H), 2.03-2.15 (m, 2H), 2.25-2.41 (m, 2H), 2.66-2.76 (m, 1H), 2.79 (s, 3H), 2.82-2.94 (m, 2H), 3.25-3.41 (m, 1H), 5.40 (s, 1H), 7.25-7.28 (m, 1H), 7.29-7.32 (m, 1H), 7.37-7.51 (m, 3H), 8.71-8.79 (m, 1H).

Example 1-183

MS ESI m/e: 509, 511 (M+H), 507, 509 (M–H).

$^1$H-NMR (CDCl$_3$, 300 MHz) δ 0.81-0.90 (m, 2H), 1.13-1.24 (m, 2H), 2.71-2.81 (m, 2H), 2.85 (s, 3H), 3.84 (s, 3H), 5.78 (s, 1H), 6.93-7.00 (m, 2H), 7.13-7.19 (m, 2H), 7.19-7.23 (m, 2H), 7.47-7.53 (m, 2H), 10.42 (brs, 1H).

Example 1-184

MS ESI m/e: 410 (M+H).

$^1$H-NMR (CDCl$_3$, 300 MHz) δ 0.75-0.88 (m, 2H), 1.09-1.22 (m, 2H), 1.85 (tt, J=7.0, 14.0 Hz, 2H), 2.26 (s, 6H), 2.40 (t, J=7.1 Hz, 2H), 2.67-2.77 (m, 1H), 2.79 (s, 3H), 3.22 (dt, J=5.5, 6.2 Hz, 3H), 5.40 (s, 1H), 7.25-7.33 (m, 2H), 7.37-7.52 (m, 3H), 8.74 (t, J=4.8 Hz, 1H).

Example 1-185

MS ESI m/e: 471, 473 (M+H), 469, 471 (M–H).

$^1$H-NMR (DMSO-d$_6$, 300 MHz) δ 2.62 (s, 3H), 3.27 (s, 3H), 5.37 (s, 1H), 7.40-7.60 (m, 7H), 7.70-7.80 (m, 1H), 10.61 (s, 1H).

Example 1-186

MS ESI m/e: 527, 529 (M+H), 525, 527 (M–H).

$^1$H-NMR (CDCl$_3$, 300 MHz) δ 0.81-0.90 (m, 2H), 1.13-1.24 (m, 2H), 2.71-2.82 (m, 1H), 2.85 (s, 3H), 3.84 (s, 3H), 5.64 (d, J=1.1 Hz, 1H), 6.94-7.01 (m, 2H), 7.17-7.24 (m, 2H), 7.29-7.33 (m, 2H), 7.34-7.40 (m, 1H), 10.35 (brs, 1H).

Example 1-187

MS ESI m/e: 459 (M+H), 457 (M–H).

$^1$H-NMR (CDCl$_3$, 300 MHz) δ 0.82-0.92 (m, 2H), 1.13-1.24 (m, 2H), 1.35 (d, J=6.0 Hz, 6H), 2.72-2.82 (m, 1H), 2.81 (s, 3H), 4.54 (sept, J=6.0 Hz, 1H), 5.63 (s, 1H), 6.85-6.94 (m, 2H), 7.12-7.20 (m, 2H), 7.29-7.35 (m, 2H), 7.38-7.53 (m, 3H), 10.15 (brs, 1H).

Example 1-188

MS ESI m/e: 513, 515 (M+H), 511, 513 (M–H).

$^1$H-NMR (DMSO-d$_6$, 300 MHz) δ 0.69-0.79 (m, 2H), 0.99-1.08 (m, 2H), 2.62-2.72 (m, 1H), 2.66 (s, 3H), 5.35 (d, J=1.1 Hz, 1H), 6.79-6.89 (m, 2H), 7.15-7.23 (m, 2H), 7.43-7.55 (m, 2H), 7.70-7.76 (m, 1H), 9.90 (brs, 1H), 10.57 (brs, 1H).

Example 1-189

MS ESI m/e: 509, 511 (M+H), 507, 509 (M–H).

$^1$H-NMR (CDCl$_3$, 300 MHz) δ 0.82-0.90 (m, 2H), 1.14-1.25 (m, 2H), 2.73-2.80 (m, 1H), 2.82 (s, 3H), 3.89 (s, 3H), 5.80 (s, 1H), 7.07-7.13 (m, 2H), 7.23-7.35 (m, 3H), 7.39-7.53 (m, 3H), 10.29 (brs, 1H).

Example 1-190

MS ESI m/e: 509, 511 (M+H), 507, 509 (M–H).

$^1$H-NMR (DMSO-d$_6$, 300 MHz) δ 0.71-0.79 (m, 2H), 0.99-1.08 (m, 2H), 2.67 (s, 3H), 2.66-2.68 (m, 1H), 3.78 (s, 3H), 5.53 (s, 1H), 6.97-7.06 (m, 3H), 7.31 (d, J=9.0 Hz, 2H), 7.41 (dd, J=9.0, 9.0 Hz, 1H), 7.62 (d, J=9.0 Hz, 2H), 10.58 (brs, H).

Example 1-191

MS ESI m/e: 527, 529 (M+H), 525, 527 (M–H).

$^1$H-NMR (DMSO-d$_6$, 300 MHz) δ 0.71-0.79 (m, 2H), 1.01-1.09 (m, 2H), 2.67 (s, 3H), 2.66-2.67 (m, 1H), 3.78 (s, 3H), 5.37 (s, 1H), 6.97-7.06 (m, 3H), 7.39-7.51 (m, 3H), 7.73 (d, J=12.0 Hz, 1H), 10.55 (brs, H).

Example 1-192

MS ESI m/e: 462 (M+H).

$^1$H-NMR (DMSO-d$_6$, 300 MHz) δ 0.71-0.79 (m, 2H), 0.99-1.08 (m, 2H), 2.55 (s, 3H), 2.60-2.71 (m, 1H), 2.92 (s, 6H), 5.01 (s, 1H), 6.56-6.66 (m, 2H), 7.18 (dd, J=12.0, 9.0 Hz, 1H), 7.39-7.51 (m, 5H), 10.00 (brs, H).

Example 1-193

MS ESI m/e: 582, 584 (M+H), 580, 582 (M–H).

$^1$H-NMR (DMSO-d$_6$, 300 MHz) δ 0.75 (m, 2H), 1.03 (m, 2H), 2.60-2.75 (m, 1H), 2.69 (s, 3H), 3.11 (brs, 4H), 3.73 (brs, 4H), 5.38 (s, 1H), 6.85 (d, J=7.6 Hz, 1H), 7.02 (brs, 2H), 7.34 (t, J=8.5 Hz, 1H), 7.40-7.55 (m, 2H), 7.73 (d, J=11.1 Hz, 1H), 10.57 (s, 1H).

Example 1-194

MS ESI m/e: 493, 495 (M+H), 491, 493 (M−H).
$^1$H-NMR (CDCl$_3$, 300 MHz) δ 0.80-0.89 (m, 2H), 1.12-1.23 (m, 2H), 2.68-2.80 (m, 1H), 2.79 (s, 3H), 4.37 (d, J=6.0 Hz, 2H), 5.33 (s, 1H), 7.18-7.33 (m, 4H), 7.39-7.52 (m, 5H), 9.14 (t, J=5.6 Hz, 1H).

Example 1-195

MS ESI m/e: 493, 495 (M+H), 491, 493 (M−H).
$^1$H-NMR (CDCl$_3$, 300 MHz) δ 0.79-0.89 (m, 2H), 1.12-1.22 (m, 2H), 2.68-2.76 (m, 1H), 2.78 (s, 3H), 4.34 (d, J=5.6 Hz, 2H), 5.34 (s, 1H), 7.20-7.31 (m, 4H), 7.39-7.53 (m, 5H), 9.11 (t, J=5.3 Hz, 1H).

Example 1-196

MS ESI m/e: 493, 495 (M+H), 491, 493 (M−H).
$^1$H-NMR (CDCl$_3$, 300 MHz) δ 0.79-0.89 (m, 2H), 1.12-1.22 (m, 2H), 2.69-2.77 (m, 1H), 2.79 (s, 3H), 4.46 (d, J=5.6 Hz, 2H), 5.36 (s, 1H), 7.17 (dt, J=1.9, 7.5 Hz, 1H), 7.24-7.33 (m, 3H), 7.35 (dt, J=1.1, 7.7 Hz, 1H), 7.39-7.51 (m, 3H), 7.59 (dd, J=1.1, 7.9 Hz, 1H), 9.16 (t, J=5.7 Hz, 1H).

Example 1-197

MS ESI m/e: 445 (M+H), 443 (M−H).
$^1$H-NMR (CDCl$_3$, 300 MHz) δ 0.83-0.92 (m, 2H), 1.14-1.25 (m, 2H), 2.72-2.83 (m, 1H), 2.80 (s, 3H), 3.11 (s, 6H), 5.44 (s, 1H), 6.53 (d, J=9.0 Hz, 1H), 7.29-7.34 (m, 2H), 7.37 (dd, J=2.6, 9.0 Hz, 1H), 7.39-7.52 (m, 3H), 8.07 (d, J=2.6 Hz, 1H), 9.96 (brs, 1H).

Example 1-198

MS ESI m/e: 495, 497 (M+H), 493, 495 (M−H).
$^1$H-NMR (DMSO-d$_6$, 300 MHz) δ 0.69-0.78 (m, 2H), 0.98-1.08 (m, 2H), 2.59 (s, 3H), 2.61-2.72 (m, 1H), 5.50 (s, 1H), 7.04 (dd, J=2.3, 8.3 Hz, 1H), 7.13 (d, J=2.3 Hz, 1H), 7.30 (d, J=8.3 Hz, 1H), 7.38-7.55 (m, 5H), 10.45 (s, 1H), 10.48 (brs, 1H).

Example 1-199

MS ESI m/e: 540, 542 (M+H), 538, 540 (M−H).
$^1$H-NMR (CDCl$_3$, 300 MHz) δ 0.82-0.91 (m, 2H), 1.14-1.23 (m, 2H), 2.71-2.82 (m, 1H), 2.93 (s, 3H), 2.96 (s, 6H), 5.66 (s, 1H), 6.52 (t, J=2.1 Hz, 1H), 6.59 (dd, J=1.9, 8.3 Hz, 1H), 6.71 (dd, J=2.6, 8.6 Hz, 1H), 7.26-7.40 (m, 4H), 10.39 (brs, 1H).

Example 1-200

MS ESI m/e: 487, 489 (M+H), 485, 487(M−H).
$^1$H-NMR (DMSO-d$_6$, 300 MHz) δ 2.62 (s, 3H), 3.27 (s, 3H), 5.47 (s, 1H), 7.40-7.60 (m, 6H), 7.63 (dd, J=2.1, 8.6 Hz, 1H), 7.91 (d, J=2.1 Hz, 1H), 10.83 (s, 1H).

Example 1-201

MS ESI m/e: 569, 571 (M+H), 567, 569 (M−H).
$^1$H-NMR (DMSO-d$_6$, 300 MHz) δ 0.75 (m, 2H), 1.03 (m, 2H), 2.45-2.60 (m, 2H), 2.60 (s, 3H), 2.67 (m, 1H), 2.85 (t, J=7.4 Hz, 2H), 5.36 (s, 1H), 7.24 (d, J=7.9 Hz, 1H), 7.32 (brs, 2H), 7.41 (t, J=7.9 Hz, 1H), 7.45-7.55 (m, 5H), 7.73 (d, J=9.2 Hz, 1H), 10.54 (s, 1H), 12.15 (brs, 1H).

Example 1-202

MS ESI m/e: 499, 501 (M+H), 497, 499 (M−H).
$^1$H-NMR (DMSO-d$_6$, 300 MHz) δ 0.74-0.82 (m, 2H), 0.98-1.06 (m, 2H), 2.63-2.70 (m, 1H), 5.74 (s, 1H), 7.25-7.33 (m, 2H), 7.38-7.55 (m, 4H), 7.63 (dd, J=2.2, 8.8 Hz, 1H), 7.92 (d, J=2.2 Hz, 1H), 10.90 (brs, 1H), 11.14 (brs, 1H).

Example 1-203

MS ESI m/e: 482 (M+H).
$^1$H-NMR (DMSO-d$_6$, 300 MHz) δ 0.77-0.79 (m, 2H), 1.02-1.17 (m, 2H), 2.18 (s, 3H), 2.34 (s, 3H), 2.57 (s, 3H), 2.65-2.68 (m, 1H), 3.66 (s, 3H), 5.24 (s, 1H), 6.98 (d, J=6.0 Hz, 1H), 7.29 (d, J=3.0 Hz, 1H), 7.40-7.56 (m, 6H), 10.35 (brs, H).

Example 1-204

MS ESI m/e: 468 (M+H).
$^1$H-NMR (DMSO-d$_6$, 300 MHz) δ 0.72-0.80 (m, 2H), 1.00-1.09 (m, 2H), 2.41 (s, 3H), 2.57 (s, 3H), 2.62-2.71 (m, 1H), 3.68 (s, 3H), 5.26 (s, 1H), 6.23 (s, 1H), 6.97 (d, J=12.0 Hz, 1H), 7.33 (s, 1H), 7.42-7.52 (m, 6H), 10.35 (brs, H).

Example 1-205

MS ESI m/e: 547 (M+H), 545 (M−H).
$^1$H-NMR (CDCl$_3$, 300 MHz) δ 0.86 (m, 2H), 1.18 (m, 2H), 2.75 (m, 1H), 2.89 (s, 3H), 2.97 (s, 6H), 3.16 (t, J=4.8 Hz, 4H), 3.85 (t, J=4.8 Hz, 4H), 5.45 (s, 1H), 6.45 (s, 1H), 6.49 (d, J=3.8 Hz, 1H), 6.75-6.80 (m, 2H), 6.91 (d, J=8.3 Hz, 1H), 7.14 (t, J=9.0 Hz, 1H), 7.33 (t, J=8.4 Hz, 1H), 9.89 (s, 1H).

Example 1-206

MS ESI m/e: 595, 597 (M+H).
$^1$H-NMR (DMSO-d$_6$, 300 MHz) δ 0.69-0.77 (m, 2H), 0.98-1.07 (m, 2H), 2.21 (s, 3H), 2.40-2.46 (m, 4H), 2.61-2.71 (m, 1H), 2.69 (s, 3H), 3.09-3.16 (m, 4H), 5.37 (s, 1H), 6.79-6.84 (m, 1H), 6.96-7.03 (m, 2H), 7.29-7.34 (m, 1H), 7.44-7.54 (m, 2H), 7.69-7.77 (m, 1H), 10.58 (brs, 1H).

Example 1-207

MS ESI m/e: 545 (M+H), 543 (M−H).
$^1$H-NMR (CDCl$_3$, 300 MHz) δ 0.81-0.92 (m, 2H), 1.14-1.25 (m, 2H), 2.72-2.82 (m, 1H), 2.82 (s, 3H), 5.69 (d, J=1.1 Hz, 1H), 7.28-7.36 (m, 2H), 7.40-7.59 (m, 6H), 10.36 (s, 1H).

Example 1-208

MS ESI m/e: 443 (M+H), 441 (M−H).
$^1$H-NMR (CDCl$_3$, 400 MHz) δ 0.81-0.91 (m, 2H), 1.16-1.23 (m, 2H), 2.73-2.80 (m, 1H), 2.82 (s, 3H), 3.12 (s, 1H), 5.80 (s, 1H), 7.26-7.33 (m, 3H), 7.35-7.52 (m, 5H), 10.50 (s, 1H).

Example 1-209

MS ESI m/e: 416 (M+H), 414 (M−H).
$^1$H-NMR (CDCl$_3$, 300 MHz) δ 0.79-0.88 (m, 2H), 1.12-1.22 (m, 2H), 2.68-2.77 (m, 1H), 2.79 (s, 3H), 4.42 (d, J=5.6 Hz, 2H), 5.37 (s, 1H), 7.26-7.35 (m, 3H), 7.38-7.52 (m, 3H), 7.65-7.72 (m, 1H), 8.57 (dd, J=1.5, 4.9 Hz, 1H), 8.63 (d, J=1.9 Hz, 1H), 9.15 (t, J=5.3 Hz, 1H)

Example 1-210

MS ESI m/e: 511, 513 (M+H), 509, 511 (M−H).
$^1$H-NMR (CDCl$_3$, 300 MHz) δ 0.80-0.90 (m, 2H), 1.13-1.23 (m, 2H), 2.70-2.78 (m, 1H), 2.79 (s, 3H), 4.43 (d, J=6.0 Hz, 2H), 5.33 (s, 1H), 6.98 (dd, J=9.0, 9.1 Hz, 1H), 7.28-7.33 (m, 2H), 7.35-7.53 (m, 5H), 9.12 (t, J=6.0 Hz, 1H).

Example 1-211

MS ESI m/e: 509, 511 (M+H), 507, 509 (M−H).
$^1$H-NMR (CDCl$_3$, 300 MHz) δ 0.83-0.92 (m, 2H), 1.14-1.25 (m, 2H), 2.73-2.84 (m, 1H), 2.81 (s, 3H), 3.83 (s, 3H), 5.46 (s, 1H), 6.89 (dd, J=3.0, 8.7 Hz, 1H), 7.21 (d, J=2.6 Hz, 1H), 7.29-7.36 (m, 3H), 7.38-7.54 (m, 3H), 10.17 (brs, 1H).

Example 1-212

MS ESI m/e: 580, 581 (M+H), 578, 580 (M−H).
$^1$H-NMR (CDCl$_3$, 300 MHz) δ 0.87 (m, 2H), 1.18 (m, 2H), 2.20 (m, 2H), 2.63 (t, J=8.1 Hz, 2H), 2.77 (m, 1H), 2.88 (s, 3H), 3.88 (t, J=7.1 Hz, 2H), 5.66 (s, 1H), 7.07 (d, J=7.9 Hz, 1H), 7.30-7.35 (m, 2H), 7.37 (d, J=9.2 Hz, 1H), 7.46 (t, J=8.1 Hz, 1H), 7.54 (d, J=8.6 Hz, 1H), 7.89 (d, J=2.0 Hz, 1H), 10.34 (s, 1H).

Example 1-213

MS ESI m/e: 513, 515 (M+H), 511, 513 (M−H).
$^1$H-NMR (DMSO-d$_6$, 300 MHz) δ 0.71-0.79 (m, 2H), 0.99-1.09 (m, 2H), 2.68 (s, 3H), 2.61-2.71 (m, 1H), 5.35 (s, 1H), 2.79-2.89 (m, 3H), 7.27 (dd, J=9.0, 9.0 Hz, 1H), 7.48-7.52 (m, 2H), 7.72 (d, J=6.0 Hz, 1H), 9.83 (brs, H), 10.53 (brs, H).

Example 1-214

MS ESI m/e: 594, 596 (M+H), 592, 594 (M−H).
$^1$H-NMR (DMSO-d$_6$, 300 MHz) δ 0.75 (m, 2H), 1.03 (m, 2H), 1.85 (brs, 4H), 2.39 (m, 2H), 2.67 (m, 4H), 3.62 (m, 2H), 5.36 (s, 1H), 7.33 (d, J=8.3 Hz, 1H), 7.35-7.40 (m, 2H), 7.45-7.55 (m, 3H), 7.74 (d, J=10.2 Hz, 1H), 10.54 (s, 1H).

Example 1-215

MS ESI m/e: 566, 568 (M+H), 564, 566 (M−H).
$^1$H-NMR (DMSO-d$_6$, 300 MHz) δ 0.70-0.80 (m, 2H), 0.99-1.11 (m, 2H), 1.90-2.01 (m, 4H), 2.64-2.74 (m, 1H), 2.74-2.75 (m, 1H), 3.13-3.27 (m, 4H), 5.39 (s, 1H), 6.54-6.65 (m, 3H), 7.20-7.30 (m, 2H), 7.45-7.55 (m, 2H), 7.71-7.78 (m, 1H), 10.60 (brs, 1H).

Example 1-216

MS ESI m/e: 580, 582 (M+H), 578, 580 (M−H).
$^1$H-NMR (DMSO-d$_6$, 300 MHz) δ 0.69-0.78 (m, 2H), 0.98-1.08 (m, 2H), 1.48-1.65 (m, 6H), 2.63-2.71 (m, 1H), 2.69 (s, 3H), 3.09-3.17 (m, 4H), 5.37 (s, 1H), 6.72-6.79 (m, 1H), 6.95-7.02 (m, 1H), 7.25-7.32 (m, 1H), 7.46-7.54 (m, 2H), 7.69-7.77 (m, 1H), 10.59 (brs, 1H).

Example 1-217

MS ESI m/e: 476 (M+H), 474 (M−H).
$^1$H-NMR (DMSO-d$_6$, 300 MHz) δ 0.71-0.80 (m, 2H), 1.01-1.13 (m, 5H), 2.58 (s, 3H), 2.61-2.72 (m, 1H), 2.90 (s, 3H), 3.42 (q, J=2.0 Hz, 2H), 5.04 (s, 1H), 6.62 (dd, J=9.0, 15.0 Hz, 2H), 7.18 (t, J=9.0 Hz, 1H), 7.40-7.59 (m, 5H), 10.01 (brs, 1H).

Example 1-218

MS ESI m/e: 584, 585 (M+H), 582, 584 (M−H).
$^1$H-NMR (DMSO-d$_6$, 300 MHz) δ 0.69-0.78 (m, 2H), 0.98-1.09 (m, 2H), 2.18 (s, 6H), 2.59 (t, J=3.0 Hz, 2H), 2.66 (s, 3H), 2.65-2.66 (m, 1H), 4.01 (t, J=4.5 Hz, 2H), 5.37 (s, 1H), 6.96-7.08 (m, 3H), 7.38-7.51 (m, 3H), 7.71 (d, J=12.0 Hz, 1H), 10.55 (brs, 1H).

Example 1-219

MS ESI m/e: 596, 598 (M+H), 594, 596 (M−H).
$^1$H-NMR (DMSO-d$_6$, 300 MHz) δ 0.75 (m, 2H), 1.03 (m, 2H), 2.67 (s, 4H), 3.75 (m, 2H), 3.98 (t, J=4.9 Hz, 2H), 4.21 (s, 2H), 5.36 (s, 1H), 7.37 (d, J=7.3 Hz, 1H), 7.40-7.60 (m, 5H), 7.73 (d, J=9.4 Hz, 1H), 10.53 (s, 1H).

Example 1-220

MS ESI m/e: 571, 573 (M+H), 569, 571 (M−H).
$^1$H-NMR (DMSO-d$_6$, 300 MHz) δ 0.74-0.76 (m, 2H), 0.99-1.10 (m, 2H), 2.65-2.67 (m, 1H), 2.66 (s, 3H), 4.71 (s, 2H), 5.37 (s, 1H), 6.99-7.08 (m, 3H), 7.41 (t, J=9.0 Hz, 1H), 7.45-7.52 (m, 2H), 7.74 (d, J=9.0 Hz, 1H), 10.55 (brs, 1H), 13.04 (brs, 1H).

Example 1-221

MS ESI m/e: 527 (M+H), 525 (M−H).
$^1$H-NMR (CDCl$_3$, 300 MHz) δ 0.81-0.91 (m, 2H), 1.14-1.25 (m, 2H), 2.71-2.82 (m, 1H), 2.82 (s, 3H), 5.82 (s, 1H), 7.01-7.09 (m, 2H), 7.28-7.35 (m, 2H), 7.39-7.54 (m, 3H), 7.66-7.74 (m, 2H), 10.42 (s, 1H).

Example 1-222

MS ESI m/e: 425 (M+H), 423 (M−H).
$^1$H-NMR (CDCl$_3$, 300 MHz) δ 0.81-0.91 (m, 2H), 1.15-1.24 (m, 2H), 2.71-2.83 (m, 1H), 2.83 (s, 3H), 3.09 (s, 1H), 5.92 (s, 1H), 7.22-7.29 (m, 2H), 7.29-7.35 (m, 2H), 7.40-7.57 (m, 5H), 10.54 (s, 1H).

Example 1-223

MS ESI m/e: 575, 577 (M+H), 573, 575 (M−H).
$^1$H-NMR (CDCl$_3$, 400 MHz) δ 0.84-0.91 (m, 2H), 1.17-1.26 (m, 2H), 2.73-2.80 (m, 1H), 2.81 (s, 3H), 3.11 (s, 3H) 5.65 (s, 1H), 7.27-7.35 (m, 2H), 7.35-7.40 (m, 1H), 7.51-7.56 (m, 1H), 7.68-7.75 (m, 1H), 8.00-8.05 (m, 2H), 10.22 (s, 1H).

Example 1-224

MS ESI m/e: 604, 606 (M+H), 602, 604 (M−H).
$^1$H-NMR (CDCl$_3$, 300 MHz) δ 0.82-0.91 (m, 2H), 1.15-1.27 (m, 2H), 2.72-2.81 (m, 1H), 2.76 (s, 6H), 2.81 (s, 3H), 5.65 (d, J=1.1 Hz, 1H), 7.29-7.34 (m, 2H), 7.35-7.43 (m, 1H), 7.45-7.51 (m, 1H), 7.63-7.72 (m, 1H), 7.83-7.89 (m, 2H), 10.25 (s, 1H).

Example 1-225

MS ESI m/e: 575, 577 (M+H), 573, 575 (M−H).
$^1$H-NMR (CDCl$_3$, 300 MHz) δ 0.82-0.91 (m, 2H), 1.16-1.27 (m, 2H), 2.72-2.83 (m, 1H), 2.83 (brs, 3H), 3.10 (s, 3H), 5.63 (brs, 1H), 7.28-7.35 (m, 2H), 7.36-7.42 (m, 1H), 7.58 (d, J=8.4 Hz, 2H), 8.10 (d, J=8.4 Hz, 2H), 10.22 (s, 1H).

Example 1-226

MS ESI m/e: 604, 606 (M+H), 602, 604 (M−H).
$^1$H-NMR (CDCl$_3$, 400 MHz) δ 0.83-0.91 (m, 2H), 1.17-1.25 (m, 2H), 2.71-2.81 (m, 1H), 2.75 (s, 6H), 2.84 (brs, 3H), 5.58 (brs, 1H), 7.26-7.35 (m, 2H), 7.35-7.40 (m, 1H), 7.52 (d, J=8.1 Hz, 2H), 7.89 (d, J=8.1 Hz, 2H), 10.21 (s, 1H).

Example 1-227

MS ESI m/e: 598, 600 (M+H), 596, 598 (M−H).
$^1$H-NMR (DMSO-d$_6$, 300 MHz) δ 0.70-0.78 (m, 2H), 0.99-1.09 (m, 2H), 1.84 (t, J=6.0 Hz, 2H), 2.13 (s, 6H), 2.34 (t, J=6.0 Hz, 2H), 2.66-2.68 (m, 1H), 2.67 (s, 3H), 4.00 (t, J=6.0 Hz, 2H), 5.37 (s, 1H), 6.96-7.09 (m, 3H), 7.40 (dd, J=6.0, 6.0 Hz, 1H), 7.48-7.51 (m, 2H), 7.74 (d, J=9.0 Hz, 1H), 10.56 (brs, 1H).

Example 1-228

MS ESI m/e: 604, 606 (M+H), 602, 604 (M−H).
$^1$H-NMR (DMSO-d$_6$, 300 MHz) δ 0.71-0.80 (m, 2H), 0.98-1.10 (m, 2H), 2.61-2.71 (m, 1H), 2.68 (s, 3H), 2.96 (s, 3H), 3.25 (s, 3H), 5.37 (s, 1H), 7.39 (d, J=6.0 Hz, 1H), 7.45-7.58 (m, 5H), 7.74 (d, J=9.0 Hz, 1H), 10.53 (brs, 1H).

Example 1-229

MS ESI m/e: 443 (M+H), 441 (M−H).
$^1$H-NMR (CDCl$_3$, 300 MHz) δ 0.81-0.90 (m, 2H), 1.14-1.24 (m, 2H), 1.27 (d, J=7.1 Hz, 6H), 2.72-2.81 (m, 1H), 2.81 (s, 3H), 2.92 (sept, J=6.8 Hz, 1H), 5.77 (s, 1H), 7.16-7.22 (m, 2H), 7.22-7.28 (m, 2H), 7.29-7.35 (m, 2H), 7.39-7.53 (m, 3H), 10.28 (brs, 1H).

Example 1-230

MS ESI m/e: 429 (M+H), 427 (M−H).
$^1$H-NMR (CDCl$_3$, 300 MHz) δ 0.82-0.91 (m, 2H), 1.15-1.24 (m, 2H), 1.25 (t, J=7.5 Hz, 3H), 2.66 (q, J=7.5 Hz, 2H), 2.72-2.81 (m, 1H), 2.81 (s, 3H), 5.76 (s, 1H), 7.15-7.24 (m, 4H), 7.29-7.36 (m, 2H), 7.39-7.53 (m, 3H), 10.29 (brs, 1H).

Example 1-231

MS ESI m/e: 426 (M+H), 424 (M−H).
$^1$H-NMR (CDCl$_3$, 300 MHz) δ 0.81-0.90 (m, 2H), 1.15-1.25 (m, 2H), 2.72-2.82 (m, 1H), 2.84 (s, 3H), 6.07 (s, 1H), 7.28-7.34 (m, 2H), 7.36-7.42 (m, 1H), 7.44-7.55 (m, 3H), 7.64-7.70 (m, 2H), 10.84 (brs, 1H).

Example 1-232

MS ESI m/e: 626, 628 (M+H), 624, 626 (M−H).
$^1$H-NMR (DMSO-d$_6$, 300 MHz) δ 0.71-0.79 (m, 2H), 1.01-1.09 (m, 2H), 2.41-2.48 (m, 4H), 2.67 (s, 3H), 2.64-2.70 (m, 3H), 3.45-3.60 (m, 4H), 4.06-4.10 (m, 2H), 5.36 (s, 1H), 7.00 (d, J=3.0 Hz, 1H), 7.03-7.05 (m, 2H), 7.38-0.53 (m, 3H), 7.72 (d, J=6.0 Hz, 1H), 10.54 (brs, 1H).

Example 1-233

MS ESI m/e: 610, 612 (M+H), 608, 610 (M−H).
$^1$H-NMR (DMSO-d$_6$, 300 MHz) δ 0.71-0.79 (m, 2H), 1.00-1.09 (m, 2H), 1.62-1.71 (m, 4H), 2.43-2.55 (m, 4H), 2.64 (s, 3H), 2.61-2.70 (m, 1H), 2.77 (t, J=3.0 Hz, 2H), 4.06 (t, J=3.0 Hz, 2H), 5.37 (s, 1H), 6.99 (d, J=3.0 Hz, 1H), 7.02-7.04 (m, 2H), 7.39 (dd, J=3.0, 3.0 Hz, 1H), 7.50-7.52 (m, 2H), 7.74 (d, J=3.0 Hz, 1H), 10.54 (brs, 1H).

Example 1-234

MS ESI m/e: 624, 626 (M+H), 622, 624 (M−H).
$^1$H-NMR (DMSO-d$_6$, 300 MHz) δ 0.71-0.79 (m, 2H), 1.01-1.09 (m, 2H), 1.32-1.41 (m, 2H), 1.41-1.52 (m, 4H), 2.37-2.46 (m, 4H), 2.60-2.71 (m, 3H), 2.67 (s, 3H), 4.07 (t, J=6.0 Hz, 2H), 5.38 (s, 1H), 7.01 (dd, J=6.0, 9.0 Hz, 1H), 7.05-7.06 (m, 2H), 7.40 (dd, J=9.0, 9.0 Hz, 1H), 7.49-7.51 (m, 2H), 7.74 (d, J=12.0 Hz, 1H), 10.55 (brs, 1H).

Example 1-235

MS ESI m/e: 612, 614 (M+H), 610, 612 (M−H).
$^1$H-NMR (DMSO-d$_6$, 300 MHz) δ 0.71-0.79 (m, 2H), 0.96 (t, J=7.5 Hz, 6H), 0.99-1.09 (m, 2H), 2.46-2.59 (m, 5H), 2.68 (s, 3H), 2.75 (t, J=3.0 Hz, 2H), 4.00 (t, J=3.0 Hz, 2H), 5.37 (s, 1H), 7.00 (dd, J=3.0, 3.0 Hz, 1H), 7.01-7.06 (m, 2H), 7.40 (dd, J=6.0, 3.0 Hz, 1H), 7.49-7.52 (m, 2H), 7.74 (d, J=18.0 Hz, 1H), 10.56 (brs, 1H).

Example 1-236

MS ESI m/e: 653, 655 (M+H), 651, 653 (M−H).
$^1$H-NMR (DMSO-d$_6$, 300 MHz) δ 0.71-0.79 (m, 2H), 0.96 (t, J=7.5 Hz, 6H), 0.99-1.09 (m, 2H), 1.80-1.91 (m, 2H), 2.13 (s, 3H), 2.46-2.59 (m, 10H), 2.60-2.73 (m, 4H), 4.00 (t, J=3.0 Hz, 2H), 5.37 (s, 1H), 7.00 (dd, J=3.0, 3.0 Hz, 1H), 7.01-7.06 (m, 2H), 7.40 (dd, J=6.0, 3.0 Hz, 1H), 7.49-7.52 (m, 2H), 7.74 (d, J=18.0 Hz, 1H), 10.56 (brs, 1H).

Example 1-237

MS ESI m/e: 444 (M+H), 442 (M−H).
$^1$H-NMR (CDCl$_3$, 300 MHz) δ 0.81-0.92 (m, 2H), 1.16-1.26 (m, 2H), 2.73-2.83 (m, 1H), 2.85 (s, 3H), 6.01 (s, 1H), 7.29-7.35 (m, 2H), 7.43-7.56 (m, 5H), 7.60-7.70 (m, 1H), 10.93 (s, 1H).

Example 1-238

MS ESI m/e: 473 (M+H), 471 (M−H).
$^1$H-NMR (DMSO-d$_6$, 400 MHz) δ 0.71-0.79 (m, 2H), 1.00-1.08 (m, 2H), 2.60 (s, 3H), 2.63-2.71 (m, 1H), 4.31 (d, J=5.8 Hz, 2H), 5.38 (t, J=5.9 Hz, 1H), 5.50 (s, 1H), 7.29-7.35 (m, 1H), 7.39-7.58 (m, 7H), 10.71 (s, 1H).

Example 1-239

MS ESI m/e: 501 (M+H), 499 (M–H).
¹H-NMR (CDCl₃, 400 MHz) δ 0.82-0.90 (m, 2H), 1.15-1.24 (m, 2H), 1.63 (s, 6H), 2.07 (s, 1H), 2.73-2.81 (m, 1H), 2.82 (s, 3H), 5.78 (s, 1H), 7.16-7.25 (m, 2H), 7.28-7.33 (m, 2H), 7.34-7.52 (m, 4H), 10.46 (s, 1H).

Example 1-240

MS ESI m/e: 445 (M+H), 443 (M–H).
¹H-NMR (CDCl₃, 400 MHz) δ 0.84-0.90 (m, 2H), 1.16-1.24 (m, 2H), 2.73-2.82 (m, 1H), 2.82 (s, 3H), 5.31 (d, J=10.9 Hz, 1H), 5.74 (d, J=17.6 Hz, 1H), 5.72 (s, 1H), 6.66 (dd, J=10.9, 17.8 Hz, 1H), 7.14-7.25 (m, 2H), 7.28-7.39 (m, 3H), 7.40-7.51 (m, 3H), 10.34 (s, 1H).

Example 1-241

MS ESI m/e: 487 (M+H), 485 (M–H).
¹H-NMR (CDCl₃, 300 MHz) δ 0.81-0.91 (m, 2H), 1.15-1.24 (m, 2H), 2.73-2.83 (m, 1H), 2.83 (s, 3H), 3.47 (s, 3H), 4.33 (s, 2H), 5.79 (s, 1H), 7.22-7.35 (m, 4H), 7.35-7.56 (m, 4H), 10.49 (s, 1H).

Example 1-242

MS ESI m/e: 447 (M+H), 445 (M–H).
¹H-NMR (CDCl₃, 400 MHz) δ 0.84-0.90 (m, 2H), 1.15-1.22 (m, 2H), 1.25 (t, J=7.6 Hz, 3H), 2.66 (q, J=7.6 Hz, 2H), 2.73-2.81 (m, 1H), 2.81 (s, 3H), 5.59 (d, J=1.2 Hz, 1H), 6.96-7.04 (m, 2H), 7.23-7.34 (m, 3H), 7.39-7.51 (m, 3H), 10.16 (s, 1H).

Example 1-243

MS ESI m/e: 555, 557 (M+H), 553, 555 (M–H).
¹H-NMR (CDCl₃, 300 MHz) δ 0.81-0.92 (m, 2H), 1.14-1.25 (m, 2H), 1.43 (t, J=4.9 Hz, 1H), 1.88 (quint, J=7.3 Hz, 2H), 2.72-2.81 (m, 1H), 2.76 (t, J=7.7 Hz, 2H), 2.82 (s, 3H), 3.65 (q, J=5.7 Hz, 2H), 5.66 (s, 1H), 7.10-7.19 (m, 2H), 7.26-7.33 (m, 3H), 7.35-7.45 (m, 2H), 10.34 (brs, 1H).

Example 1-244

MS ESI m/e: 486, 488 (M+H), 484, 486 (M–H).
¹H-NMR(DMSO-d₆, 300 MHz) δ 1.19 (t, J=6.0 Hz, 3H), 2.50-2.53 (m, 1H), 2.62 (s, 3H), 3.95 (q, J=7.0 Hz, 2H), 5.37 (s, 1H), 7.48-7.52 (m, 2H), 7.60 (dd, J=3.0, 3.0 Hz, 1H), 7.74 (d, J=12.0 Hz, 1H), 7.97 (d, J=6.0 Hz, 1H), 8.73 (d, J=45.0 Hz, 1H), 10.58 (brs, 1H).

Example 1-245

MS ESI m/e: 554, 556 (M+H), 552, 554 (M–H).
¹H-NMR (DMSO-d₆, 300 MHz) δ 0.69-0.79 (m, 2H), 0.99-1.09 (m, 2H), 2.04 (s, 3H), 2.63-2.68 (m, 1H), 2.66 (s, 3H), 5.35 (s, 1H), 7.08 (d, J=9.0 Hz, 1H), 7.41 (dd, J=6.0, 6.0 Hz, 1H), 7.49-7.51 (m, 2H), 7.61-7.77 (m, 3H), 10.18 (brs, 1H), 10.54 (brs, 1H).

Example 1-246

MS ESI m/e: 500 (M+H), 498 (M–H).
¹H-NMR (CDCl₃, 300 MHz) δ 0.82-0.91 (m, 2H), 1.14-1.25 (m, 2H), 2.38 (s, 6H), 2.72-2.83 (m, 1H), 2.83 (s, 3H), 3.48 (s, 2H), 5.77 (d, J=0.7 Hz, 1H), 7.20-7.55 (m, 8H), 10.45 (s, 1H).

Example 1-247

MS ESI m/e: 489 (M+H), 487 (M–H).
¹H-NMR (DMSO-d₆, 300 MHz) δ 0.71-0.81 (m, 2H), 0.99-1.10 (m, 2H), 2.61 (s, 3H), 2.64-2.74 (m, 1H), 5.57 (s, 1H), 6.58 (d, J=16.1 Hz, 1H), 7.40-7.64 (m, 8H), 7.81 (d, J=12.1 Hz, 1H), 10.80 (s, 1H), 12.44 (brs, 1H).

Example 1-248

MS ESI m/e: 491 (M+H), 489 (M–H).
¹H-NMR (DMSO-d₆, 400 MHz) δ 0.72-0.78 (m, 2H), 0.99-1.07 (m, 2H), 2.59 (t, J=7.6 Hz, 2H), 2.58 (s, 3H), 2.63-2.70 (m, 1H), 2.86 (t, J=7.5 Hz, 2H), 5.25 (d, J=1.2 Hz, 1H), 7.12-7.17 (m, 1H), 7.24-7.30 (m, 1H), 7.35-7.54 (m, 6H), 10.40 (s, 1H), 12.18 (s, 1H).

Example 1-249

MS ESI m/e: 447 (M+H), 445 (M–H).
¹H-NMR (DMSO-d₆, 300 MHz) δ 0.72-0.79 (m, 2H), 0.99-1.07 (m, 2H), 2.59 (s, 3H), 2.63-2.70 (m, 1H), 5.45 (s, 1H), 7.25-7.30 (m, 2H), 7.31-7.37 (m, 2H), 7.41-7.55 (m, 5H), 10.49 (brs, 1H).

Example 1-250

MS ESI m/e: 501 (M+H), 499 (M–H).
¹H-NMR (DMSO-d₆, 300 MHz) δ 0.71-0.78 (m, 2H), 1.00-1.08 (m, 2H), 2.62 (s, 1H), 2.66-2.71 (m, 1H), 5.76 (s, 1H), 7.41-7.55 (m, 7H), 7.76 (d, J=8.3 Hz, 2H), 10.86 (brs, 1H).

Example 1-251

MS ESI m/e: 458 (M+H), 456 (M–H).
¹H-NMR (CDCl₃, 300 MHz) δ 0.72-0.82 (m, 2H), 0.99-1.09 (m, 2H), 2.58 (s, 3H), 2.63-2.74 (m, 1H), 5.13 (d, J=1.1 Hz, 1H), 6.45-6.50 (m, 1H), 7.33-7.61 (m, 8H), 10.28 (brs, 1H), 11.28 (brs, 1H).

Example 1-252

MS ESI m/e: 582, 584 (M+H), 580, 582 (M–H).
¹H-NMR (CDCl₃, 300 MHz) δ 0.82-0.91 (m, 2H), 1.14-1.25 (m, 2H), 1.76-1.90 (m, 2H), 2.26-2.38 (m, 2H), 2.26 (brs, 6H), 2.65-2.73 (m, 2H), 2.74-2.80 (m, 1H), 2.83 (s, 3H), 5.65 (d, J=0.7 Hz, 1H), 7.10-7.16 (m, 2H), 7.24-7.29 (m, 1H), 7.30-7.34 (m, 2H), 7.34-7.44 (m, 2H), 10.34 (brs, 1H).

Example 1-253

MS ESI m/e: 584, 586 (M+H), 582, 584 (M–H).
¹H-NMR (CDCl₃, 300 MHz) δ 0.82-0.90 (m, 2H), 1.15-1.23 (m, 2H), 2.73-2.80 (m, 1H), 2.93 (s, 3H), 2.97 (s, 3H), 3.34 (s, 3H), 3.44-3.56 (m, 4H), 5.66 (d, J=1.1 Hz, 2H), 6.55-6.60 (m, 2H), 6.70-6.76 (m, 1H), 7.22-7.40 (m, 4H), 10.39 (brs, 1H).

Example 1-254

MS ESI m/e: 457 (M+H), 455 (M−H).
$^1$H-NMR (CDCl$_3$, 400 MHz) δ 0.82-0.89 (m, 2H), 1.15-1.23 (m, 2H), 2.06 (s, 3H), 2.72-2.80 (m, 1H), 2.82 (s, 3H), 5.74 (s, 1H), 7.14-7.21 (m, 2H), 7.28-7.36 (m, 3H), 7.39-7.51 (m, 3H), 10.38 (s, 1H).

Example 1-255

MS ESI m/e: 624, 626 (M+H), 622, 624 (M−H).
$^1$H-NMR (CDCl$_3$, 300 MHz) δ 0.81-0.91 (m, 2H), 1.13-1.24 (m, 2H), 1.74-1.90 (m, 2H), 2.28-2.38 (m, 2H), 2.38-2.46 (m, 4H), 2.65-2.72 (m, 2H), 2.73-2.80 (m, 1H), 2.83 (s, 3H), 3.68-3.74 (m, 4H), 5.65 (d, J=1.1 Hz, 1H), 7.10-7.17 (m, 2H), 7.23-7.28 (m, 1H), 7.29-7.33 (m, 2H), 7.34-7.44 (m, 2H), 10.33 (brs, 1H).

Example 1-256

MS ESI m/e: 549 (M+H), 547 (M−H).
$^1$H-NMR (DMSO-d$_6$, 300 MHz) δ 0.66-0.77 (m, 2H), 0.89-1.05 (m, 2H), 2.54-2.61 (m, 1H), 2.56 (s, 3H), 7.36-7.45 (m, 4H), 7.53-7.63 (m, 3H), 7.65-7.71 (m, 2H), 12.88 (brs, 1H).

Example 1-257

MS ESI m/e: 638 (M+H), 636 (M−H).
$^1$H-NMR (DMSO-d$_6$, 300 MHz) δ 0.74 (m, 2H), 1.03 (m, 2H), 2.65 (s, 4H), 3.02 (s, 3H), 5.38 (s, 1H), 7.13 (d, J=8.6 Hz, 1H), 7.20-7.40 (m, 3H), 7.46 (t, J=8.1 Hz, 1H), 7.63 (d, J=9.3 Hz, 1H), 7.81 (d, J=10.1 Hz, 1H), 10.00 (s, 1H), 10.54 (s, 1H).

Example 1-258

MS ESI m/e: 461 (M+H), 459 (M−H).
$^1$H-NMR (CDCl$_3$, 300 MHz) δ 0.83-0.91 (m, 2H), 0.96 (t, J=7.3 Hz, 3H), 1.14-1.25 (m, 2H), 1.58-1.72 (m, 2H), 2.60 (t, J=7.7 Hz, 2H), 2.72-2.82 (m, 1H), 2.82 (s, 3H), 5.61 (d, J=1.1 Hz, 1H), 6.94-7.04 (m, 2H), 7.24-7.36 (m, 3H), 7.41-7.53 (m, 3H), 10.18 (s, 1H).

Example 1-259

MS ESI m/e: 521 (M+H), 519 (M−H).
$^1$H-NMR (CDCl$_3$, 300 MHz) δ 0.83-0.92 (m, 2H), 1.17-1.27 (m, 2H), 2.72-2.82 (m, 1H), 2.82 (s, 3H), 3.12 (s, 3H), 3.14 (s, 1H), 5.80 (d, J=0.7 Hz, 1H), 7.28-7.36 (m, 2H), 7.37-7.45 (m, 1H), 7.51-7.57 (m, 1H), 7.68-7.77 (m, 1H), 8.01-8.07 (m, 2H), 10.40 (s, 1H).

Example 1-260

MS ESI m/e: 536 (M+H), 534 (M−H).
$^1$H-NMR (CDCl$_3$, 300 MHz) δ 0.82-0.93 (m, 2H), 1.29-1.28 (m, 2H), 2.71-2.81 (m, 1H), 2.89 (s, 3H), 3.10 (s, 3H), 3.15 (s, 1H), 5.82 (s, 1H), 6.81-6.88 (m, 2H), 7.08 (d, J=9.0 Hz, 1H), 7.21-7.39 (m, 3H), 7.39-7.51 (m, 2H), 10.49 (brs, H).

Example 1-261

MS ESI m/e: 499, 501 (M+H).
$^1$H-NMR (CDCl$_3$, 300 MHz) δ 1.30 (t, J=7.0 Hz, 3H), 3.63 (s, 3H), 4.13 (q, J=7.0 Hz, 2H), 5.57 (s, 2H), 5.78 (s, 1H), 7.20-7.50 (m, 8H), 10.33 (s, 1H).

Example 1-262

MS ESI m/e: 604, 606 (M+H), 602, 604 (M−H).
$^1$H-NMR (DMSO-d$_6$, 300 MHz) δ 0.71-0.78 (m, 2H), 0.99-1.07 (m, 2H), 1.18 (t, J=7.5 Hz, 3H), 2.61-2.70 (m, 4H), 3.13 (q, J=7.0 Hz, 2H), 5.35 (s, 1H), 7.08-7.14 (m, 1H), 7.25-7.34 (m, 2H), 7.41-7.54 (m, 3H), 7.71-7.77 (m, 1H), 10.04 (brs, 1H), 10.53 (s, 1H).

Example 1-263

MS ESI m/e: 570, 572 (M+H), 568, 570 (M−H).
$^1$H-NMR (DMSO-d$_6$, 300 MHz) δ 0.71-0.79 (m, 2H), 0.99-1.07 (m, 2H), 2.63-2.73 (m, 1H), 2.66 (s, 3H), 3.99 (d, J=6.0 Hz, 2H), 5.36 (s, 1H), 5.65 (t, J=6.0 Hz, 1H), 7.10-7.15 (m, 1H), 7.39-7.52 (m, 3H), 7.71-7.85 (m, 3H), 9.91 (brs, 1H), 10.54 (brs, 1H).

Example 1-264

MS ESI m/e: 512, 514 (M+H), 510, 512 (M−H).
$^1$H-NMR (DMSO-d$_6$, 300 MHz) δ 0.69-0.77 (m, 2H), 0.97-1.08 (m, 2H), 2.62-2.71 (m, 1H), 2.74 (s, 3H), 5.35 (d, J=1.5 Hz, 1H), 5.38 (brs, 2H), 6.47-6.53 (m, 1H), 6.54-6.57 (m, 1H), 6.58-6.63 (m, 1H), 7.11 (t, J=7.9 Hz, 1H), 7.44-7.53 (m, 2H), 7.70-7.77 (m, 1H), 10.55 (brs, 1H).

Example 1-265

MS ESI m/e: 459 (M+H), 457 (M−H).
$^1$H-NMR (CDCl$_3$, 300 MHz) δ 0.66-0.74 (m, 2H), 0.83-0.91 (m, 2H), 0.97-1.06 (m, 2H), 1.14-1.24 (m, 2H), 1.85-1.96 (m, 1H), 2.72-2.81 (m, 1H), 2.81 (s, 3H), 5.58 (d, J=1.1 Hz, 1H), 6.82-6.92 (m, 2H), 7.21-7.29 (m, 1H), 7.29-7.36 (m, 2H), 7.39-7.53 (m, 3H), 10.16 (s, 1H).

Example 1-266

MS ESI m/e: 584, 586 (M+H), 582, 584 (M−H).
$^1$H-NMR (DMSO-d$_6$, 300 MHz) δ 0.71-0.78 (m, 2H), 0.99-1.08 (m, 2H), 2.63-2.71 (m, 1H), 2.66 (s, 3H), 3.32 (s, 3H), 3.37 (s, 3H), 4.00 (brs, 2H), 5.36 (d, J=0.8 Hz, 1H), 7.10-7.16 (m, 1H), 7.40-7.52 (m, 3H), 7.71-7.80 (m, 3H), 10.00 (brs, 1H), 10.54 (brs, 1H).

Example 1-267

MS ESI m/e: 658, 660 (M+H), 656, 658 (M−H).
$^1$H-NMR (CDCl$_3$, 300 MHz) δ 0.70-0.79 (m, 2H), 0.99-1.10 (m, 2H), 2.62-2.76 (m, 1H), 2.66 (s, 3H), 4.48-4.64 (m, 2H), 5.36 (s, 1H), 7.17 (d, J=9.0 Hz, 1H), 7.28-7.33 (m, 2H), 7.43-7.52 (m, 3H), 7.74 (d, J=12.0 Hz, 1H), 10.52 (brs, 1H), 10.72 (brs, 1H).

Example 1-268

MS ESI m/e: 554 (M+H), 552 (M−H).
$^1$H-NMR (CDCl$_3$, 300 MHz) δ 0.83-0.92 (m, 2H), 1.14-1.24 (m, 2H), 1.26 (t, J=7.7 Hz, 3H), 1.37 (t, J=7.3 Hz, 3H), 2.67 (q, J=7.6 Hz, 2H), 2.71-2.81 (m, 1H), 2.85 (s, 3H), 3.17

(q, J=7.5 Hz, 2H), 5.60 (d, J=1.1 Hz, 1H), 6.94-7.08 (m, 4H), 7.22-7.33 (m, 3H), 7.38-7.47 (m, 1H), 10.15 (s, 1H).

Example 1-269

MS ESI m/e: 541, 543 (M+H), 539, 541 (M−H).
$^1$H-NMR (DMSO-d$_6$, 300 MHz) δ 0.70-0.79 (m, 2H), 0.98-1.10 (m, 2H), 2.60 (s, 3H), 2.62-2.71 (m, 1H), 5.37 (d, J=1.1 Hz, 1H), 7.43-7.57 (m, 2H), 7.61-7.78 (m, 3H), 7.95-8.05 (m, 2H), 10.54 (brs, 1H), 13.34 (brs, 1H).

Example 1-270

MS ESI m/e: 540, 542 (M+H), 538, 540 (M−H).
$^1$H-NMR (DMSO-d$_6$, 300 MHz) δ 0.71-0.80 (m, 2H), 0.98-1.09 (m, 2H), 2.61 (s, 3H), 2.63-2.74 (m, 1H), 5.38 (s, 1H), 7.45-7.58 (m, 3H), 7.58-7.65 (m, 2H), 7.70-7.78 (m, 1H), 7.90 (brs, 1H), 7.94-8.00 (m, 1H), 8.11 (brs, 1H), 10.54 (brs, 1H).

Example 1-271

MS ESI m/e: 618, 620 (M+H), 616, 618 (M−H).
$^1$H-NMR (DMSO-d$_6$, 300 MHz) δ 0.71-0.77 (m, 2H), 0.92 (t, J=7.5 Hz, 3H), 1.00-1.07 (m, 2H), 1.66 (q, J=7.0 Hz, 2H), 2.62-2.70 (m, 4H), 3.05-3.13 (m, 2H), 5.36 (s, 1H), 7.09-7.13 (m, 1H), 7.23-7.32 (m, 2H), 7.41-7.53 (m, 3H), 7.71-7.77 (m, 1H), 10.05 (brs, 1H), 10.53 (s, 1H).

Example 1-272

MS ESI m/e: 618, 620 (M+H), 616, 618 (M−H).
$^1$H-NMR (DMSO-d$_6$, 300 MHz) δ 0.71-0.78 (m, 2H), 0.99-1.08 (m, 2H), 1.23 (d, J=6.0 Hz, 6H), 2.62-2.70 (m, 4H), 3.19-3.29 (m, 1H), 5.36 (s, 1H), 7.07-7.13 (m, 1H), 7.26-7.34 (m, 2H), 7.39-7.54 (m, 3H), 7.71-7.76 (m, 1H), 10.00 (brs, 1H), 10.53 (s, 1H).

Example 1-273

MS ESI m/e: 469 (M+H), 467 (M−1).
$^1$H-NMR (CDCl$_3$, 300 MHz) δ 0.80-0.90 (m, 2H), 1.10-1.30 (m, 2H), 2.78 (m, 1H), 2.83 (s, 3H), 5.97 (s, 1H), 7.30-7.35 (m, 2H), 7.35-7.55 (m, 5H), 7.65 (d, J=8.5 Hz, 2H), 10.67 (s, 1H).

Example 1-274

MS ESI m/e: 652 (M+H), 650 (M−H).
$^1$H-NMR (DMSO-d$_6$, 300 MHz) δ 0.70-0.79 (m, 2H), 0.98-1.08 (m, 2H), 1.17 (t, J=7.3 Hz, 3H), 2.61-2.71 (m, 1H), 2.64 (s, 3H), 3.13 (q, J=7.3 Hz, 2H), 5.38 (brs, 1H), 7.09-7.15 (m, 2H), 7.24-7.38 (m, 3H), 7.40-7.49 (m, 1H), 7.60-7.67 (m, 1H), 7.81 (dd, J=1.8, 9.9 Hz, 1H), 10.04 (s, 1H).

Example 1-275

MS ESI m/e: 540 (M+H), 538 (M−H).
$^1$H-NMR (CDCl$_3$, 400 MHz) δ 0.83-0.91 (m, 2H), 1.15-1.23 (m, 2H), 1.26 (t, J=7.6 Hz, 3H), 2.67 (q, J=7.6 Hz, 2H), 2.72-2.80 (m, 1H), 2.85 (s, 3H), 3.05 (s, 3H), 5.60 (d, J=1.2 Hz, 1H), 6.98-7.05 (m, 2H), 7.05-7.10 (m, 1H), 7.23-7.31 (m, 4H), 7.40-7.47 (m, 1H), 10.16 (s, 1H).

Example 1-276

MS ESI m/e: 653, 655 (M+H).
$^1$H-NMR (DMSO-d$_6$, 300 MHz) δ 0.70-0.79 (m, 2H), 0.87 (t, J=7.2 Hz, 3H), 1.00-1.08 (m, 2H), 1.22-1.36 (m, 2H), 1.43-1.54 (m, 2H), 2.15 (t, J=7.3 Hz, 2H), 2.63-2.72 (m, 1H), 2.66 (s, 3H), 3.86 (d, J=5.3 Hz, 2H), 5.36 (s, 1H), 7.05-7.12 (m, 1H), 7.40-7.52 (m, 3H), 7.61-7.77 (m, 3H), 8.08-8.15 (m, 1H), 10.20 (brs, 1H), 10.54 (brs, 1H).

Example 1-277

MS ESI m/e: 597, 599 (M+H), 595, 597 (M−H).
$^1$H-NMR (DMSO-d$_6$, 300 MHz) δ 0.70-0.78 (m, 2H), 0.99-1.07 (m, 2H), 2.28 (s, 6H), 2.64-2.70 (m, 1H), 2.67 (s, 3H), 3.09 (brs, 2H), 5.36 (d, J=1.1 Hz, 1H), 7.10-7.14 (m, 1H), 7.40-7.52 (m, 3H), 7.71-7.79 (m, 3H), 9.97 (brs, 1H), 10.54 (brs, 1H).

Example 1-278

MS ESI m/e: 568, 570 (M+H), 566, 568 (M−H).
$^1$H-NMR (DMSO-d$_6$, 300 MHz) δ 0.71-0.78 (m, 2H), 0.99-1.11 (m, 5H), 2.33 (q, J=7.0 Hz, 2H), 2.63-2.71 (m, 4H), 5.36 (s, 1H), 7.04-7.10 (m, 1H), 7.42 (t, J=7.5 Hz, 1H), 7.46-7.54 (m, 2H), 7.61-7.67 (m, 1H), 7.70-7.77 (m, 2H), 10.08 (s, 1H), 10.54 (s, 1H).

Example 1-279

MS ESI m/e: 582, 584 (M+H), 580, 582 (M−H).
$^1$H-NMR (DMSO-d$_6$, 300 MHz) δ 0.71-0.78 (m, 2H), 0.91 (t, J=7.5 Hz, 3H), 0.99-1.07 (m, 2H), 1.60 (q, J=8.0 Hz, 2H), 2.29 (t, J=7.5 Hz, 2H), 2.63-2.71 (m, 4H), 5.36 (s, 1H), 7.42 (t, J=7.5 Hz, 1H), 7.46-7.54 (m, 2H), 7.62-7.76 (m, 3H), 10.09 (s, 1H), 10.54 (s, 1H).

Example 1-280

MS ESI m/e: 644, 646 (M+H), 642, 644 (M−H).
$^1$H-NMR (DMSO-d$_6$, 300 MHz) δ 0.68-0.80 (m, 2H), 0.97-1.08 (m, 2H), 2.61-2.72 (m, 1H), 2.64 (s, 3H), 5.36 (d, J=0.7 Hz, 1H), 6.88-7.01 (m, 1H), 7.05-7.17 (m, 2H), 7.23-7.34 (m, 1H), 7.47 (dd, J=2.3, 8.7 Hz, 1H), 7.52 (t, J=8.1 Hz, 1H), 7.73 (dd, J=1.5, 10.2 Hz, 1H), 10.56 (brs, 1H).

Example 1-281

MS ESI m/e: 485 (M+H), 483 (M−H).
$^1$H-NMR (CDCl$_3$, 300 MHz) δ 0.71-0.81 (m, 2H), 1.00-1.10 (m, 2H), 2.60 (s, 3H), 2.61-2.72 (m, 1H), 5.52 (s, 1H), 7.41-7.56 (m, 9H), 10.62 (brs, 1H).

Example 1-282

MS ESI m/e: 624, 626 (M+H), 622, 624 (M−H).
$^1$H-NMR (CDCl$_3$, 300 MHz) δ 0.71-0.81 (m, 2H), 0.97-1.10 (m, 2H), 2.61-2.72 (m, 1H), 2.65 (s, 3H), 5.07 (s, 2H), 5.36 (s, 1H), 7.19 (d, J=9.0 Hz, 1H), 7.28-7.38 (m, 2H), 7.42-7.56 (m, 3H), 7.74 (d, J=9.0 Hz, 1H), 10.53 (brs, 1H), 10.64 (brs, 1H).

Example 1-283

MS ESI m/e: 526, 528 (M+H), 524, 526 (M−H).
$^1$H-NMR (CDCl$_3$, 300 MHz) δ 0.71-0.79 (m, 2H), 0.99-1.09 (m, 2H), 2.66 (d, J=6.0 Hz, 3H), 2.64-2.67 (m, 1H), 2.74 (s, 3H), 5.36 (s, 1H), 5.92-5.98 (m, 1H), 6.50-6.60 (m, 3H), 7.19 (t, J=7.5 Hz, 1H), 7.49-7.54 (m, 2H), 7.74 (d, J=12.0 Hz, 1H), 10.57 (brs, 1H).

Example 1-284

MS ESI m/e: 652, 654 (M+H), 650, 652 (M−H).
$^1$H-NMR (CDCl$_3$, 300 MHz) δ 0.68-0.80 (m, 2H), 0.99-1.09 (m, 2H), 2.33 (s, 3H), 2.61-2.70 (m, 1H), 5.35 (s, 1H), 7.04 (d, J=12.0 Hz, 1H), 7.13 (d, J=6.0 Hz, 1H), 7.30-7.38 (m, 2H), 7.49-7.62 (m, 5H), 7.73-7.80 (m, 3H), 10.48 (brs, 1H), 10.52 (brs, 1H).

Example 1-285

MS ESI m/e: 465 (M+H), 463 (M−H).
$^1$H-NMR (DMSO-d$_6$, 300 MHz) δ 0.71-0.78 (m, 2H), 1.01-1.07 (m, 2H), 2.53 (s, 3H), 2.59 (s, 3H), 2.64-2.72 (m, 1H), 5.25 (d, J=1.1 Hz, 1H), 7.17 (dd, J=1.9, 8.7 Hz, 1H), 7.32 (dd, J=1.9, 11.3 Hz, 1H), 7.39-7.55 (m, 6H), 10.41 (brs, 1H).

Example 1-286

MS ESI m/e: 558 (M+H), 556 (M−H).
$^1$H-NMR (DMSO-d$_6$, 300 MHz) δ 0.72-0.78 (m, 2H), 0.99-1.07 (m, 2H), 2.53 (s, 3H), 2.63-2.69 (m, 1H), 2.65 (s, 3H), 3.02 (s, 3H), 5.25 (d, J=1.1 Hz, 1H), 7.11-7.19 (m, 2H), 7.24-7.35 (m, 3H), 7.39-7.50 (m, 2H), 9.99 (brs, 1H), 10.39 (brs, 1H).

Example 1-287

MS ESI m/e: 582, 584 (M+H), 580, 582 (M−H).
$^1$H-NMR (DMSO-d$_6$, 300 MHz) δ 0.70-0.78 (m, 2H), 0.99-1.12 (m, 8H), 2.53-2.70 (m, 5H), 5.36 (s, 1H), 7.05-7.11 (m, 1H), 7.42 (t, J=7.5 Hz, 1H), 7.46-7.55 (m, 2H), 7.62-7.68 (m, 1H), 7.70-7.77 (m, 2H), 10.05 (s, 1H), 10.54 (s, 1H).

Example 1-288

MS ESI m/e: 576, 578 (M+H), 574, 576 (M−H).
$^1$H-NMR (DMSO-d$_6$, 300 MHz) δ 0.72-0.80 (m, 2H), 1.00-1.08 (m, 2H), 2.60-2.70 (m, 4H), 5.37 (s, 1H), 7.47-7.58 (m, 4H), 7.65-7.77 (m, 3H), 7.88-7.93 (m, 2H), 10.52 (s, 1H).

Example 1-289

MS ESI m/e: 550 (M+H), 548 (M−H).
$^1$H-NMR (DMSO-d$_6$, 300 MHz) δ 0.70-0.78 (m, 2H), 0.99-1.09 (m, 2H), 1.18 (t, J=7.3 Hz, 3H), 2.63-2.71 (m, 1H), 2.66 (s, 3H), 3.13 (q, J=7.5 Hz, 2H), 4.32 (s, 1H), 5.51 (s, 1H), 7.09-7.15 (m, 1H), 7.24-7.35 (m, 2H), 7.36-7.41 (m, 1H), 7.41-7.49 (m, 1H), 7.50-7.61 (m, 2H), 10.04 (s, 1H), 10.72 (s, 1H).

Example 1-290

MS ESI m/e: 518 (M+H), 516 (M−H).
$^1$H-NMR (DMSO-d$_6$, 400 MHz) δ 0.71-0.78 (m, 2H), 1.00-1.08 (m, 2H), 2.61-2.71 (m, 1H), 2.66 (s, 3H), 3.03 (s, 3H), 4.19 (s, 1H), 5.64 (s, 1H), 7.11-7.16 (m, 1H), 7.24-7.29 (m, 1H), 7.30-7.37 (m, 3H), 7.43-7.49 (m, 1H), 7.51-7.56 (m, 2H), 10.01 (s, 1H), 10.70 (s, 1H).

Example 1-291

MS ESI m/e: 483 (M+H), 481 (M−H).
$^1$H-NMR (DMSO-d$_6$, 300 MHz) δ 0.70-0.80 (m, 2H), 0.98-1.10 (m, 2H), 2.60 (s, 3H), 2.62-2.73 (m, 1H), 3.68 (q, J=11.6 Hz, 2H), 5.54 (s, 1H), 7.30-7.38 (m, 2H), 7.39-7.56 (m, 7H), 10.60 (brs, 1H).

Example 1-292

MS ESI m/e: 554, 556 (M+H), 552, 554 (M−H).
$^1$H-NMR (DMSO-d$_6$, 300 MHz) δ 0.71-0.81 (m, 2H), 0.98-1.09 (m, 2H), 2.60 (s, 3H), 2.63-2.71 (m, 1H), 2.79 (d, J=4.5 Hz, 3H), 5.38 (d, J=1.1 Hz, 1H), 7.45-7.55 (m, 2H), 7.57-7.65 (m, 2H), 7.71-7.77 (m, 1H), 7.84-7.89 (m, 1H), 7.89-7.95 (m, 1H), 8.57 (q, J=5.3 Hz, 1H), 10.53 (brs, 1H).

Example 1-293

MS ESI m/e: 447 (M+H), 445 (M−H).
$^1$H-NMR (DMSO-d$_6$, 300 MHz) δ 0.71-0.80 (m, 2H), 0.99-1.08 (m, 2H), 2.59 (s, 3H), 2.62-2.73 (m, 1H), 3.00 (dt, J=25.2, 6.0 Hz, 2H), 4.67 (dt, J=47.1, 6.4 Hz, 2H), 5.46 (s, 1H), 7.23-7.29 (m, 2H), 7.33-7.39 (m, 2H), 7.40-7.56 (m, 5H), 10.51 (brs, 1H).

Example 1-294

MS ESI m/e: 590, 592 (M+H), 588, 590 (M−H).
$^1$H-NMR (DMSO-d$_6$, 300 MHz) δ 0.71-0.79 (m, 2H), 1.00-1.09 (m, 2H), 2.42 (s, 3H), 2.58-2.70 (m, 4H), 5.37 (s, 1H), 7.45-7.54 (m, 2H), 7.70-7.80 (m, 3H), 7.82-7.88 (m, 2H), 10.51 (s, 1H).

Example 1-295

MS ESI m/e: 604, 606 (M+H), 602, 604 (M−H).
$^1$H-NMR (DMSO-d$_6$, 300 MHz) δ 0.72-0.79 (m, 2H), 0.96 (t, J=6.0 Hz, 3H), 1.01-1.08 (m, 2H), 2.58-2.71 (m, 4H), 2.74-2.84 (m, 2H), 5.37 (s, 1H), 7.46-7.55 (m, 2H), 7.69-7.79 (m, 4H), 7.84-7.90 (m, 2H), 10.51 (s, 1H).

Example 1-296

MS ESI m/e: 504 (M+H), 502 (M−H).
$^1$H-NMR (CDCl$_3$, 300 MHz) δ 0.81-0.91 (m, 2H), 1.12-1.23 (m, 2H), 1.26 (t, J=7.5 Hz, 3H), 2.16 (s, 3H), 2.66 (q, J=7.6 Hz, 2H), 2.72-2.82 (m, 1H), 2.86 (s, 3H), 5.59 (d, J=1.5 Hz, 1H), 6.95-7.08 (m, 3H), 7.22-7.32 (m, 1H), 7.33-7.55 (m, 3H), 7.70 (s, 1H), 10.18 (s, 1H).

Example 1-297

MS ESI m/e: 602 (M+H), 600 (M−H).
$^1$H-NMR (DMSO-d$_6$, 300 MHz) δ 0.68-0.79 (m, 2H), 0.98-1.09 (m, 2H), 2.04 (s, 3H), 2.63-2.71 (m, 1H), 2.66 (s, 3H), 5.38 (d, J=1.5 Hz, 1H), 7.04-7.10 (m, 1H), 7.29-7.38

(m, 1H), 7.38-7.46 (m, 1H), 7.60-7.72 (m, 3H), 7.81 (dd, J=1.8, 10.2 Hz, 1H), 10.15 (s, 1H), 10.55 (s, 1H).

Example 1-298

MS ESI m/e: 532 (M+H), 530 (M−H).
$^1$H-NMR (DMSO-$d_6$, 300 MHz) δ 0.70-0.80 (m, 2H), 0.98-1.09 (m, 2H), 1.18 (t, J=7.3 Hz, 3H), 2.61-2.72 (m, 1H), 2.65 (s, 3H), 3.13 (q, J=7.5 Hz, 2H), 4.18 (s, 1H), 5.65 (s, 1H), 7.08-7.15 (m, 1H), 7.24-7.31 (m, 1H), 7.31-7.38 (m, 3H), 7.41-7.49 (m, 1H), 7.51-7.57 (m, 2H), 10.04 (s, 1H), 10.70 (s, 1H).

Example 1-299

MS ESI m/e: 667, 669 (M+H), 665, 667 (M−H).
$^1$H-NMR (DMSO-$d_6$, 300 MHz) δ 0.71-0.77 (m, 2H), 0.83 (t, J=7.4 Hz, 3H), 0.98-1.07 (m, 2H), 1.19-1.29 (m, 2H), 1.39-1.49 (m, 2H), 2.04 (t, J=7.5 Hz, 2H), 2.45-2.53 (m, 2H), 2.63-2.70 (m, 1H), 2.66 (s, 3H), 3.27-3.35 (m, 2H), 5.35 (d, J=1.1 Hz, 1H), 7.05-7.11 (m, 1H), 7.42 (t, J=8.1 Hz, 1H), 7.47-7.52 (m, 2H), 7.60-7.67 (m, 1H), 7.70-7.77 (m, 2H), 7.87-7.94 (m, 1H), 10.17 (brs, 1H), 10.54 (brs, 1H).

Example 1-300

MS ESI m/e: 457 (M+H), 455 (M−1).
$^1$H-NMR (CDCl$_3$, 300 MHz) δ 0.80-0.90 (m, 2H), 1.10-1.30 (m, 2H), 1.34 (s, 9H), 2.77 (m, 1H), 2.81 (s, 3H), 5.79 (s, 1H), 7.20 (d, J=8.5 Hz, 2H), 7.30-7.35 (m, 2H), 7.35-7.55 (m, 5H), 10.29 (s, 1H).

Example 1-301

MS ESI m/e: 580 (M+H), 578 (M−1).
$^1$H-NMR (DMSO-$d_6$, 300 MHz) δ 0.75 (brs, 2H), 1.05 (m, 2H), 2.68 (s, 4H), 3.03 (s, 3H), 3.32 (s, 3H), 5.68 (s, 1H), 7.15 (d, J=8.9 Hz, 1H), 7.27 (d, J=8.1 Hz, 1H), 7.47 (t, J=8.0 Hz, 1H), 7.64 (d, J=8.4 Hz, 1H), 7.75-7.90 (m, 2H), 10.01 (s, 1H), 10.95 (s, 1H).

Example 1-302

MS ESI m/e: 620 (M+H), 618 (M−H).
$^1$H-NMR (DMSO-$d_6$, 400 MHz) δ 0.71-0.78 (m, 2H), 0.99-1.07 (m, 2H), 2.62-2.69 (m, 1H), 2.65 (s, 3H), 3.02 (s, 3H), 5.54 (s, 1H), 7.10-7.19 (m, 3H), 7.23-7.28 (m, 1H), 7.29-7.32 (m, 1H), 7.42-7.49 (m, 1H), 7.74-7.80 (m, 2H), 10.00 (s, 1H), 10.57 (s, 1H).

Example 1-303

MS ESI m/e: 625, 627 (M+H), 623, 625 (M−H).
$^1$H-NMR (DMSO-$d_6$, 300 MHz) δ 0.69-0.78 (m, 2H), 0.99-1.09 (m, 2H), 2.34-2.56 (m, 6H), 2.61-2.71 (m, 1H), 2.74 (s, 3H), 3.08-3.19 (m, 2H), 3.50-3.62 (m, 4H), 5.36 (s, 1H), 5.77 (brs, 1H), 6.53-6.70 (m, 3H), 7.18 (dd, J=9.0, 6.0 Hz, 1H), 7.40-7.50 (m, 2H), 7.74 (d, J=9.0 Hz, 1H), 10.56 (brs, 1H).

Example 1-304

MS ESI m/e: 572, 574 (M+H), 570, 572 (M−H).
$^1$H-NMR (DMSO-$d_6$, 300 MHz) δ 0.74-0.79 (m, 2H), 1.00-1.08 (m, 2H), 2.62-2.68 (m, 4H), 3.02 (s, 3H), 5.53 (s, 1H), 7.12-7.14 (m, 1H), 7.22-7.35 (m, 4H), 7.42-7.44 (m, 1H), 7.60-7.62 (m, 2H), 10.00 (brs, 1H), 10.57 (brs, 1H).

Example 1-305

MS ESI m/e: 584, 586 (M+H), 582, 584 (M−H).
$^1$H-NMR (DMSO-$d_6$, 300 MHz) δ 0.69-0.80 (m, 2H), 0.97-1.08 (m, 2H), 2.47 (t, J=7.2 Hz, 2H), 2.62-2.71 (m, 1H), 2.67 (s, 3H), 3.70 (q, J=5.9 Hz, 2H), 4.69 (t, J=5.1 Hz, 1H), 5.36 (d, J=1.1 Hz, 1H), 7.07 (dd, J=2.6, 7.9 Hz, 1H), 7.42 (t, J=8.1 Hz, 1H), 7.48-7.55 (m, 2H), 7.62-7.69 (m, 1H), 7.71-7.77 (m, 1H), 10.13 (brs, 1H), 10.54 (brs, 1H).

Example 1-306

MS ESI m/e: 611, 613 (M+H), 609, 611 (M−H).
$^1$H-NMR (DMSO-$d_6$, 300 MHz) δ 0.69-0.79 (m, 2H), 0.98-1.08 (m, 2H), 2.16 (s, 6H), 2.39-2.48 (m, 2H), 2.51-2.59 (m, 2H), 2.63-2.72 (m, 1H), 2.67 (s, 3H), 5.35 (d, J=1.1 Hz, 1H), 7.05-7.11 (m, 1H), 7.42 (t, J=8.1 Hz, 1H), 7.47-7.55 (m, 2H), 7.61-7.67 (m, 1H), 7.69-7.77 (m, 2H), 10.22 (brs, 1H), 10.54 (brs, 1H).

Example 1-307

MS ESI m/e: 583, 585 (M+H), 581, 583 (M−H).
$^1$H-NMR (DMSO-$d_6$, 300 MHz) δ 0.70-0.79 (m, 2H), 0.98-1.08 (m, 2H), 1.04 (t, J=7.2 Hz, 3H), 2.62-2.74 (m, 1H), 2.68 (s, 3H), 3.09 (quint, J=6.8 Hz, 2H), 5.35 (d, J=1.1 Hz, 1H), 6.16 (t, J=5.8 Hz, 1H), 6.88-6.95 (m, 1H), 7.32 (t, J=7.9 Hz, 1H), 7.36-7.42 (m, 1H), 7.45-7.57 (m, 3H), 7.71-7.77 (m, 1H), 8.73 (brs, 1H), 10.55 (brs, 1H).

Example 1-308

MS ESI m/e: 584, 586 (M+H), 582, 584 (M−H).
$^1$H-NMR (DMSO-$d_6$, 300 MHz) δ 0.70-0.78 (m, 2H), 0.98-1.08 (m, 2H), 1.24 (t, J=7.2 Hz, 3H), 2.61-2.72 (m, 1H), 2.66 (s, 3H), 4.12 (q, J=6.9 Hz, 2H), 5.36 (d, J=1.1 Hz, 1H), 7.00-7.05 (m, 1H), 7.39 (t, J=7.9 Hz, 1H), 7.43-7.55 (m, 3H), 7.60-7.65 (m, 1H), 7.70-7.78 (m, 1H), 9.85 (brs, 1H), 10.54 (brs, 1H).

Example 1-309

MS ESI m/e: 619, 621 (M+H), 617, 619 (M−H).
$^1$H-NMR (DMSO-$d_6$, 300 MHz) δ 0.68-0.80 (m, 2H), 0.98-1.07 (m, 2H), 2.60-2.71 (m, 1H), 2.63 (s, 3H), 2.67 (s, 6H), 5.35 (d, J=1.1 Hz, 1H), 7.09-7.15 (m, 1H), 7.21-7.27 (m, 2H), 7.43 (t, J=8.5 Hz, 1H), 7.47-7.54 (m, 2H), 7.70-7.76 (m, 1H), 10.11 (brs, 1H), 10.54 (brs, 1H).

Example 1-310

MS ESI m/e: 500 (M+H), 498 (M−H).
$^1$H-NMR (DMSO-$d_6$, 300 MHz) δ 0.70-0.79 (m, 2H), 0.98-1.08 (m, 2H), 2.05 (s, 3H), 2.63-2.72 (m, 1H), 2.67 (s, 3H), 4.32 (s, 1H), 5.51 (brs, 1H), 7.04-7.12 (m, 1H), 7.35-7.46 (m, 2H), 7.50-7.61 (m, 2H), 7.62-7.67 (m, 1H), 7.67-7.72 (m, 1H), 10.16 (s, 1H), 10.75 (s, 1H).

Example 1-311

MS ESI m/e: 666 (M+H), 664 (M−H).
$^1$H-NMR (DMSO-$d_6$, 400 MHz) δ 0.71-0.77 (m, 2H), 0.92 (t, J=7.5 Hz, 3H), 1.00-1.07 (m, 2H), 1.59-1.71 (m, 2H), 2.62-2.70 (m, 1H), 2.64 (s, 3H), 3.09 (t, J=7.4 Hz, 2H), 5.38 (d, J=1.2 Hz, 1H), 7.08-7.14 (m, 1H), 7.23-7.37 (m, 3H), 7.41-7.48 (m, 1H), 7.61-7.66 (m, 1H), 7.79-7.84 (m, 1H), 10.54 (s, 1H).

Example 1-312

MS ESI m/e: 753, 755 (M+H), 751, 753 (M−H).
$^1$H-NMR (CDCl$_3$, 300 MHz) δ 0.81-0.89 (m, 2H), 1.14-1.22 (m, 2H), 2.70-2.79 (m, 1H), 2.81 (s, 3H), 3.21-3.32 (m, 2H), 3.57-3.68 (m, 2H), 5.07 (s, 2H), 5.57-5.67 (m, 1H), 5.65 (d, J=1.1 Hz, 1H), 7.04-7.09 (m, 1H), 7.21-7.40 (m, 11H), 7.74-7.80 (m, 1H), 10.34 (brs, 1H).

Example 1-313

MS ESI m/e: 619, 621 (M+H), 617, 619 (M−H).
$^1$H-NMR (DMSO-d$_6$, 300 MHz) δ 0.72-0.79 (m, 2H), 0.99-1.09 (m, 2H), 2.63-2.70 (m, 1H), 2.66 (s, 3H), 3.09-3.19 (m, 2H), 3.37-3.49 (m, 2H), 5.36 (d, J=0.9 Hz, 1H), 7.17-7.24 (m, 1H), 7.30-7.39 (m, 2H), 7.47-7.54 (m, 3H), 7.73-7.77 (m, 1H), 7.93-8.14 (m, 3H), 10.39 (brs, 1H), 10.52 (brs, 1H).

Example 1-314

MS ESI m/e: 703, 705 (M+H), 701, 703 (M−H).
$^1$H-NMR (DMSO-d$_6$, 300 MHz) δ 0.71-0.78 (m, 2H), 0.82 (t, J=7.2 Hz, 3H), 0.99-1.08 (m, 2H), 1.15-1.27 (m, 1H), 1.37-1.47 (m, 2H), 2.01 (t, J=7.5 Hz, 2H), 2.62-2.70 (m, 1H), 2.65 (s, 3H), 3.17-3.25 (m, 2H), 3.33-3.43 (m, 2H), 5.36 (d, J=1.1 Hz, 1H), 7.11-7.18 (m, 1H), 7.25-7.30 (m, 1H), 7.33-7.36 (m, 1H), 7.42-7.54 (m, 3H), 7.72-7.77 (m, 1H), 7.87-7.94 (m, 1H), 10.08 (brs, 1H), 10.53 (brs, 1H).

Example 1-315

MS ESI m/e: 659, 661 (M+H), 657, 659 (M−H).
$^1$H-NMR (DMSO-d$_6$, 300 MHz) δ 0.72-0.79 (m, 2H), 1.01-1.09 (m, 2H), 2.14 (s, 3H), 2.32-2.39 (m, 4H), 2.60-2.72 (m, 4H), 2.83-2.97 (m, 4H), 5.37 (s, 1H), 7.46-7.55 (m, 2H), 7.71-7.87 (m, 5H), 10.51 (s, 1H).

Example 1-316

MS ESI m/e: 646, 648 (M+H), 644, 646 (M−H).
$^1$H-NMR DMSO-d$_6$, 300 MHz) δ 0.72-0.79 (m, 2H), 1.01-1.10 (m, 2H), 2.60-2.71 (m, 4H), 2.81-2.94 (m, 4H), 3.58-3.67 (m, 4H), 5.38 (s, 1H), 7.47-7.55 (m, 2H), 7.71-7.88 (m, 5H), 10.50 (s, 1H).

Example 1-317

MS ESI m/e: 644, 646 (M+H), 642, 644 (M−H).
$^1$H-NMR (DMSO-d$_6$, 300 MHz) δ 0.71-0.79 (m, 2H), 1.00-1.09 (m, 2H), 1.32-1.41 (m, 2H), 1.47-1.58 (m, 4H), 2.58-2.73 (m, 4H), 2.82-2.92 (m, 4H), 5.37 (s, 1H), 7.46-7.54 (m, 2H), 7.71-7.84 (m, 5H), 10.51 (s, 1H).

Example 1-318

MS ESI m/e: 630, 632 (M+H), 628, 630 (M−H).
$^1$H-NMR (DMSO-d$_6$, 300 MHz) δ 0.71-0.79 (m, 2H), 1.01-1.10 (m, 2H), 1.59-1.69 (m, 4H), 2.58 (s, 3H), 2.63-2.71 (m, 1H), 3.03-3.22 (m, 4H), 5.37 (s, 1H), 7.46-7.55 (m, 2H), 7.71-7.82 (m, 3H), 7.87-7.92 (m, 2H), 10.51 (s, 1H).

Example 1-319

MS ESI m/e: 666 (M+H), 664 (M−H).
$^1$H-NMR (DMSO-d$_6$, 300 MHz) δ 0.70-0.79 (m, 2H), 0.99-1.08 (m, 2H), 1.23 (d, J=6.6 Hz, 6H), 2.61-2.71 (m, 1H), 2.64 (s, 3H), 5.38 (s, 1H), 7.08-7.15 (m, 1H), 7.27-7.38 (m, 3H), 7.39-7.47 (m, 1H), 7.60-7.66 (m, 1H), 7.78-7.84 (m, 1H), 9.99 (brs, 1H), 10.54 (s, 1H).

Example 1-320

MS ESI m/e: 564 (M+H), 562 (M−H).
$^1$H-NMR (DMSO-d$_6$, 300 MHz) δ 0.70-0.79 (m, 2H), 0.92 (t, J=7.3 Hz, 3H), 0.99-1.09 (m, 2H), 1.58-1.74 (m, 2H), 2.62-2.72 (m, 1H), 2.66 (s, 3H), 3.05-3.14 (m, 2H), 4.32 (s, 1H), 5.51 (s, 1H), 7.09-7.16 (m, 1H), 7.24-7.34 (m, 2H), 7.35-7.50 (m, 2H), 7.50-7.61 (m, 2H), 10.04 (brs, 1H), 10.73 (s, 1H).

Example 1-321

MS ESI m/e: 564 (M+H), 562 (M−H).
$^1$H-NMR (DMSO-d$_6$, 300 MHz) δ 0.70-0.79 (m, 2H), 0.99-1.08 (m, 2H), 1.23 (d, J=6.6 Hz, 6H), 2.62-2.71 (m, 1H), 2.65 (s, 1H), 3.18-3.30 (m, 1H), 4.31 (s, 1H), 5.51 (s, 1H), 7.08-7.14 (m, 1H), 7.26-7.35 (m, 2H), 7.35-7.48 (m, 2H), 7.50-7.61 (m, 2H), 10.00 (brs, 1H), 10.73 (s, 1H).

Example 1-322

MS ESI m/e: 655 (M+H), 653 (M−H).
$^1$H-NMR (DMSO-d$_6$, 300 MHz) δ 0.69-0.79 (m, 2H), 0.99-1.09 (m, 2H), 2.61-2.71 (m, 4H), 3.02 (s, 3H), 5.49 (s, 1H), 7.15 (d, J=9.0 Hz, 1H), 7.25-7.31 (m, 2H), 7.38-7.49 (m, 2H), 7.74-7.77 (m, 1H), 8.00 (s, 1H), 9.99 (brs, 1H), 10.76 (brs, 1H).

Example 1-323

MS ESI m/e: 625, 627 (M+H), 623, 625 (M−H).
$^1$H-NMR (DMSO-d$_6$, 300 MHz) δ 0.70-0.79 (m, 2H), 0.98-1.09 (m, 2H), 1.70 (quint, J=7.2 Hz, 2H), 2.11 (s, 6H), 2.21 (t, J=7.2 Hz, 2H), 2.33 (t, J=7.3 Hz, 2H), 2.62-2.72 (m, 1H), 2.66 (s, 3H), 5.35 (d, J=1.1 Hz, 1H), 7.04-7.11 (m, 1H), 7.41 (t, J=8.1 Hz, 1H), 7.45-7.54 (m, 2H), 7.60-7.67 (m, 1H), 7.69-7.78 (m, 2H), 10.13 (brs, 1H), 10.54 (brs, 1H).

Example 1-324

MS ESI m/e: 583, 585 (M+H), 581, 583 (M−H).
$^1$H-NMR (DMSO-d$_6$, 300 MHz) δ 0.69-0.79 (m, 2H), 0.97-1.08 (m, 2H), 2.62-2.74 (m, 1H), 2.69 (s, 3H), 2.92 (s, 6H), 5.35 (d, J=1.1 Hz, 1H), 6.94-7.01 (m, 1H), 7.34 (t, J=8.1 Hz, 1H), 7.46-7.54 (m, 2H), 7.54-7.61 (m, 2H), 7.70-7.77 (m, 1H), 8.51 (brs, 1H), 10.54 (brs, 1H).

Example 1-325

MS ESI m/e: 569, 571 (M+H), 567, 569 (M−H).
$^1$H-NMR (DMSO-d$_6$, 300 MHz) δ 0.69-0.80 (m, 2H), 0.98-1.09 (m, 2H), 2.63 (d, J=4.9 Hz, 3H), 2.65-2.73 (m, 1H), 2.68 (s, 3H), 5.35 (d, J=1.1 Hz, 1H), 6.00-6.08 (m, 1H), 6.89-6.95 (m, 1H), 7.33 (t, J=7.9 Hz, 1H), 7.38-7.45 (m, 1H), 7.46-7.52 (m, 2H), 7.52-7.56 (m, 1H), 7.69-7.77 (m, 1H), 8.77 (brs, 1H), 10.55 (brs, 1H).

Example 1-326

MS ESI m/e: 465 (M+H), 463 (M−H).
$^1$H-NMR (DMSO-d$_6$, 300 MHz) δ 0.70-0.80 (m, 2H), 0.99-1.08 (m, 2H), 2.59 (s, 3H), 2.62-2.72 (m, 1H), 3.21 (dt,

J=4.5, 18.3 Hz, 2H), 5.50 (s, 1H), 6.27 (tt, J=4.3, 56.3 Hz, 1H), 7.26-7.34 (m, 2H), 7.34-7.56 (m, 7H), 10.55 (brs, 1H).

Example 1-327

MS ESI m/e: 585, 587 (M+H), 583, 585 (M−1).
$^1$H-NMR (DMSO-d$_6$, 300 MHz) δ 0.75 (brs, 2H), 1.03 (m, 2H), 2.68 (s, 4H), 3.61 (s, 3H), 5.36 (s, 1H), 7.00-7.10 (m, 1H), 7.38 (t, J=8.1 Hz, 1H), 7.45-7.55 (m, 2H), 7.65-7.80 (m, 3H), 9.12 (s, 1H), 9.63 (s, 1H), 10.54 (s, 1H).

Example 1-328

MS ESI m/e: 457 (M+H), 455 (M−H).
$^1$H-NMR (DMSO-d$_6$, 300 MHz) δ 0.74-0.81 (m, 2H), 1.01-1.10 (m, 2H), 2.60 (s, 3H), 2.65-2.74 (m, 1H), 5.50 (s, 1H), 7.32 (dd, J=1.9, 8.7 Hz, 1H), 7.40-7.56 (m, 6H), 7.82-7.87 (m, 2H), 8.07 (d, J=8.3 Hz, 1H), 10.63 (brs, 1H).

Example 1-329

MS ESI m/e: 437 (M+H), 435 (M−H).
$^1$H-NMR (CDCl$_3$, 400 MHz) δ 2.89 (s, 3H), 7.15-7.55 (m, 5H), 10.35 (s, 1H).

Example 1-330

MS ESI m/e: 347 (M+H), 345 (M−H).
$^1$H-NMR (CDCl$_3$, 300 MHz) δ 3.41 (s, 3H), 3.53 (s, 3H), 3.56 (s, 3H), 7.15-7.23 (m, 2H), 7.32-7.38 (m, 2H), 10.45 (s, 1H).

Example 1-331

MS ESI m/e: 458 (M+H), 456 (M−H).
$^1$H-NMR (CDCl$_3$, 300 MHz) δ 0.40-0.57 (m, 4H), 1.24-1.37 (m, 1H), 2.81 (s, 3H), 2.97 (s, 6H), 3.91 (d, J=7.0 Hz, 2H), 5.61 (s, 1H), 6.70-6.77 (m, 2H), 7.10-7.17 (m, 2H), 7.33-7.54 (m, 5H), 10.22 (s, 1H).

Example 1-332

MS ESI m/e: 495 (M+H), 496, 493 (M−H), 494.
$^1$H-NMR (DMSO-d$_6$, 300 MHz) δ 2.70 (s, 3H), 3.84 (s, 3H), 5.88 (s, 1H), 7.36-7.55 (m, 10H), 7.46 (d, J=9.0 Hz, 2H), 7.99 (d, J=9.0 Hz, 2H), 10.85 (brs, 1H).

Example 1-333

MS ESI m/e: 604, 606 (M+H), 602, 604 (M−H).
$^1$H-NMR(DMSO-d$_6$, 400 MHz)δ 0.66-0.74(m, 2H), 0.98-1.06(m, 2H), 1.56(s, 3H), 2.60-2.69(m, 1H), 2.74(s, 3H), 3.03(s, 3H), 6.80(t, J=8.9 Hz, 1H), 7.10-7.15(m, 1H), 7.25-7.36(m, 3H), 7.46(t, J=8.0 Hz, 1H), 7.59-7.64(m, 1H), 9.99(s, 1H), 10.17(s, 1H).

Example 1-334

MS ESI m/e: 556(M+H), 554(M−H).
$^1$H-NMR(DMSO-d$_6$, 300 MHz) δ 0.69-0.78(m, 2H), 0.99-1.08(m, 2H), 2.74(s, 3H), 2.61-2.72(m, 1H), 2.69-2.79 (m, 2H), 2.98-3.09(m, 2H), 5.36(s, 1H), 5.92(brs, 1H), 6.51-6.68(m, 3H), 7.15-7.20(m, 2H), 7.49-7.50(m, 2H), 7.72-7.75(m, 1H), 10.60(brs, 1H).

Example 1-335

MS ESI m/e: 654(M+H), 652(M−H).
$^1$H-NMR(DMSO-d$_6$, 300 MHz) δ 0.67-0.81(m, 2H), 0.96-1.09(m, 2H), 2.36(s, 3H), 2.61-2.69(m, 1H), 5.35(s, 1H), 7.08(d, J=9.0 Hz, 1H), 7.16(d, J=9.0 Hz, 1H), 7.31-7.39(m, 2H), 7.48-7.53(m, 2H), 7.57-7.62(m, 1H), 7.74(d, J=9.0 Hz, 1H), 8.10(d, J=9.0 Hz, 1H), 8.77-8.80(m, 1H), 8.88-8.90(m, 1H), 10.52(brs, 1H), 10.69(brs, 1H).

Example 1-336

MS ESI m/e: 532(M+H), 530(M−H).
$^1$H-NMR(DMSO-d$_6$, 300 MHz) δ 0.71-0.80(m, 2H), 0.99-1.09(m, 2H), 2.25(s, 3H), 2.61-2.73(m, 1H), 2.64(s, 3H), 3.01(s, 3H), 4.17(s, 1H), 5.27(s, 1H), 7.14-7.48(m, 7H), 9.98(brs, 1H), 10.50(brs, 1H).

Example 1-337

MS ESI m/e: 552(M+H), 550(M−H).
$^1$H-NMR(DMSO-d$_6$, 300 MHz) δ 0.68-0.78(m, 2H), 0.99-1.10(m, 2H), 2.66(s, 3H), 2.61-2.76(m, 1H), 3.01(s, 3H), 4.31(s, 1H), 5.61(s, 1H), 7.13(d, J=12.0 Hz, 1H), 7.22-7.32(m, 2H), 7.41-7.51(m, 2H), 7.61(d, J=6.0 Hz, 1H), 7.74(s, 1H), 9.98(brs, 1H), 10.90(brs, 1H).

Example 1-338

MS ESI m/e: 558 (M+H), 556 (M−H).
$^1$H-NMR(DMSO-d$_6$, 300 MHz)δ 0.70-0.81(m, 2H), 0.99-1.08(m, 2H), 2.61-2.71(m, 1H), 2.65(s, 3H), 3.02(dt, J=18.8, 3.4 Hz, 2H), 3.02(s, 3H), 4.69(dt, J=47.1, 3.0 Hz, 2H), 5.28(s, 1H), 7.10-7.16(m, 1H), 7.17-7.23(m, 1H), 7.23-7.29 (m, 1H), 7.29-7.39(m, 2H), 7.41-7.50(m, 2H), 10.00(brs, 1H), 10.43(s, 1H).

Example 1-339

MS ESI m/e: 690(M+H), 688(M−H).
$^1$H-NMR(DMSO-d$_6$, 300 MHz) δ 0.69-0.79(m, 2H), 0.98-1.09(m, 2H), 2.22-2.32(m, 4H), 2.64(s, 3H), 2.60-2.71 (m, 3H), 3.25-3.41(m, 2H), 3.41-3.51(m, 4H), 5.34(s, 1H), 7.09(d, J=6.0 Hz, 1H), 7.23-7.35(m, 2H), 7.40-7.51(m, 3H), 7.73(d, J=12.0 Hz, 1H), 10.08(brs, 1H), 10.52(brs, 1H).

Example 1-340

MS ESI m/e: 634(M+H), 632(M−H).
$^1$H-NMR(DMSO-d$_6$, 300 MHz) δ 0.70-0.79(m, 2H), 0.98-1.09(m, 2H), 2.22(s, 3H), 2.60-2.69(m, 1H), 2.63(s, 3H), 3.01(s, 3H), 5.14(s, 1H), 7.13(d, J=9.0 Hz, 2H), 7.22-7.30(m, 2H), 7.41-7.48(m, 1H), 7.61-7.64(m, 1H), 7.74(s, 1H), 9.98(brs, 1H), 10.32(brs, 1H).

Example 1-341

MS ESI m/e: 522 (M+H), 520 (M−H).
$^1$H-NMR(CDCl$_3$, 300 MHz)δ 0.70-0.80(m, 2H), 0.97-1.09(m, 2H), 2.06(s, 3H), 2.54(s, 3H), 2.63-2.72(m, 1H), 2.66(s, 3H), 5.23-5.26(m, 2H), 7.05-7.20(m, 2H), 7.28-7.49 (m, 3H), 7.61-7.73(m, 2H), 10.17(brs, 1H), 10.41(brs, 1H).

Example 1-342

MS ESI m/e: 522 (M+H), 520 (M–H).
$^1$H-NMR(DMSO-d$_6$, 300 MHz)δ 0.69-0.79(m, 2H), 0.97-1.10(m, 2H), 2.04(s, 3H), 2.60-2.73(m, 1H), 2.65(s, 3H), 3.02(dt, J=25.2, 2.8 Hz, 2H), 4.69(dt, J=47.1, 3.2 Hz, 2H), 5.27(s, 1H), 7.02-7.11(m, 1H), 7.16-7.23(m, 1H), 7.29-7.49 (m, 3H), 7.61-7.71(m, 2H), 10.16(brs, 1H), 10.44(brs, 1H).

Example 1-343

MS ESI m/e: 475 (M+H), 473 (M–H).
$^1$H-NMR(CDCl$_3$, 300 MHz)δ 0.85-0.94(m, 2H), 1.16-1.24(m, 2H), 2.75-2.83(m, 1H), 2.82(s, 3H), 5.54-5.58(m, 1H), 7.30-7.38(m, 3H), 7.43-7.54(m, 5H), 7.63-7.69(m, 1H), 10.28(brs, 1H).

Example 2-1

MS ESI m/e: 472 (M+H), 470 (M–H).
$^1$H-NMR (DMSO-d$_6$, 400 MHz) δ 2.68 (s, 3H), 7.34-7.39 (m, 2H), 7.41-7.61 (m, 10H), 7.80-7.87 (m, 2H), 11.34 (s, 1H).

Example 2-2

MS ESI m/e: 592 (M+H), 590 (M–H).
$^1$H-NMR (DMSO-d$_6$, 300 MHz) δ 0.70-0.82 (m, 2H), 1.01-1.13 (m, 2H), 2.64-2.75 (m, 1H), 2.67 (s, 3H), 3.05 (s, 3H), 7.19-7.27 (m, 1H), 7.27-7.34 (m, 1H), 7.35-7.39 (m, 1H), 7.45-7.54 (m, 2H), 7.71 (dd, J=3.0, 12.0 Hz, 1H), 8.51 (t, J=9.0 Hz, 1H), 10.05 (s, 1H), 11.61 (d, J=3.0 Hz, 1H).

Example 3-1

MS ESI m/e: 493, 495 (M+H), 491, 493 (M–H).
$^1$H-NMR (CDCl$_3$, 400 MHz) δ 0.77-0.82 (m, 2H), 1.09-1.15 (m, 2H), 1.36 (s, 3H), 2.72-2.74 (m, 1H), 3.20 (s, 3H), 6.86 (d, 2H), 7.28-7.32 (m, 2H), 7.34-7.51 (m, 5H), 11.36 (s, 1H).

Example 3-2

MS ESI m/e: 479, 481 (M+H), 477, 479 (M–H).
$^1$H-NMR (CDCl$_3$, 400 MHz) δ 0.83-0.90 (m, 2H), 1.10-1.18 (m, 2H), 2.67-2.76 (m, 1H), 3.11 (s, 3H), 5.00 (s, 1H), 7.02 (d, J=8.6 Hz, 2H), 7.10-7.15 (m, 2H), 7.19-7.25 (m, 1H), 7.34-7.41 (m, 2H), 7.63-7.70 (m, 2H), 11.71 (s, 1H).

Example 3-3

MS ESI m/e: 479, 481 (M+H), 477, 479 (M–H).
$^1$H-NMR (CDCl$_3$, 300 MHz) δ 0.83-0.92 (m, 2H), 1.09-1.19 (m, 2H), 2.67-2.78 (m, 1H), 3.13 (s, 3H), 5.06 (s, 1H), 6.87-6.94 (m, 2H), 7.21-7.28 (m, 2H), 7.45-7.60 (m, 5H), 11.68 (s, 1H).

Example 3-4

MS ESI m/e: 604 (M+H), 606, 602 (M–H), 604.
$^1$H-NMR (DMSO-d$_6$, 300 MHz) δ 0.65-0.69 (m, 2H), 0.93-0.98 (m, 2H), 1.25 (s, 3H), 2.59-2.64 (m, 1H), 3.01 (s, 3H), 3.08 (s, 3H), 7.08-7.13 (m, 2H), 7.21-7.25 (m, 2H), 7.39-7.43 (m, 2H), 7.70-7.74 (m, 1H), 9.90 (brs, 1H), 11.09 (brs, 1H).

Example 3-5

MS ESI m/e: 618 (M+H), 620, 616 (M–H), 618.
$^1$H-NMR (DMSO-d$_6$, 300 MHz) δ 0.64-0.69 (m, 2H), 0.92-0.98 (m, 2H), 1.19 (t, J=9.8 Hz, 3H), 1.24 (s, 3H), 2.58-2.64 (m, 1H), 3.11 (q, J=9.8 Hz, 2H), 3.08 (s, 3H), 7.07-7.13 (m, 2H), 7.21-7.25 (m, 2H), 7.37-7.42 (m, 2H), 7.70-7.74 (m, 2H), 9.95 (brs, 1H), 11.09 (brs, 1H).

Example 3-6

MS ESI m/e: 604 (M+H), 606, 602 (M–H), 604.
$^1$H-NMR (DMSO-d$_6$, 300 MHz) δ 0.64-0.69 (m, 2H), 0.92-0.99 (m, 2H), 1.25 (s, 3H), 2.04 (s, 3H), 2.58-2.66 (m, 1H), 3.08 (s, 3H), 7.01-7.13 (m, 2H), 7.33-7.43 (m, 2H), 7.58-7.60 (m, 2H), 7.70-7.74 (m, 1H), 10.10 (brs, 1H), 11.09 (brs, 1H).

Example 3-7

MS ESI m/e: 652 (M+H), 650 (M–H).
$^1$H-NMR (DMSO-d$_6$, 300 MHz) δ 0.62-0.72 (m, 2H), 0.91-1.01 (m, 2H), 1.25 (s, 3H), 2.57-2.67 (m, 1H), 3.01 (s, 3H), 3.08 (s, 3H), 6.92 (t, J=9.0 Hz, 1H), 7.09-7.14 (m, 1H), 7.20-7.26 (m, 2H), 7.37-7.45 (m, 1H), 7.52-7.58 (m, 1H), 7.79 (dd, J=1.8, 9.0 Hz, 1H), 9.89 (s, 1H), 11.08 (s, 1H).

Example 3-8

MS ESI m/e: 550 (M+H), 548 (M–H).
$^1$H-NMR (DMSO-d$_6$, 300 MHz) δ 0.62-0.71 (m, 2H), 0.90-1.01 (m, 2H), 1.26 (s, 3H), 2.56-2.66 (m, 1H), 3.01 (s, 3H), 3.10 (s, 3H), 4.30 (s, 1H), 7.05-7.16 (m, 2H), 7.20-7.27 (m, 2H), 7.32 (dd, J=1.7, 9.0 Hz, 1H), 7.37-7.45 (m, 1H), 7.52 (dd, J=1.7, 12.0 Hz, 1H), 9.90 (s, 1H), 11.10 (s, 1H).

Example 3-9

MS ESI m/e: 639 (M+H), 638, 637 (M–H).
$^1$H-NMR (DMSO-d$_6$, 300 MHz) δ 0.65-0.73 (m, 2H), 0.93-0.98 (m, 2H), 1.26 (s, 3H), 2.58-2.65 (m, 1H), 3.05 (s, 3H), 3.08 (s, 3H), 7.11 (dd, J=10.1 Hz, 13.0 Hz, 1H), 7.32 (d, J=11.6 Hz, 1H), 7.42 (d, J=10.1 Hz, 1H), 7.48 (s, 1H), 7.63 (d, J=11.6 Hz, 1H), 7.72 (d, J=13.0 Hz, 1H), 9.65 (brs, 1H), 11.08 (brs, 1H).

Example 4-1

MS ESI m/e: 616 (M+H), 614 (M–H).
$^1$H-NMR(DMSO-d$_6$, 400 MHz)δ 0.63-0.70(m, 2H), 0.91-1.00(m, 2H), 1.25(s, 3H), 2.04(s, 3H), 2.58-2.66(m, 1H), 3.07(s, 3H), 6.92(t, J=8.8 Hz, 1H), 7.00-7.05(m, 1H), 7.36(t, J=8.2 Hz, 1H), 7.52-7.63(m, 3H), 7.79(dd, J=2.0, 10.4 Hz, 1H), 10.10(s, 1H), 11.08(s, 1H).

Example 4-2

MS ESI m/e: 666 (M+H), 664 (M–H).
$^1$H-NMR(DMSO-d$_6$, 300 MHz)δ 0.62-0.71(m, 2H), 0.91-1.01(m, 2H), 1.19(t, J=7.2 Hz, 3H), 1.24(s, 3H), 2.56-2.67 (m, 1H), 3.08(s, 3H), 3.11(q, J=7.2 Hz, 2H), 6.92(t, J=8.7 Hz, 1H), 7.09(d, J=8.1 Hz, 1H), 7.21-7.28(m, 2H), 7.40(t, J=8.3 Hz, 1H), 7.55(d, J=8.1 Hz, 1H), 7.79(dd, J=1.8, 10.5 Hz, 1H), 9.94(s, 1H), 11.08(s, 1H).

Example 4-3

MS ESI m/e: 514 (M+H), 512 (M−H).
$^1$H-NMR(DMSO-$d_6$, 400 MHz)δ 0.63-0.70(m, 2H), 0.91-0.99(m, 2H), 1.26(s, 3H), 2.04(s, 3H), 2.58-2.66(m, 1H), 3.10(s, 3H), 4.30(s, 1H), 7.01-7.06(m, 1H), 7.09(t, J=8.4 Hz, 1H), 7.31(dd, J=1.6, 8.4 Hz, 1H), 7.36(t, J=7.8 Hz, 1H), 7.52(dd, J=1.6, 11.6 Hz, 1H), 7.57-7.63(m, 2H), 10.10(s, 1H), 11.10(s, 1H)

Example 4-4

MS ESI m/e: 568,570(M+H), −566,568(M−H)
$^1$H-NMR(DMSO-$d_6$, 300 MHz) 0.61-0.65(m, 2H), 0.90-0.95(m, 2H), 1.20(s, 3H), 2.04(s, 3H), 2.56-2.61(m, 1H), 3.04(s, 3H), 7.07(dd, J=8.6, 10.7 Hz, 1H), 7.25(d, J=8.8 Hz, 2H), 7.38(d, J=10.7 Hz, 1H), 7.60(d, J=8.8 Hz, 2H), 7.69(d, J=8.6 Hz, 1H), 10.07(s, 1H), 11.05(s, 1H)

Example 4-5

MS ESI m/e: 556,558(M+1).
$^1$H-NMR(DMSO-$d_6$, 400 MHz)δ 0.63-0.67(m, 2H), 0.91-0.96(m, 2H), 1.17(s, 3H), 2.56-2.62(m, 1H), 3.05(s, 3H), 7.11(dd, J=8.6, 10.4 Hz, 1H), 7.40(d, J=8.6 Hz, 1H), 7.66(d, J=9.3 Hz, 2H), 7.69(dd, J=2.1, 10.4 Hz, 1H), 8.30(d, J=9.3 Hz, 2H), 10.94(s, 1H)

Example 4-6

MS ESI m/e: 564 (M+H), 562 (M−H).
$^1$H-NMR(DMSO-$d_6$, 400 MHz)δ 0.64-0.70(m, 2H), 0.92-0.99(m, 2H), 1.19(t, J=7.4 Hz, 3H), 1.25(s, 3H), 2.57-2.65(m, 1H), 3.10(s, 3H), 3.11(q, J=7.4 Hz, 2H), 4.31(s, 1H), 7.06-7.12(m, 2H), 7.22-7.27(m, 2H), 7.32(dd, J=1.6, 8.0 Hz, 1H), 7.40(t, J=8.0 Hz, 1H), 7.52(dd, J=1.6, 11.6 Hz, 1H), 9.95(s, 1H), 11.10(s, 1H).

Example 4-7

MS ESI m/e: 490 (M+H), 488 (M−H).
$^1$H-NMR(DMSO-$d_6$, 400 MHz)δ 0.64-0.71(m, 2H), 0.91-0.99(m, 2H), 1.25(s, 3H), 2.04(s, 3H), 2.60-2.67(m, 1H), 3.05(s, 3H), 7.02-7.06(m, 1H), 7.13-7.19(m, 1H), 7.20-7.29(m, 2H), 7.33-7.41(m, 2H), 7.57-7.63(m, 2H), 10.10(s, 1H), 11.23(s, 1H).

Example 4-8

MS ESI m/e: 604, 606(M+H), 602, 604(M−H).
1H-NMR(DMSO-d6, 300 MHz)δ 0.63-0.69(m, 2H), 0.92-0.99(m, 2H), 1.23(s, 3H), 2.57-2.67(m, 1H), 3.04(s, 3H), 3.07(s, 3H), 7.08-7.14(m, 1H), 7.26(d, J=9.0 Hz, 2H), 7.34(d, J=9.0 Hz, 2H), 7.39-7.44(m, 1H), 7.70-7.75(m, 1H), 9.96(s, 1H), 11.08(s, 1H)

Example 4-9

MS ESI m/e: 518 (M+H), 516 (M−H).
$^1$H-NMR(DMSO-$d_6$, 400 MHz)δ 0.64-0.71(m, 2H), 0.92-1.00(m, 2H), 1.19(t, J=7.6 Hz, 3H), 1.24(s, 3H), 2.04(s, 3H), 2.59-2.67(m, 1H), 2.62(q, J=7.6 Hz, 2H), 3.03(s, 3H), 7.01-7.11(m, 3H), 7.23(d, J=11.6 Hz, 1H), 7.36(t, J=8.2 Hz, 1H), 7.56-7.63(m, 2H), 10.10(s, 1H), 11.23(s, 1H).

Example 4-10

MS ESI m/e: 603, 605 (M+H), 601, 603 (M−H).
$^1$H-NMR(CDCl$_3$, 300 MHz)δ 0.77-0.84(m, 2H), 1.11-1.18(m, 2H), 1.32(t, J=7.3 Hz, 3H), 1.33(s, 3H), 2.70-2.78(m, 1H), 3.15(q, J=7.5 Hz, 2H), 3.20(s, 3H), 6.89(t, J=8.3 Hz, 1H), 7.28-7.32(m, 1H), 7.36(dd, J=2.3, 9.8 Hz, 1H), 7.60-7.69(m, 2H), 7.86-7.93(m, 2H), 11.28(s, 1H).

Example 4-11

MS ESI m/e: 516 (M+H), 514 (M−H).
$^1$H-NMR(DMSO-$d_6$, 400 MHz)δ 0.64-0.71(m, 2H), 0.92-1.00(m, 2H), 1.25(s, 3H), 2.04(s, 3H), 2.59-2.67(m, 1H), 3.07(s, 3H), 5.32(d, J=11.1 Hz, 1H), 5.89(d, J=17.6 Hz, 1H), 6.73(dd, J=10.9, 17.6 Hz, 1H), 7.01-7.06(m, 1H), 7.11(t, J=8.6 Hz, 1H), 7.28-7.33(m, 1H), 7.33-7.40(m, 1H), 7.51-7.57(m, 1H), 7.57-7.63(m, 2H), 10.10(s, 1H), 11.22(s, 1H).

Example 4-12

MS ESI m/e: 729 (M+H), 727 (M−H).
$^1$H-NMR(DMSO-$d_6$, 300 MHz)δ 0.65-0.68 (m, 2H), 0.83 (t, J=7.3 Hz, 3H), 0.93-0.97 (m, 2H), 1.23-1.26 (m, 5H), 1.40-1.50 (m, 2H), 2.04 (t, J=7.5 Hz, 2H), 2.48-2.50 (m, 2H), 2.59-2.64 (m, 1H), 3.08 (s, 3H), 3.28-3.33 (m, 2H), 6.92 (t, J=8.7 Hz, 1H), 7.03 (d, J=7.9 Hz, 1H), 7.36 (t, J=8.1 Hz, 1H), 7.56-7.59 (m, 2H), 7.64-7.66 (m, 1H), 7.79 (dd, J=10.4, 1.7 Hz, 1H), 7.90 (t, J=5.7 Hz, 1H), 10.10 (s, 1H), 11.08 (s, 1H).

Example 4-13

MS ESI m/e: 603 (M+H), 601 (M−H).
$^1$H-NMR(DMSO-$d_6$, 300 MHz)δ 0.66-0.69 (m, 2H), 0.83 (t, J=7.2 Hz, 3H), 0.93-0.98 (m, 2H), 1.17-1.29 (m, 5H), 1.40-1.50 (m, 2H), 2.04 (t, J=7.3 Hz, 2H), 2.47-2.51 (m, 2H), 2.61-2.65 (m, 1H), 3.05 (s, 3H), 3.29-3.33 (m, 2H), 7.04 (d, J=9.0 Hz, 1H), 7.19-7.34 (m, 5H), 7.59 (d, J=8.7 Hz, 1H), 7.66 (s, 1H), 7.91 (t, J=5.3 Hz, 1H), 10.10 (s, 1H), 11.23 (s, 1H).

Example 4-14

MS ESI m/e: 685 (M+H), 683 (M−H).
$^1$H-NMR(DMSO-$d_6$, 300 MHz)δ 0.64-0.70(m, 2H), 0.82 (t, J=7.3 Hz, 3H), 0.90-0.98(m, 2H), 1.14-1.28(m, 4H), 1.25(s, 3H), 1.37-1.49(m, 2H), 1.45(s, 6H), 2.04(t, J=7.3 Hz, 2H), 2.58-2.65(m, 1H), 3.07(s, 3H), 3.27-3.34(m, 2H), 5.49(brs, 1H), 6.99-7.11(m, 2H), 7.18-7.25(m, 1H), 7.31-7.42(m, 2H), 7.55-7.67(m, 2H), 7.85-7.93(m, 1H), 10.09(s, 1H), 11.14(s, 1H).

Example 4-15

MS ESI m/e: 590 (M+H), 588 (M−H).
$^1$H-NMR(CDCl$_3$, 300 MHz)δ 1.42(s, 3H), 2.16(s, 3H), 3.21(s, 3H), 3.37(s, 3H), 6.69(t, J=8.3 Hz, 1H), 7.04-7.10(m, 1H), 7.31-7.55(m, 5H), 7.70(s, 1H), 11.41(s, 1H).

Example 4-16

MS ESI m/e: 626 (M+H), 624 (M−H).
$^1$H-NMR(DMSO-$d_6$, 300 MHz)δ 1.26(s, 3H), 3.01(s, 3H), 3.09(s, 3H), 3.21(s, 3H), 6.93(t, J=8.3 Hz, 1H), 7.11-

7.15(m, 1H), 7.20-7.28(m, 2H), 7.42(t, J=8.3 Hz, 1H), 7.52-7.57(m, 1H), 7.76-7.81(m, 1H), 9.94(br, 1H), 11.21(br, 1H).

Example 4-17

MS ESI m/e: 630 (M+H), 628 (M−H).
$^1$H-NMR(CDCl$_3$, 300 MHz)δ 0.75-0.81(m, 2H), 1.05-1.15(m, 5H), 1.41(s, 3H), 2.15(s, 3H), 2.68-2.77(m, 1H), 3.90-4.00(m, 2H), 6.72(t, J=8.3 Hz, 1H), 6.97-7.03(m, 1H), 7.30-7.54(m, 5H), 7.65-7.69(m, 1H), 11.07(s, 1H).

Example 4-18

MS ESI m/e: 666 (M+H), 664 (M−H).
$^1$H-NMR(CDCl$_3$, 300 MHz)δ 0.75-0.81(m, 2H), 1.06-1.15(m, 5H), 1.39(s, 3H), 2.68-2.76(m, 1H), 3.02(s, 3H), 3.90-4.00(m, 2H), 6.74(t, J=8.3 Hz, 1H), 6.93-6.99(m, 1H), 7.07-7.13(m, 1H), 7.20-7.26(m, 2H), 7.38-7.54(m, 3H), 11.07(s, 1H).

Example 4-19

MS ESI m/e: 654 (M+H), 652 (M−H).
$^1$H-NMR(DMSO-d$_6$, 300 MHz)δ 1.13(t, J=6.8 Hz, 3H), 1.20(t, J=7.2 Hz, 3H), 1.25(s, 3H), 3.08(s,3H), 3.12(q, J=7.4 Hz, 2H), 3.87(d, J=7.1 Hz, 2H), 6.94(t, J=8.6 Hz, 1H), 7.12(d, J=8.0 Hz, 1H), 7.25(d, J=8.4 Hz, 1H), 7.29(s, 1H), 7.41(t, J=8.0 Hz, 1H), 7.55(d, J=8.5 Hz, 1H), 7.79(d, J=10.5 Hz, 1H), 9.98 (s,1H), 11.24 (s, 1H).

Example 4-20

MS ESI m/e: 640 (M+H), 638 (M−H).
$^1$H-NMR(DMSO-d$_6$, 300 MHz)δ 1.13(t, J=6.8 Hz, 3H), 1.26(s, 3H), 3.02(s, 3H), 3.09(s, 3H), 3.88(q, J=6.8 Hz, 2H), 6.95(t, J=8.5 Hz, 1H), 7.11-7.18(m, 1H), 7.21-7.30(m, 2H), 7.43(t, J=7.7 Hz, 1H), 7.55(d, J=9.0 Hz, 1H), 7.76-7.82(m, 1H), 9.94(brs, 1H), 11.24(brs, 1H).

Example 4-21

MS ESI m/e: 604 (M+H), 602 (M−H).
$^1$H-NMR(DMSO-d$_6$, 300 MHz)δ 1.13(t, J=6.8 Hz, 3H), 1.26(s, 3H), 2.04(s, 3H), 3.08(s, 3H), 3.87(q, J=7.5 Hz, 2H), 6.94(t, J=8.5 Hz, 1H), 7.05-7.11(m, 1H), 7.37(t, J=7.9 Hz, 1H), 7.51-7.60(m, 2H), 7.65-7.71(m, 1H), 7.78(d, J=10.2 Hz, 1H), 10.10(brs, 1H), 11.23(brs, 1H).

Example 4-22

MS ESI m/e: 666 (M+H), 664 (M−H).
$^1$H-NMR(DMSO-d$_6$, 400 MHz)δ 0.47(t, J=7.2 Hz, 3H), 0.63-0.69(m, 2H), 0.90-0.97(m, 2H), 1.76-1.94(m, 2H), 2.57-2.63(m, 1H), 3.00(s, 3H), 3.07(s, 3H), 6.93(t, J=8.8 Hz, 1H), 7.12-7.16(m, 1H), 7.23-7.30(m, 2H), 7.42(t, J=8.0 Hz, 1H), 7.53-7.58(m, 1H), 7.79(dd, J=1.6, 10.0 Hz, 1H), 9.91(s, 1H), 11.07(s, 1H).

Example 4-23

MS ESI m/e: 680 (M+H), 678 (M−H).
$^1$H-NMR(DMSO-d$_6$, 300 MHz)δ 0.47(t, J=7.4 Hz, 3H), 0.61-0.70(m, 2H), 0.89-0.98(m, 2H), 1.20(t, J=7.4 Hz, 3H), 1.74-1.95(m, 2H), 2.55-2.65(m, 1H), 3.07(s, 3H), 3.11(q, J=7.4 Hz, 2H), 6.92(t, J=8.6 Hz, 1H), 7.11(d, J=7.8 Hz, 1H), 7.22-7.31(m, 2H), 7.40(t, J=7.9 Hz, 1H), 7.56(d, J=8.7 Hz, 1H), 7.79(d, J=10.2 Hz, 1H), 9.97(s, 1H), 11.07(s, 1H).

Example 4-24

MS ESI m/e: 630 (M+H), 628 (M−H).
$^1$H-NMR(DMSO-d$_6$, 300 MHz)δ 0.47(t, J=7.2 Hz, 3H), 0.60-0.69(m, 2H), 0.87-0.98(m, 2H), 1.79-1.93(m, 2H), 2.04 (s, 3H), 2.56-2.66(m, 1H), 3.07(s, 3H), 6.92(t, J=8.6 Hz, 1H), 7.07(d, J=8.4 Hz, 1H), 7.37(t, J=8.1 Hz, 1H), 7.53-7.69(m, 3H), 7.79(d, J=10.2 Hz, 1H), 10.09(s, 1H), 11.07(s, 1H).

Example 4-25

MS ESI m/e: 554 (M+H), 552 (M−H).
$^1$H-NMR(DMSO-d$_6$, 300 MHz)δ 0.64-0.73(m, 2H), 0.91-1.01(m, 2H), 1.19(t, J=7.5 Hz, 3H), 1.24(s, 3H), 2.57-2.68 (m, 1H), 2.62(q, J=7.4 Hz, 2H), 3.01(s, 3H), 3.03(s, 3H), 7.03-7.15(m, 3H), 7.19-7.27(m, 3H), 7.41(t, J=8.1 Hz, 1H), 9.89(s, 1H), 11.24(s, 1H).

Example 4-26

MS ESI m/e: 568 (M+H), 566 (M−H).
$^1$H-NMR(DMSO-d$_6$, 300 MHz)δ 0.62-0.73(m, 2H), 0.91-1.01(m, 2H), 1.18 (t, J=7.5 Hz, 3H), 1.19(t, J=7.2 Hz, 3H), 1.23(s, 3H), 2.57-2.68(m, 1H), 2.62(q, J=7.5 Hz, 2H), 3.03 (s, 3H), 3.11(q, J=7.2 Hz, 2H), 7.03-7.13(m, 3H), 7.19-7.27 (m, 3H), 7.40(t, J=8.1 Hz, 1H), 9.94(s, 1H), 11.24(s, 1H).

Example 4-27

MS ESI m/e: 528 (M+H), 526 (M−H).
$^1$H-NMR(DMSO-d$_6$, 300 MHz)δ 0.48(t, J=7.4 Hz, 3H), 0.60-0.70(m, 2H), 0.88-0.98(m, 2H), 1.77-1.92(m, 2H), 2.04 (s, 3H), 2.55-2.66(m, 1H), 3.10(s, 3H), 4.30(s, 1H), 7.04-7.14(m, 2H), 7.28-7.41(m, 2H), 7.52(d, J=11.7 Hz, 1H), 7.58-7.68(m, 2H), 10.09(s, 1H), 11.08(s, 1H).

Example 4-28

MS ESI m/e: 564 (M+H), 562 (M−H).
$^1$H-NMR(DMSO-d$_6$, 400 MHz)δ 0.48(t, J=7.2 Hz, 3H), 0.63-0.69(m, 2H), 0.90-0.97(m, 2H), 1.78-1.93(m, 2H), 2.56-2.64(m, 1H), 3.01(s, 3H), 3.10(s, 3H), 4.31(s, 1H), 7.09(t, J=8.4 Hz, 1H), 7.13-7.17(m, 1H), 7.23-7.34(m, 3H), 7.42(t, J=8.0 Hz, 1H), 7.52(dd, J=2.0, 11.6 Hz, 1H), 9.92(s, 1H), 11.08(s, 1H).

Example 4-29

MS ESI m/e: 578 (M+H), 576 (M−H).
$^1$H-NMR(DMSO-d$_6$, 300 MHz)δ 0.47(t, J=7.1 Hz, 3H), 0.61-0.70(m, 2H), 0.88-0.98(m, 2H), 1.20(t, J=7.2 Hz, 3H), 1.75-1.95(m, 2H), 2.55-2.64(m, 1H), 3.10(s, 3H), 3.11(q, J=7.2 Hz, 2H), 4.30(s, 1H), 7.04-7.14(m, 2H), 7.23-7.35(m, 3H), 7.40(t, J=7.8 Hz, 1H), 7.52(d, J=11.4 Hz, 1H), 9.97(s, 1H), 11.08(s, 1H).

Example 4-30

MS ESI m/e: 532 (M+H), 530 (M−H).
$^1$H-NMR(DMSO-d$_6$, 400 MHz)δ 0.46(t, J=7.4 Hz, 3H), 0.64-0.70(m, 2H), 0.90-0.97(m, 2H), 1.19(t, J=7.6 Hz, 3H), 1.80-1.90(m, 2H), 2.04(s, 3H), 2.57-2.67(m, 1H), 2.63(q, J=7.6 Hz, 2H), 3.02(s, 3H), 7.04-7.13(m, 3H), 7.23(d,

J=12.0 Hz, 1H), 7.37(t, J=8.0 Hz, 1H), 7.61(d, J=7.6 Hz, 1H), 7.64(t, J=2.0 Hz, 1H), 10.09(s, 1H), 11.24(s, 1H).

Example 4-31

MS ESI m/e: 568 (M+H), 566 (M−H).
$^1$H-NMR(DMSO-$d_6$, 400 MHz)δ 0.47(t, J=7.2 Hz, 3H), 0.63-0.71(m, 2H), 0.90-0.98(m, 2H), 1.19(t, J=7.4 Hz, 3H), 1.74-1.96(m, 2H), 2.57-2.67(m, 1H), 2.63(q, J=7.4 Hz, 2H), 3.01(s, 3H), 3.02(s, 3H), 7.06-7.11(m, 2H), 7.12-7.17(m, 1H), 7.20-7.30(m, 3H), 7.42(t, J=8.0 Hz, 1H), 9.91(s, 1H), 11.24(s, 1H).

Example 4-32

MS ESI m/e: 582 (M+H), 580 (M−H).
$^1$H-NMR(DMSO-$d_6$, 400 MHz)δ 0.46(t, J=7.2 Hz, 3H), 0.64-0.70(m, 2H), 0.90-0.98(m, 2H), 1.19(t, J=7.6 Hz, 3H), 1.20(t, J=7.6 Hz, 3H), 1.75-1.93(m, 2H), 2.58-2.68(m, 1H), 2.63(q, J=7.6 Hz, 2H), 3.02(s, 3H), 3.10(q, J=7.6 Hz, 2H), 7.05-7.14(m, 3H), 7.20-7.31(m, 3H), 7.40(t, J=8.0 Hz, 1H), 9.97(s, 1H), 11.23(s, 1H).

Example 4-33

MS ESI m/e: 681(M+H), 679(M−H).
$^1$H-NMR(DMSO-$d_6$, 300 MHz) δ 0.61-0.69(m, 2H), 0.90-1.00(m, 2H), 1.22(s, 3H), 2.52-2.63(m, 1H), 2.67(s, 6H), 3.06(s, 3H), 6.88-6.94(m, 1H), 7.02-7.09(m, 1H), 7.18-7.21(m, 2H), 7.31-7.39(m, 1H), 7.51-7.56(m, 1H), 7.75-7.81(m, 1H), 10.01(brs, 1H), 11.06(brs, 1H).

Example 4-34

MS ESI m/e: 723(M+H), 721(M−H).
$^1$H-NMR(DMSO-$d_6$, 300 MHz) δ 0.61-0.70(m, 2H), 0.90-0.99(m, 2H), 1.24(s, 3H), 2.55-2.64(m, 1H), 3.06(s, 3H), 2.99-3.10(m, 4H), 3.43-3.53(m, 4H), 6.88-6.92(m, 1H), 7.05-7.09(m, 2H), 7.14-7.22(m, 1H), 7.31-7.40(m, 1H), 7.51-7.59(m, 1H), 7.75-7.81(m, 1H), 10.21(brs, 1H), 11.08(brs, 1H).

Example 4-35

MS ESI m/e: 519 (M+H), 517 (M−H).
$^1$H-NMR(DMSO-$d_6$, 300 MHz)δ 0.64-0.71(m, 2H), 0.92-1.00(m, 2H), 1.26(s, 3H), 2.59-2.67(m, 1H), 2.73(t, J=7.0 Hz, 2H), 3.02-3.12(m, 2H), 3.05(s, 3H), 7.04-7.43(m, 6H), 7.58-7.63(m, 1H), 7.67(s, 1H), 7.77-7.88(m, 3H), 10.39(s, 1H), 11.23(s, 1H).

Example 4-36

MS ESI m/e: 645 (M+H), 643 (M−H).
$^1$H-NMR(DMSO-$d_6$, 300 MHz)δ 0.62-0.70(m, 2H), 0.92-0.98(m, 2H), 1.26(s, 3H), 2.59-2.66(m, 1H), 2.72(t, J=7.2 Hz, 2H), 3.03-3.13(m, 2H), 3.08(s, 3H), 6.93(t, J=8.4 Hz, 1H), 7.03-7.08(m, 1H), 7.39(t, J=8.4 Hz, 1H), 7.53-7.68(m, 3H), 7.72-7.85(m, 4H), 10.37(s, 1H), 11.08(s, 1H).

Example 4-37

MS ESI m/e: 650(M+H), 648(M−H).
$^1$H-NMR(DMSO-$d_6$, 300 MHz)δ 0.64-0.69(m, 2H), 0.92-0.99(m, 2H), 1.31(s, 3H), 2.06(s, 3H), 2.57-2.64(m, 1H), 3.08(s, 3H), 6.93(dd, J=9.3,11.1 Hz, 1H), 7.19(s, 1H), 7.46(s, 1H), 7.55(d, J=9.3 Hz, 1H), 7.79(d, J=11.1 Hz, 1H), 7.83(s, 1H), 10.27(s, 1H), 11.03(s, 1H)

Example 4-38

MS ESI m/e: 564 (M+H), 562 (M−H).
$^1$H-NMR(CDCl$_3$, 300 MHz)δ 0.75-0.81(m, 2H), 1.06-1.16(m, 5H), 1.40(s, 3H), 2.69-2.76(m, 1H), 3.03(s, 3H), 3.13(s, 1H), 3.92-4.01(m, 2H), 6.77-6.84(m, 1H), 6.92(t, J=8.1 Hz, 1H), 7.08-7.13(m, 1H), 7.18-7.33(m, 4H), 7.42(t, J=8.1 Hz, 1H), 11.11(s, 1H).

Example 4-39

MS ESI m/e: 568 (M+H), 566 (M−H).
$^1$H-NMR(CDCl$_3$, 300 MHz)δ 0.75-0.83(m, 2H), 1.02(t, J=7.0 Hz, 3H), 1.07-1.15(m, 2H), 1.24(t, J=7.7 Hz, 3H), 1.38(s, 3H), 2.60-2.76(m, 3H), 3.02(s, 3H), 3.90-4.00(m, 2H), 6.77(s, 1H), 6.94-7.03(m, 3H), 7.08-7.13(m, 1H), 7.19-7.27(m, 2H), 7.41(t, J=7.7 Hz, 1H), 11.19(s, 1H).

Example 4-40

MS ESI m/e: 552 (M+H), 550 (M−H).
$^1$H-NMR(DMSO-$d_6$, 300 MHz)δ 1.13(t, J=6.9 Hz, 3H), 1.20(t, J=7.3 Hz, 3H), 1.26(s, 3H), 3.11(s,3H), 3.12(q, J=7.4 Hz, 2H), 3.87(q, J=7.1 Hz, 2H), 4.30(s, 1H), 7.05-7.15(m, 2H), 7.20-7.35(m,3H), 7.41(t, J=8.0 Hz, 1H), 7.52(d, J=11.6 Hz, 1H), 9.99(s, 1H), 11.25(s, 1H).

Example 4-41

MS ESI m/e: 556 (M+H), 554 (M−H).
$^1$H-NMR(DMSO-$d_6$, 300 MHz)δ 1.10-1.25(m,12H), 2.62 (q, J=7.6 Hz, 2H), 3.03(s,3H), 3.12(q, J=7.3 Hz, 2H), 3.88(q, J=6.9 Hz, 2H), 7.05-7.15(m,3H), 7.20-7.30(m,3H), 7.41(t, J=8.0 Hz, 1H), 9.98(s,1H), 11.41(s,1H).

Example 4-42

MS ESI m/e: 538 (M+H), 536 (M−H).
$^1$H-NMR(DMSO-$d_6$, 300 MHz)δ 1.13(t, J=7.2 Hz, 3H), 1.27(s, 3H), 3.03(s, 3H), 3.11(s, 3H), 3.87(q, J=6.8 Hz, 2H), 4.30(s, 1H), 7.05-7.18(m, 2H), 7.20-7.35(m, 3H), 7.43(t, J=7.9 Hz, 1H), 7.52(d, J=11.3 Hz, 1H), 9.94(brs, 1H), 11.25(brs, 1H).

Example 4-43

MS ESI m/e: 502 (M+H), 500 (M−H).
$^1$H-NMR(DMSO-$d_6$, 300 MHz)δ 1.13(t, J=7.0 Hz, 3H), 1.27(s, 3H), 2.05(s, 3H), 3.11(s, 3H), 3.87(q, J=7.1 Hz, 2H), 4.30(s, 1H), 7.04-7.15(m, 2H), 7.28-7.34(m, 1H), 7.37(t, J=8.1 Hz, 1H), 7.49-7.60(m, 2H), 7.66-7.70(m, 1H), 10.10(brs, 1H), 11.24(brs, 1H).

Example 4-44

MS ESI m/e: 542 (M+H), 540 (M−H).
$^1$H-NMR(DMSO-$d_6$, 300 MHz)δ 1.14(t, J=7.2 Hz, 3H), 1.19(t, J=7.5 Hz, 3H), 1.25(s, 3H), 2.63(q, J=7.5 Hz, 2H), 3.02(s, 3H), 3.03(s, 3H), 3.89(q, J=7.0 Hz, 2H), 7.04-7.18(m, 3H), 7.20-7.30(m, 3H), 7.42(t, J=8.1 Hz, 1H), 9.93(brs, 1H), 11.41(brs, 1H).

Example 4-45

MS ESI m/e: 506 (M+H), 504 (M−H).
$^1$H-NMR(DMSO-d$_6$, 300 MHz)δ 1.14(t, J=6.2 Hz, 3H), 1.19(t, J=7.5 Hz, 3H), 1.25(s, 3H), 2.05(s, 3H), 2.63(q, J=7.5 Hz, 2H), 3.03(s, 3H), 3.89(q, J=6.8 Hz, 2H), 7.04-7.15(m, 3H), 7.23(d, J=12.0 Hz, 1H), 7.37(t, J=8.1 Hz, 1H), 7.53-7.60(m, 1H), 7.65-7.70(m, 1H), 10.10(brs, 1H), 11.41(brs, 1H).

Example 4-46

MS ESI m/e: 528 (M+H), 526 (M−H).
$^1$H-NMR(CDCl$_3$, 300 MHz)δ 0.75-0.82(m, 2H), 1.06-1.16(m, 5H), 1.42(s, 3H), 2.17(s, 3H), 2.68-2.78(m, 1H), 3.13(s, 1H), 3.92-4.01(m, 2H), 6.90(t, J=7.9 Hz, 1H), 6.99-7.06(m, 1H), 7.22-7.46(m, 5H), 7.63-7.68(m, 1H), 11.10(s, 1H).

Example 4-47

MS ESI m/e: 532 (M+H), 530 (M−H).
$^1$H-NMR(CDCl$_3$, 300 MHz)δ 0.75-0.83(m, 2H), 1.02(t, J=7.0 Hz, 3H), 1.08-1.16(m, 2H), 1.24(t, J=7.5 Hz, 3H), 1.40(s, 3H), 2.16(s, 3H), 2.61-2.77(m, 3H), 3.91-4.00(m, 2H), 6.93-7.05(m, 4H), 7.26-7.48(m, 3H), 7.59-7.64(m, 1H), 11.19(s, 1H).

Example 4-48

MS ESI m/e: 488 (M+H), 486 (M−H).
$^1$H-NMR(CDCl$_3$, 300 MHz)δ 1.42(s, 3H), 2.15(s, 3H), 3.13(s, 1H), 3.23(s, 3H), 3.38(s, 3H), 6.86(t, J=8.7 Hz, 1H), 7.03-7.10(m, 1H), 7.22-7.41(m, 5H), 7.70(s, 1H), 11.46(s, 1H).

Example 4-49

MS ESI m/e: 524 (M+H), 522 (M−H).
$^1$H-NMR(CDCl$_3$, 300 MHz)δ 1.41(s, 3H), 3.04(s, 3H), 3.14(s, 1H), 3.23(s, 3H), 3.38(s, 3H), 6.75(s, 1H), 6.89(t, J=8.5 Hz, 1H), 7.11-7.17(m, 1H), 7.18-7.33(m, 4H), 7.43(t, J=8.1 Hz, 1H), 11.47(s, 1H).

Example 4-50

MS ESI m/e: 492 (M+H), 490 (M−H).
$^1$H-NMR(CDCl$_3$, 300 MHz)δ 1.24(t, J=7.5 Hz, 3H), 1.41(s, 3H), 2.15(s, 3H), 2.65(q, J=7.7 Hz, 2H), 3.18(s, 3H), 3.38(s, 3H), 6.88-7.11(m, 4H), 7.32-7.46(m, 3H), 7.63-7.69(m, 1H), 11.45(s, 1H).

Example 4-51

MS ESI m/e: 528 (M+H), 526 (M−H).
$^1$H-NMR(CDCl$_3$, 300 MHz)δ 1.24(t, J=7.5 Hz, 3H), 1.39(s, 3H), 2.65(q, J=7.3 Hz, 2H), 3.03(s, 3H), 3.18(s, 3H), 3.38(s, 3H), 6.84(s, 1H), 6.90-7.03(m, 1H), 7.11-7.17(m, 1H), 7.19-7.30(m, 2H), 7.42(t, J=8.1 Hz, 1H), 11.46(s, 1H).

Example 4-52

MS ESI m/e: 528 (M+H), 526 (M−H).
$^1$H-NMR(DMSO-d$_6$, 400 MHz)δ 0.64-0.70(m, 2H), 0.91-0.99(m, 2H), 1.25(s, 3H), 2.04(s, 3H), 2.05(s, 3H), 2.58-2.66(m, 1H), 3.07(s, 3H), 7.01-7.10(m, 2H), 7.20-7.25(m, 1H), 7.32-7.43(m, 2H), 7.57-7.63(m, 2H), 10.10(s, 1H), 11.14(s, 1H).

Example 4-53

MS ESI m/e: 532 (M+H), 530 (M−H).
$^1$H-NMR(DMSO-d$_6$, 400 MHz)δ 0.64-0.71(m, 2H), 0.89(t, J=7.4 Hz, 3H), 0.92-0.99(m, 2H), 1.24(s, 3H), 1.54-1.65(m, 2H), 2.04(s, 3H), 2.57(t, J=7.5 Hz, 2H), 2.60-2.67(m, 1H), 3.02(s, 3H), 7.01-7.12(m, 3H), 7.18-7.24(m, 1H), 7.33-7.39(m, 1H), 7.58-7.62(m, 2H), 10.10(s, 1H), 11.24(s, 1H).

Example 4-54

MS ESI m/e: 653(M+H), 651(M−H).
$^1$H-NMR(DMSO-d$_6$, 300 MHz) δ 0.60-0.71(m, 2H), 0.90-1.01(m, 2H), 1.27(s, 3H), 2.58-2.67(m, 1H), 3.08(s, 3H), 6.89-7.01(m, 2H), 7.09-7.23(m, 4H), 7.30-7.39(m, 1H), 7.51-7.59(m, 1H), 7.73-7.83(m, 1H), 9.69(brs, 1H), 11.09(brs, 1H).

Example 4-55

MS ESI m/e: 637 (M+H), 635 (M−H).
$^1$H-NMR(DMSO-d$_6$, 300 MHz)δ 0.69(m,2H), 0.96(m, 2H), 1.17(s,3H), 2.62(m,1H), 3.09(s,3H), 3.26(s,3H), 6.95(t, J=8.6 Hz, 1H), 7.56(d, J=8.7 Hz, 1H), 7.70-7.85(m,3H), 7.90-8.00(m,2H), 11.04(s,1H).

Example 4-56

MS ESI m/e: 504 (M+H), 502 (M−H).
$^1$H-NMR(DMSO-d$_6$, 400 MHz)δ 0.65-0.71(m, 2H), 0.92-0.99(m, 2H), 1.24(s, 3H), 2.04(s, 3H), 2.32(s, 3H), 2.58-2.67(m, 1H), 3.02(s, 3H), 7.00-7.10(m, 3H), 7.20(d, J=12.0 Hz, 1H), 7.36(t, J=8.2 Hz, 1H), 7.56-7.63(m, 2H), 10.10(s, 1H), 11.24(s, 1H).

Example 4-57

MS ESI m/e: 558 (M+H), 556 (M−H).
$^1$H-NMR(DMSO-d$_6$, 400 MHz)δ 0.64-0.71(m, 2H), 0.90-0.99(m, 2H), 1.24(s, 3H), 1.46-1.57(m, 2H), 1.58-1.69(m, 2H), 1.71-1.83(m, 2H), 1.97-2.07(m, 2H), 2.04(s, 3H), 2.58-2.68(m, 1H), 2.93-3.06(m, 1H), 3.03(s, 3H), 7.00-7.14(m, 3H), 7.24(dd, J=1.2, 12.0 Hz, 1H), 7.36(t, J=8.2 Hz, 1H), 7.57-7.63(m, 1H), 10.10(s, 1H), 11.22(s, 1H).

Example 4-58

MS ESI m/e: 651 (M+H), 649 (M−H).
$^1$H-NMR(DMSO-d$_6$, 300 MHz)δ 0.65-0.71(m, 2H), 0.93-1.00(m, 2H), 1.10(t, J=7.3 Hz, 3H), 1.17(s, 3H), 2.56-2.66(m, 1H), 3.09(s, 3H), 3.29-3.40(m, 2H), 6.95(t, J=8.7 Hz, 1H), 7.52-7.58(m, 1H), 7.73-7.82(m, 3H), 7.88-7.95(m, 2H), 11.04(s, 1H).

Example 4-59

MS ESI m/e: 721(M+H), 719(M−H).
$^1$H-NMR(DMSO-d$_6$, 300 MHz) δ 0.61-0.71(m, 2H), 0.91-1.01(m, 2H), 1.26(s, 3H), 1.35-1.60(m, 6H), 2.59-2.67(m, 1H), 2.99-3.12(m, 4H), 3.07(s, 3H), 6.89-6.94(m, 1H), 7.04-7.06(m, 1H), 7.13-7.17(m, 1H), 7.34-7.39(m, 1H), 7.54-7.57(m, 1H), 7.77-7.80(m, 1H), 10.06(brs, 1H), 11.06(brs, 1H).

Example 4-60

MS ESI m/e: 630(M+H), 628(M−H).
$^1$H-NMR(DMSO-$d_6$, 300 MHz) δ 0.63-0.72(m, 2H), 0.91-1.01(m, 2H), 1.09(t, J=7.5 Hz, 3H), 1.27(s, 3H), 2.34(q, J=7.0 Hz, 2H), 2.59-2.70(m, 1H), 3.09(s, 3H), 6.91-7.08(m, 2H), 7.34-7.40(m, 1H), 7.56-7.69(m, 3H), 7.78-7.82(m, 1H), 10.03(brs, 1H), 11.09(brs, 1H).

Example 4-61

MS ESI m/e: 533 (M+H), 531 (M−H).
$^1$H-NMR(DMSO-$d_6$, 300 MHz)δ 0.64-0.73(m, 2H), 0.91-1.01(m, 2H), 1.22(s, 3H), 2.04(s, 3H), 2.58-2.68(m, 1H), 2.92(s, 6H), 2.98(s, 3H), 6.55(dd, J=3.0, 9.1 Hz, 1H), 6.62(dd, J=2.6, 14.3 Hz, 1H), 6.99-7.11(m, 2H), 7.35(t, J=7.9 Hz, 1H), 7.55-7.62(m, 2H), 10.09(brs, 1H), 11.27(brs, 1H).

Example 4-62

MS ESI m/e: 673(M+H), 671(M−H)
$^1$H-NMR(DMSO-$d_6$, 300 MHz) 0.63-0.69(m, 2H), 0.91-0.98(m, 2H), 1.33(s, 3H), 2.03(s, 6H), 3.08(s, 3H), 6.91(dd, J=10.5,9.6 Hz, 1H), 7.28(s, 2H), 7.55(d, J=9.6 Hz, 1H), 7.78(d, J=10.5 Hz, 1H), 10.09(s, 1H), 7.92(s, 1H), 11.09(s, 1H)

Example 4-63

MS ESI m/e: 646.0(M+H), 644.0(M−H).
$^1$H-NMR(DMSO-$d_6$, 300 MHz)δ 0.63-0.69(m, 2H), 0.91-0.98(m, 2H), 1.28(s, 3H), 2.08(s, 3H), 2.57-2.65(m, 1H), 3.07(s, 3H), 3.89(s, 3H), 6.91(dd, J=12.0, 9.0 Hz, 1H), 7.07(s, 2H), 7.55(d, J=9.0 Hz, 1H), 7.79(d, J=12.0 Hz, 1H), 7.95(s, 1H), 9.27(s, 1H), 11.12(s, 1H)

Example 4-64

$^1$H-NMR: 685.9,687.9,684.0,685.9
$^1$H-NMR(DMSO-$d_6$, 300 MHz)δ 0.64-0.70(m, 2H), 0.92-0.99(m, 2H), 1.31(s, 3H), 2.57-2.63(m, 1H), 3.08(s, 6H), 6.94(dd, J=9.0, 12.0 Hz, 1H), 7.22-7.22(m, 1H), 7.27-7.27(m, 2H), 7.56(d, J=9.0 Hz, 1H), 7.79(d, J=12.0 Hz, 1H), 10.16(s, 1H), 11.04(s, 1H)

Example 4-65

MS ESI m/e: 571.1 (M+H),569.2 (M−H).
$^1$H-NMR(DMSO-$d_6$, 300 MHz)δ 0.64-0.69(m, 2H), 0.93-1.00(m, 2H), 1.35(s, 3H), 2.04(s, 6H), 2.59-2.67(m, 1H), 3.11(s, 3H), 4.32(s, 1H), 7.09(dd, J=9.0, 12.0 Hz, 1H), 7.30(s, 2H), 7.33(d, J=9.0 Hz, 1H), 7.53(d, J=12.0 Hz, 1H), 7.94(s, 1H), 10.11(s, 2H), 11.12(s, 1H)

Example 4-66

MS ESI m/e: 616.0(M+H),614.0(M−H).
$^1$H-NMR(DMSO-$d_6$, 300 MHz)δ 0.63-0.68(m, 2H), 0.92-0.99(m, 2H), 1.23(s, 3H), 2.07(s, 3H), 2.58-2.66(m, 1H), 3.07(s, 3H), 6.92(dd, J=9.0, 9.0 Hz, 1H), 7.28(d, J=9.0 Hz, 2H), 7.55(d, J=9.0 Hz, 1H), 7.64(d, J=9.0 Hz, 1H), 7.79(d, J=9.0 Hz, 1H), 10.10(s, 1H), 11.06(s, 1H)

Example 4-67

MS ESI m/e: 530 (M+H), 528 (M−H).
$^1$H-NMR(DMSO-$d_6$, 300 MHz)δ 0.62-0.76(m, 4H), 0.90-1.03(m, 4H), 1.24(s, 3H), 1.88-2.02(m, 1H), 2.04(s, 3H), 2.58-2.68(m, 1H), 3.01(s, 3H), 6.92-7.11(m, 4H), 7.35(t, J=8.6 Hz, 1H), 7.55-7.64(m, 2H), 10.09(s, 1H), 11.23(s, 1H).

Example 4-68

MS ESI m/e: 660 (M+H), 658 (M−H).
$^1$H-NMR(DMSO-$d_6$, 300 MHz)δ 0.56-0.64(m, 2H), 0.85-0.95(m, 2H), 1.26(s, 3H), 2.04(s, 3H), 2.46-2.60(m, 1H), 3.20(brs, 3H), 3.46-3.55(m, 2H), 4.01-4.11(m, 2H), 6.91(t, J=8.5 Hz, 1H), 6.97-7.07(m, 1H), 7.35(t, J=7.8 Hz, 1H), 7.45(d, J=8.4 Hz, 1H), 7.54-7.67(m, 2H), 7.73(d, J=9.9 Hz, 1H), 10.09(s, 1H), 10.13(s, 1H).

Example 4-69

MS ESI m/e: 696 (M+H), 694 (M−H).
$^1$H-NMR(DMSO-$d_6$, 300 MHz)δ 0.56-0.66(m, 2H), 0.81-0.97(m, 2H), 1.26(s, 3H), 2.50-2.59(m, 1H), 3.00(s, 3H), 3.19(s, 3H), 3.50(t, J=5.3 Hz, 2H), 4.05(t, J=5.1 Hz, 2H), 6.90(t, J=8.9 Hz, 1H), 7.07-7.15(m, 1H), 7.18-7.27(m, 2H), 7.35-7.50(m, 2H), 7.69-7.78(m, 1H), 9.90(brs, 1H), 10.16(brs, 1H).

Example 4-70

MS ESI m/e: 652.0 (M+H),650.0(M−H).
$^1$H-NMR(DMSO-$d_6$, 400 MHz)δ 0.60-0.64(m, 2H), 0.89-0.94(m, 2H), 1.19(s, 3H), 2.55-2.62(m, 1H), 2.99(s, 3H), 3.03(s, 3H), 6.88(dd, J=8.0, 8.0 Hz, 1H), 7.21(d, J=8.0 Hz, 2H), 7.29(d, J=8.0 Hz, 2H), 7.51(d, J=8.0 Hz, 1H), 7.75(d, J=8.0 Hz, 1H), 9.91(s, 1H), 11.02(s, 1H)

Example 4-71

MS ESI m/e: 514.1(M+H), 512.2 (M−H).
$^1$H-NMR(DMSO-$d_6$, 300 MHz)δ 0.63-0.69(m, 2H), 0.91-0.99(m, 2H), 1.24(s, 3H), 2.07(s, 3H), 2.59-2.66(m, 1H), 3.10(s, 3H), 4.30(s, 1H), 7.09(dd, J=8.7, 8.4 Hz, 1H), 7.28(d, J=8.4 Hz, 2H), 7.31(d, J=8.7 Hz, 1H), 7.52(d, J=8.4 Hz, 1H), 7.64(d, J=8.4 Hz, 1H), 10.10(s, 1H), 11.08(s, 1H)

Example 4-72

MS ESI m/e: 559 (M+H), 557 (M−H).
$^1$H-NMR(DMSO-$d_6$, 300 MHz)δ 0.62-0.72(m, 2H), 0.90-1.01(m, 2H), 1.18(s, 3H), 2.57-2.67(m, 1H), 3.07(s, 3H), 6.93(t, J=8.5 Hz, 1H), 7.34-7.50(m, 5H), 7.52-7.58(m, 1H), 7.79(dd, J=1.5, 10.2 Hz, 1H), 11.06(brs, 1H).

Example 4-73

MS ESI m/e: 668(M+H), 666(M−H).
$^1$H-NMR(DMSO-$d_6$, 300 MHz) δ 0.62-0.72(m, 2H), 0.92-1.01(m, 2H), 1.30(s, 3H), 2.60-2.69(m, 1H), 3.10(s, 3H), 6.91-6.99(m, 1H), 7.06-7.11(m, 1H), 7.38-7.42(m, 1H), 7.52-7.60(m, 1H), 7.75-7.95(m, 5H), 9.98(brs, 1H), 11.09(brs, 1H), 12.68(brs, 1H).

MS ESI m/e: 681(M+H), 679(M−H).
$^1$H-NMR(DMSO-$d_6$, 300 MHz) δ 0.64-0.72(m, 2H), 0.90-1.02(m, 2H), 1.31(s, 3H), 2.60-2.69(m, 1H), 3.09(s, 3H), 3.89(s, 3H), 6.09-6.11(m, 1H), 6.90-6.97(m, 1H), 7.01-

7.11(m, 3H), 7.37-7.42(m, 1H), 7.52-7.60(m, 1H), 7.73-7.84 (m, 3H), 9.90(brs, 1H), 11.10(brs, 1H).

Example 4-74

MS ESI m/e: 647 (M+H), 645 (M−H).
$^1$H-NMR(DMSO-$d_6$, 300 MHz)δ 0.64-0.69(m, 2H), 0.92-0.99(m, 2H), 1.27(s, 3H), 2.58-2.66(m, 1H), 3.08(s, 3H), 3.62(s, 3H), 6.92(t, J=8.6 Hz, 1H), 6.99-7.02(m, 1H), 7.33(t, J=8.1 Hz, 1H), 7.54-7.57(m, 1H), 7.61-7.66(m, 2H), 7.79 (dd, J=1.8, 10.2 Hz, 1H), 9.05(s, 1H), 9.58(s, 1H), 11.08(s, 1H).

Example 4-75

MS ESI m/e: 518.0 (M+H), 516.0(M−H).
$^1$H-NMR(DMSO-$d_6$, 300 MHz)δ 0.64-0.70(m, 2H), 0.92-1.00(m, 2H), 1.19(t, J=7.8 Hz, 3H), 1.23(s, 3H), 2.07(s, 3H), 2.57-2.65(m, 1H), 2.63(q, J=7.8 Hz, 2H), 3.02(s, 3H), 7.07-7.09(m, 2H), 7.21-7.25(m, 1H), 7.28(d, J=9.0 Hz, 2H), 7.63(d, J=8.7 Hz, 2H), 10.10(s, 1H), 11.22(s, 1H)

Example 4-76

MS ESI m/e: 550.1 (M+H), 548.1(M−H)
$^1$H-NMR(DMSO-$d_6$, 300 MHz)δ 0.63-0.69(m, 2H), 0.91-0.99(m, 2H), 1.24(s, 3H), 2.07(s, 3H), 2.59-2.66(m, 1H), 3.10(s, 3H), 4.30(s, 1H), 7.09(dd, J=8.7, 8.4 Hz, 1H), 7.28(d, J=8.4 Hz, 2H), 7.31(d, J=8.7 Hz, 1H), 7.52(d, J=8.4 Hz, 1H), 7.64(d, J=8.4 Hz, 2H), 10.10(s, 1H), 11.08(s, 1H)

Example 4-77

MS ESI m/e: 666.0 (M+H), 664.0 (M−H).
$^1$H-NMR(DMSO-$d_6$, 300 MHz)δ 0.63-0.69(m, 2H), 0.92-0.99(m, 2H), 1.21(t, J=7.4 Hz, 3H), 1.23(s, 3H), 2.58-2.65 (m, 1H), 3.14(q, J=7.4 Hz, 2H), 6.92(dd, J=7.5, 10.5 Hz, 1H), 7.26(d, J=9.0 Hz, 2H), 7.32(d, J=9.0 Hz, 2H), 7.55(d, J=7.5 Hz, 1H), 7.79(d, J=10.5 Hz, 1H), 9.98(s, 1H), 11.06(s, 1H)

Example 4-78

MS ESI m/e: 554.2 (M+H), 552.1 (M−H)
$^1$H-NMR(DMSO-$d_6$, 300 MHz)δ 0.64-0.70(m, 2H), 0.92-0.99(m, 2H), 1.19(t, J=7.5 Hz, 3H), 1.22(s, 3H), 2.55-2.63 (m, 1H), 2.63(q, J=7.5 Hz, 2H), 3.02(s, 3H), 3.04(s, 3H), 7.07-7.09(m, 2H), 7.21-7.25(m, 1H), 7.25(d, J=9.3 Hz, 2H), 7.34(d, J=9.3 Hz, 2H), 9.95(s, 1H), 11.22(s, 1H)

Example 4-79

MS ESI m/e: 664 (M+H), 662 (M−H).
$^1$H-NMR(DMSO-$d_6$, 400 MHz)δ 0.28-0.34(m, 2H), 0.69-0.77(m, 2H), 1.06(brs, 3H), 2.30-2.37(m, 1H), 2.99(s, 3H), 4.21(t, J=9.2 Hz, 2H), 4.72(t, J=8.6 Hz, 2H), 6.50-6.57(m, 1H), 7.06-7.11(m, 1H), 7.14-7.24(m, 3H), 7.29-7.35(m, 1H), 7.35-7.41(m, 1H), 9.91(brs, 1H).

Example 4-80

MS ESI m/e: 661 (M+H), 659 (M−H).
$^1$H-NMR(DMSO-$d_6$, 300 MHz)δ 0.65-0.69(m, 2H), 0.93-0.98(m, 2H), 1.27(s, 3H), 2.60-2.65(m, 1H), 3.05(s, 3H), 3.08(s, 3H), 3.67(s, 3H), 6.92(t, J=8.5 Hz, 1H), 7.00-7.03(m, 1H), 7.34(t, J=7.9 Hz, 1H), 7.54-7.57(m, 1H), 7.61-7.67(m, 2H), 7.77-7.81(m, 1H), 9.24(s, 1H), 11.08(s, 1H).

Example 4-81

MS ESI m/e: 617 (M+H), 615 (M−H).
$^1$H-NMR(DMSO-$d_6$, 300 MHz)δ 0.63-0.70(m, 2H), 0.92-0.98(m, 2H), 1.28(s, 3H), 2.59-2.66(m, 1H), 3.08(s, 3H), 5.89(s, 2H), 6.87-6.94(m, 2H), 7.28(t, J=7.9 Hz, 1H), 7.35-7.45(m, 2H), 7.53-7.56(m, 1H), 7.75-7.81(m, 1H), 8.71(s, 1H), 11.09(s, 1H).

Example 4-82

MS ESI m/e: 632 (M+H), 630 (M−H).
$^1$H-NMR(DMSO-$d_6$, 300 MHz)δ 0.64-0.69(m, 2H), 0.92-0.98(m, 2H), 1.25(s, 3H), 2.60-2.64(m, 1H), 3.08(s, 3H), 3.99(d, J=6.0 Hz, 2H), 5.64(t, J=6.0 Hz, 1H), 6.92(t, J=8.5 Hz, 1H), 7.05-7.08(m, 1H), 7.37(t, J=7.9 Hz, 1H), 7.53-7.56 (m, 1H), 7.71-7.81(m, 3H), 9.83(s, 1H), 11.07(s, 1H).

Example 4-83

MS ESI m/e: 511, 513 (M+H), 509, 511 (M−H).
$^1$H-NMR(DMSO-$d_6$, 300 MHz)δ 1.20(s, 3H), 3.08(s, 3H), 3.22(s, 3H), 3.50(t, J=6.2 Hz, 2H), 4.04(t, J=6.2 Hz, 2H), 7.07(d, J=8.7 Hz, 2H), 7.35-7.51(m, 5H), 7.55(d, J=8.7 Hz, 2H), 11.06(s, 1H).

Example 4-84

MS ESI m/e: 511, 513 (M+H), 509, 511 (M−H).
$^1$H-NMR(DMSO-$d_6$, 300 MHz)δ 1.22(s, 3H), 3.08(s, 3H), 4.50(s, 2H), 7.08(d, J=8.7 Hz, 2H), 7.38-7.52(m, 5H), 7.55(d, J=8.7 Hz, 2H), 10.89(s, 1H).

Example 4-85

MS ESI m/e: 497, 499 (M+H), 495, 497 (M−H).
$^1$H-NMR(DMSO-$d_6$, 300 MHz)δ 1.20(s, 3H), 3.08(s, 3H), 3.53(q, J=6.3 Hz, 2H), 3.94(t, J=6.4 Hz, 2H), 4.77(t, J=5.8 Hz, 1H), 7.06(d, J=9.0 Hz, 2H), 7.37-7.51(m, 5H), 7.55(d, J=9.0 Hz, 2H), 11.10(s, 1H).

Example 4-86

MS ESI m/e: 524, 526 (M+H), 522, 524 (M−H).
$^1$H-NMR(DMSO-$d_6$, 300 MHz)δ 1.20(s, 3H), 2.16(s, 6H), 2.42(t, J=6.8 Hz, 2H), 3.08(s, 3H), 3.94(t, J=7.2 Hz, 2H), 7.07(d, J=9.0 Hz, 2H), 7.37-7.51(m, 5H), 7.56(d, J=8.7 Hz, 2H), 11.07(s, 1H).

Example 4-87

MS ESI m/e: 681(M+H), 679(M−H).
$^1$H-NMR(DMSO-$d_6$, 300 MHz) δ 0.64-0.72(m, 2H), 0.90-1.02(m, 2H), 1.31(s, 3H), 2.60-2.69(m, 1H), 3.09(s, 3H), 3.89(s, 3H), 6.09-6.11(m, 1H), 6.90-6.97(m, 1H), 7.01-7.11(m, 3H), 7.37-7.42(m, 1H), 7.52-7.60(m, 1H), 7.73-7.84 (m, 3H), 9.90(brs, 1H), 11.10(brs, 1H).

Example 4-88

MS ESI m/e: 614(M+H), 612(M−H).
$^1$H-NMR(DMSO-$d_6$, 300 MHz) δ 0.62-0.72(m, 2H), 0.91-1.01(m, 2H), 1.31(s, 3H), 2.55-2.68(m, 1H), 3.09(s, 3H), 3.57(s, 2H), 6.87-6.96(m, 3H), 7.25-7.28(m, 1H), 7.55-7.58(m, 1H), 7.78-7.81(m, 1H), 10.49(brs, 1H), 11.08(brs, 1H).

Example 4-89

MS ESI m/e: 668(M+H), 666(M−H).
$^1$H-NMR(DMSO-$d_6$, 300 MHz) δ 0.62-0.71(m, 2H), 0.91-1.01(m, 2H), 1.29(s, 3H), 2.60-2.70(m, 1H), 3.08(s, 3H), 6.93(dd, J=9.0, 9.0 Hz, 1H), 7.08(d, J=9.0 Hz, 1H), 7.40(dd, J=9.0, 9.0 Hz, 1H), 7.56(d, J=9.0 Hz, 1H), 7.70(s, 1H), 7.80(d, J=9.0 Hz, 2H), 8.05(s, 1H), 8.38(s, 1H), 9.96(brs, 1H), 11.08(brs, 1H), 13.27(brs, 1H).

Example 4-90

MS ESI m/e: 603 (M+H), 601 (M−H).
$^1$H-NMR(DMSO-$d_6$, 300 MHz)δ 0.64-0.71(m, 2H), 0.93-1.00(m, 2H), 1.19(s, 3H), 2.58-2.66(m, 1H), 3.08(s, 3H), 6.95(t, J=8.5 Hz, 1H), 7.46-7.58(m, 3H), 7.79(dd, J=1.5, 10.2 Hz, 1H), 8.01(d, J=8.7 Hz, 2H), 11.01(s, 1H), 13.14(br, 1H).

Example 4-91

MS ESI m/e: 602 (M+H), 600 (M−H).
$^1$H-NMR(DMSO-$d_6$, 300 MHz)δ 0.64-0.71(m, 2H), 0.92-1.00(m, 2H), 1.19(s, 3H), 2.59-2.65(m, 1H), 3.08(s, 3H), 6.94(t, J=8.7 Hz, 1H), 7.42-7.49(m, 3H), 7.53-7.58(m, 1H), 7.76-7.81(m, 1H), 7.94(d, J=8.7 Hz, 2H), 8.07(brs, 1H), 11.02(s, 1H).

Example 4-92

MS ESI m/e: 616 (M+H), 614 (M−H).
$^1$H-NMR(DMSO-$d_6$, 300 MHz)δ 0.64-0.70(m, 2H), 0.92-1.00(m, 2H), 1.18(s, 3H), 2.58-2.66(m, 1H), 2.81(d, J=4.5 Hz, 3H), 3.08(s, 3H), 6.94(t, J=8.7 Hz, 1H), 7.47(d, J=8.6 Hz, 2H), 7.52-7.58(m, 1H), 7.76-7.82(m, 1H), 7.90(d, J=8.6 Hz, 2H), 8.51-8.56(m, 1H), 11.02(brs, 1H).

Example 4-93

MS ESI m/e: 630 (M+H), 628 (M−H).
$^1$H-NMR(DMSO-$d_6$, 300 MHz)δ 0.64-0.70(m, 2H), 0.92-1.00(m, 2H), 1.22(s, 3H), 2.59-2.66(m, 1H), 2.93(brs, 3H), 3.00(brs, 3H), 3.08(s, 3H), 6.94(t, J=8.5 Hz, 1H), 7.42-7.49(m, 4H), 7.53-7.57(m, 1H), 7.77-7.81(m, 1H), 11.04(s, 1H).

Example 4-94

MS ESI m/e: 617 (M+H), 615 (M−H).
$^1$H-NMR(DMSO-$d_6$, 300 MHz)δ 0.64-0.69(m, 2H), 0.92-0.99(m, 2H), 1.19(s, 3H), 2.58-2.65(m, 1H), 3.07(s, 3H), 3.63(s, 2H), 6.92(t, J=8.7 Hz, 1H), 7.28-7.36(m, 4H), 7.53-7.57(m, 1H), 7.75-7.81(m, 1H), 11.07(br, 1H), 12.39(br, 1H).

Example 4-95

MS ESI m/e: 661 (M+H), 659 (M−H).
$^1$H-NMR(DMSO-$d_6$, 300 MHz)δ 0.61-0.71(m, 2H), 0.90-1.00(m, 2H), 1.28(s, 3H), 2.55-2.68(m, 1H), 3.08(s, 3H), 3.14(q, J=5.6 Hz, 2H), 3.43(q, J=5.6 Hz, 2H), 4.74(t, J=5.6 Hz, 1H), 6.20(t, J=5.6 Hz, 1H), 6.83-6.97(m, 2H), 7.22-7.38(m, 2H), 7.48(s, 1H), 7.54(d, J=9.0 Hz, 1H), 7.78(d, J=10.5 Hz, 1H), 8.75(s, 1H), 11.08(s, 1H).

Example 4-96

MS ESI m/e: 784 (M+H), 782 (M−H).
$^1$H-NMR(DMSO-$d_6$, 300 MHz)δ 0.62-0.71(m, 2H), 0.90-1.02(m, 2H), 1.24(s, 3H), 2.57-2.69(m, 1H), 3.00(q, J=6.7 Hz, 4H), 3.07(s, 3H), 3.35(q, J=6.7 Hz, 2H), 3.89(t, J=6.7 Hz, 2H), 4.60(t, J=5.7 Hz, 1H), 6.86-7.05(m, 3H), 7.10-7.21(m, 2H), 7.35(t, J=7.8 Hz, 1H), 7.55(d, J=7.8 Hz, 1H), 7.71(t, J=5.7 Hz, 1H), 7.79(dd, J=1.8, 9.6 Hz, 1H), 9.88(s, 1H), 11.09(s, 1H).

Example 4-97

MS ESI m/e: 530 (M+H), 528 (M−H).
$^1$H-NMR(DMSO-$d_6$, 300 MHz)δ 0.63-0.71(m, 2H), 0.91-1.00(m, 2H), 1.25(s, 3H), 2.04(s, 3H), 2.10(s, 3H), 2.58-2.68(m, 1H), 3.07(s, 3H), 5.16(s, 1H), 5.52(s, 1H), 7.04(d, J=6.9 Hz, 1H), 7.11(t, J=8.6 Hz, 1H), 7.32-7.40(m, 2H), 7.51(dd, J=1.8, 12.6 Hz, 1H), 7.56-7.63(m, 2H), 10.10(s, 1H), 11.22(s, 1H).

Example 4-98

MS ESI m/e: 532 (M+H), 530 (M−H).
$^1$H-NMR(DMSO-$d_6$, 400 MHz)δ 0.60-0.73(m, 2H), 0.89-1.00(m, 2H), 1.20(d, J=6.4 Hz, 6H), 1.24(s, 3H), 2.04(s, 3H), 2.56-2.68(m, 1H), 2.84-2.97(m, 1H), 3.03(s, 3H), 6.97-7.16(m, 3H), 7.19-7.29(m, 1H), 7.35(t, J=8.0 Hz, 1H), 7.53-7.66(m, 2H), 10.10(s, 1H), 11.22(s, 1H).

Example 4-99

MS ESI m/e: 634.0 (M+H), 632.1 (M−H).
$^1$H-NMR(DMSO-$d_6$, 300 MHz)δ 0.63-0.69(m, 2H), 0.91-0.98(m, 2H), 1.28(s, 3H), 2.09(s, 3H), 2.57-2.66(m, 1H), 3.07(s, 3H), 6.92(dd, J=9.0, 8.7 Hz, 1H), 7.14-7.19(m, 1H), 7.33(dd, J=8.7, 10.5 Hz, 1H), 7.55(d, J=8.7 Hz, 1H), 7.79(d, J=12.0 Hz, 1H), 7.88-7.92(m, 1H), 9.87(s, 1H), 11.09(s, 1H)

Example 4-100

MS ESI m/e: 646 (M+H), 644 (M−H).
$^1$H-NMR(DMSO-$d_6$, 300 MHz)δ 0.52-0.62(m, 2H), 0.82-0.96(m, 2H), 1.28(s, 3H), 2.04(s, 3H), 2.44-2.59(m, 1H), 3.58-3.65(m, 2H), 4.01-4.08(m, 2H), 5.58(t, J=4.5 Hz, 1H), 6.91(t, J=8.6 Hz, 1H), 6.99-7.08(m, 1H), 7.30-7.45(m, 2H), 7.57-7.65(m, 2H), 7.66-7.75(m, 1H), 10.09(brs, 1H), 10.12(brs, 1H).

Example 4-101

MS ESI m/e: 670.0 (M+H), 668.0 (M−H)
$^1$H-NMR(DMSO-$d_6$, 300 MHz)δ 0.60-0.67(m, 2H), 0.89-0.96(m, 2H), 1.35(s, 3H), 2.56-2.62(m, 1H), 2.60(s, 3H), 3.09(s, 3H), 6.49-6.56(m, 1H), 6.84-6.99(m, 3H), 7.22(dd, J=2.4, 7.5 Hz, 1H), 7.46-7.52(m, 1H)

Example 4-102

MS ESI m/e: 532.1 (M+H), 530.2 (M−H).
$^1$H-NMR(DMSO-$d_6$, 300 MHz)δ 0.65-0.69 (m, 2H), 0.92-0.94 (m, 2H), 1.29 (s, 3H), 2.09 (s, 3H), 2.59-2.63 (m, 1H), 3.10 (s, 3H), 4.29 (s, 1H), 7.06-7.54 (m, 5H), 7.90 (d, 1H, J=6.6 Hz), 9.86 (s, 1H), 11.11 (s, 1H).

Example 4-103

MS ESI m/e: 615.1 (M+H), 613.1 (M−H)
$^1$H-NMR(DMSO-d$_6$, 300 MHz)δ 0.63-0.71(m, 2H), 0.91-0.98(m, 2H), 1.23(s, 3H), 2.57-2.65(m, 1H), 3.07(s, 3H), 6.88-6.96(m, 4H), 7.55(d, J=8.7 Hz, 1H), 7.78(d, J=10.5 Hz, 1H), 10.76(s, 1H), 10.79(s, 1H), 11.10(s, 1H)

Example 4-104

MS ESI m/e: 638 (M+H), 636 (M−H).
$^1$H-NMR(DMSO-d$_6$, 300 MHz)δ 0.64-0.70(m, 2H), 0.93-0.99(m, 2H), 1.19(s, 3H), 2.57-2.65(m, 1H), 3.08(s, 3H), 6.90-6.98(m, 1H), 7.48(s, 2H), 7.52-7.61(m, 3H), 7.75-7.82(m, 1H), 7.89(d, J=8.6 Hz, 2H), 11.00(s, 1H).

Example 4-105

MS ESI m/e: 536 (M+H), 534 (M−H).
$^1$H-NMR(DMSO-d$_6$, 300 MHz)δ 0.63-0.71(m, 2H), 0.91-1.00(m, 2H), 1.24(s, 3H), 2.04(s, 3H), 2.51(s, 3H), 2.59-2.65(m, 1H), 3.04(s, 3H), 7.00-7.14(m, 3H), 7.27-7.40(m, 2H), 7.56-7.62(m, 2H), 10.09(brs, 1H), 11.22(brs, 1H).

Example 4-106

MS ESI m/e: 572 (M+H), 570 (M−H).
$^1$H-NMR(DMSO-d$_6$, 300 MHz)δ 0.62-0.72(m, 2H), 0.91-1.01(m, 2H), 1.24(s, 3H), 2.51(s, 3H), 2.60-2.67(m, 1H), 3.01(s, 3H), 3.04(s, 3H), 7.05-7.15(m, 3H), 7.20-7.34(m, 3H), 7.40(t, J=4.1 Hz, 1H), 9.88(s, 1H), 11.22(s, 1H).

Example 4-107

MS ESI m/e: 599(M+H), 597(M−H).
$^1$H-NMR(DMSO-d$_6$, 300 MHz)δ 0.66-0.72(m, 2H), 0.93-0.98(m, 2H), 1.12(d, J=3.0 Hz, 3H), 2.60-2.67(m, 1H), 3.08(s, 3H), 6.90-6.97(m, 1H), 7.15-7.25(m, 1H), 7.54-7.57(m, 2H), 7.64-7.69(m, 1H), 7.77-7.81(m, 1H), 8.31(d, J=3.8 Hz, 1H), 11.12(d, J=3.4 Hz, 1H), 12.60(d, J=14.3 Hz, 1H).

Example 4-108

MS ESI m/e: 657 (M+H), 655 (M−H).
$^1$H-NMR(DMSO-d$_6$, 300 MHz)δ 0.62-0.74(m, 2H), 0.90-1.01(m, 2H), 1.26(s, 3H), 2.58-2.70(m, 1H), 3.08(s, 3H), 4.06(s, 2H), 6.92(t, J=8.6 Hz, 1H), 7.36-7.47(m, 3H), 7.51-7.60(m, 2H), 7.78(dd, J=1.8, 10.2 Hz, 1H), 8.31(s, 1H), 11.04(s, 1H).

Example 4-109

MS ESI m/e: 657 (M+H), 655 (M−H).
$^1$H-NMR(DMSO-d$_6$, 300 MHz)δ 0.62-0.71(m, 2H), 0.90-0.99(m, 2H), 1.26(s, 3H), 2.56-2.67(m, 1H), 3.08(s, 3H), 4.44(s, 2H), 6.93(t, J=8.7 Hz, 1H), 7.13(d, J=7.5 Hz, 1H), 7.45(t, J=8.1 Hz, 1H), 7.50-7.58(m, 2H), 7.71-7.82(m, 2H), 11.10(s, 1H), 11.23(s, 1H).

Example 4-110

MS ESI m/e: 643 (M+H), 641 (M−H).
$^1$H-NMR(DMSO-d$_6$, 300 MHz)δ 0.62-0.72(m, 2H), 0.90-1.00(m, 2H), 1.27(s, 3H), 2.58-2.67(m, 1H), 3.08(s, 3H), 3.60-3.86(m, 2H), 4.16-4.32(m, 2H), 6.84-6.97(m, 2H), 7.28(t, J=7.8 Hz, 1H), 7.40-7.73(m, 2H), 7.55(d, J=8.4 Hz, 1H), 7.78(dd, J=1.5, 10.2 Hz, 1H), 9.15-9.51(brs, 1H), 11.09(s, 1H).

Example 4-111

MS ESI m/e: 613 (M+H), 611 (M−H).
$^1$H-NMR(DMSO-d$_6$, 300 MHz)δ 0.65-0.74(m, 2H), 0.91-1.01(m, 2H), 1.11(s, 3H), 2.58-2.69(m, 1H), 3.08(s, 3H), 3.89(s, 3H), 6.94(t, J=8.4 Hz, 1H), 7.26-7.34(m, 1H), 7.51-7.58(m, 1H), 7.59-7.67(m, 2H), 7.74-7.84(m, 1H), 8.27(s, 1H), 11.10(brs, 1H).

Example 4-112

MS ESI m/e: 613 (M+H), 611 (M−H).
$^1$H-NMR(DMSO-d$_6$, 300 MHz)δ 0.63-0.74(m, 2H), 0.91-1.02(m, 2H), 1.13(s, 3H), 2.57-2.69(m, 1H), 3.08(s, 3H), 4.09(s, 3H), 6.94(t, J=8.5 Hz, 1H), 7.39-7.47(m, 1H), 7.51-7.60(m, 1H), 7.66-7.74(m, 2H), 7.75-7.83(m, 1H), 8.09(s, 1H), 11.10(brs, 1H).

Example 4-113

MS ESI m/e: 602 (M+H), 600 (M−H).
$^1$H-NMR(DMSO-d$_6$, 300 MHz, 120° C.)δ 0.72(m,2H), 0.95(m,2H), 1.30(s,3H), 2.67(m,1H), 3.12(s,3H), 6.88(t, J=8.4 Hz, 1H), 7.07(dd, J=1.8, 8.8 Hz, 1H), 7.36(t, J=7.9 Hz, 1H), 7.40-7.55(m,3H), 7.67(dd, J=1.8, 10.3 Hz, 1H), 8.39(brs,1H), 9.84(brs,1H), 10.90(s,1H).

Example 4-114

MS ESI m/e: 679 (M+H), 677 (M−H).
$^1$H-NMR(DMSO-d$_6$, 400 MHz)δ 0.62-0.72(m, 2H), 0.91-1.01(m, 2H), 1.25(s, 3H), 2.59-2.66(m, 1H), 3.08(s, 3H), 3.48-3.56(m, 2H), 3.84(t, J=6.4 Hz, 2H), 6.92(t, J=8.6 Hz, 1H), 7.09(d, J=8.0 Hz, 1H), 7.16-7.26(m, 2H), 7.44(t, J=8.2 Hz, 1H), 7.55(d, J=8.0 Hz, 1H), 7.74-7.83(m, 2H), 11.10(s, 1H).

Example 4-115

MS ESI m/e: 599 (M+H), 597 (M−H).
$^1$H-NMR(DMSO-d$_6$, 300 MHz)δ 0.65-0.73(m, 2H), 0.91-1.00(m, 2H), 1.14(s, 3H), 2.59-2.67(m, 1H), 3.09(s, 3H), 6.92(t, J=4.1 Hz, 1H), 7.11-7.16(m, 1H), 7.53-7.59(m, 2H), 7.76-7.83(m, 2H), 8.14(s, 1H), 11.10(s, 1H), 13.20(s, 1H).

Example 4-116

MS ESI m/e: 685.9 (M+H), 684.0 (M−H).
$^1$H-NMR(DMSO-d$_6$, 300 MHz)δ 0.62-0.70(m, 2H), 0.92-0.98(m, 2H), 1.26(s, 3H), 2.57-2.65(m, 1H), 3.08(s, 3H), 3.09(s, 3H), 6.94(dd, J=9.0, 8.7 Hz, 1H), 7.38(dd, J=2.3, 8.6 Hz, 1H), 7.51-7.57(m, 3H), 7.63(d, J=2.3 Hz, 1H), 7.78(dd, J=1.5, 10.2 Hz, 1H), 9.59(s, 1H), 11.01(s, 1H)

Example 4-117

MS ESI m/e: 666.0 (M+H), 664.1 (M−H).
$^1$H-NMR(DMSO-d$_6$, 300 MHz)δ 0.61-0.68(m, 2H), 0.90-0.97(m, 2H), 1.23(s, 3H), 2.30(s, 3H), 2.55-2.63(m, 1H), 3.09(s, 3H), 6.88-6.95(m, 1H), 7.15-7.34(m, 3H), 7.47-7.57(m, 2H), 7.70-7.80(m, 2H).

Example 4-118

MS ESI m/e: 630 (M+H), 628 (M–H).
$^1$H-NMR(CDCl$_3$, 300 MHz)δ 0.75-0.81(m, 2H), 1.09-1.15(m, 2H), 1.47(s, 3H), 2.70-2.77(m, 1H), 3.20(s, 3H), 4.66(s, 2H), 6.70(t, J=8.5 Hz, 1H), 6.81-6.88(m, 2H), 7.00(d, J=8.3 Hz, 1H), 7.43-7.55(m, 2H), 8.12(s, 1H), 11.31(s, 1H).

Example 4-119

MS ESI m/e: 612 (M+H), 610 (M–H).
$^1$H-NMR(DMSO-d$_6$, 300 MHz)δ 1.21(s, 3H), 3.09(s, 3H), 3.21(s, 3H), 6.96(t, J=8.5 Hz, 1H), 7.48(s, 2H), 7.53-7.64(m, 3H), 7.76-7.81(m, 1H), 7.90(d, J=8.3 Hz, 2H), 11.13(s, 1H).

Example 4-120

MS ESI m/e: 573 (M+H), 571 (M–H).
$^1$H-NMR(DMSO-d$_6$, 300 MHz)δ 0.66-0.69 (m, 2H), 0.94-0.98 (m, 2H), 1.26 (s, 3H), 2.50 (s, 3H), 2.61-2.66 (m, 1H), 3.04 (s, 3H), 6.98 (d, J=7.3 Hz, 1H), 7.10-7.19 (m, 6H), 7.31-7.33 (m, 2H), 9.66 (s, 1H), 11.23 (s, 1H).

Example 4-121

MS ESI m/e: 600 (M+H), 598 (M–H).
$^1$H-NMR(CDCl$_3$, 300 MHz)δ 0.80-0.90(m, 2H), 1.11-1.20(m, 2H), 1.27(s, 3H), 2.74-2.83(m, 1H), 3.24(s, 3H), 6.75(t, J=8.3 Hz, 1H), 7.37(dd, J=1.9, 8.7 Hz, 1H), 7.45-7.57(m, 2H), 7.80(brs, 3H), 11.37(s, 1H).

Example 4-122

MS ESI m/e: 671 (M+H), 669 (M–H).
$^1$H-NMR(DMSO-d$_6$, 400 MHz)δ 0.60-0.67(m, 2H), 0.87-0.95(m, 2H), 1.21(s, 3H), 2.24(brs, 3H), 2.54-2.61(m, 1H), 2.69(brs, 2H), 3.04(s, 3H), 3.07(brs, 2H), 3.62(brs, 2H), 6.89(t, J=8.7 Hz, 1H), 7.24-7.29(m, 1H), 7.30-7.35(m, 2H), 7.40-7.46(m, 1H), 7.48-7.53(m, 1H), 7.72-7.77(m, 1H), 11.01(s, 1H).

Example 4-123

MS ESI m/e: 628(M+H), 626(M–H).
$^1$H-NMR(DMSO-d$_6$, 300 MHz) δ 0.61-0.71(m, 2H), 0.90-1.00(m, 2H), 1.30(s, 3H), 2.50(t, J=7.5 Hz, 2H), 2.55-2.67(m, 1H), 2.95(t, J=7.5 Hz, 2H), 3.09(s, 3H), 6.87-6.95(m, 3H), 7.24(d, J=9.0 Hz, 1H), 7.57(d, J=9.0 Hz, 1H), 7.80(d, J=9.0 Hz, 1H), 10.11(brs, 1H), 11.07(brs, 1H).

Example 4-124

MS ESI m/e: 643 (M+H), 641 (M–H).
$^1$H-NMR(DMSO-d$_6$, 300 MHz)δ 0.63-0.72(m, 2H), 0.90-1.00(m, 2H), 1.27(s, 3H), 2.58-2.67(m, 1H), 3.08(s, 3H), 3.41(t, J=8.3 Hz, 2H), 3.85(t, J=8.3 Hz, 2H), 6.92(t, J=8.5 Hz, 1H), 6.98(d, J=7.8 Hz, 1H), 7.05(s, 1H), 7.37(t, J=8.1 Hz, 1H), 7.49(d, J=8.1 Hz, 1H), 7.55(d, J=8.4 Hz, 1H), 7.67-7.71(m, 1H), 7.79(dd, J=1.8, 10.5 Hz, 1H), 11.11(s, 1H).

Example 4-125

MS ESI m/e: 644 (M+H), 642 (M–H).
$^1$H-NMR(DMSO-d$_6$, 300 MHz)δ 0.62-0.72(m, 2H), 0.89-1.01(m, 2H), 1.25(s, 3H), 2.56-2.68(m, 1H), 3.08(s, 3H), 4.07(t, J=8.4 Hz, 2H), 4.45(t, J=8.4 Hz, 2H), 6.92(t, J=8.3 Hz, 1H), 7.14(d, J=8.1 Hz, 1H), 7.46(t, J=8.1 Hz, 1H), 7.51-7.60(m, 2H), 7.65-7.69(m, 1H), 7.78(d, J=9.3 Hz, 1H), 11.10(s, 1H).

Example 4-126

MS ESI m/e: 616 (M+H), 614 (M–H).
$^1$H-NMR(DMSO-d$_6$, 300 MHz)δ 0.62-0.73(m, 2H), 0.90-1.00(m, 2H), 1.24(s, 3H), 2.57-2.67(m, 1H), 3.08(s, 3H), 6.93(t, J=8.6 Hz, 1H), 7.08(dd, J=2.4, 8.7 Hz, 1H), 7.18(d, J=2.1 Hz, 1H), 7.34(d, J=8.1 Hz, 1H), 7.55(d, J=8.7 Hz, 1H), 7.79(dd, J=1.5, 10.5 Hz, 1H), 11.08(s, 1H), 11.80(s, 1H).

Example 4-127

MS ESI m/e: 638 (M+H), 636 (M–H).
$^1$H-NMR(DMSO-d$_6$, 300 MHz)δ 0.64-0.72(m, 2H), 0.90-1.01(m, 2H), 1.19(s, 3H), 2.57-2.66(m, 1H), 3.09(s, 3H), 6.94(t, J=8.7 Hz, 1H), 7.51(brs, 2H), 7.53-7.58(m, 1H), 7.61-7.70(m, 2H), 7.76-7.88(m, 3H), 11.05(brs, 1H).

Example 4-128

MS ESI m/e: 642 (M+H), 640 (M–H).
$^1$H-NMR(DMSO-d$_6$, 300 MHz)δ 0.59-0.72(m, 2H), 0.88-1.01(m, 2H), 1.27(s, 3H), 1.29(s, 6H), 2.55-2.67(m, 1H), 3.07(s, 3H), 6.86-6.97(m, 2H), 7.34(d, J=7.9 Hz, 1H), 7.55(dd, J=1.1, 7.9 Hz, 1H), 7.78(dd, J=1.1, 10.6 Hz, 1H), 10.44(brs, 1H), 11.07(s, 1H).

Example 4-129

MS ESI m/e: 574(M+H), 572(M–H).
$^1$H-NMR(DMSO-d$_6$, 300 MHz) δ 0.59-0.69(m, 2H), 0.89-0.99(m, 2H), 1.35(s, 3H), 2.52-2.66(m, 1H), 3.07(s, 3H), 5.25(brs, 2H), 6.46(d, J=6.0 Hz, 1H), 6.53(s, 1H), 6.55(d, J=9.0 Hz, 1H), 6.90(dd, J=9.0, 9.0 Hz, 1H), 7.06(dd, J=9.0, 9.0 Hz, 1H), 7.55(d, J=9.0 Hz, 1H), 7.78(d, J=9.0 Hz, 1H), 11.06(brs, 1H).

Example 4-130

MS ESI m/e: 640 (M+H), 638 (M–H).
$^1$H-NMR(DMSO-d$_6$, 300 MHz)δ 0.60-0.71(m, 2H), 0.89-1.00(m, 2H), 1.29(s, 3H), 1.47-1.55(m, 2H), 1.58-1.68(m, 2H), 2.55-2.68(m, 1H), 3.07(s, 3H), 6.87-6.96(m, 3H), 7.02(d, J=7.9 Hz, 1H), 7.52-7.58(m, 1H), 7.78(dd, J=1.9, 10.2 Hz, 1H), 10.66(brs, 1H), 11.07(brs, 1H).

Example 4-131

MS ESI m/e: 472 (M+H), 470 (M–H).
$^1$H-NMR(DMSO-d$_6$, 300 MHz)δ 0.59-0.70(m, 2H), 0.89-1.01(m, 2H), 1.36(s, 3H), 2.56-2.67(m, 1H), 3.10(s, 3H), 4.28(s, 1H), 5.24(s, 2H), 6.42-6.62(m, 3H), 6.99-7.14(m, 2H), 7.26-7.36(m, 1H), 7.46-7.57(m, 1H), 11.08(s, 1H).

Example 4-132

MS ESI m/e: 716(M+H), 714(M–H).
$^1$H-NMR(DMSO-d$_6$, 300 MHz) δ 0.62-0.74(m, 2H), 0.91-1.04(m, 2H), 1.28(s, 3H), 1.36(s, 9H), 2.48(s, 3H), 2.59-2.69(m, 1H), 3.08(s, 3H), 6.94(t, J=8.6 Hz, 1H), 7.17-7.24(m, 2H), 7.38-7.57(m, 3H), 7.79(d, J=10.3 Hz, 1H), 11.0(brs, 1H).

Example 4-133

MS ESI m/e: 694(M+H), 692(M−H).
$^1$H-NMR(DMSO-d$_6$, 400 MHz) δ 0.62-0.71(m, 2H), 0.92-1.01(m, 2H), 1.17(s, 3H), 1.95(s, 3H), 2.59-2.69(m, 1H), 3.08(s, 3H), 3.54(s, 3H), 6.94(d, J=9.0 Hz, 1H), 7.52-7.60(m, 5H), 7.79(d, J=10.4 Hz, 1H), 11.0(brs, 1H).

Example 4-134

MS ESI m/e: 620(M+H), 618(M−H).
$^1$H-NMR(DMSO-d$_6$, 300 MHz) δ 1.27(s, 3H), 2.06(s, 3H), 3.10(s, 3H), 3.49-3.60(m, 2H), 3.89-4.01(m, 2H), 4.78(brs, 1H), 6.95(t, J=8.7 Hz, 1H), 7.03-7.10(m, 1H), 7.41(t, J=8.0 Hz, 1H), 7.51-7.60(m, 2H), 7.68(s, 1H), 7.78-7.82(m, 1H), 10.1(brs, 1H), 11.3(brs, 1H).

Example 4-135

MS ESI m/e: 634(M+H), 632(M−H).
$^1$H-NMR(DMSO-d$_6$, 300 MHz) δ 1.27(s, 3H), 2.65-2.79(m, 2H), 2.06(s, 3H), 3.09(s, 3H), 3.39-3.50(m, 2H), 3.82-3.94(m, 2H), 4.46(brs, 1H), 6.95(t, J=8.7 Hz, 1H), 7.07-7.10(m, 1H), 7.38(t, J=8.0 Hz, 1H), 7.55-7.58(m, 2H), 7.68(s, 1H), 7.78-7.81(m, 1H), 10.1(brs, 1H), 11.3(brs, 1H).

Example 4-136

MS ESI m/e: 650 (M+H), 648 (M−1).
$^1$H-NMR(DMSO-d$_6$, 300 MHz)δ 1.27(s,3H), 2.05(s,3H), 3.09(s,3H), 3.70-3.90(m, 2H), 4.02(q, J=7.8 Hz 1H), 4.55(t, J=5.7 Hz, 1H), 4.77(d, J=5.4 Hz, 1H), 6.94(t, J=8.7 Hz, 1H), 7.05(d, J=7.5 Hz, 1H), 7.37(t, J=8.1 Hz, 1H), 7.56(d, J=8.7 Hz, 2H), 7.68(s, 1H), 7.79(dd, J=1.5, 10.2 Hz, 1H), 10.10(s, 1H), 11.30(s, 1H).

Example 4-137

MS ESI m/e: 650 (M+H), 648 (M−1).
$^1$H-NMR(DMSO-d$_6$, 300 MHz)δ 1.27(s,3H), 2.05(s,3H), 3.09(s,3H), 3.70-3.90(m, 2H), 4.02(q, J=7.1 Hz, 1H), 4.55(brs, 1H), 4.77(d, J=3.9 Hz, 1H), 6.94(t, J=8.5 Hz, 1H), 7.04(d, J=8.7 Hz, 1H), 7.37(t, J=8.1 Hz, 1H), 7.56(d, J=8.7 Hz, 2H), 7.68(s, 1H), 7.79(dd, J=2.4, 10.8 Hz, 1H), 10.10(s, 1H), 11.30(s, 1H).

Example 4-138

MS ESI m/e: 723(M+H), 721(M−H).
$^1$H-NMR(DMSO-d$_6$, 300 MHz) δ 0.65-0.72(m, 2H), 0.91-1.01(m, 2H), 1.27(s, 3H), 1.91(s, 3H), 2.59-2.69(m, 1H), 2.93(s, 6H), 3.10(s, 3H), 6.98(t, J=8.6 Hz, 1H), 7.43-7.60(m, 5H), 7.80(d, J=10.3 Hz, 1H), 11.0(brs, 1H).

Example 4-139

MS ESI m/e: 630 (M+H), 628 (M−H).
$^1$H-NMR(DMSO-d$_6$, 400 MHz)δ 0.63-0.71(m, 2H), 0.92-1.00(m, 2H), 1.26(s, 3H), 1.82(brs, 3H), 2.58-2.67(m, 1H), 3.08(s, 3H), 3.16(brs, 3H), 6.94(t, J=8.7 Hz, 1H), 7.30-7.46(m, 3H), 7.47-7.60(m, 2H), 7.76-7.82(m, 1H), 11.02(s, 1H).

Example 4-140

MS ESI m/e: 658 (M+H), 656 (M−H).
$^1$H-NMR(DMSO-d$_6$, 400 MHz) δ 0.61-0.72(m, 2H), 0.92-1.01(m, 2H), 1.28(s, 3H), 2.20(s, 6H), 2.58-2.66(m, 1H), 3.08(s, 3H), 6.94(t, J=8.6 Hz, 1H), 7.29-7.35(m, 1H), 7.36-7.40(m, 1H), 7.42-7.48(m, 1H), 7.51-7.58(m, 2H), 7.75-7.82(m, 1H), 11.00(s, 1H).

Example 4-141

MS ESI m/e: 633 (M+H), 631 (M−H).
$^1$H-NMR(DMSO-d$_6$, 300 MHz)δ 1.27(s, 3H), 1.81-1.93(m, 2H), 2.05(s, 3H), 2.75-2.87(m, 2H), 3.09(s, 3H), 3.91(t, 2H, J=6.2 Hz), 6.93(t, 1H, J=8.5 Hz), 7.04-7.10(m, 1H), 7.38(t, 1H, J=8.1 Hz), 7.48-7.59(m, 2H), 7.69-7.86(m, 5H), 10.18(s, 1H), 11.21(s, 1H).

Example 4-142

MS ESI m/e: 664 (M+H), 662 (M−H).
$^1$H-NMR(DMSO-d$_6$, 300 MHz)δ 1.26(s, 3H), 1.46-1.57(m, 1H), 1.65-1.80(m, 1H), 2.05(s, 3H), 3.08(s, 3H), 3.15-3.36(m, 2H), 3.40-3.51(m, 1H), 3.78-3.91(m, 1H), 3.98-4.11(m, 1H), 4.46-4.56(m, 2H), 6.94(t, 1H, J=8.7 Hz), 7.04-7.10(m, 1H), 7.37(t, 1H, J=8.1 Hz), 7.52-7.59(m, 2H), 7.65-7.69(m, 1H), 7.79(dd, 1H, J=1.9, 10.5 Hz), 10.10(s, 1H), 11.28(s, 1H).

Example 4-143

MS ESI m/e: 664 (M+H), 662 (M−H).
$^1$H-NMR(DMSO-d$_6$, 300 MHz)δ 1.26(s, 3H), 1.43-1.59(m, 1H), 1.67-1.79(m, 1H), 2.04(s, 3H), 3.08(s, 3H), 3.15-3.32(m, 2H), 3.40-3.50(m, 1H), 3.78-3.91(m, 1H), 3.97-4.10(m, 1H), 4.45-4.54(m, 2H), 6.94(t, 1H, J=8.7 Hz), 7.04-7.09(m, 1H), 7.37(t, 1H, J=8.1 Hz), 7.53-7.59(m, 2H), 7.65-7.69(m, 1H), 7.79(dd, 1H, J=1.9, 10.2 Hz), 10.10(s, 1H), 11.27(s, 1H).

Example 4-144

MS ESI m/e: 648 (M+H), 646 (M−H).
$^1$H-NMR(CDCL3, 300 MHz)δ 1.42(s, 3H), 1.53-1.82(m, 4H), 2.17(s, 3H), 3.21(s, 3H), 3.68(t, 2H, J=6.2 Hz), 3.96-4.04(m, 2H), 6.70(t, 1H, J=8.3 Hz), 7.05-7.12(m, 1H), 7.22-7.56(m, 6H), 7.70(s, 1H), 11.47(s, 1H).

Example 4-145

MS ESI m/e: 670 (M+H), 668 (M−H).
$^1$H-NMR(DMSO-d$_6$, 300 MHz)δ 1.26 (s, 3H), 1.66-1.75 (m, 2H), 3.02 (s, 3H), 3.08 (s, 3H), 3.42 (q, 2H, J=5.9 Hz), 3.88-3.91 (m, 2H), 4.45 (t, 1H, J=5.1 Hz), 6.94 (t, 1H, J=8.6 Hz), 7.12-7.15 (m, 1H), 7.23-7.29 (m, 2H), 7.42 (t, 1H, J=7.9 Hz), 7.54-7.57 (m, 1H), 7.78 (dd, 1H, J=10.5, 1.7 Hz), 9.92 (s, 1H), 11.26 (s, 1H).

Example 4-146

MS ESI m/e: 634 (M+H), 632 (M−H).
$^1$H-NMR(DMSO-d$_6$, 400 MHz)δ 1.25(s, 3H), 1.66-1.75(m, 2H), 3.08(s, 3H), 3.42(q, 2H, J=4.5 Hz), 3.86-3.93(m, 2H), 4.46(t, 1H, J=3.8 Hz), 6.95(t, 1H, J=6.4 Hz), 7.11(dd, 1H, J=1.7, 6.4 Hz), 7.22(d, 1H, J=1.6 Hz), 7.35(d, 1H, J=6.4 Hz), 7.53-7.58(m, 1H), 7.79(dd, 1H, J=1.4, 7.8 Hz), 11.27(s, 1H), 11.84(s, 1H).

Example 4-147

MS ESI m/e: 577 (M+H), 575 (M–H).
$^1$H-NMR(DMSO-d$_6$, 300 MHz)δ 1.19(s, 3H), 1.65-1.76 (m, 2H), 3.08(s, 3H), 3.43(q, 2H, J=5.9 Hz), 3.86-3.94(m, 2H), 4.46(t, 1H, J=5.3 Hz), 6.95(t, 1H, J=8.7 Hz), 7.38-7.51 (m, 5H), 7.52-7.58(m, 1H), 7.79(dd, 1H, J=1.9, 10.2 Hz), 11.25(s, 1H).

Example 4-148

MS ESI m/e: 650 (M+H), 648 (M–H).
$^1$H-NMR(DMSO-d$_6$, 300 MHz)δ 1.26 (s, 3H), 1.70-1.72 (m, 2H), 3.08 (s, 3H), 3.42 (q, 2H, J=5.7 Hz), 3.89-3.91 (m, 2H), 3.99 (d, 2H, J=5.9 Hz), 4.44 (t, 1H, J=5.3 Hz), 5.64 (t, 1H, J=6.1 Hz), 6.94 (t, 1H, J=8.6 Hz), 7.11 (d, 1H, J=7.0 Hz), 7.39 (t, 1H, J=8.3 Hz), 7.55 (d, 1H, J=8.1 Hz), 7.70-7.81 (m, 3H), 9.83 (s, 1H), 11.25 (s, 1H).

INDUSTRIAL APPLICABILITY

The compound of the present invention shows superior p15 protein inducing action and/or p27 protein inducing action and/or MEK inhibitory action.

In addition, the compound of the present invention shows superior antitumor activity, and anti-rheumatism activity.

Therefore, the compound can be a pharmaceutical agent effective for the prophylaxis or treatment of a disease caused by undesirable cell proliferation, particularly, tumor or rheumatism.

This application is based on patent application Nos. 174770/2004 and 327111/2004 filed in Japan, the contents of which are hereby incorporated by reference.

What is claimed is:

1. A compound represented by the following formula [I] or a pharmaceutically acceptable salt, hydrate, or solvate thereof:

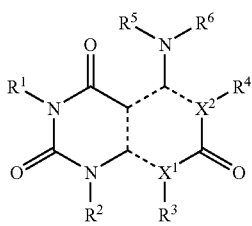

wherein
the moiety is

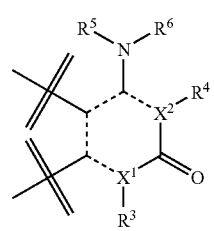

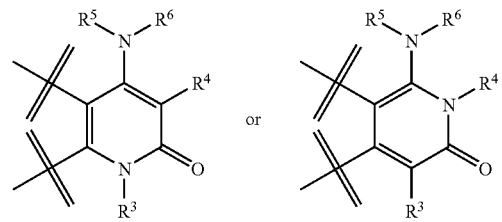

$R^1$ and $R^6$ are the same or different and each is
a $C_{1-6}$ alkyl group,
a $C_{2-6}$ alkenyl group,
  wherein the $C_{1-6}$ alkyl group and the $C_{2-6}$ alkenyl group are optionally substituted by 1 to 3 substituents selected from the following group A, or

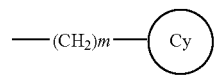

wherein m is 0 or an integer of 1 to 4,
  ring Cy is a $C_{3-12}$ carbon ring group or a heterocyclic group,
    wherein the heterocyclic group is a saturated or unsaturated ring group having, besides carbon atom, 1 to 4 hetero atoms selected from an oxygen atom, a nitrogen atom and a sulfur atom, the $C_{3-12}$ carbon ring group and the heterocyclic group are optionally substituted by 1 to 5 substituents selected from the following group B,
$R^2$ is
a $C_{2-6}$ alkenyl group,
  wherein the $C_{2-6}$ alkenyl group is optionally substituted by 1 to 3 substituents selected from the following group A, or

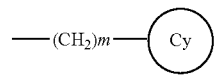

wherein m is 0 or an integer of 1 to 4,
  ring Cy is a $C_{3-12}$ carbon ring group or a heterocyclic group,
    wherein the heterocyclic group is a saturated or unsaturated ring group having, besides carbon atom, 1 to 4 hetero atoms selected from an oxygen atom, a nitrogen atom and a sulfur atom, the $C_{3-12}$ carbon ring group and the heterocyclic group are optionally substituted by 1 to 5 substituents selected from the following group B,
$R^3$, $R^4$, and $R^5$ are the same or different and each is
a hydrogen atom,
a hydroxyl group,
a $C_{1-6}$ alkyl group,
a $C_{2-6}$ alkenyl group,
  wherein the $C_{1-6}$ alkyl group and the $C_{2-6}$ alkenyl group are optionally substituted by 1 to 3 substituents selected from the following group A,
a $C_{3-12}$ carbon ring group or
a heterocyclic group, wherein the heterocyclic group is a saturated or unsaturated ring group having, besides carbon atom, 1 to 4 hetero atoms selected from an oxygen atom, a nitrogen atom and a sulfur atom, and the $C_{3-12}$ carbon ring group and the heterocyclic group are optionally substituted by 1 to 5 substituents selected from the following group B, or $R^2$ and $R^3$ are optionally linked to form a $C_{1-4}$ alkylene group, or $R^4$ and $R^5$ are optionally linked to form a $C_{1-4}$ alkylene group, wherein group A is a group consisting of
1) a halogen atom,
2) a nitro group,
3) a cyano group,
4) a $C_{1-4}$ alkyl group,
5) —$OR^{A1}$ wherein $R^{A1}$ is a hydrogen atom or a $C_{1-4}$ alkyl group,
6) —$SR^{A2}$ wherein $R^{A2}$ is a hydrogen atom or a $C_{1-4}$ alkyl group,
7) —$NR^{A3}R^{A4}$ wherein $R^{A3}$ and $R^{A4}$ are the same or different and each is a hydrogen atom or a $C_{1-4}$ alkyl group,
8) —$COOR^{A5}$ wherein $R^{A5}$ is a hydrogen atom or a $C_{1-4}$ alkyl group,
9) —$NR^{A6}COR^{A7}$ wherein $R^{A6}$ is a hydrogen atom or a $C_{1-4}$ alkyl group, $R^{A7}$ is a $C_{1-4}$ alkyl group, a $C_{3-12}$ carbon ring group or a heterocyclic group,
10) —$NR^{A8}COOR^{A9}$ wherein $R^{A8}$ and $R^{A9}$ are the same or different and each is a hydrogen atom or a $C_{1-4}$ alkyl group,
11) a $C_{3-12}$ carbon ring group and
12) a heterocyclic group,
    wherein the heterocyclic group is a saturated or unsaturated ring group having, besides carbon atom, 1 to 4 hetero atoms selected from an oxygen atom, a nitrogen atom and a sulfur atom,
    each of the $C_{1-4}$ alkyl groups of the above-mentioned 4), $R^{A1}$, $R^{A2}$, $R^{A3}$, $R^{A4}$, $R^{A5}$, $R^{A6}R^{A7}$, $R^{A8}$ and $R^{A9}$ is optionally substituted by the same or different 1 to 3 substituents selected from the following group C, and
    each of the $C_{3-12}$ carbon ring groups of the above-mentioned 11) and $R^{A7}$, and the heterocyclic groups of 12) and $R^{A7}$ is optionally substituted by the same or different 1 to 5 substituents selected from the following group C group B is a group consisting of
1) a halogen atom,
2) a nitro group,
3) a cyano group,
4) a $C_{1-8}$ alkyl group,
5) a $C_{2-4}$ alkenyl group,
6) a $C_{2-4}$ alkynyl group,
7) —$OR^{B1}$ wherein $R^{B1}$ is a hydrogen atom or a $C_{1-4}$ alkyl group,
8) —$SR^{B2}$ wherein $R^{B2}$ is a hydrogen atom or a $C_{1-4}$ alkyl group,
9) —$NR^{B3}R^{B4}$ wherein $R^{B3}$ is a hydrogen atom, a $C_{1-4}$ alkyl group, a $C_{3-12}$ carbon ring group or a heterocyclic group, and $R^{B4}$ is a hydrogen atom or a $C_{1-4}$ alkyl group,
10) —$NR^{B5}COR^{B6}$ wherein $R^{B5}$ is a hydrogen atom or a $C_{1-4}$ alkyl group, and $R^{B6}$ is a hydrogen atom, a $C_{1-4}$ alkyl group, a $C_{3-12}$ carbon ring group or a heterocyclic group,
11) —$NR^{B7}COOR^{B8}$ wherein $R^{B7}$ and $R^{B8}$ are the same or different and each is a hydrogen atom or a $C_{1-4}$ alkyl group,
12) —$NR^{B9}CONR^{B10}R^{B11}$ wherein $R^{B9}$, $R^{B10}$ and $R^{B11}$ are the same or different and each is a hydrogen atom or a $C_{1-4}$ alkyl group,
13) —$NR^{B12}CONR^{B13}OR^{B14}$ wherein $R^{B12}$, $R^{B13}$ and $R^{B14}$ are the same or different and each is a hydrogen atom or a $C_{1-4}$ alkyl group,
14) —$NR^{B15}SO_2R^{B16}$ wherein $R^{B15}$ is a hydrogen atom or a $C_{1-4}$ alkyl group, and $R^{B16}$ is a $C_{1-4}$ alkyl group, a $C_{3-12}$ carbon ring group or a heterocyclic group,
15) —$SO_2$—$R^{B17}$ wherein $R^{B17}$ is a $C_{1-4}$ alkyl group or a heterocyclic group,
16) —$SO_2NR^{B18}R^{B19}$ wherein $R^{B18}$ and $R^{B19}$ are the same or different and each is a hydrogen atom or a $C_{1-4}$ alkyl group,
17) —$P(=O)(R^{B20})(R^{B21})$ wherein $R^{B20}$ and $R^{B21}$ are the same or different and each is a $C_{1-4}$ alkyl group,
18) —$COOR^{B22}$ wherein $R^{B22}$ is a hydrogen atom or a $C_{1-4}$ alkyl group,
19) —$CONR^{B23}R^{B24}$ wherein $R^{B23}$ and $R^{B24}$ are the same or different and each is a hydrogen atom or a $C_{1-4}$ alkyl group,
20) —$NR^{B25}SO_2NR^{B26}R^{B27}$ wherein $R^{B25}$, $R^{B26}$ and $R^{B27}$ are the same or different and each is a hydrogen atom or a $C_{1-4}$ alkyl group,
21) —$NR^{B28}SO_2NR^{B29}CONR^{B30}R^{B31}$ wherein $R^{B28}$, $R^{B29}$, $R^{B30}$ and $R^{B31}$ are the same or different and each is a hydrogen atom or a $C_{1-4}$ alkyl group,
22) a $C_{3-12}$ carbon ring group and
23) a heterocyclic group
    wherein each of the "$C_{1-8}$ alkyl group" of the above-mentioned 4), and the $C_{1-4}$ alkyl groups for $R^{B1}$ to $R^{B31}$ is optionally substituted by the same or different 1 to 3 substituents selected from the above-mentioned group A,
    each of the $C_{2-4}$ alkenyl group of 5) and the $C_{2-4}$ alkynyl group of 6) is optionally substituted by the same or different 1 to 3 substituents selected from the above-mentioned group A,
    the heterocyclic group is a saturated or unsaturated ring group having, besides carbon atom, 1 to 4 hetero atoms selected from an oxygen atom, a nitrogen atom and a sulfur atom, and
    each of the $C_{3-12}$ carbon ring group of the above-mentioned 22), $R^{B3}$, $R^{B6}$ and $R^{B16}$, and the heterocyclic group of the above-mentioned 23), $R^{B3}$, $R^{B6}$, $R^{B16}$ and $R^{B17}$ is optionally substituted by the same or different 1 to 5 substituents selected from the following group C, and group C is a group consisting of
1) a halogen atom,
2) a cyano group,
3) a $C_{1-4}$ alkyl group,
4) —$OR^{C1}$ wherein $R^{C1}$ is a hydrogen atom or a $C_{1-4}$ alkyl group,
5) —$NR^{C2}R^{C3}$ wherein $R^{C2}$ and $R^{C3}$ are the same or different and each is a hydrogen atom or a $C_{1-4}$ alkyl group,
6) —$COOR^{C4}$ wherein $R^{C4}$ is a hydrogen atom or a $C_{1-4}$ alkyl group and
7) an oxo group,
provided that when $R^2$ is a phenyl group, then $R^1$ is not a phenyl group.

2. The compound of claim 1 or a pharmaceutically acceptable salt, hydrate, or solvate thereof, wherein the compound is represented by the following formula: [I-1]

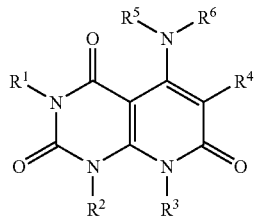

[I-1]

wherein each symbol in the formula is as defined in claim 1.

3. The compound of claim 1 or a pharmaceutically acceptable salt, hydrate, or solvate thereof, wherein the compound is represented by the following formula: [I-3]

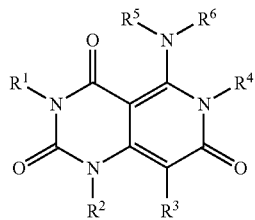

[I-3]

wherein each symbol in the formula is as defined in claim 1.

4. The compound of any one of claims 1, 2 and 3, or a pharmaceutically acceptable salt, hydrate, or solvate thereof, wherein $R^1$ is a $C_{1-6}$ alkyl group.

5. The compound of any one of claims 1, 2 and 3, or a pharmaceutically acceptable salt, hydrate, or solvate thereof, wherein $R^1$ is

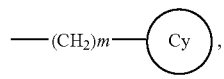

wherein m is 0, and ring Cy is a $C_{3-12}$ carbon ring group,
wherein the $C_{3-12}$ carbon ring group is optionally substituted by 1 to 5 substituents selected from group B of claim 1.

6. The compound of claim 5 or a pharmaceutically acceptable salt, hydrate, or solvate thereof, wherein $R^1$ is a $C_{3-8}$ cycloalkyl group.

7. The compound of claim 6 or a pharmaceutically acceptable salt, hydrate, or solvate thereof, wherein $R^1$ is a cyclopropyl group.

8. The compound of any one of claims 1, 2 and 3, or a pharmaceutically acceptable salt, hydrate, or solvate thereof, wherein $R^2$ is

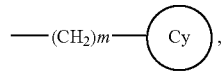

wherein m is 0, and ring Cy is a $C_{3-12}$ carbon ring group or a heterocyclic group,
wherein the $C_{3-12}$ carbon ring group and the heterocyclic group are optionally substituted by 1 to 5 substituents selected from group B of claim 1.

9. The compound of any one of claims 1, 2 and 3, or a pharmaceutically acceptable salt, hydrate, or solvate thereof, wherein $R^3$ is a $C_{1-6}$ alkyl group.

10. The compound of any one of claims 1, 2 and 3, or a pharmaceutically acceptable salt, hydrate, or solvate thereof, wherein $R^4$ is a hydrogen atom.

11. The compound of any one of claims 1, 2 and 3, or a pharmaceutically acceptable salt, hydrate, or solvate thereof, wherein $R^5$ is a hydrogen atom.

12. The compound of any one of claims 1, 2 and 3, or a pharmaceutically acceptable salt, hydrate, or solvate thereof, wherein $R^6$ is

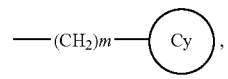

wherein m is 0, and ring Cy is a $C_{3-12}$ carbon ring group or a heterocyclic group,
wherein the $C_{3-12}$ carbon ring group and the heterocyclic group are optionally substituted by 1 to 5 substituents selected from group B of claim 1.

13. The compound of claim 1, which is N-{3-[3-cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]-phenyl}-acetamide or a pharmaceutically acceptable salt, hydrate, or solvate thereof.

14. The compound of claim 13, wherein the compound is the sodium salt thereof.

15. The compound of claim 13, wherein the compound is the hydrate thereof.

16. The compound of claim 13, wherein the compound is the acetic acid solvate thereof.

17. The compound of claim 13, wherein the compound is the dimethylsulfoxide solvate thereof.

18. The compound of claim 13, wherein the compound is the ethanol solvate thereof.

19. The compound of claim 13, wherein the compound is the nitromethane solvate thereof.

20. The compound of claim 13, wherein the compound is the chlorobenzene solvate thereof.

21. The compound of claim 13, wherein the compound is the 1-pentanol solvate thereof.

22. The compound of claim 13, wherein the compound is the isopropyl alcohol solvate thereof.

23. The compound of claim 13, wherein the compound is the ethylene glycol solvate thereof.

24. The compound of claim 13, wherein the compound is the 3-methylbutanol solvate thereof.

25. A pharmaceutical composition comprising
(a) a compound of claim 1 or 13 or a pharmaceutically acceptable salt, hydrate, or solvate thereof, and
(b) a pharmaceutically acceptable carrier.

26. A pharmaceutical composition comprising
(a) a compound of claim 1 or 13 or a pharmaceutically acceptable salt, hydrate, or solvate thereof,
(b) at least one antitumor compound that is not a compound of the formula [I]or a pharmaceutically acceptable salt, hydrate, or solvate thereof, and
(c) a pharmaceutically acceptable carrier.

* * * * *